US012653879B2

(12) United States Patent (10) Patent No.: US 12,653,879 B2

Delany et al. (45) Date of Patent: Jun. 16, 2026

---

(54) OUTER MEMBRANE VESICLES

(71) Applicant: GLAXOSMITHKLINE BIOLOGICALS SA, Rixensart (BE)

(72) Inventors: Isabel Delany, Siena (IT); Giulia Giordano, Siena (IT); Rosanna Leuzzi, Siena (IT); Immaculada Margarit Y Ros, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 394 days.

(21) Appl. No.: 18/025,273

(22) PCT Filed: Sep. 9, 2021

(86) PCT No.: PCT/EP2021/074744

§ 371 (c)(1),
(2) Date: Mar. 8, 2023

(87) PCT Pub. No.: WO2022/053535

PCT Pub. Date: Mar. 17, 2022

(65) Prior Publication Data

US 2023/0321213 A1 Oct. 12, 2023

(30) Foreign Application Priority Data

Sep. 11, 2020 (EP) ..................................... 20195709

(51) Int. Cl.
| | |
|---|---|
| *A61K 39/095* | (2006.01) |
| *A61K 39/00* | (2006.01) |
| *A61K 39/39* | (2006.01) |
| *A61P 31/04* | (2006.01) |
| *C12N 1/20* | (2006.01) |
| *C12N 1/205* | (2026.01) |
| *C12N 1/36* | (2006.01) |
| *C12R 1/36* | (2006.01) |

(52) U.S. Cl.
CPC ............ *A61K 39/095* (2013.01); *A61K 39/39* (2013.01); *A61P 31/04* (2018.01); *C12N 1/205* (2021.05); *C12N 1/36* (2013.01); *A61K 2039/521* (2013.01); *A61K 2039/55505* (2013.01); *C12R 2001/36* (2021.05)

(58) Field of Classification Search
None
See application file for complete search history.

(56) References Cited

U.S. PATENT DOCUMENTS

2009/0035328 A1* 2/2009 Granoff ................ A61K 39/095
435/69.3

FOREIGN PATENT DOCUMENTS

| WO | 2013006055 A1 | 1/2013 |
|---|---|---|
| WO | 2017129752 A1 | 8/2017 |
| WO | 2018042017 A2 | 3/2018 |

OTHER PUBLICATIONS

Zhu et al. Infection and Immunity, vol. 73, No. 11, p. 7558-7568, 2005.*
GenBank accession #AAW88912 Jul. 1, 2015.*
NCBI accession AE004969 Jul. 1, 2015.*
NCBI WP_003689500 Oct. 22, 2019.*
PCT/EP2021/074744 International Search Report and Written Opinion, mailed Nov. 17, 2021 (10 pages).
21st International Pathogenic Neisseria Conference, Jan. 23, 2018 (Jan. 23, 2018)—Jan. 28, 2018 (Jan. 28, 2018), pp. 1-264, p. 240, OP174.
Jordan, Philip W., et al: "Strain-specific differences in Neisseria gonorrhoeae associated with the phase variable gene repertoire", BMC Microbiology, 2005.5:21, Apr. 27, 2005 (Apr. 27, 2005) p. 21 (12 pages).
Weiyan Zhu et al: "Vaccines for Gonorrhea: Can We Rise to the Challenge?", Frontiers in Microbiology, vol. 2, Jan. 1, 2011 (Jan. 1, 2011).

* cited by examiner

*Primary Examiner* — Oluwatosin A Ogunbiyi

(57) ABSTRACT

The present invention relates to the field of neisserial vaccine compositions (particularly gonococcal vaccine compositions) and the use of such compositions in medicine. More particularly, the present invention relates to genetically modified gonococci of strain FA1090 and outer membrane vesicles obtained therefrom. The invention also provides a process for preparing the genetically modified gonococci of the invention as well as immunogenic compositions and vaccines comprising the outer membrane vesicles of the invention.

21 Claims, 55 Drawing Sheets

Specification includes a Sequence Listing.

Distribution by Country

F62

FA1090

MS11

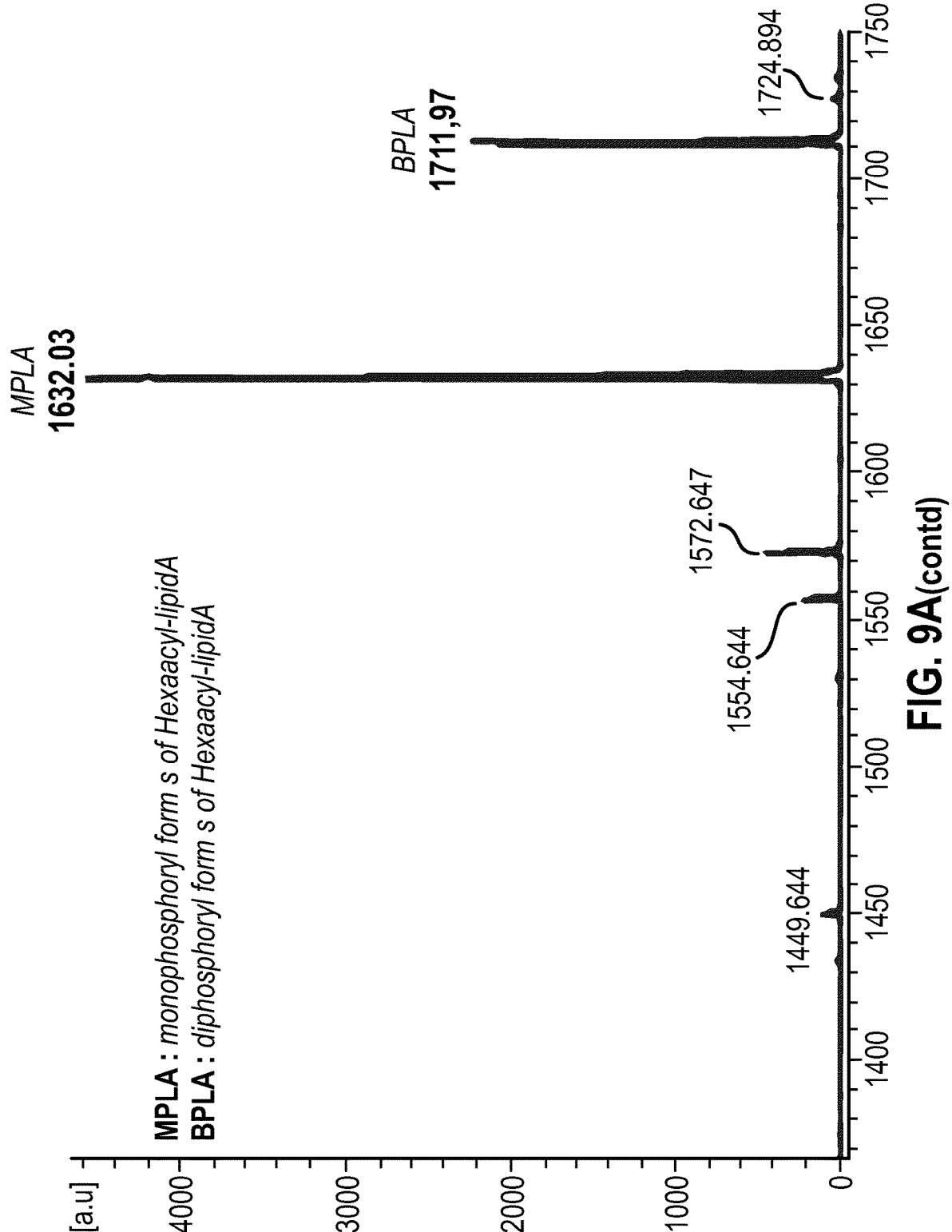
MPLA : monophosphoryl form s of Hexaacyl-lipidA
BPLA : diphosphoryl form s of Hexaacyl-lipidA
FIG. 9A(contd)

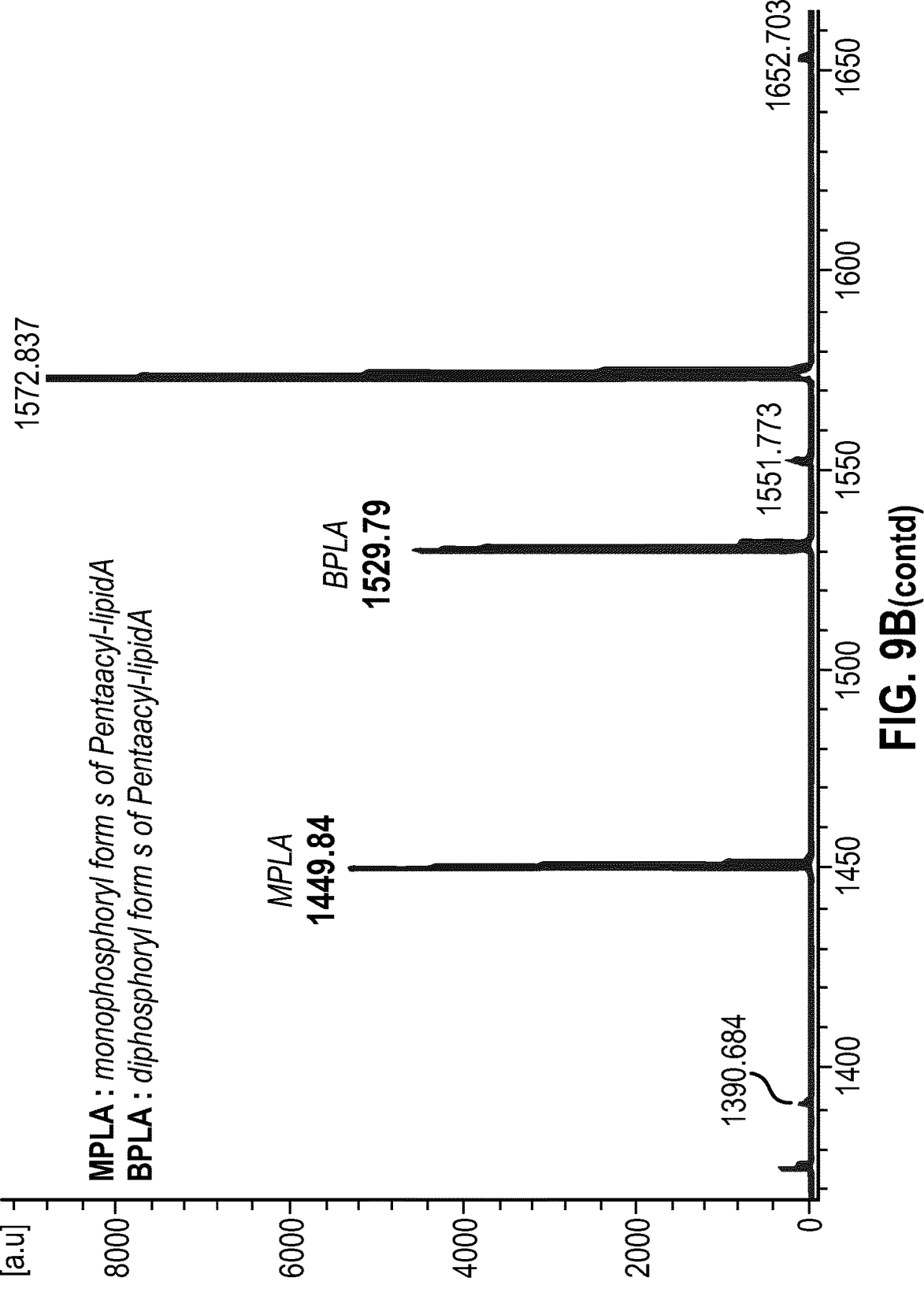
MPLA : *monophosphoryl form s of Pentaacyl-lipidA*
BPLA : *diphosphoryl form s of Pentaacyl-lipidA*
FIG. 9B(contd)

FIG. 12

```
CCGGCATCGACGCTGATGCTCGGTCAGGCGGCGGGAGCGGCATTGGCGCTTTGGTCAGCCATAAGCTGCCCGTTTCGGAATA
CACGGCCCTTGCCAGGTCAAAACCAGGCGGTCGGCAAAGGCGGCAAAGGCGGCGAAAGCAACCAGGTGCAGCATATGGTGGTGCAAATGC
TGGGACTTTCGGGAACGCCGCAGGCGGGATGCGGCGGACGGGTCTTGCCGTGCCGCTGACCCGCCTTACGCAACCACGGGCTT
GCCGCCAAACTCAATCCTTCGGGATGCCAGGTCAGCTGCCGGAAGGTTTCAATAGTTTGTATTTGCCGCCT
GAAAAGAAAATGTGTACCGCGAATGAAAATTTATATTTTTTGTACTGGTGTTTTGCAGTTTCTGCCGTTTGCGCTGCACAA
GATTGCCGCGGCCTGATCGGTTCGCTTGCCTACCTTCTGGTCAAACCGCCGTATCGGCGAAATCAATTTGGCAAAATGTT
TTCCCGAATGGGACGGACGAAGAAAAGCGTAAAACCGTGTTGAAACAGCATTCAACATGCCGGCAATAAGCTCGAATACGGC
TTATATTGGTACGCGTCTGCCAAATGCCTGAAATCGCTGGTGCGCTACCGCGGTGGCGGTTAATCGGCGGTTACCGCGTGCCGCTGA
GGGGGAAAAGTCATCATCCTGTACCCGCCACTTTACCGCGTTCGAGATGGCGGTGTACGGCGTTAATCAGGATGTCCCGCTGA
TCAGTATGTATTCCCACCAAAAAAACAAGATATTGGACGAACAGATTTTGAAAGGCCGCAACCGCTATCACAACGTCTTCCTT
ATCGGGGCGGCCACCGAAGGGCTGCGCGCCCTCGTCAAACAGTTCCGCAAAAGCAGTGCGCCGTTCCTGTATCTGCCCGATCAGGA
TTTTCCGACGCAACAATTCGGTTTTTTGTGGATTTTTTCGGCATTCCCCGTCCGCGCAACGATTACCGGCTTGCAATTCTATCCCGCTTGGAAA
TTGCAAATGCAAAAGTGATACCCCGTGTTTTTTGTGGATTTTTTCGGCATTCCCCGTCCGCGCAACGCGCAACCGGAACA
TCCTTTCCGAGTGAAGAGCGCAAGCGGTTTCAAAACCCGGAAGGCAGCCCCGATTTTTACTGACTACACAGGATTGCCGGACGCGGTTTT
ATATTTCTGGCTGCGCACAAGCGGTTTCAAAACCCGGAAGGCAGCCCCGATTTTTACTGACTACACAGGATTGCCGGACGCGGTTTT
TCAGCGGTTGCTGCGCACAAGCGGTTTCAAAACCCGATTGTTTTTGGAATTTGAAACCCGGTTTTAAAGGCTTATTCCGAGAACA
AACGGTTCAGTTGTTTGTAAAAACAATGCTTTTTTAAAATATATATAGTAGTGATTAACAAAACCAATACGGCGTGCTTCGGCTTCA
AAGGGGAGTGGATGCCGAAAAACCCGGTTAATATATATATAGTAGTGATTAACAAAACCAATACGGCGTGCTTCGGCCTTGT
AAGAGAACGATTCCCTAAGGTGCTGAAGCACCAGCGAATCGGTTCCGTACTATTTGTACTCGTTCTGCCGCCTTGT
CCTGATTTTGTTAATCCACTATAAAAATAAATTTGTTTAAAAACATAAAGTTGTAAACAAGTATCTCATATAAGCCTTTTTC
ATTAAAACAGATAGTCAGATATTTGTGCTAAAAATTTATATAAATTATATAAATTCAAGTTATAAAAAATATATGGAATT
TTATTTTGTTTATTTTATAATTTTAAGCA
``` lpxL1 gene

ATG – start codon lpxL1

TACCCGCACTTTA ... TTTTCCGACGC / CAGGA Borders of the UP and DOWN cassettes of recombination

TGA – stop codon lpxL1

FIG. 13

```
AACCCCGATTGTTTTGGGAATTTGAAACCCGGGTTGTACAAACAGGATTGCCGGACGGTTTAACGGTTCAGTTGTTTGTA
AAAACAATGCTTTTTTAAAATTGACAAAAACGAAATCGGTTTAAAGGCTTATTCCGAGAACAAAGGGGAGTGGATGCCGAA
AACCCGGTTAATATATTATAGTGGATTAACAAAAACCAATACGGCGTTGCTTCGCTTAGCTCAAAGAGAACGATTCCCTAAG
GTGCTGAAGCACCAAGCGAATCGGTTCCGTACTATTGTGTCTCGCGGCTTCGCCGCCTTGTCCTGATTTTTGTTAATCCA
CTATAAAATTAAATTGTTTAAAACATAAAGTTGTAAACAAGTATCTCATATAAGCCTTTTTCATTAAACAGATAGTCAGAT
ATTTTGTGCTAAAAATTTATATAATATTAAATTAATATCAAGTTATAAAAATATATGGAATTTTATTTGTTTATTTATAA
TTTTAAGCA
```

*lpxL1* gene

ATG – start codon *lpxL1*

TGA – stop codon *lpxL1*

Borders of the UP and DOWN cassettes of recombination

*kanR cassette* – antibiotic (kanamycin) resistance cassette

CAACGGCAATCGTGCGATATGGAAAAAATCCCCTAAAGTAATGACACGGAATTGATTTTTCGGCATGATAGACTATCAGGAA
ACAGGCTGTTTTACGGTTGTTGTTTTCAGGCGTTGAGTATTGACAGTCCGCCCCCCCTGTTTCTTTATAGTGGAGACTGAAATATCCG
ATTTGCCGCCATGTTTCTACAGCGGCCTGTGTATGTTGGCAATTCAGCAGTTGCTTCTGTATCTGCTGTACAAATCTAATGAGGG
AATAAAATGACCAAACAGCTGAAATTAAGCGCATTATTCGTTGCATTTCGTTGCTTCGCTTCCGGCACTGCTGTTGCGGGGCGAGGCGTC
CGTTCAGGGTTACACCGTAAGCGTAAGCGCGTAGCGAAATCGAACGAAATCGTACGCAACACTATGGAGAATGCTGAGAAAAACGCCTACTTTG
ATAAAGCAAGCCAAGGTCGCGTAGAAGGTCGGGGGCGATGGGAATGCGGGTTGCCGTCCCCGAGCCCGACCCGCCCGTCGCCGTTGTGGAG
CAGGCTCCTCAATATGTTGATGAAACCATTTCCCTGTCTGCCAAAACCCTGGTTTCGGTTTCGATAAGGATTCATTGCGCGCCGA
AGCTCAAGACAACCTGAAAGTATTGGCGCAACGCCTGAGTCGAACCAATGTCCAATCTGTCCGCGTCGAAGGCCATACCGACT
TTATGGGTTCTGAAAAAATACAATCAGGCTCTGTCCGAACGCCGCATACGTAGTGGCAAACAACCTGGTCAGCAACGGCGTA
CCTGCTTCTAGAATTTCTGCTGTCCGGCTTGGGCGAATCTCAAGCGGCAAATGACTCAAGTTGTCAAGCCCGCGTAGAGTGTGAAAATCC
GGGTGCGAAAGCCTCTAAAGCCAAAAAACGTGAGGCTCGAATTGCATGTATCGAACCTGACCGCCGTAGATGTGAAAATCC
GCAGCATCGTAACCCGTCAGGTTGTGCCGGCACGCAATCATCACCACACTAAGGCTAGGTAATATCTTGCCGATGCATGAGG
TTAGCGGATTTTGTACCGGGTACTGTTGCAATATTCGTGAAACGTCGGCCGGTATCGATGATGTGAAACAAACCCCGCTTTTG
CGGGGTTTGTTTTTTGGGTGGTTTTCTGAAACGGCTATCGTCAGAATCGGGTTCGCAGGTTCGGATTCGATTCATG
TTTGTGTCCCATTGCCGCGCTTTATAGTGGATTAACAAAAAATCCACTATATCGGTTGAAACCTCGATTTTAAGGCGGTAGGATGTGGGT
CAAGGCGAGGCAACGCCGTACCGGTTTAAATTAATCGTATCGATAATTCATACAAATTCACGCCCTTTCCCCCTCATTGGG
TTGCCCATAGCAAGGGAATCCTTTCGTATGCCGGCCACTGTATGCCGGATATGGTTTTATCATCATCCCT
AAATGGATGGAATCGTGCCCGATGTGTGCCCGATGTGTGCCCGATATGGTTTTATCATCATCCCT

*rmp* gene

ATG – start codon *rmp*

TAA – stop codon *rmp*

Borders of the UP and DOWN cassettes of recombination

FIG. 15

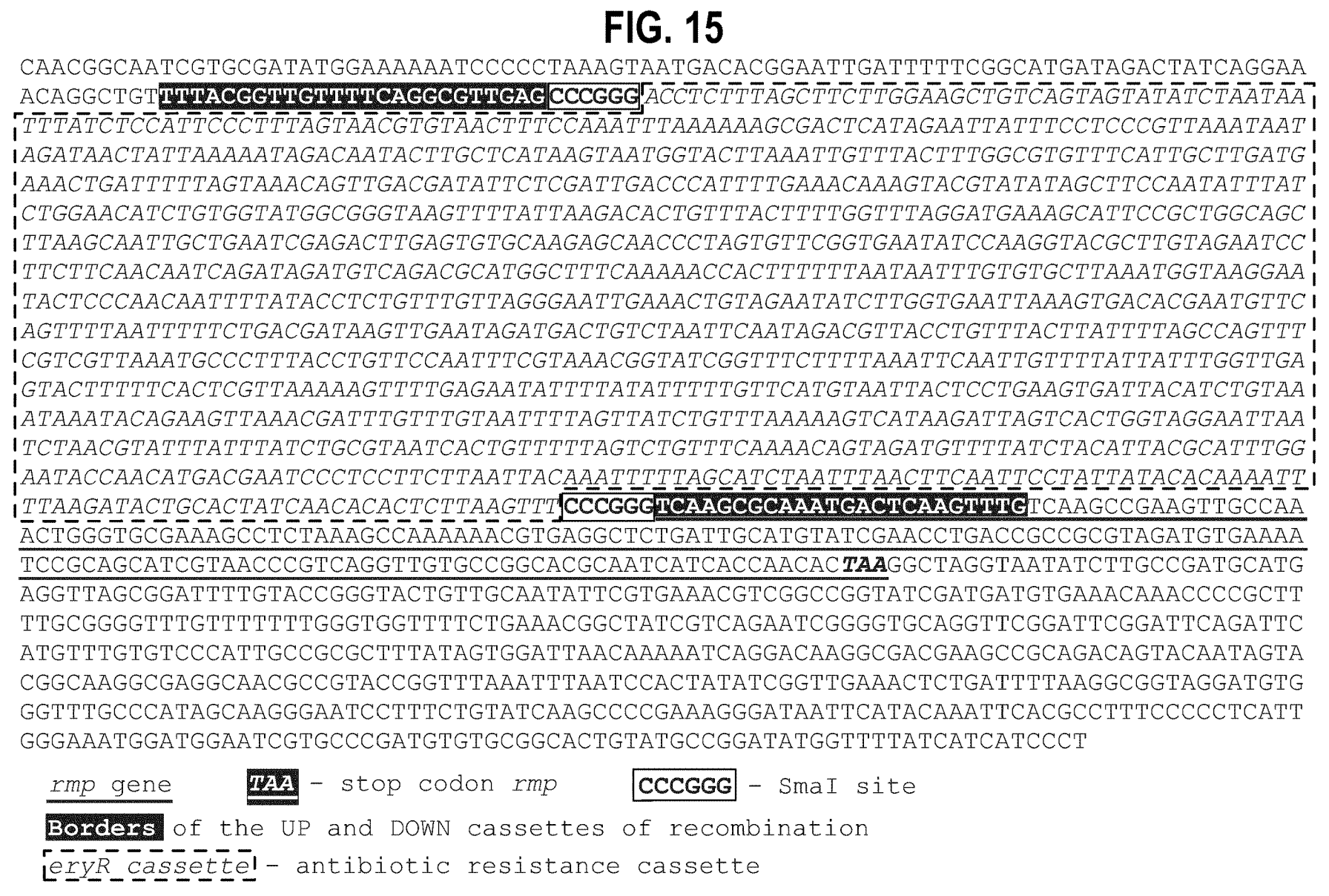

_rmp_ gene

TAA - stop codon _rmp_

Borders of the UP and DOWN cassettes of recombination

_eryR cassette_ - antibiotic resistance cassette

CCCGGG - SmaI site

Centrality hTLR4 activation

■ FA1090 nOMV

● FA1090 ΔlpxL1 (#GMMA2)

▲ FA1090 ΔlpxL1ΔrmpM (GMMA3)

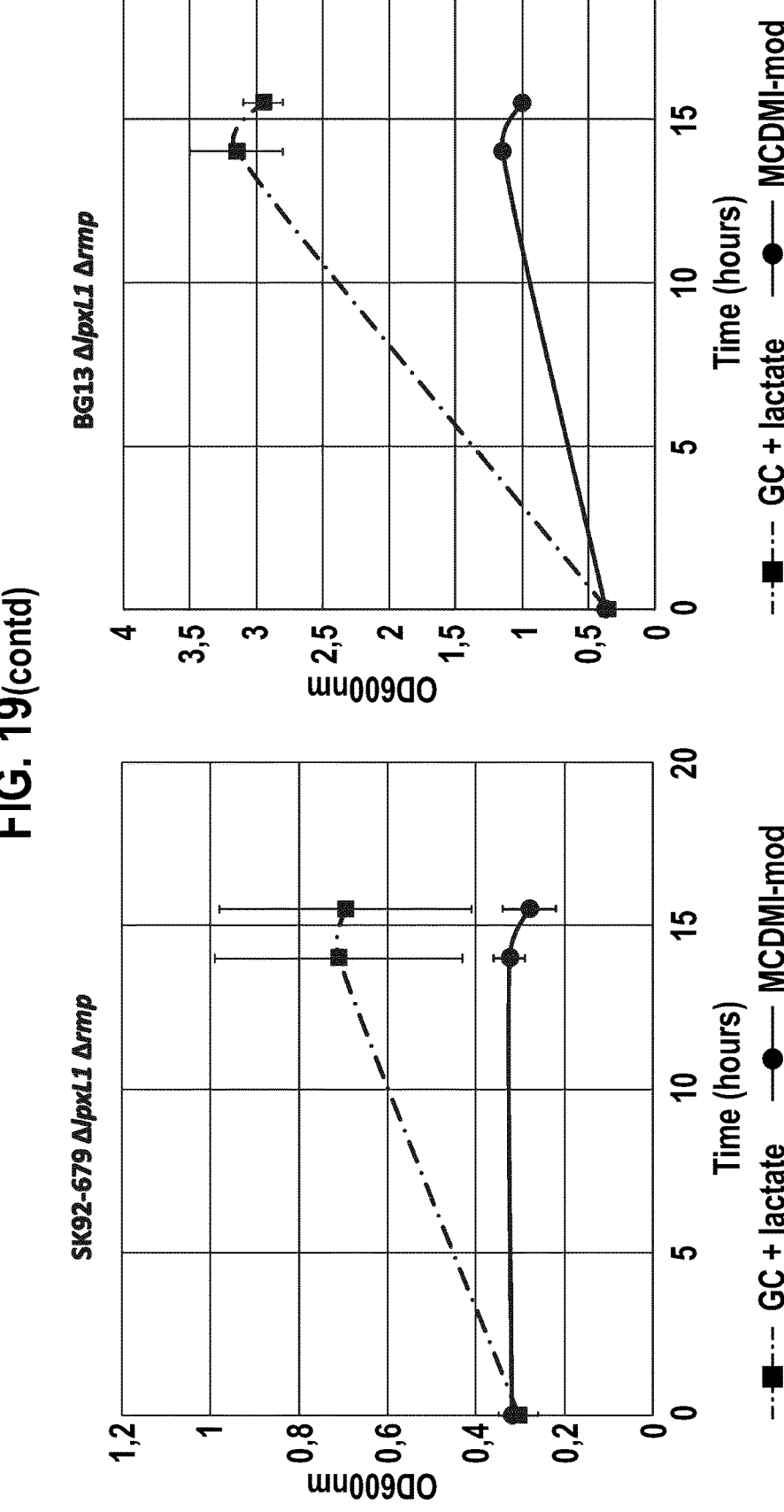
FIG. 19(contd)

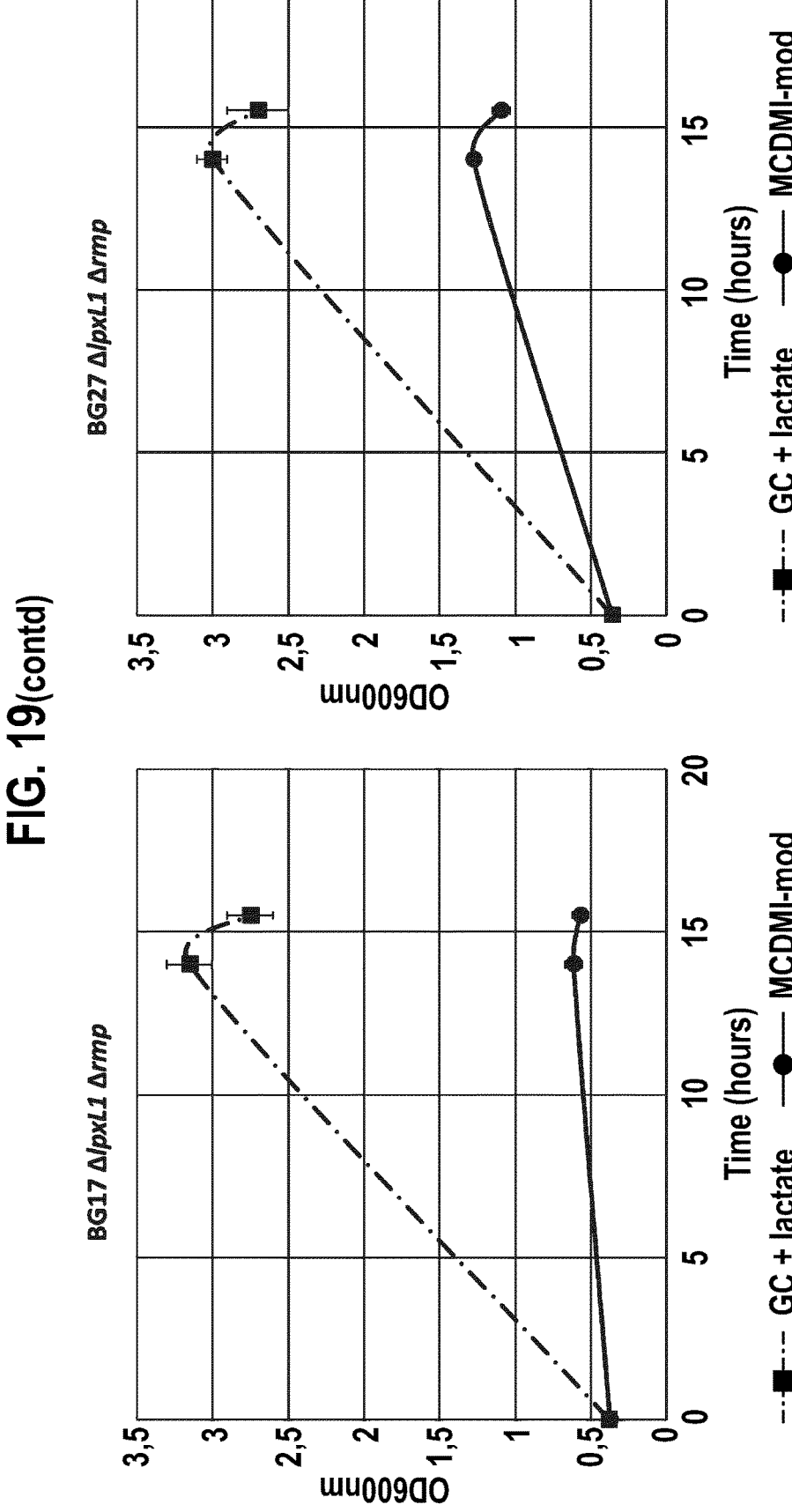
FIG. 19(contd)

FIG. 20A

Volumetric productivity

FIG. 20B

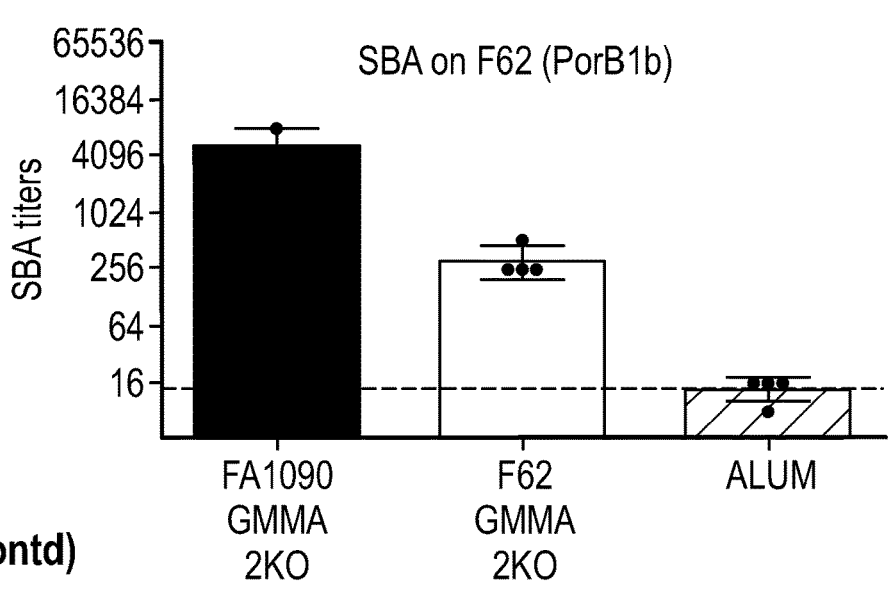
FIG. 21(contd)
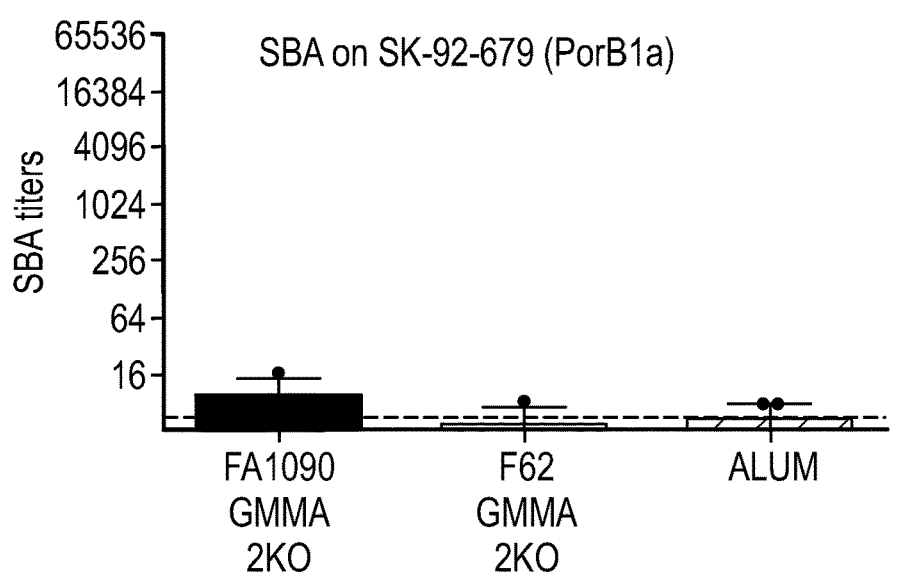

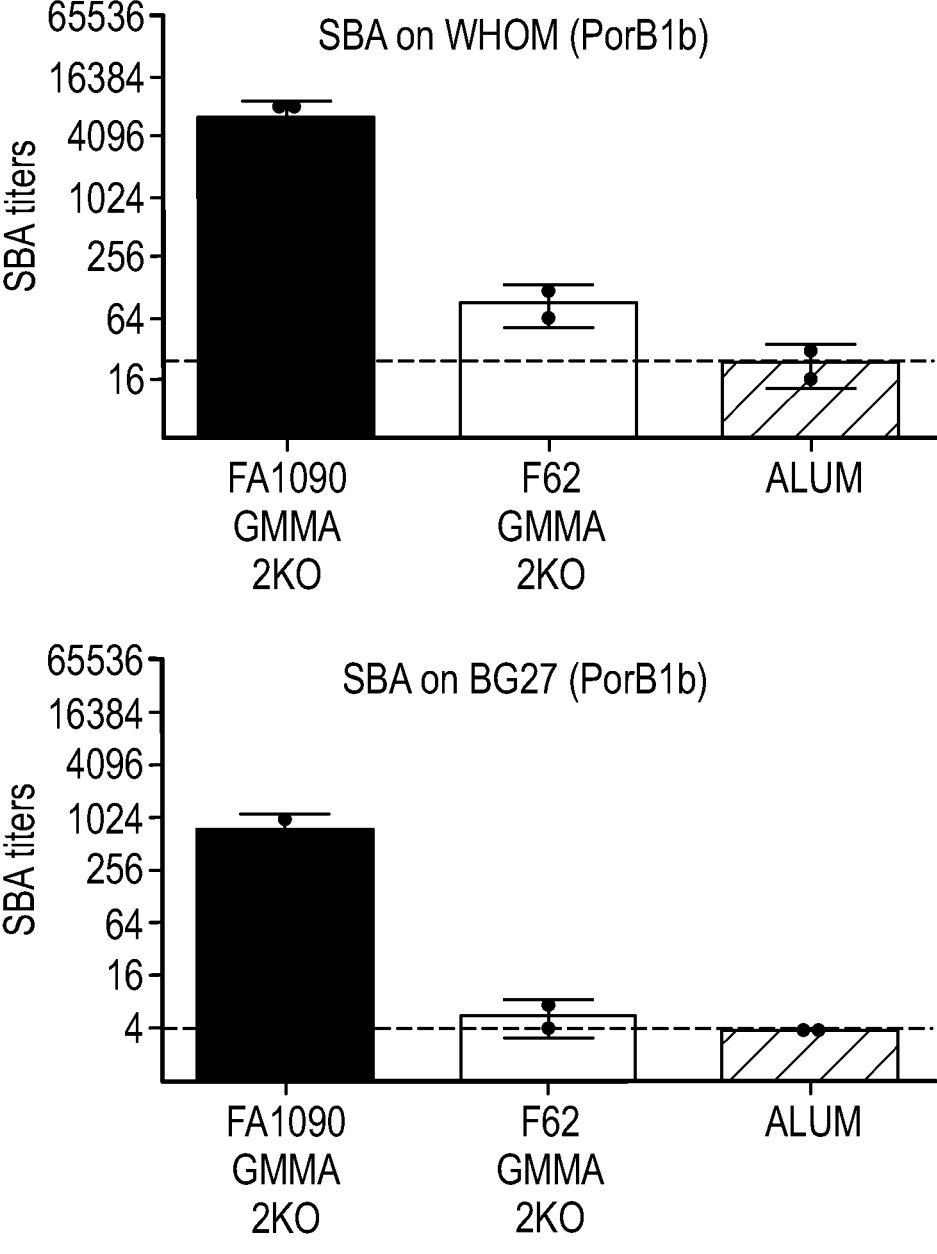
FIG. 21(contd)

FA1090

SK92-679

WHO-M

Luminex assay with RMP coated beads hSBA titers of pooled sera at 4wp2 and 2wp3 against the homologous FA1090 strain

Individual hSBA titers at 2wp3 against the homologous and the heterologous Ng strains O Alum   ⊘ Bexsero   ◉ GMMA TRD 4   ⊕ GMMA TRD 5   ⊖ GMMA TRD 9

FIG. 25A(contd)

Individual hSBA titers at 2wp3 against the homologous and the heterologous Ng strains O Alum   ⊘ Bexsero   ◐ GMMA TRD 4   ⊕ GMMA TRD 5   ⊖ GMMA TRD 9

FIG. 25A(contd)
Individual hSBA titers at 2wp3 against the homologous and the heterologous Ng strains
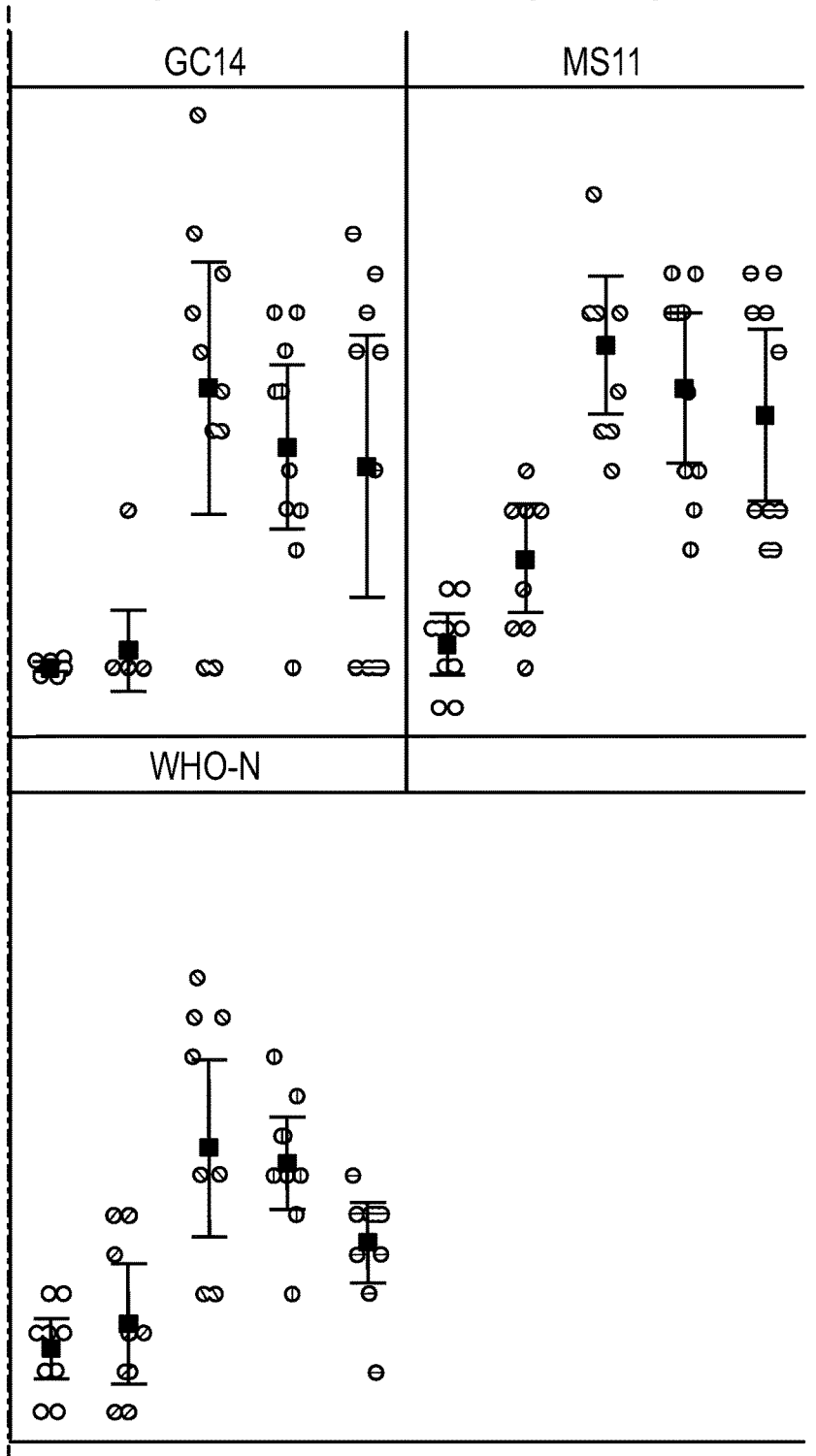
O Alum  ⊘ Bexsero  ⊗ GMMA TRD 4  ⊕ GMMA TRD 5  ⊖ GMMA TRD 9

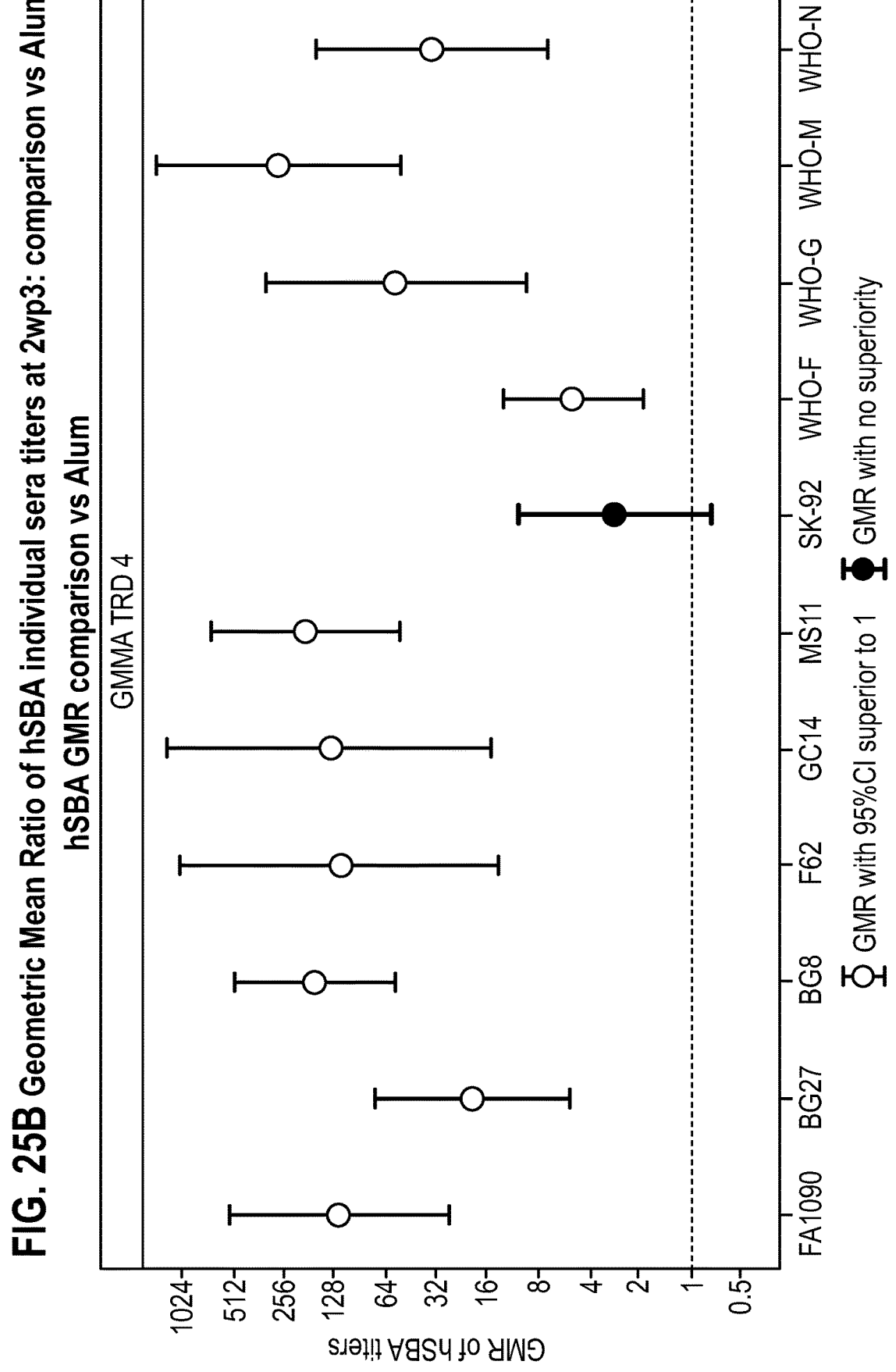
FIG. 25B Geometric Mean Ratio of hSBA individual sera titers at 2wp3: comparison vs Alum

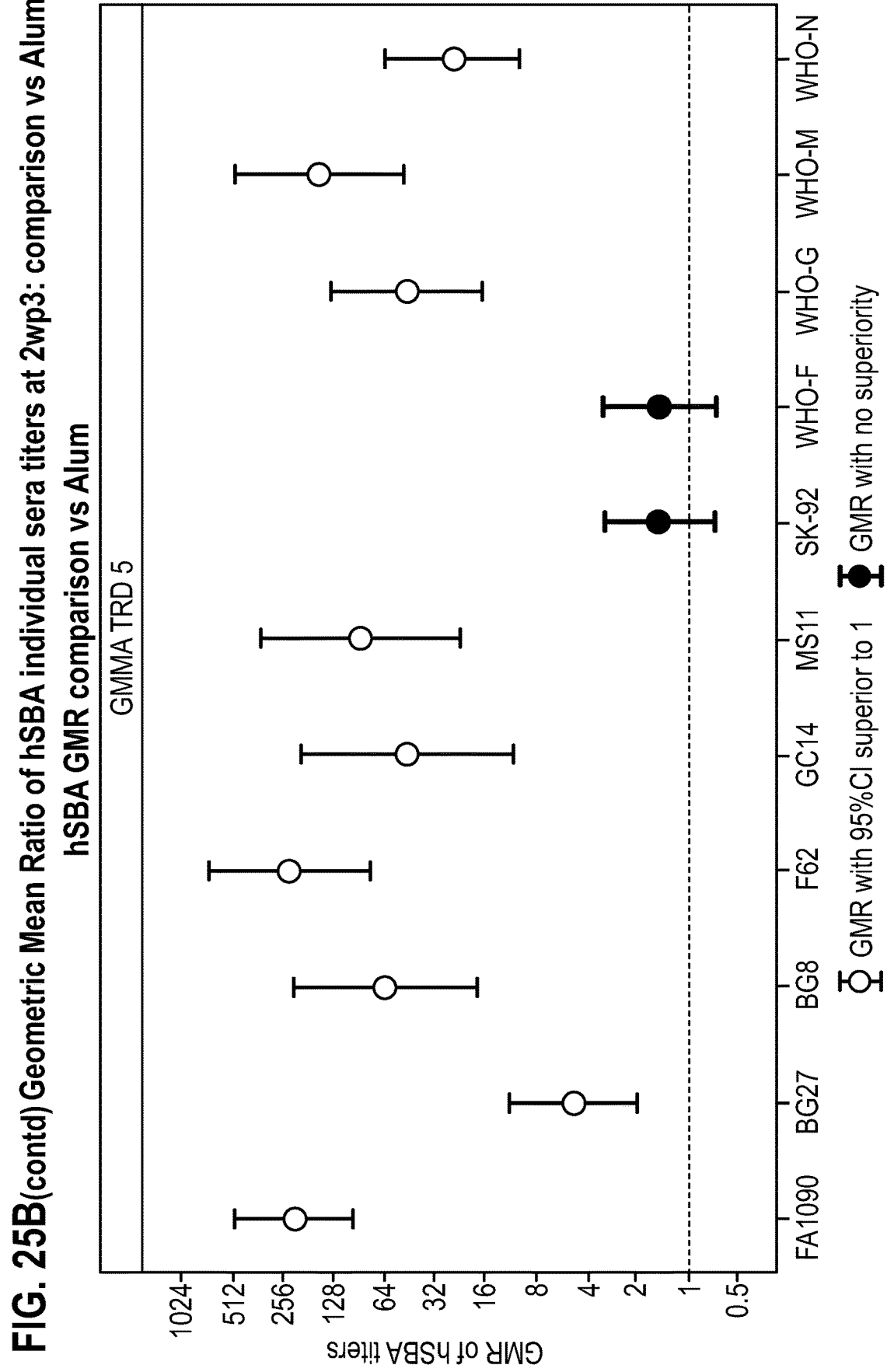
FIG. 25B(contd) Geometric Mean Ratio of hSBA individual sera titers at 2wp3: comparison vs Alum FIG. 25B(contd) Geometric Mean Ratio of hSBA individual sera titers at 2wp3: comparison vs Alum FIG. 25C Geometric Mean Ratio of hSBA individual sera titers at 2wp3: comparison vs Bexsero FIG. 25C(contd) Geometric Mean Ratio of hSBA individual sera titers at 2wp3: comparison vs Bexsero FIG. 25C(contd) Geometric Mean Ratio of hSBA individual sera titers at 2wp3: comparison vs Bexsero Anti-Ng GMMA IgG titers of pooled sera at 4wp2 and 2wp3

Anti-Ng GMMA IgG titers of individual sera at 2wp3 with 95% Confidence Interval

IgG in sera by Luminex at 2wp3

Anti-Ng GMMA IgG titers of individual sera at GMR with 95% Confidence Interval

Anti-Ng GMMA IgG titers of individual vaginal washes at 2wp3 with 95% Confidence Interval

Anti-Ng GMMA IgG titers of individual vaginal washes at GMR with 95% Confidence Interval

Anti-Ng GMMA IgA titers of individual vaginal washes at 2wp3 with 95% Confidence Interval

Anti-Ng GMMA IgA titers of individual vaginal washes at GMR with 95% Confidence Interval

Vaginal washes - Luminex IgA GMR and 95'%'CI

|  | LCI | GMR | UCI |
|---|---|---|---|
| TRD 9 / Bexsero | 4.5 | 26.2 | 151.0 |
| TRD 5 / Bexsero | 6.3 | 29.7 | 140.3 |
| TRD 4 / Bexsero | 13.4 | 43.1 | 138.7 |
| TRD 9 / Alum | 7.5 | 40.5 | 219.1 |
| TRD 5 / Alum | 10.5 | 46.0 | 200.9 |
| TRD 4 / Alum | 23.5 | 66.8 | 189.6 |

1  2    10    100    1000

GMRs with 95% CI

Global PorB phylogeny in Ng

FIG. 31

FA1090_2KO and GC_0817560 PorB alignment with extracellular Loops (1-8) identification and diversity.

PorB

|  |  |  |
|---|---|---|
| FA1090_2KO (201) | 1 | MKKSLIALTLAALPVAAMADVTLYGAIKAGVQ|TYRSVEHTDGKVSKVETGSEIA|DFGSKI |
| GC_0817560 (726) | 1 |                  F |

*Loop 1*

|  |  |  |
|---|---|---|
| FA1090_2KO (201) | 61 | GFKGQEDLGNGLKAVWQLEQGASVAG|NTGWGN|KQSFVGLKGGFGTIR|GSLNSPLKNTG |
| GC_0817560 (726) | 61 |                           A        V |

*Loop 2*

|  |  |  |
|---|---|---|
| FA1090_2KO (201) | 121 | ANVNAWESGKFTGN|VLEISGMA|QREHRY|LSVRYDSPEFAGFSGSVQY|APKDNSGSNGE|SY |
| GC_0817560 (726) | 121 |               D        K |

*Loop 3*

*Loop 4*

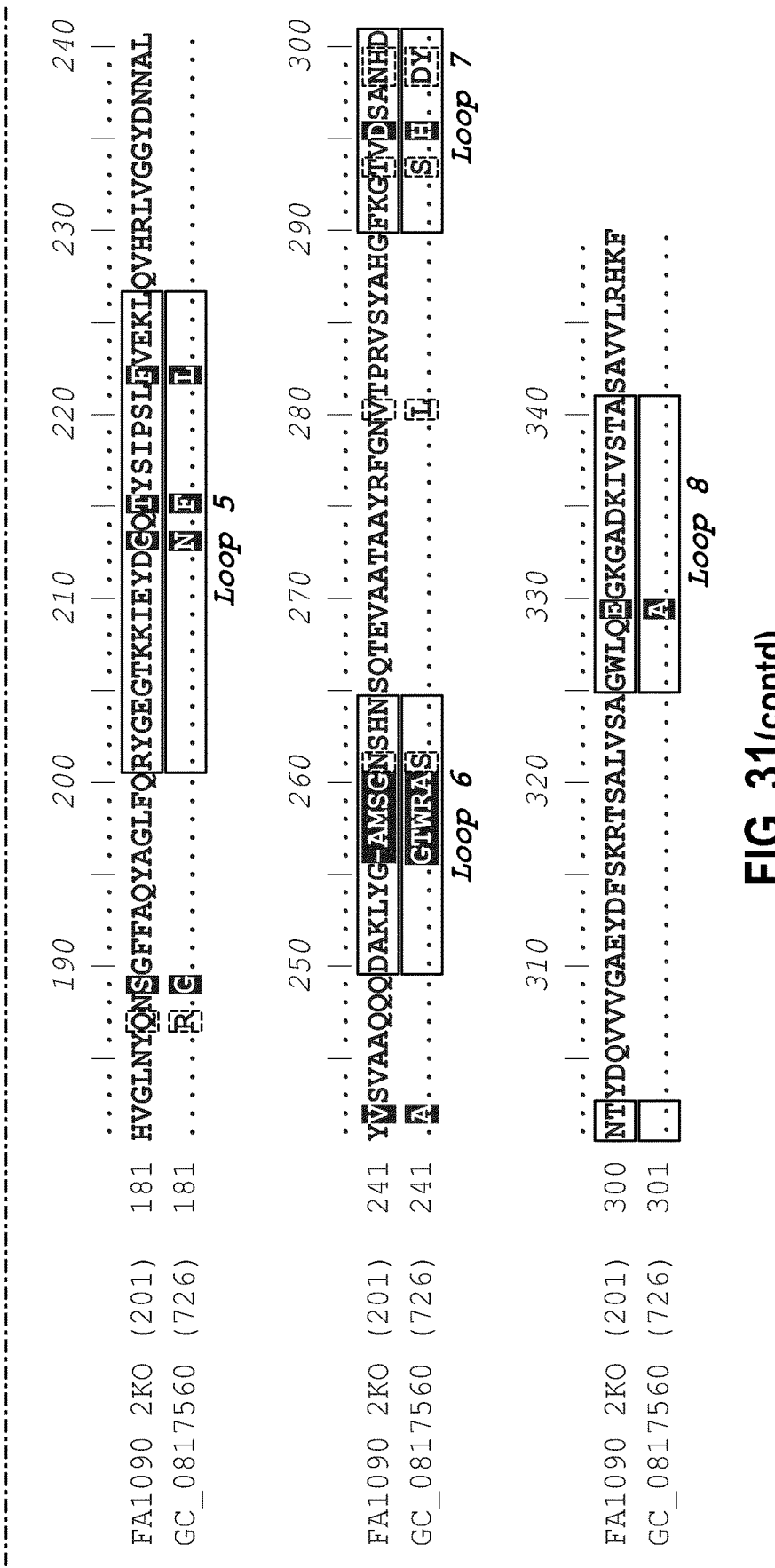
FIG. 31(contd)

OUTER MEMBRANE VESICLES

TECHNICAL FIELD

This invention relates to genetically modified *Neisseria gonorrhoeae* bacteria and outer membrane vesicles obtained therefrom. The outer membrane vesicles are particularly useful in immunogenic compositions and vaccines, e.g. vaccines for use in medicine.

BACKGROUND

The Gram-negative diplococci *Neisseria gonorrhoeae*, is an obligate human pathogen that causes the sexually transmitted infection (STI), gonorrhoea. Gonococcal disease typically presents as a mucosal infection of the genital tract, rectum, pharynx or eye.

*Neisseria gonorrhoeae* infection is a considerable global health concern with an estimated incidence of more than 106 million cases per year worldwide (WHO, 2018). Gonorrhoea is the second most reported communicable disease in the US (CDC 2019) and its prevalence world-wide appears to be increasing. For example, prevalence in Australia has increased by 63% over the past 5 years (Kirby *Institute. HIV, viral hepatitis and sexually transmissible infections in Australia: Annual Surveillance Report* 2017) and by 63% in the US between 2014 and 2018 (*CDC, Sexually Transmitted Disease Surveillance* 2018). However, because asymptomatic infections are common (occurring in up to 80% of infected females and 40% of infected males) the true prevalence of *N. gonorrhoeae* is not fully understood.

Left untreated, or if undiagnosed, *N. gonorrhoeae* infection can lead to serious consequences. Such consequences include endometritis, pelvic inflammatory disease, urogenital tract abscesses, adverse pregnancy outcomes, neonatal complications (including blindness) and infertility. Furthermore, infection with *N. gonorrhoeae* increases the risk of acquiring and transmitting Human Immunodeficiency Virus (HIV) (Hayes R, Watson Jones D, Celum C, van de Wngert J, Wasserheit J. *Treatment of sexually transmitted infections for HIV prevention: end of the road or new beginning? AIDS* 2010; 24: S15-26).

The control of *N. gonorrhoeae* is largely based on antibiotic treatment. This approach is however compromised by the rapid and continued emergence of antimicrobial resistance (AMR). *N. gonorrhoeae* has developed resistance to many antibiotics that were previously successful in treating the infection. This had left cephalosporins as the last line of defence for gonorrhoea treatment. However, strains with high-level resistance to the expanded spectrum cephalosporins (i.e. ceftriaxone and cefixime) have now been isolated from around the world (Unemo M, Jensen J S. *Antimicrobial-resistant sexually transmitted infections: gonorrhoea and Mycoplasma genitalium. Nat Rev Urol* 2017; 14: 139-152).

In an effort to end STI epidemics as major public health concerns, the WHO recently released a draft global health strategy with a global target goal of 90% reduction in *N. gonorrhoeae* incidence by 2030 (*WHO, Global Health Sector Strategy on sexually transmitted infections, 2016-2021*, 20 Dec. 2017). Given the ability of the gonococcus to develop AMR, a gonococcal vaccine will be key to the long-term control of gonorrhoea (Edwards J L, Jennings M P, Seib K L *Neisseria gonorrhoeae vaccine development: hope on the horizon? Current Opinion in Infectious Diseases*: June 2018-Volume 31-Issue 3-p 246-250), (Gottlieb S L, Jerse A E, et al. *Advancing vaccine development for*

*gonorrhoea and the Global STI Vaccine Roadmap. Sex Health.* 2019; 16(5): 426-432. doi: 10.1071/SH19060).

To date gonococcal vaccine development has however been challenging with no gonococcal-specific vaccine candidates demonstrating clinical protection. However, a recent retrospective case-control study found that reduced rates of gonorrhoea occurred among sexual health clinic patients (ages 15-30 years) following their vaccination with the outer membrane vesicle (OMV) vaccine MeNZB, directed to Neisseria meningitidis serogroup B (i.e. cross-protection). However, the efficacy of MeNZB against N gonorrhoeae was relatively low (estimated to be 31%) (Petousis-Harris H, Paynter J, Morgan J, et al. *Effectiveness of a Group B OMV meningococcal vaccine against gonorrhoea in New Zealand—a case control study. Lancet* 2017; 390: 1603-1610).

OMVs are a complex mix of outer membrane components that are naturally released from Gram-negative bacteria, such as N meningitidis and *N. gonorrhoeae* (Van Der Pol L, Stork M, Van Der Ley P. *Outer membrane vesicles as platform vaccine technology. Biotechnol J* 2015; 10: 1689-1706). The observation of cross-protection of the MeNZB OMV based vaccine provided, for the first time, evidence that an OMV based vaccine approach may be effective in protecting subjects against gonorrhoea. In this regard, Liu and colleagues showed that intravaginal inoculation with a microencapsulated interleukin-12 plus gonococcal OMVs can confer protection to mice against *N. gonorrhoeae* infection (Liu Y, Hammer LA, Liu W et al. *Experimental vaccine induces Th1-driven immune responses and resistance to Neisseria gonorrhoeae infection in a murine model. Mucosal Immunol* 2017; 10: 1594-1608). However, other attempts to use gonococcal OMVs as vaccine candidates gave inconclusive results. For example, a gonococcal OMV-based vaccine candidate was immunogenic in terms of inducing serum and mucosal antibodies but failed in a mouse challenge study (Freixeiro et al, *A genetically modified native outer membrane vesicle vaccine administered by a subcutaneous/intranasal route failed to accelerate clearance of gonococcus in a heterologous mouse challenge study. 21st International Pathogenic Neisseria Conference* Sep. 23-28, 2018, Oral Poster Presentation Abstract OP174).

There remains a need for an effective gonorrhoea vaccine. The inventors of the present application surprisingly discovered that a genetically modified gonococcus, produced specifically in the background strain FA1090, resulted in a gonococcus with improved properties in terms of its utility as a vaccine strain. In particular, the genetically modified gonococcus was a) capable of being grown in liquid culture and, b) produced productive levels of OMVs compared to other gonococcal strains with the same genetic modifications. Furthermore, said genetically modified FA1090 gonococcus blebbed OMVs with improved immunogenic properties, such as their ability to induce significant crossbactericidal antibody titres. This was surprising by itself. It was particularly surprising in view of genomic analyses that suggested that *Neisseria gonorrhoeae* of strain FA1090 was genomically diverse (i.e. peripheral) compared to the genomes of over 4000 comparator gonococci.

SUMMARY OF THE INVENTION

The inventors of the present application have discovered that by generating a genetically modified gonococcus, specifically in the background strain FA1090, they were able to produce a vaccine strain with surprising properties. In particular, the inventors found that a genetically modified gonococcal bacterium of strain FA1090, was both capable of being transferred into liquid culture and produced productive levels of OMVs compared to other gonococcal strains with the same genetic modifications. Furthermore, OMVs blebbed from said genetically modified FA1090 gonococcus were highly immunogenic and induced significant cross-bactericidal antibody titres. Given this preclinical data, a vaccine based on the outer-membrane vesicles disclosed herein is capable of displaying clinical efficacy in the prevention of gonococcal infection and disease in humans.

Thus, in a first aspect there is provided a genetically modified gonococcal bacterium of strain FA1090, comprising genetic modification(s) that:

a) decreases or abolishes expression and/or function of the lipid A biosynthesis lauroyl acyltransferase (lpxl1) gene, mRNA, and/or polypeptide; and b) decreases or abolishes expression and/or function of the reduction modifiable protein (rmp) gene, mRNA, and/or polypeptide.

In a further aspect there is provided, a process for producing the gonococcal bacterium the process comprising either:

a) decreasing or abolishing the expression and/or function of the lpxl1 gene mRNA and/or polypeptide in a gonococcal FA1090 bacterium to produce a first gonococcal FA1090 bacterium and decreasing or abolishing the expression and/or function of the rmp gene mRNA and/or polypeptide from the first gonococcal FA1090 bacterium to produce a second gonococcal FA1090 bacterium; or b) decreasing or abolishing the expression and/or function of the rmp gene mRNA and/or polypeptide from the first gonococcal FA1090 bacterium to produce a first gonococcal FA1090 bacterium and decreasing or abolishing the expression and/or function of the lpxl1 gene mRNA and/or polypeptide from the first gonococcal FA1090 bacterium to produce a second gonococcal FA1090 bacterium.

In a further aspect there is a provided the use of the gonococcal bacterium in the production of outer membrane vesicles.

In a further aspect there is provided an outer membrane vesicle obtained or obtainable from an FA1090 strain gonococcus, wherein said outer membrane vesicle comprises either reduced levels or no detectable level of both lpxl1 and rmp polypeptides.

In a further aspect there is provided an outer membrane vesicle (OMV) from a genetically modified FA1090 strain gonococcus, said genetically modified FA1090 strain gonococcus comprising genetic modification(s) that a) decreases or abolishes expression and/or function of the lpxl1 gene, lpxl1 mRNA, and/or Lpxl1 polypeptide; and b) decreases or abolishes expression and/or function of the rmp gene, rmp mRNA, and/or Rmp polypeptide, said OMV comprising: i) reduced levels of Rmp polypeptide compared to the levels of Rmp polypeptide in a comparator OMV from a *N. gonorrhoeae* strain FA1090 that lacks said genetic modifications; and ii) reduced levels of hexa-acylated lipid A compared to the levels of hexa-acylated lipid A from the comparator OMV.

In a further aspect there is provided an outer membrane vesicle obtained or obtainable from the gonococcal bacterium of the invention.

In a further aspect there is provided an immunogenic composition comprising an outer membrane vesicle of the invention.

In a further aspect there is provided a vaccine comprising either the outer membrane vesicle of the invention or the immunogenic composition of the invention and a pharmaceutically acceptable excipient.

In a further aspect there is provided the immunogenic composition of the invention or vaccine of the invention for use in medicine.

In a further aspect there is provided the immunogenic composition of the invention or vaccine of the invention, for use in immunising a subject against Neisseria infection for example *N. gonorrhoea* infection.

In a further aspect there is provided the immunogenic composition of the invention or vaccine of the invention for use in the treatment or prevention of disease caused by Neisseria for example *N. gonorrhoea.*

In a further aspect there is provided a method for the treatment or prevention of disease caused by Neisseria (for example *N. gonorrhoea*) in a subject in need thereof, said method comprising administering to said subject a therapeutically effective amount of the immunogenic composition of the invention or vaccine of the invention.

In a further aspect there is provided, a method for immunizing a subject in need thereof against Neisseria (for example *N. gonorrhoea*), comprising administering an immunologically effective amount of the immunogenic composition of the invention or vaccine of the invention to the subject.

In a further aspect there is provided a method for raising an immune response in a subject, comprising administering an immunogenic composition of the invention or vaccine of the invention to a subject.

In a further aspect there is provided the use of the immunogenic composition of the invention or the vaccine of the invention in the manufacture of a medicament for the treatment or prevention of disease caused by Neisseria.

In a further aspect there is provided the use of the immunogenic composition of the invention or the vaccine of the invention in the manufacture of a medicament for the treatment or prevention of disease caused by *N. gonorrhoea.*

In a further aspect there is provided the immunogenic composition or vaccine for use, the method or the use of the invention wherein at least 2 doses of the composition are administered to a subject.

In a further aspect there is provided the immunogenic composition or vaccine for use, the method or the use of the invention wherein the subjects are adolescents and/or adults.

In a further aspect there is provided the immunogenic composition or vaccine for use, the method or the use of the invention wherein the subject is at increased risk of infection with *N. gonorrhoea* relative to the average risk in the general population.

In a further aspect there is provided the immunogenic composition or vaccine for use, method or the use of the invention wherein the subject is co-immunised against one or more further infectious agents.

In a further aspect there is provided the immunogenic composition or vaccine for use, the method or the use of the invention wherein said immunogenic composition or vaccine is administered via the intramuscular or intraperitoneal route of administration.

Figure 11:
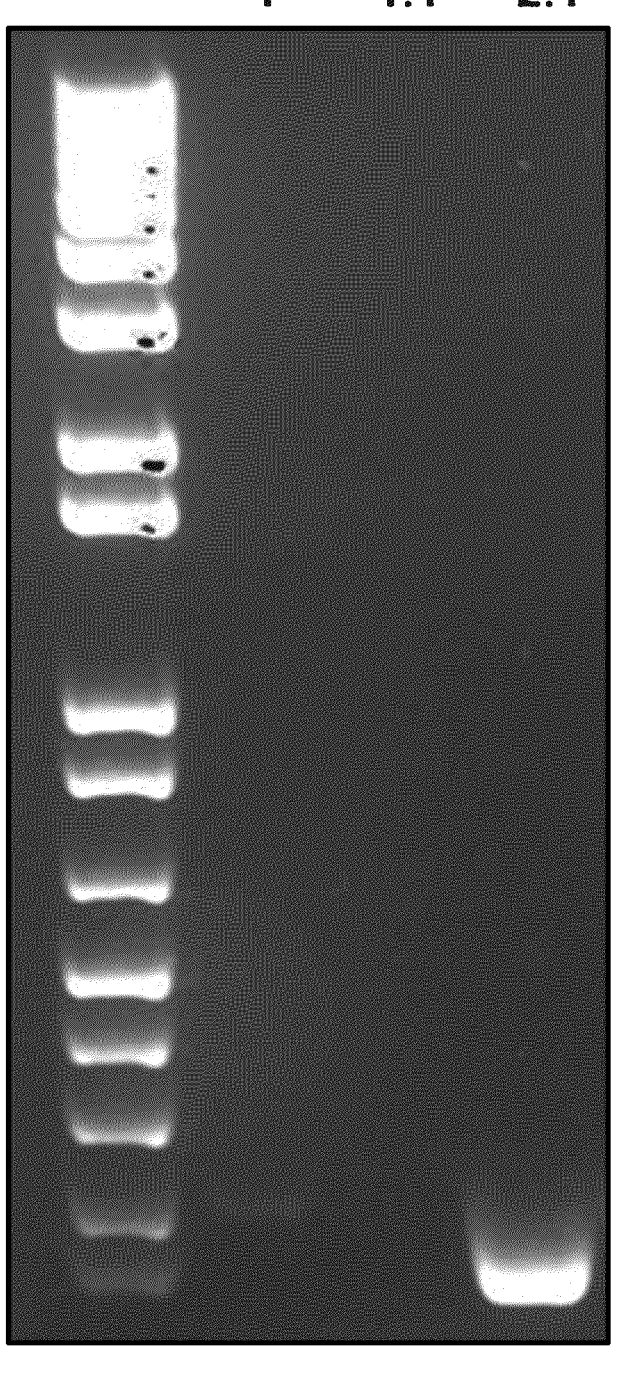

FIG. 11: Agarose gel of the PCR internal check of FA1090 ΔlpxL1Δrmp clones. PCRs were performed with primers specific for the original population (the cells from which 2KO mutant was generated in this case FA1090 ΔlpxL1) and PCR products were separated by electrophoresis in a 1% agarose gel. The presence of a band is correlated with the presence of residual original cells in the population. The 1 kb plus ladder was used as marker.

FIG. 12: Locus of lpxL1 extracted from unmodified FA1090 isolate.

Figure 13:
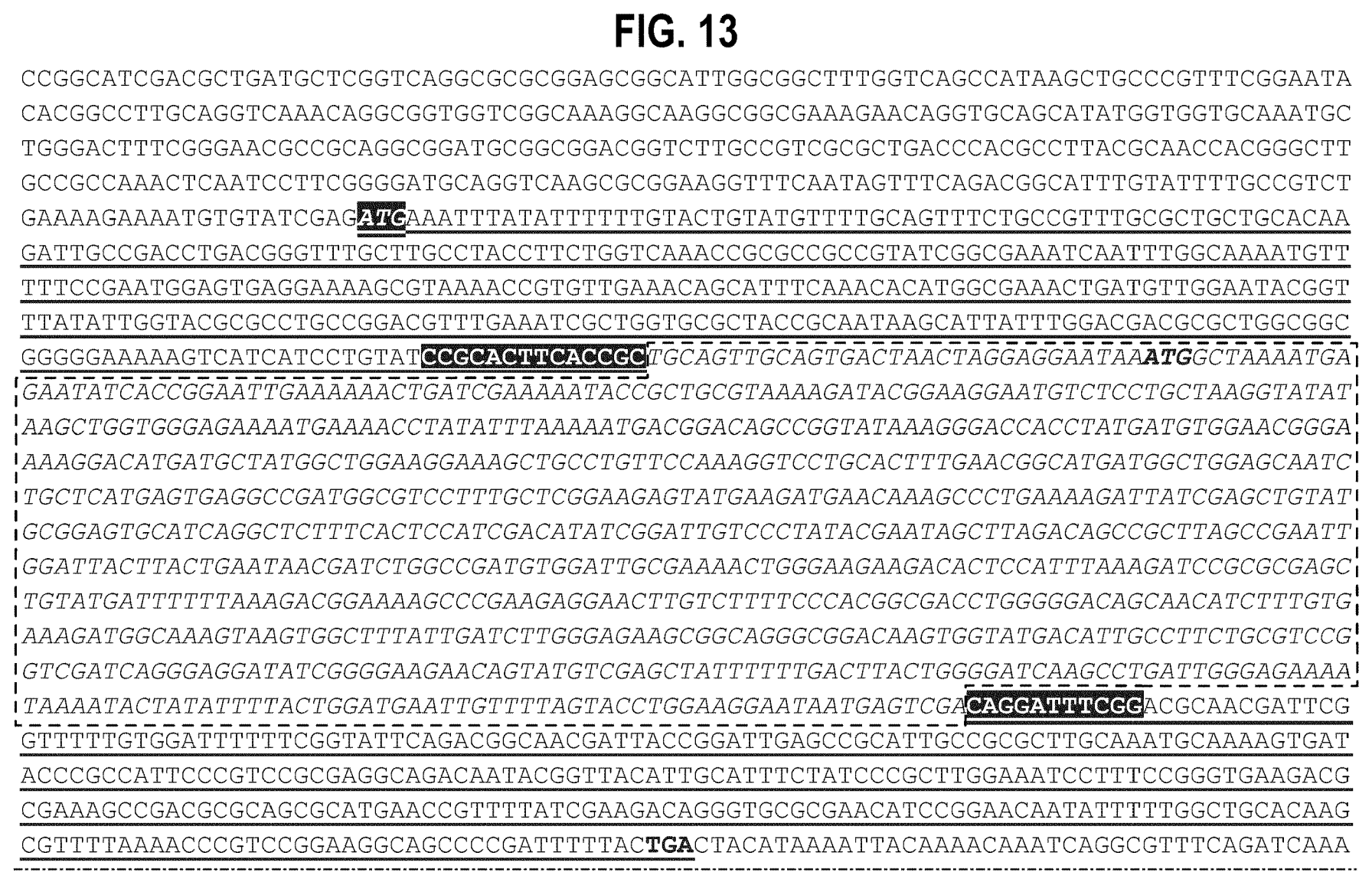

FIG. 13: Locus of lpxL1 extracted from the FA1090 Δlpxl1, Δrmp strain.

FIG. 14: Locus of rmp extracted from unmodified FA1090 isolate.

FIG. 15: Locus of rmp extracted from the FA1090 Δlpxl1, Δrmp strain.

Figure 16:
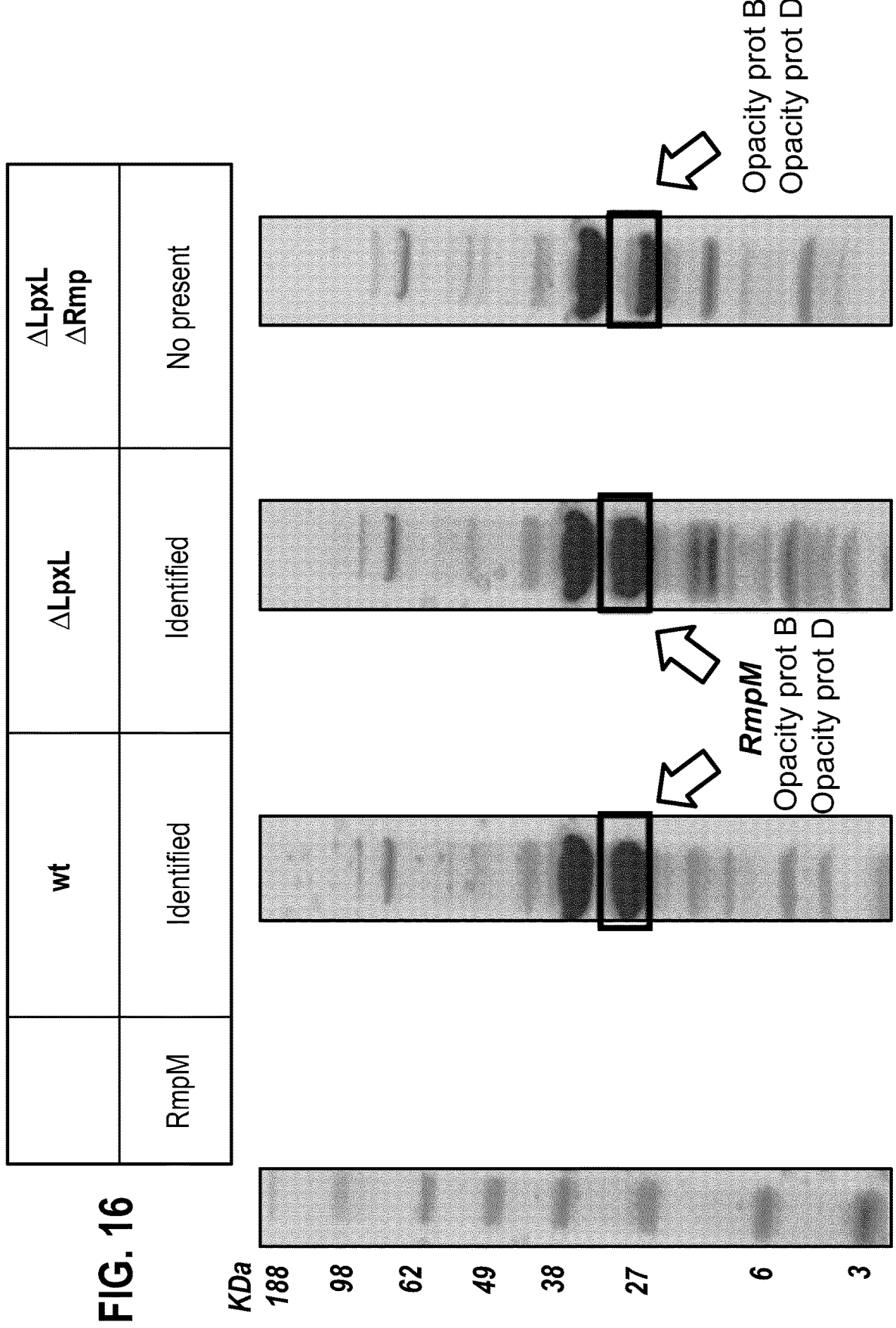

FIG. 16: SDS-PAGE pattern of OMVs blebbed from wild-type FA1090, Δlpxl1 FA1090 (1KO) and Δlpxl1, Δrmp (2KO) FA1090. The protein content of the bands which migrated with an apparent molecular weight of ~28 kDa were identified.

Figure 17:
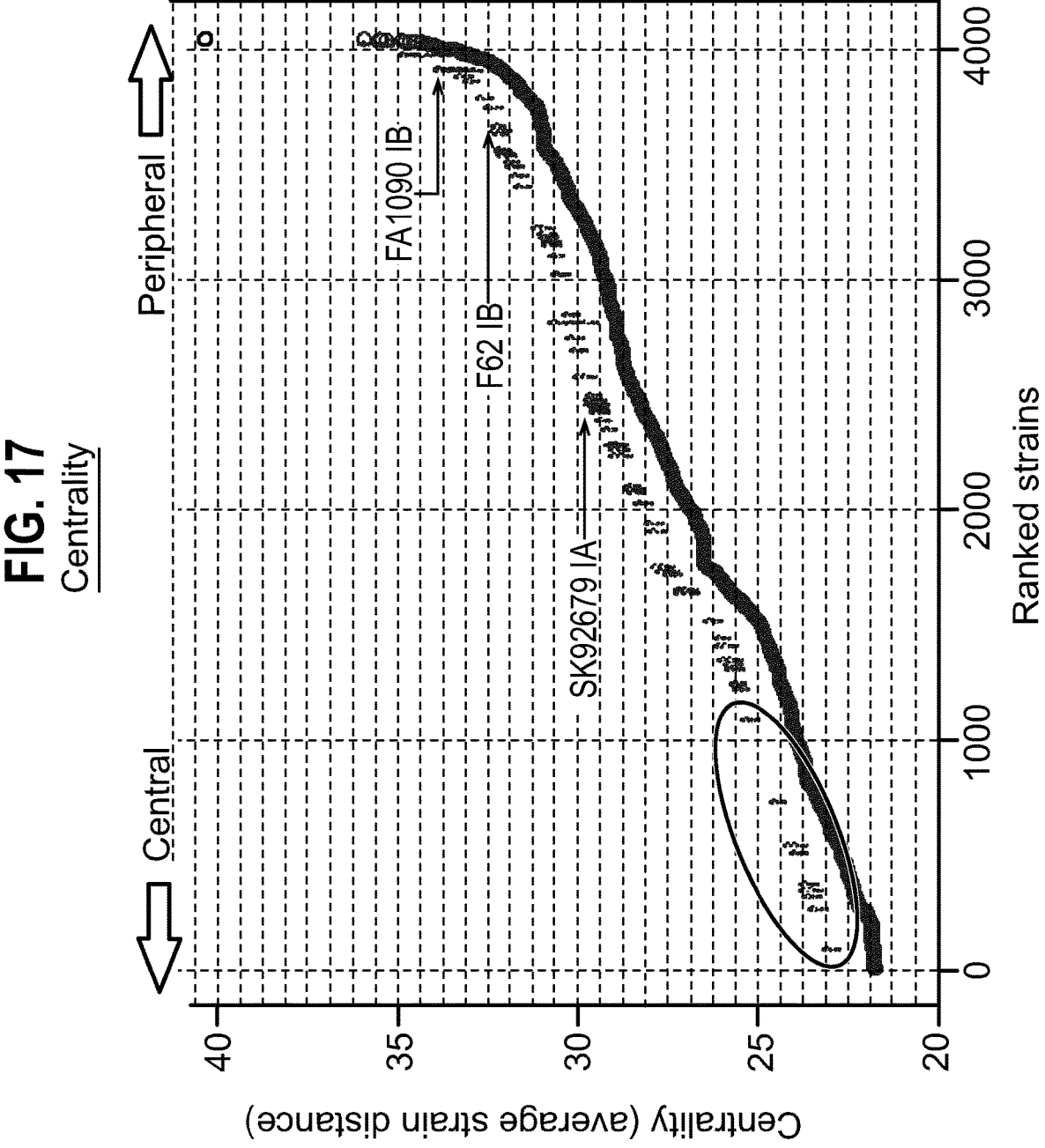

FIG. 17: Centrality defined as average distance of each strain with respect to each other. Phylogenetic average distance of each strain from all the others ('centrality'), based on schema allelic variations of 59 protein loci.

Figure 18:
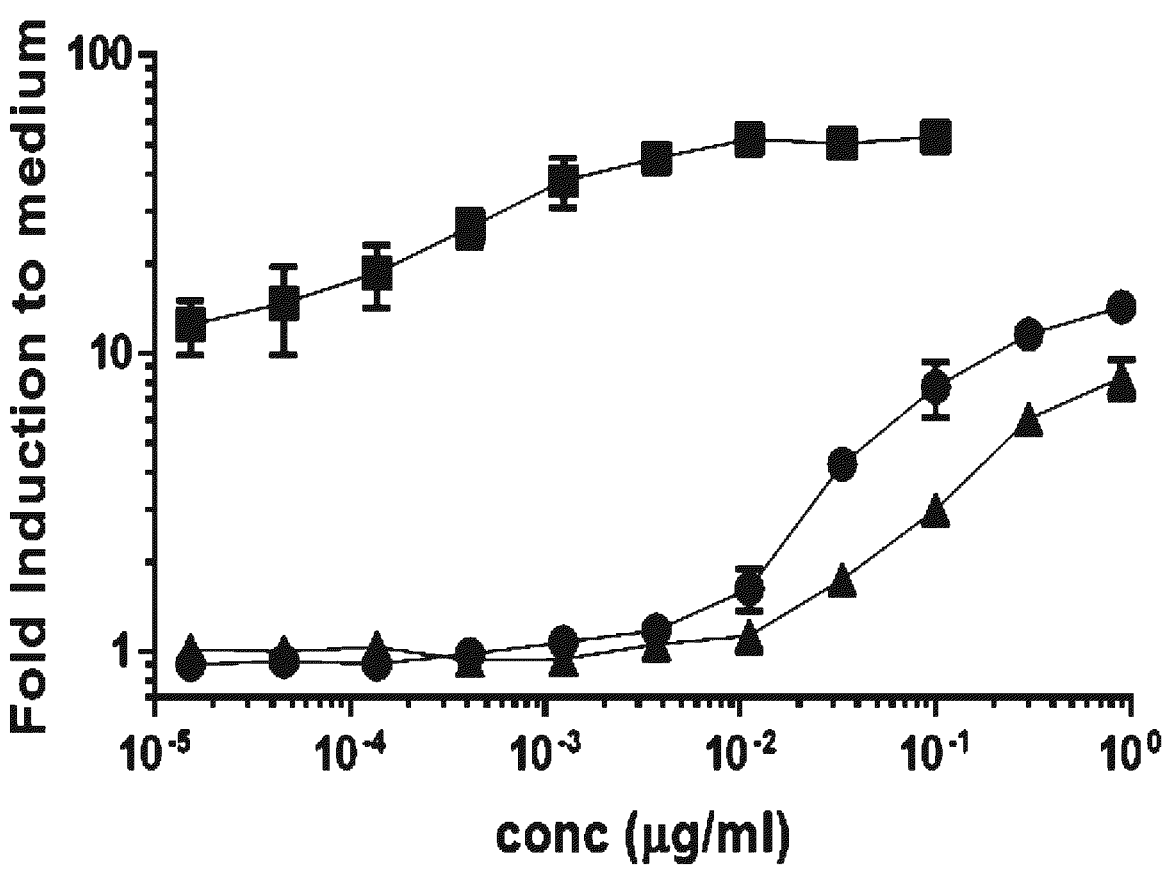

FIG. 18: TLR4 activation by OMVs from WT and mutant FA1090. HEK293-NF-kBluc/hTLR4 cells were stimulated in-vitro with different concentration (protein based) of OMV from wild-type (WT) FA1090 or OMV prepared from FA1090 Δlpxl1 (or 1KO) mutant (#GMMA2) and FA1090 Δlpxl1,Δrmp (or 2KO) mutant (#GMMA3). Cells were then lysed and TLR4-mediated NF-kB activation was quantified measuring luciferase induction with luminescence. Cell activation is expressed as fold induction over medium treated cells.

Figure 19:
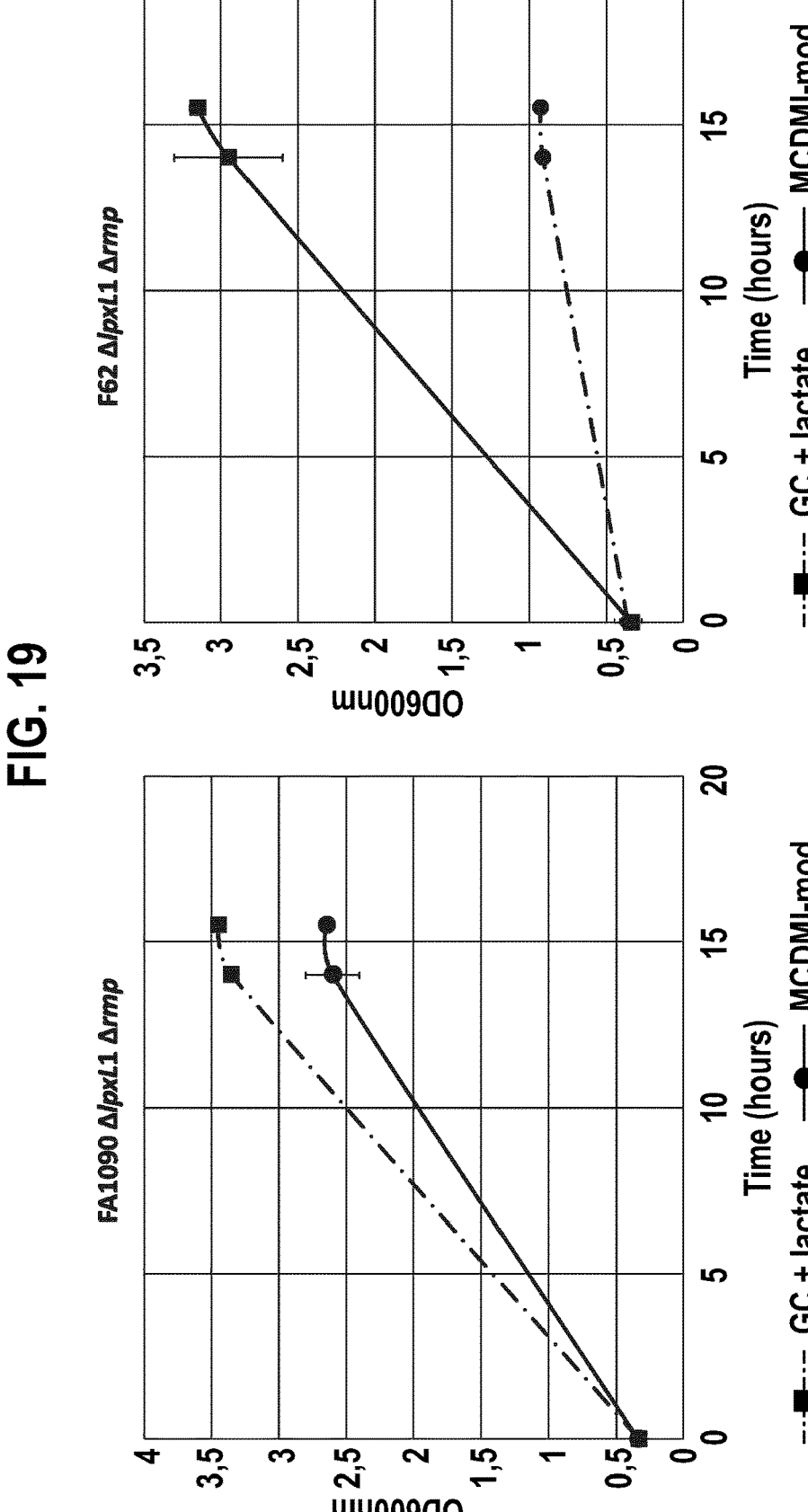

FIG. 19: Growth profiles of six double-mutant gonococci (Δlpxl1,Δrmp) in two tested media preparations. Growth was monitored over a period of 16 hours and was measured based on optical density (OD) measured at 600 nm.

Figure 20A:
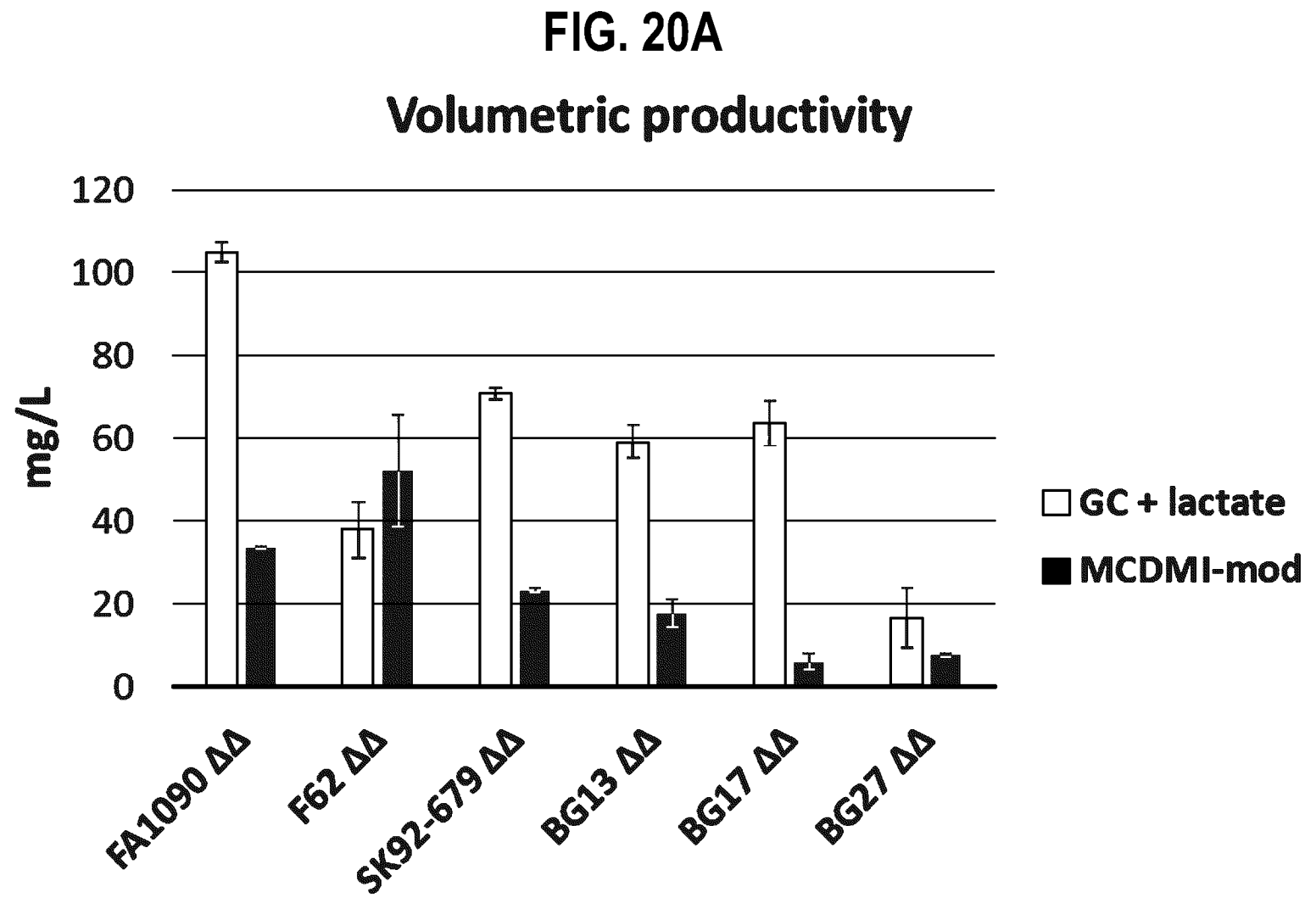

FIG. 20A: The OMV volumetric productivity is shown for the six 2KO gonococci (Δlpxl1,Δrmp) in two growth media. For each sample fluorescence was recorded with and without dye addition and background fluorescence of supernatants without dye were subtracted from the dye-treated samples values.

A blank with medium only was also subtracted. OMV concentration in culture supernatant is shown (in mg/L) as evaluated by value extrapolation from a standard curve. Data is reported as an average of two biological replicates for each strain and growth condition.

Figure 20B:
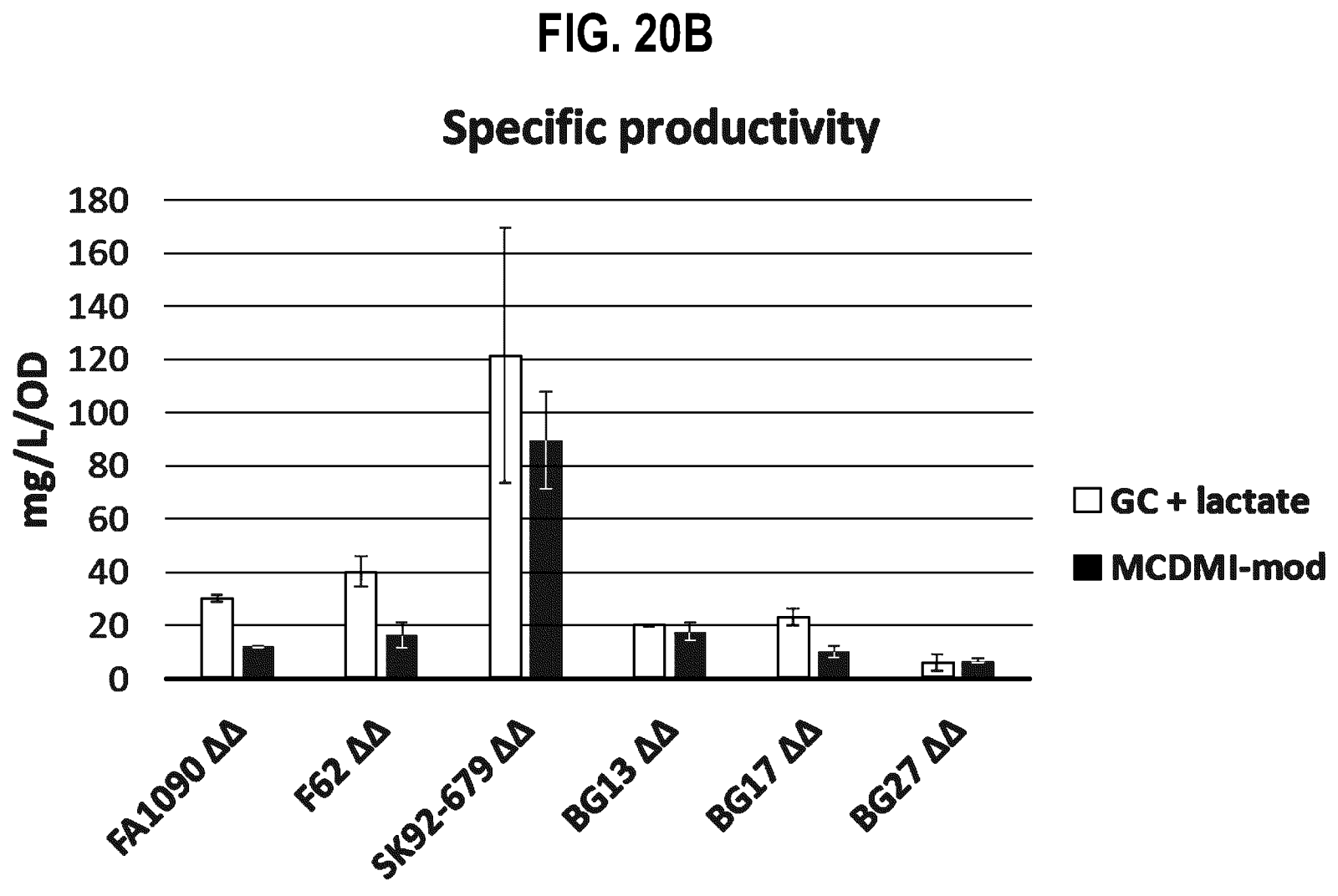

FIG. 20B: Results from FIG. 20A normalized to the different optical density at 600 nm wavelength (OD600 nm) reached by each strain in each condition to compare the specific productivity.

Figure 21:
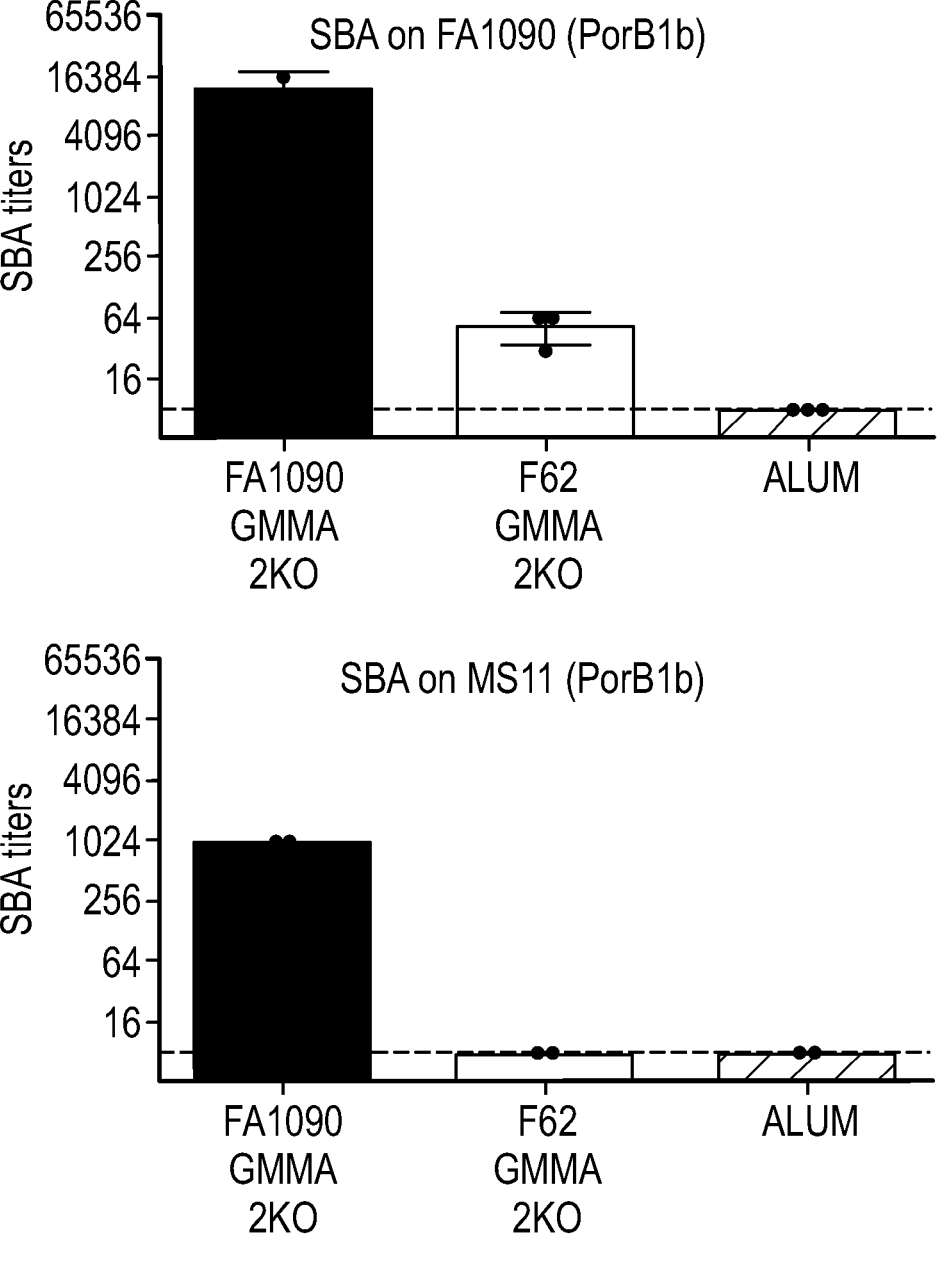

FIG. 21: Immunogenicity of OMVs (referred to as GMMA therein) blebbed from both from double-mutant FA1090 (Δlpxl1,Δrmp) and double-mutant F62 (Δlpxl1, Δrmp). 7-week-old CD1 female mice were immunized IP two times at 4 weeks interval with OMVs from FA1090 2KO or F62 2KO formulated in Alum or with Alum alone. Functional antibodies were measured by hSBA against the indicated strains in sera collected two weeks after the second immunization using human serum as complement source.

Figure 22A:
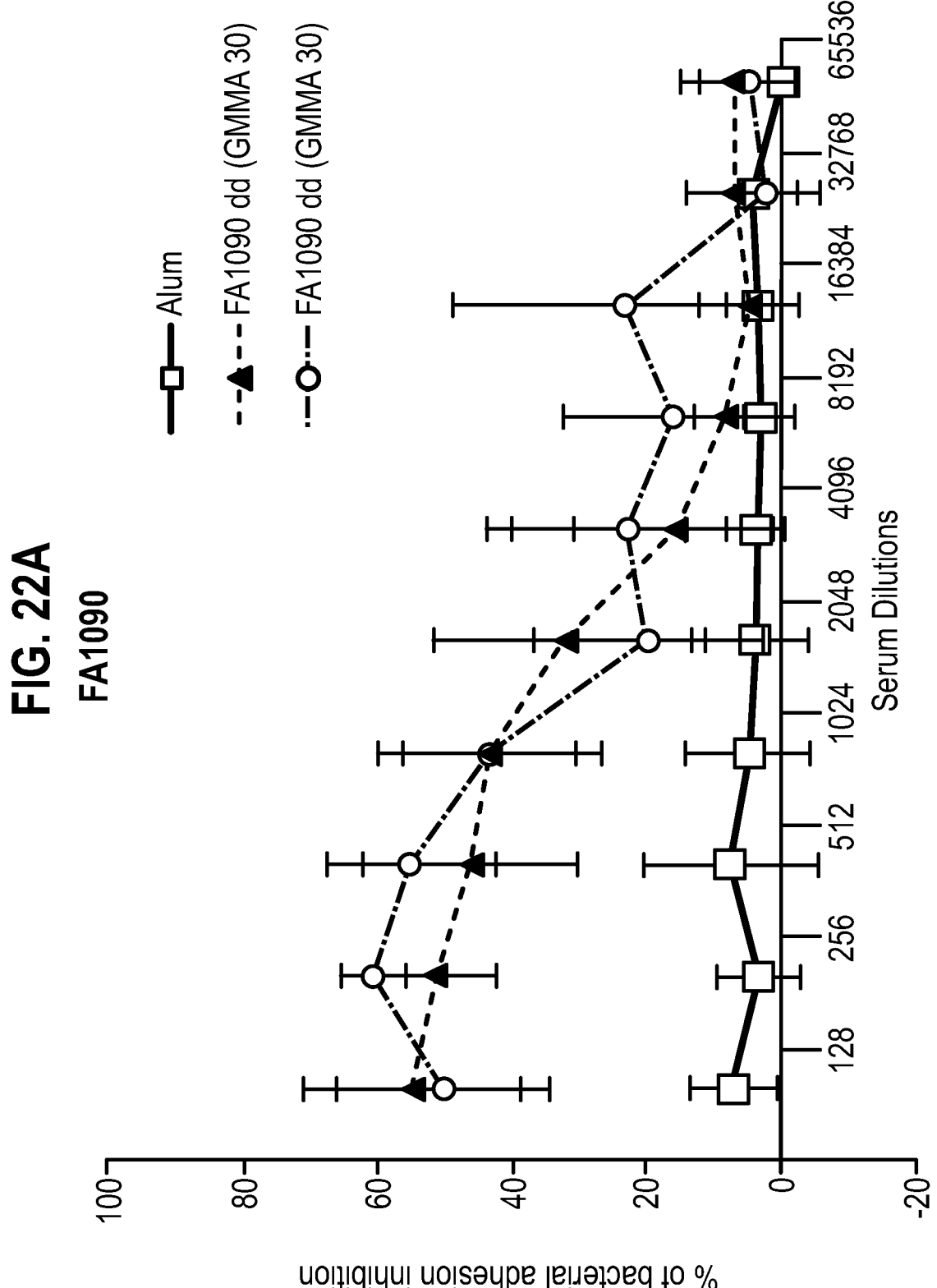
Figure 22B:
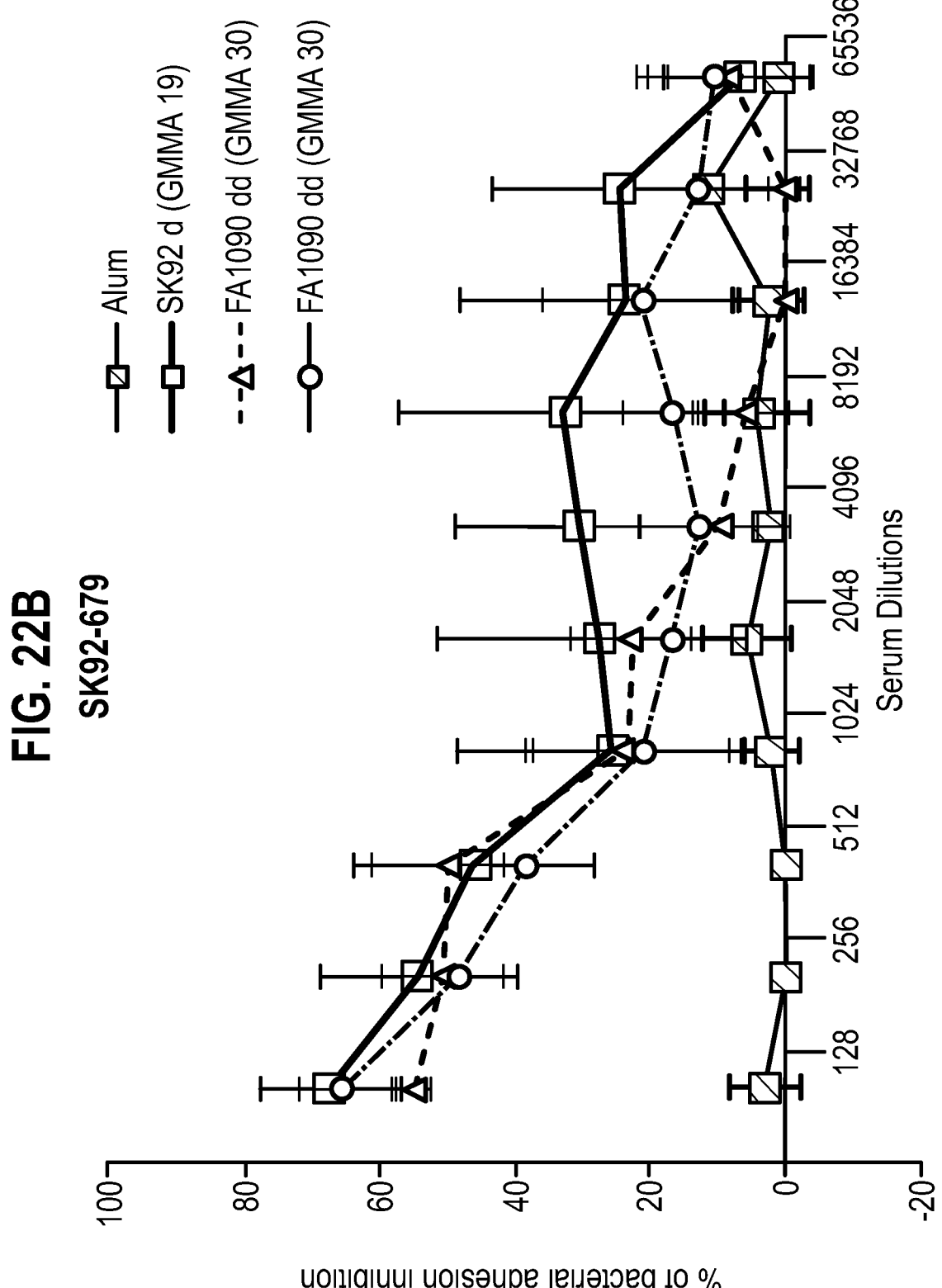
Figure 22C:
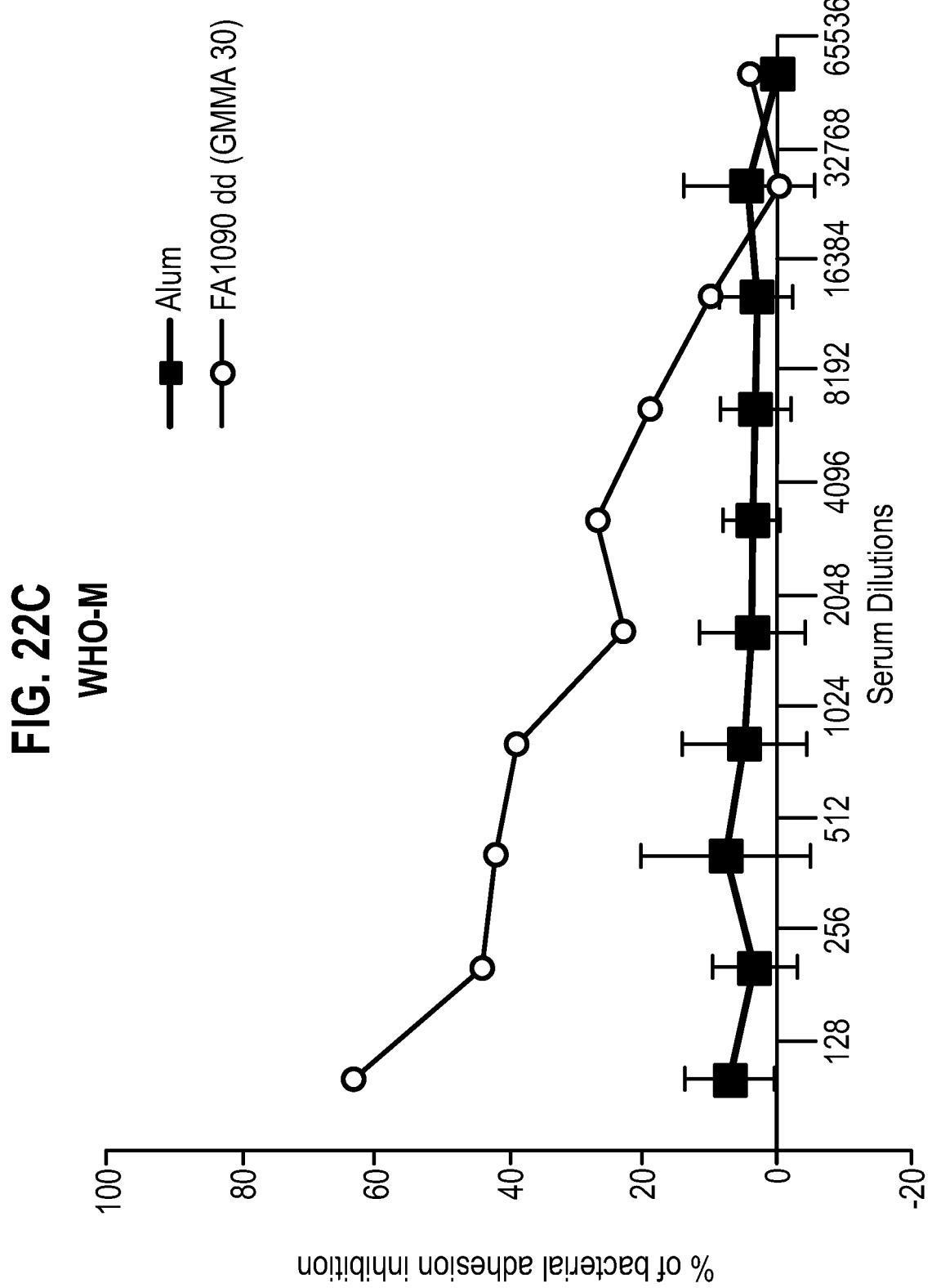

FIG. 22A, FIG. 22B and FIG. 22C: Bacterial adhesion inhibition (BAI) results for strains FA1090 (FIG. 22A), SK920679 (FIG. 22B), and WHO-M (FIG. 22C) are shown for dilutions of serum from seven-week-old CD1 female mice that were immunized IP two times at 4 weeks interval with OMVs (referred to as GMMA therein) obtained from the FA1090 double-mutant (Δlpxl1,Δrmp, labelled as "dd" in the Figure) in two separate experiments. OMV's were formulated in Alum and an Alum only control was also tested as negative control. Functional antibodies were measured by BAI with the indicated strains (FA1090 (FIG. 22A), SK92-679 (FIG. 22B) and WHO-M (FIG. 22C)). "dd"=delta, delta i.e. FA1090ΔΔ (referring to the double mutant Δlpxl1,Δrmp).

Figure 23:
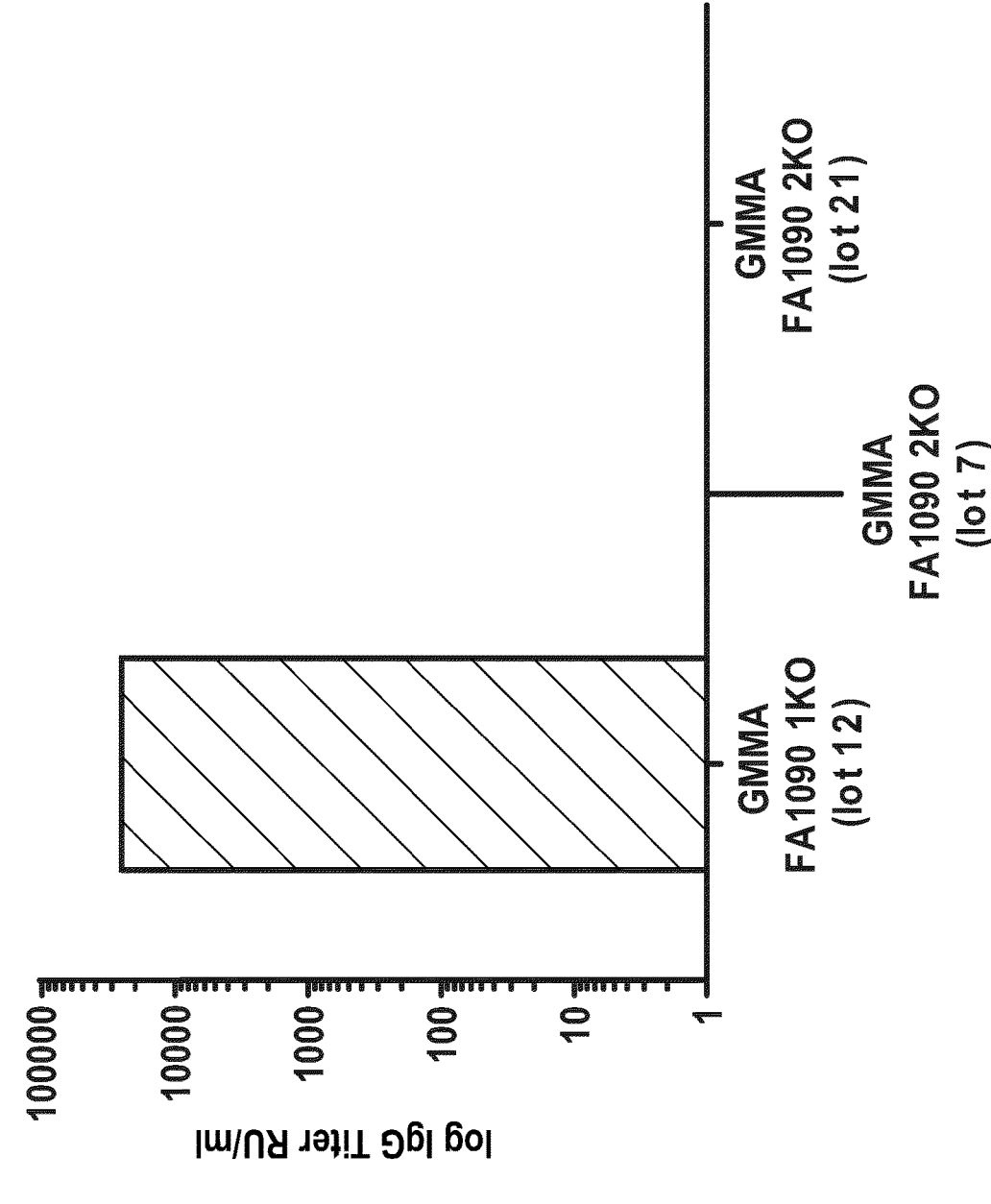

FIG. 23: OMVs (referred to as GMMA therein) from FA1090 Δlpxl1,Δrmp (2KO) do not induce anti-rmp antibodies. 7-week-old CD1 female mice were immunized IP two times at 4 weeks interval with OMVs from FA1090 Δlpxl1 (single-mutant) or FA1090 Δlpxl1,Δrmp (double-mutant) formulated in Alum and 2 weeks after the second immunization anti-rmp IgG were measured on pooled sera with a Luminex-based immunoassay.

Figure 24:
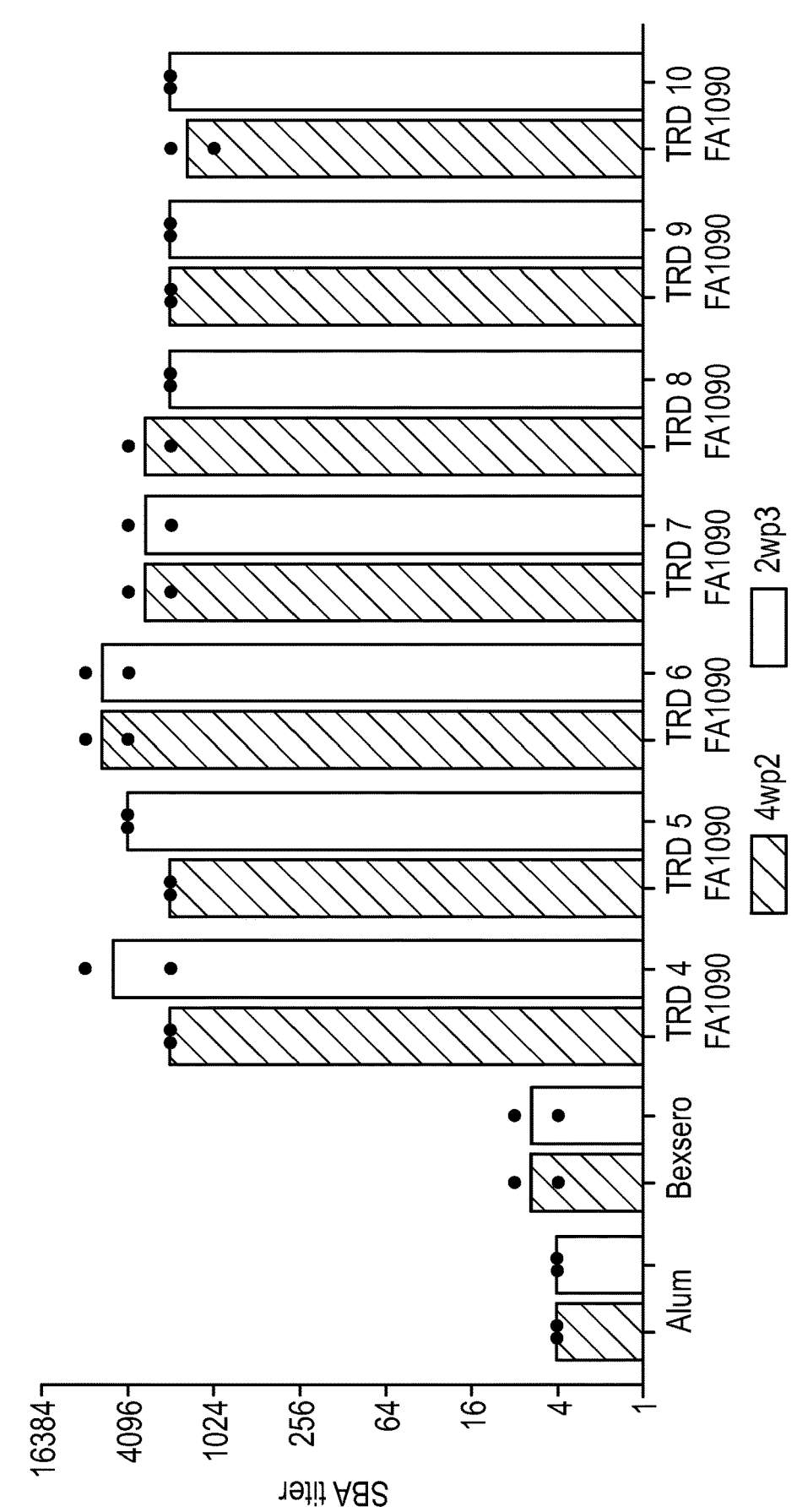

FIG. 24: hSBA titres measured against the FA1090 homologous strain on pooled 4wp2 and 2wp3 sera from CD1 mice immunized with Alum, Bexsero, or the 7 FA1090 2KO OMV vaccine lots (TRD4-TRD10). Bars represent the mean titre of two independent experiments. Dots represent single titres.

Figure 25A:
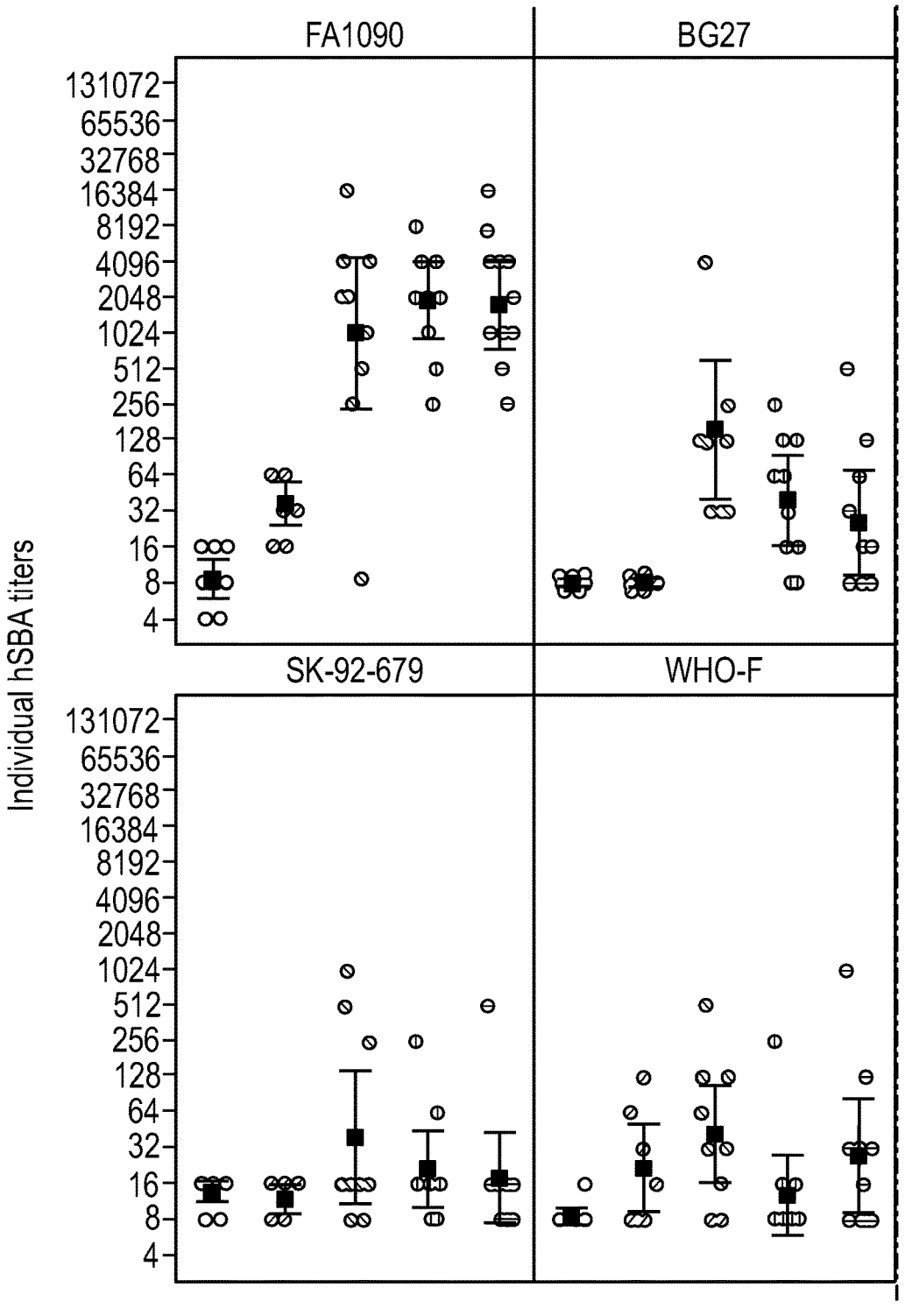

FIG. 25A: Individual hSBA titre were measured against the indicated gonococcus strains on individual sera from CD1 mice immunized with Alum, Bexsero, or the FA1090 2KO OMV vaccine lots TRD4, TRD 5 and TRD9. Data is reported together with GMT (95% CI).

Figure 25B:
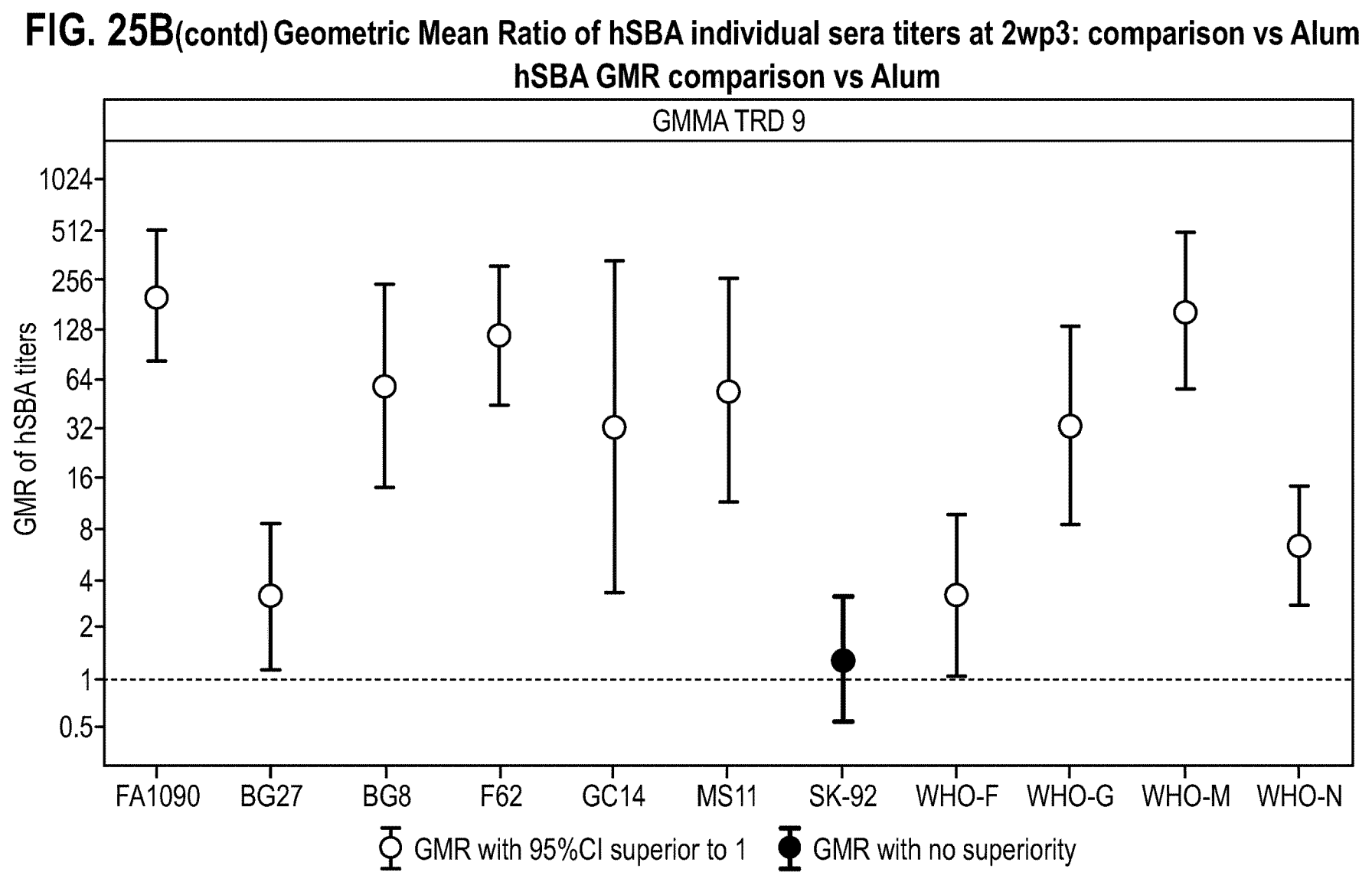
Figure 25C:
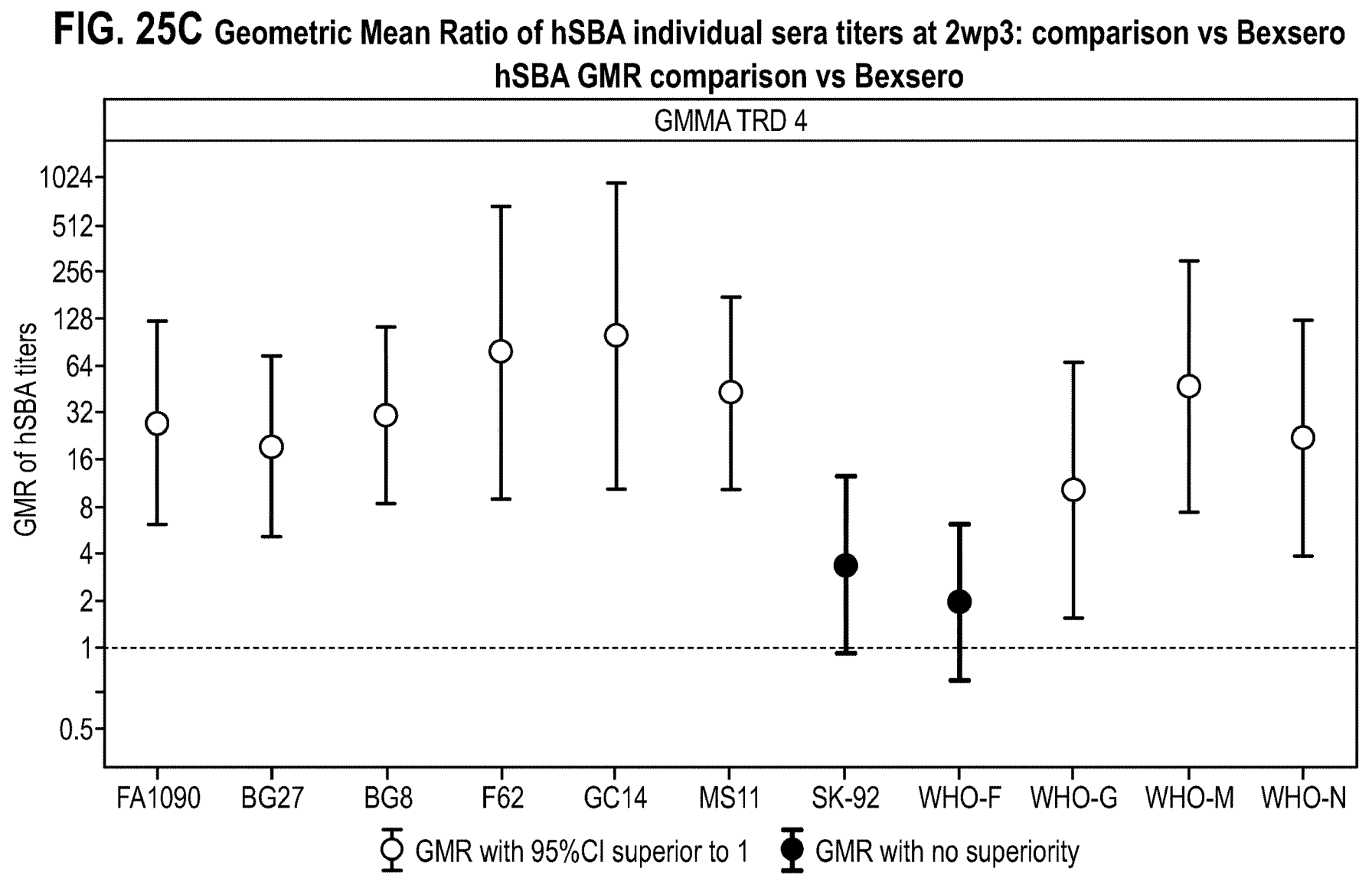
Figure 25C:
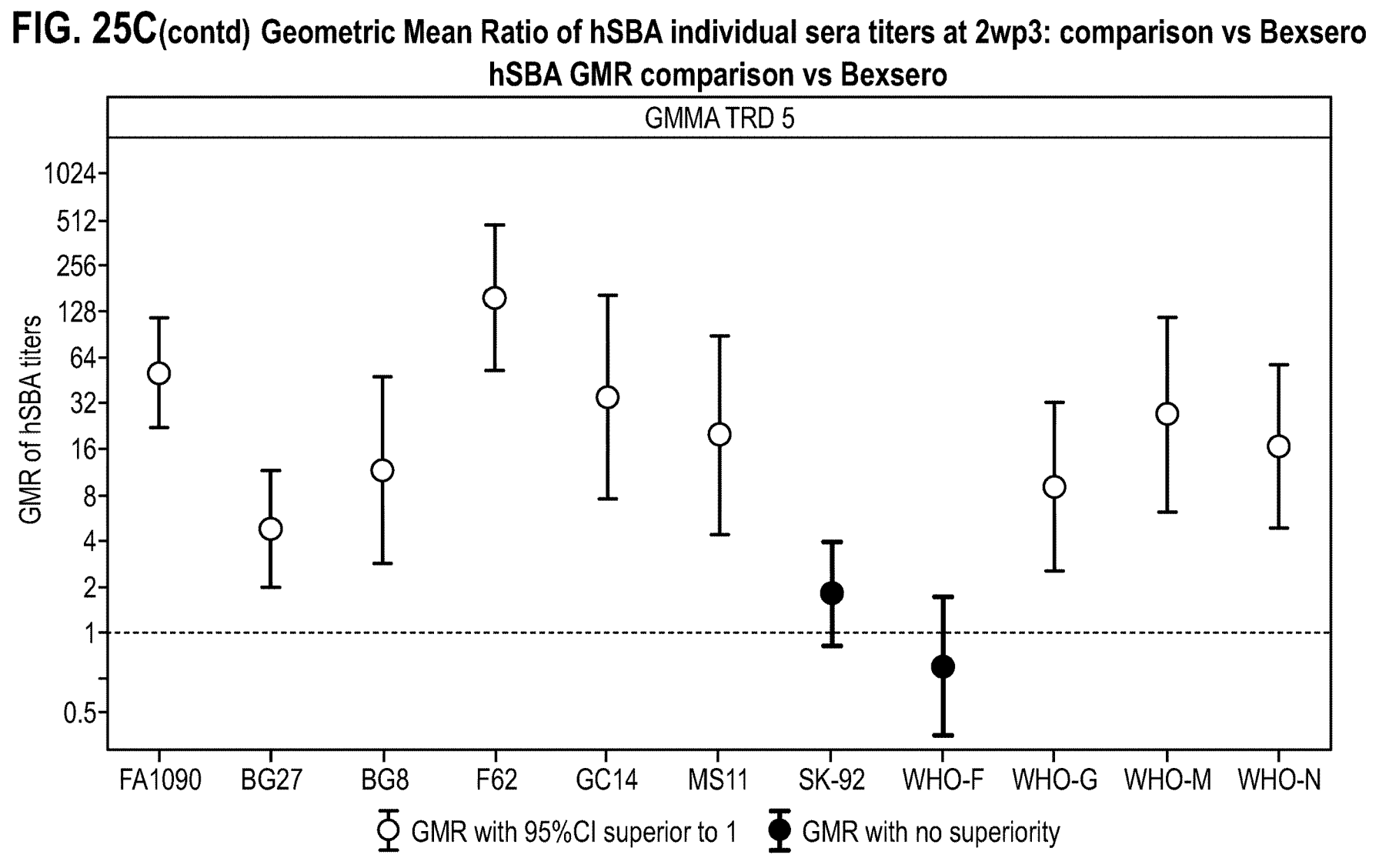
Figure 25C:
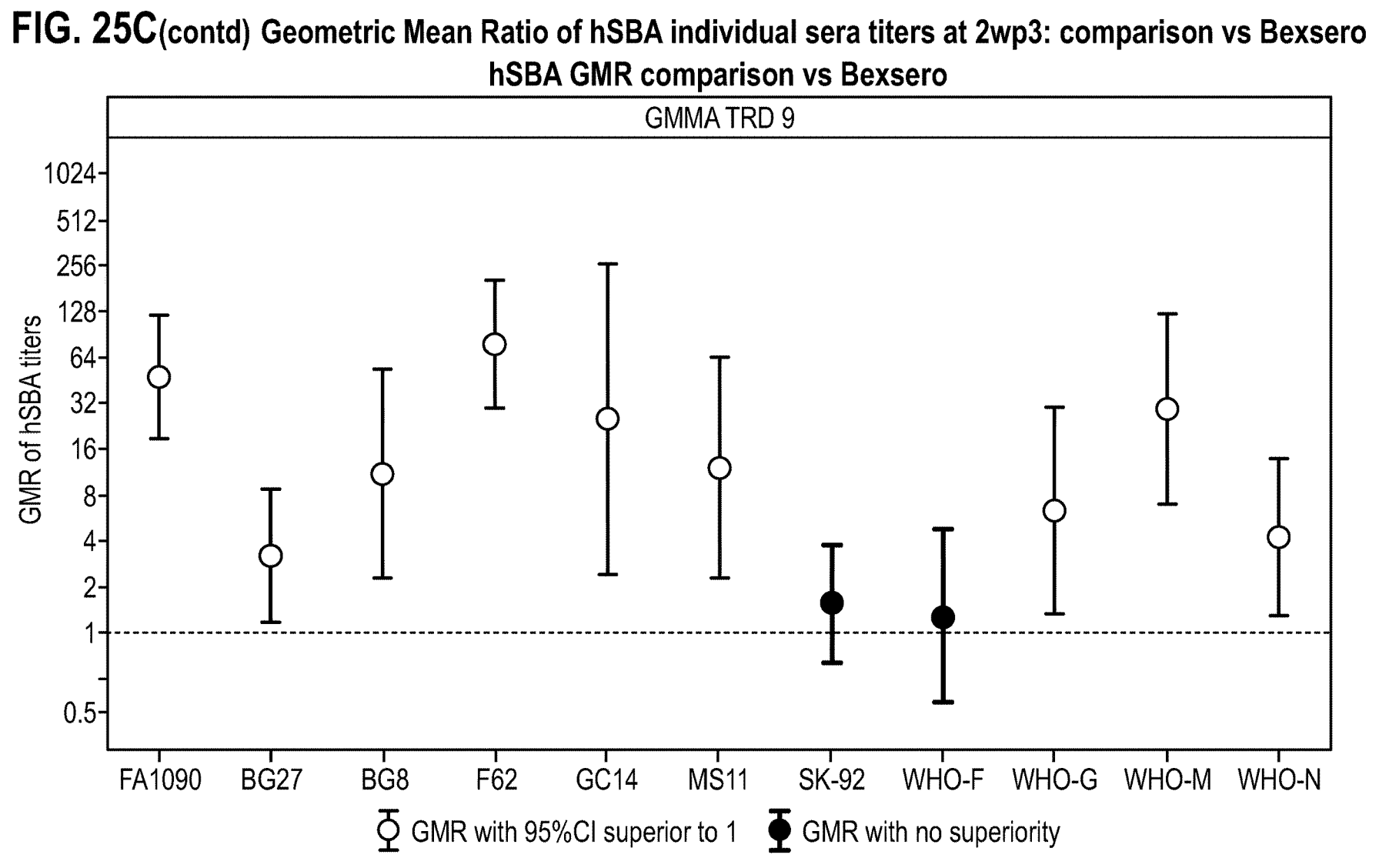

FIG. 25B and FIG. 25C: hSBA GMR with 95% CI revealed superiority of the titres for the FA1090 2KO OMV vaccine lots TRD4, TRD 5 and TRD9 compared to Alum (FIG. 25B) and Bexsero (FIG. 25C) for at least 9 out of 11 tested strains.

Figure 26:
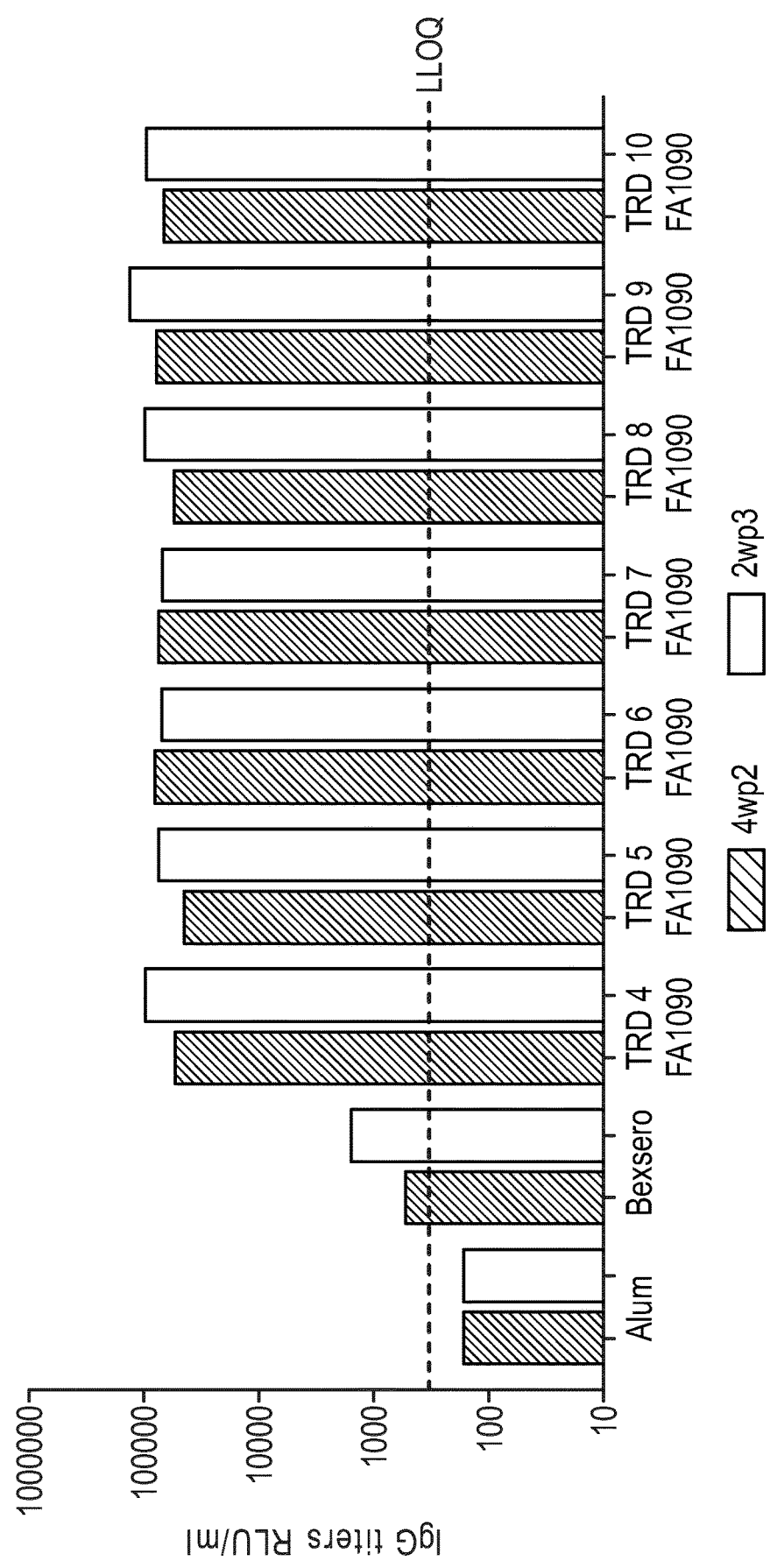

FIG. 26: Anti-OMV IgG were measured by Luminex in the sera from pooled group of mice immunized as indicated. IgG titres of all 7 FA1090 2KO OMV vaccine lots and the Bexsero titres are reported. Dotted line indicates the Lower Limit of Quantification, LLOQ=329.

Figure 27A:
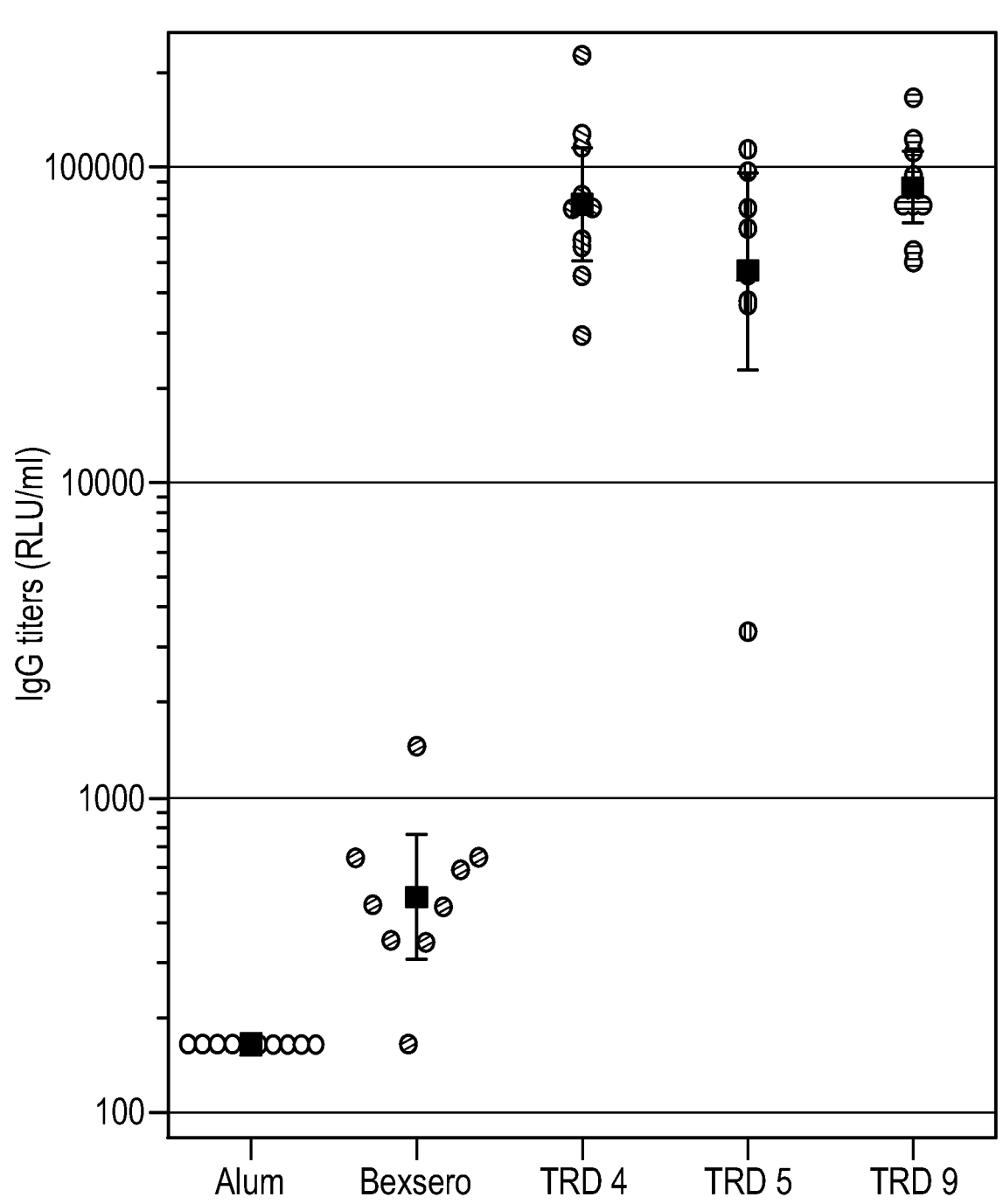

FIG. 27A: Anti-OMV IgG was measured by Luminex in the sera from individual mice immunized as indicated. Individual titres and GMT with 95% CI are reported.

Figure 27B:
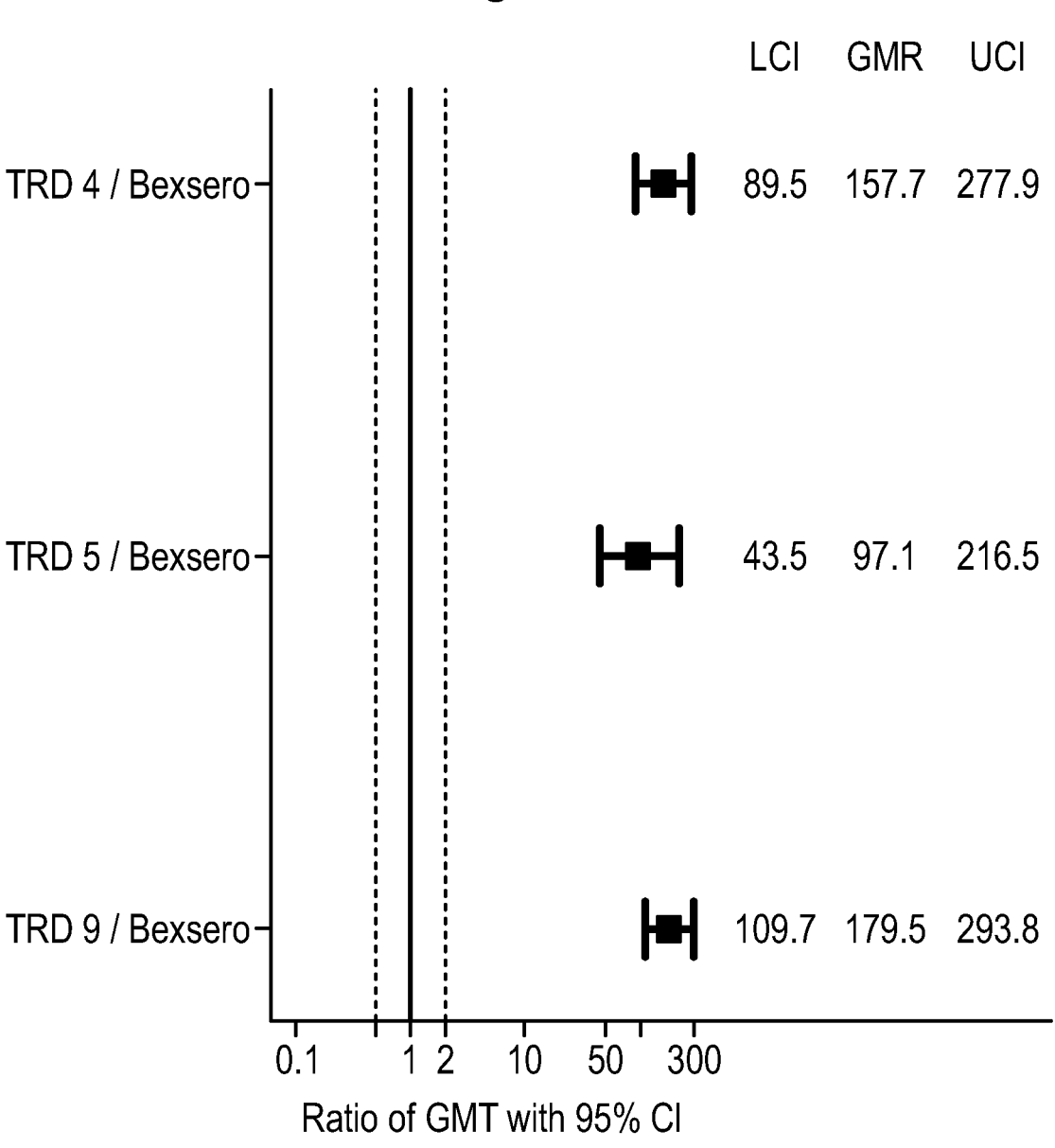

FIG. 27B: Anti-OMV IgG was measured by Luminex in the sera from individual mice immunized as indicated. GMR with upper and lower 95% CI of the titres from different FA1090 2KO OMV lots and the Bexsero titres are reported.

Figure 28A:
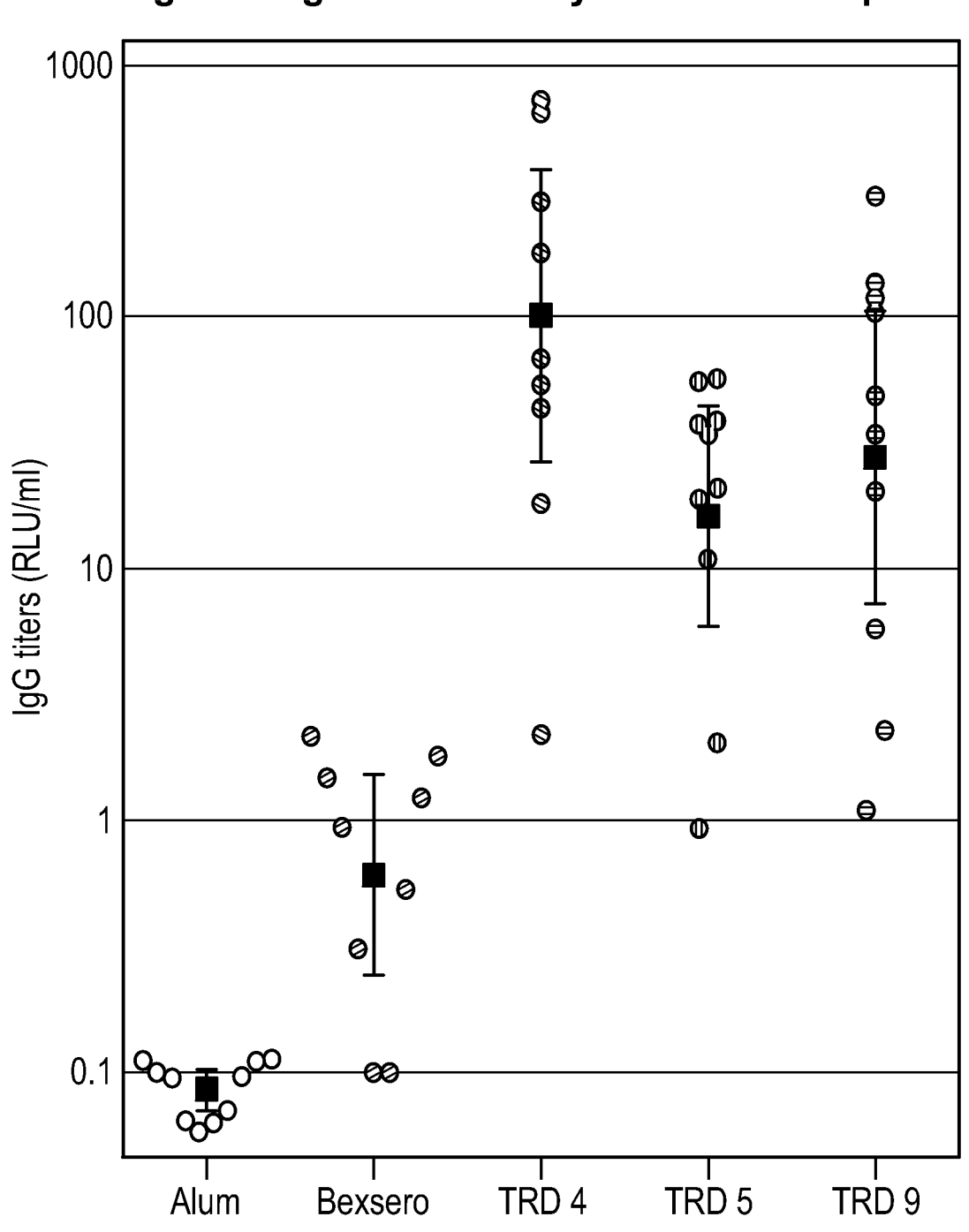

FIG. 28A: Anti-OMV IgG were measured by Luminex in the vaginal washes from individual mice immunized as indicated. Individual titres and GMT with 95% CI are reported FIG. 28B: Anti-OMV IgG were measured by Luminex in the vaginal washes from individual mice immunized as indicated. GMR with upper and lower 95% CI of the titres from different FA1090 2KO OMV vaccine lots and the Bexsero titres or the Alum titres are reported.

Figure 29A:
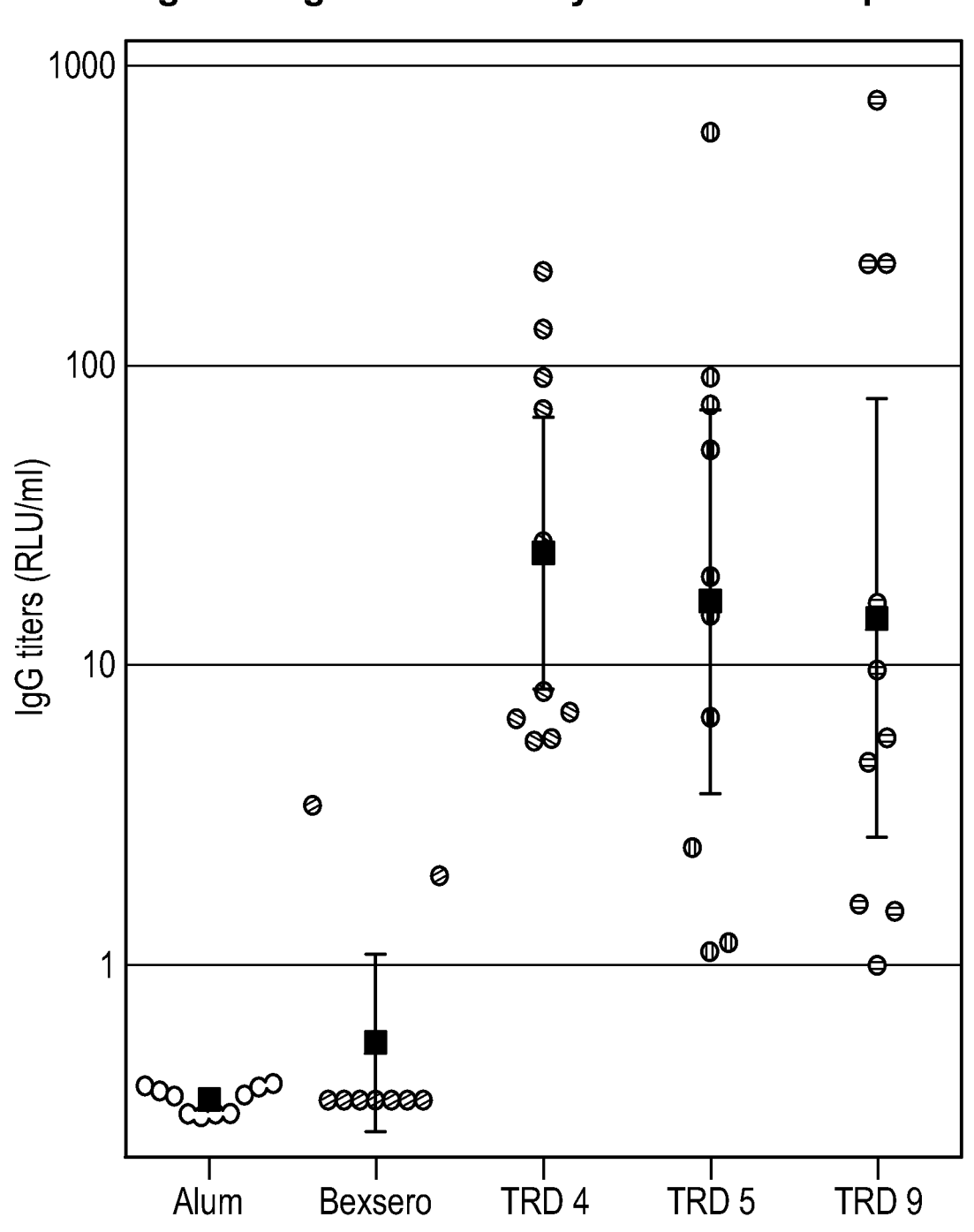

FIG. 29A: Anti-OMV IgA were measured by Luminex in the vaginal washes from individual mice immunized as indicated. Individual titres and GMT with 95% CI are reported FIG. 29B: Anti-OMV IgA were measured by Luminex in the vaginal washes from individual mice immunized as indicated. GMR with upper and lower 95% CI of the titres from different FA1090 2KO OMV vaccine lots and the Bexsero titres or the Alum titres are reported.

Figure 30:
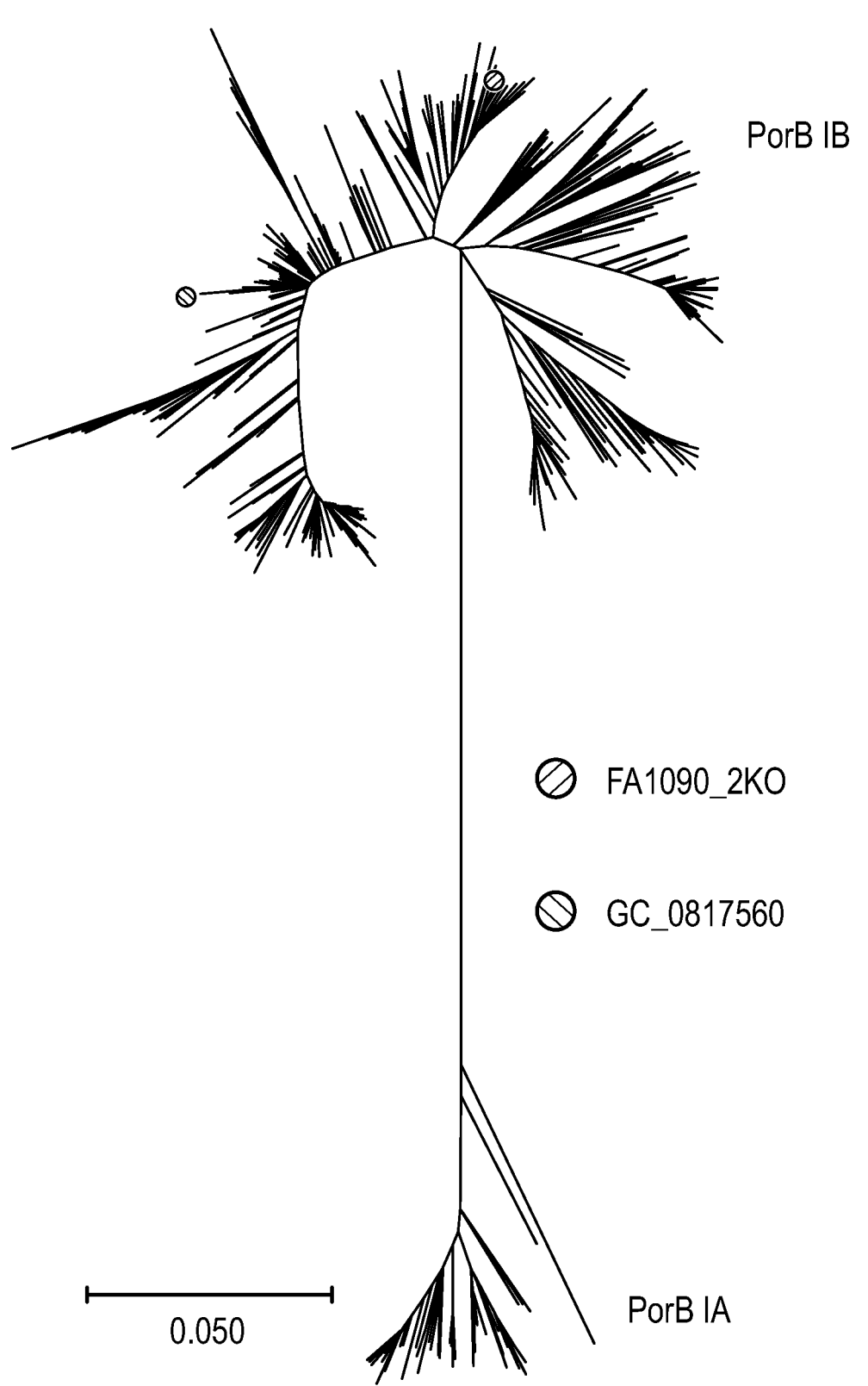

FIG. 30: Global PorB phylogeny in *N. gonorrhoeae*.

FIG. 31: FA1090 2KO and GC_0817560 PorB alignment with extracellular Loops (1-8) identification and diversity.

Figure 32:
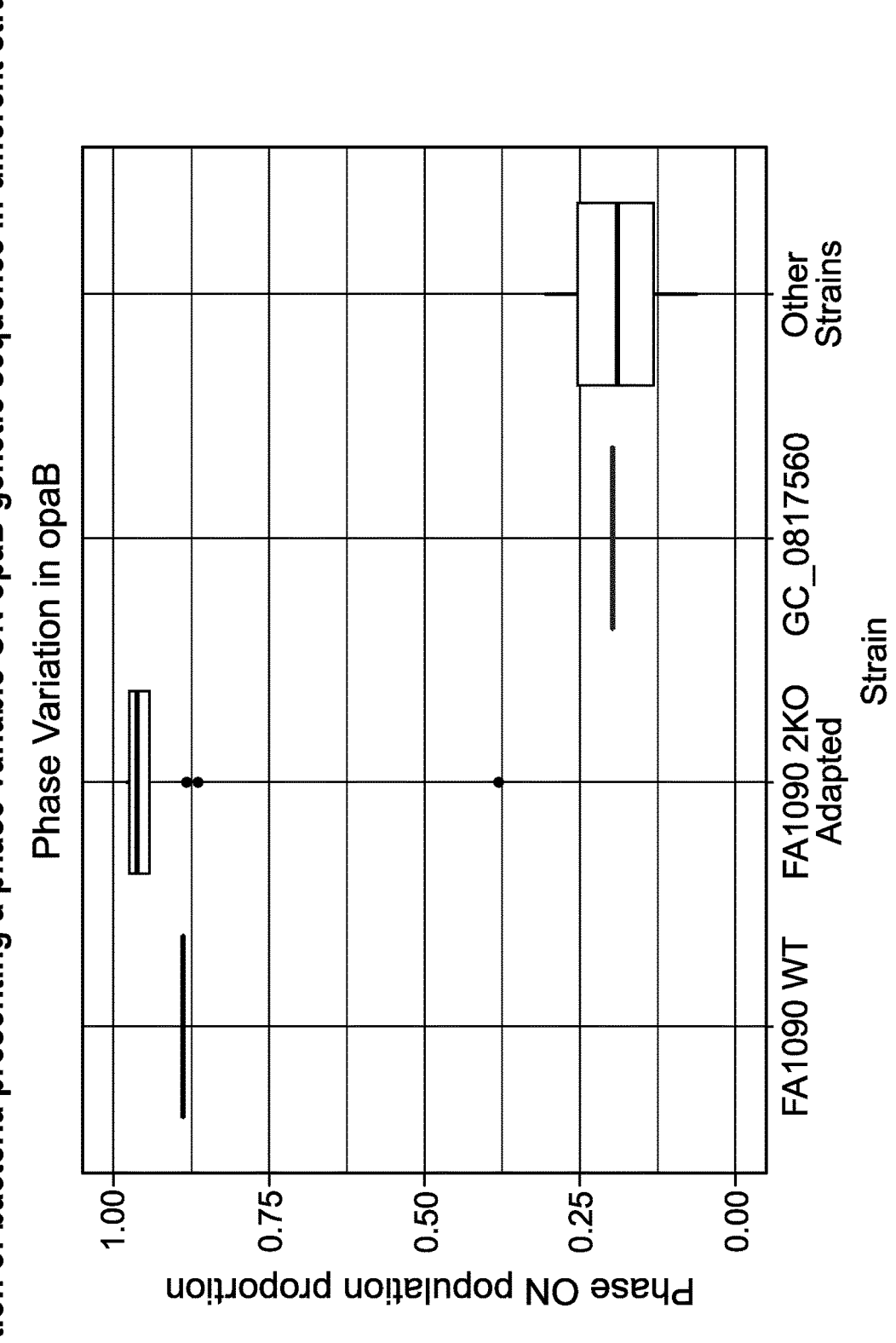

FIG. 32: Proportion of bacteria presenting a phase variable ON opaB genetic sequence in different strains. The percentage of bacteria predicted to be phase ON in one (FA1090 WT and GC_0817560 strains) or in multiple (FA1090 2KO and Other Strains) samples is reported.

DETAILED DESCRIPTION

Terminology

To facilitate review of the various embodiments of this disclosure, the following explanations of terms are provided. Additional terms and explanations are provided in the context of this disclosure.

Unless otherwise explained or defined herein, all technical and scientific terms used herein have the same meaning as commonly understood by one of ordinary skill in the art to which this disclosure belongs. For example, definitions of common terms in molecular biology can be found in Benjamin Lewin, *Genes V*, published by Oxford University Press, 1994 (ISBN 0-19-854287-9); Kendrew et al. (eds.), *The Encyclopaedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

All references, including publications of patent and or patent applications cited within this patent specification are incorporated by reference herein.

As used herein, gene identifiers formatted in italics refers to the gene or mRNA thereto (e.g. lpxl1 refers to the lpxl1 gene). As used herein gene identifiers that are non-italicized refers to the protein or polypeptide (e.g. lpxl1 refers to the lpxl1 protein). As used herein, "lpxl1 gene mRNA and/or polypeptide" refers to "lpxl1 gene mRNA and/or lpxl1 polypeptide". As used herein, "rmp gene mRNA and/or polypeptide" refers to "lpxl1 gene mRNA and/or rmp polypeptide". The abbreviation WT corresponds to "wild-type".

Reference to "lipooligosaccharide" (or LOS) may also be referred to as "lipopolysaccharide" (or LPS).

Amino acids refers to an amino acid selected from the group consisting of alanine (ala, A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), valine (val, V).

A "subject" as used herein is an animal, preferably a mammal, including humans, non-human primates and non-primate mammals such as members of the rodent genus (including but not limited to mice and rats), the Cavia genus (including but not limited to guinea pigs) and members of the order Lagomorpha (including but not limited to rabbits). As used herein, the subject is most preferably a human.

As used herein, "immune response" means the sequence of events occurring at the molecular, cellular or tissue level (i.e. at any level of biological organisation) in response to an antigen. In the context of the present disclosure, "immune response" may be the sequence of cellular (cell mediated) and/or humoral (antibody mediated) events occurring in response to an antigen (e.g. antigens on the surface of bacteria, viruses, fungi etc.) or in response to antigens present on the surface of an OMV or antigens in the form of an immunogenic fragment, immunogenic composition or vaccine. As used herein, "immunogenicity" means the ability of an antigen to elicit an immune response.

As used herein, "adjuvant" means a compound or substance (or combination of compounds or substances) that, when administered to a subject in conjunction with an antigen or antigens, for example as part of an immunogenic composition or vaccine, increases or enhances the subject's immune response to the administered antigen or antigens (compared to the immune response obtained in the absence of adjuvant). With respect to the present disclosure an adjuvant administered to subject in conjunction with outer membrane vesicles increases or enhances the subject's immune response to antigen or antigens present in the surface of the OMVs.

As used herein the term "protect" in the context of infection, diseases or conditions caused by Neisseria (most particularly N gonorrhoeae) means to protect via prophylaxis. Protection may for example relate to a reduction in the incidence of an infection, disease or condition caused by Neisseria (in symptomatic and asymptomatic states) leading to the control of the disease and/or to the control of associated reproductive health adverse outcomes caused by Neisseria. Protection may lead to a reduction in the number of clinical visits. The term protect (or protection) may herein be used in relation to protection against the primary infection by Neisseria in terms of prevention of acute diseases (cervicitis and urethritis), reduction of the impact of antimicrobial resistance, gonococcal-related HIV acquisition and long-term reproductive complications occurring as a result of said infection. Protection may be achieved against disease causing gonococcal infections in different anatomical sites (urogenital, anorectal, oropharyngeal). As used herein the term "prevent" (or prevention) means that, as a result of increased protection, diseases or conditions caused by N gonorrhoeae are substantially averted resulting in improved population health outcomes.

As used herein the term "treat" (or treatment) in the context of infection, diseases or conditions caused by Neisseria (most particularly *N. gonorrhoea*) means to treat via administration, post-infection any *N. gonorrhoea* causing symptom, effect or phenotype. Treatment may mean to decrease the severity or frequency of symptoms of the condition or disease in a subject, slow or eliminate the progression of the condition and/or totally or partially eliminate the symptoms of the disease or condition in the subject. Treatment of an infection, disease or condition caused by *N. gonorrhoea* includes ameliorating, stabilising, reducing or eliminating the symptoms, effects or phenotypes caused by *N. gonorrhoea* in humans. Treatment of an infection, disease or condition caused by *N. gonorrhoea* also may include clearing or killing the bacteria.

As used herein the term "genetic modification(s)" means any alteration to the constitution, structure or operation of the genetic material in a cell to provide a specified effect (e.g. decreasing or abolishing expression). The skilled person is aware of numerous means to decrease or abolish gene and/or protein expression in comparison to that of a non-modified (e.g. naturally occurring bacterium) or a bacterium comprising the wild type gene of interest. The genetic material within a cell relates to either DNA or RNA. As such, the term genetic modification as used herein, means any artificial alteration to the constitution, structure or operation of either gonococcal DNA or RNA such as to decrease and/or abolish expression and/or function of the specified genes. As used herein, "genetically modified" with regards to gonococcal bacterium refers to a gonococcus that has had its genetic material artificially altered. Genetically modified gonococcal bacteria do not include wild type gonococcal bacteria. A genetically modified gonococcal bacterium includes for example a gonococcal bacterium into which an exogenous polynucleotide has been introduced. A genetically modified gonococcal bacterium also refers to a bacterium that has been genetically manipulated such that endogenous nucleotides have been altered to include a mutation, such as a deletion, an insertion, a substitution or a combination thereof. For instance, an endogenous coding and/or non-coding region could be deleted or replaced. Such genetic modifications may result either in depleted and/or abolished expression of a polypeptide and/or may result in a polypeptide having a different amino acid sequence than was encoded by the endogenous polynucleotide. Another example of a genetically modified gonococcal bacterium is one having an altered regulatory sequence, such as a promotor, to result in increased or decreased expression of an operably linked endogenous coding region.

As used herein the term "gene deletion" or "gene knockout" refers to a combination of genetic techniques that has the potential to render a specific gene inoperable or inactive. In some embodiments a gene deletion decreases or abolishes expression of a polypeptide from the gene. In some embodiments both the mRNA and protein are reduced or eliminated. In certain embodiments the expression of gene is substantially decreased or abolished. Substantially decreased means that the expression of a gene is reduced by at least 70%, at least 80%, at least 90%, at least 95% or at least 98% when compared to an endogenous level of expression of a gene. In a certain embodiment the expression of a gene is abolished. Abolished means that, using techniques to monitor the expression of either the mRNA transcribed from a gene, or the expression of protein translated from a particular mRNA, no level of detection is observed. Expression of a gene can be determined by a suitable technique (e.g., by measuring transcript levels by RT/Q-PCR or expressed protein levels by immunoassay e.g. Western Blot). Such techniques are known to the person skilled in the art. Gene deletion or gene knockout, might include not only deletion of genetic elements but also addition, substitution or modification, such that the gene is inoperable or inactive, i.e. insertion of a genetic sequence may cause mistranslation of the gene, by for example, incorporating an early stop codon, or by causing a missense translation. Genes may for example be deleted by replacement of the gene, or a fragment of said gene, with a different heterologous gene (e.g. an antibiotic resistance gene) for example by homologous recombination.

As used herein the "Δ" symbol is used herein to refer to a bacterial strain from which the sequence of the gene recited after the Δ symbol has been deleted/knocked out in line with the definition of "gene deletion" or "gene knockout".

As used herein the term "outer membrane vesicle(s)" or "OMV(s)" relates to proteoliposomic vesicles obtained by disruption of, or blebbing from the outer membrane of Gram-negative bacteria, to form vesicles therefrom that retains antigens from the outer membrane. Gram-negative bacteria naturally shed OMVs which are released into the growth medium. Heterologous antigens are expressed in the Gram-negative bacteria such that they assemble in the membrane that is then released into the culture supernatant. OMVs from such bacteria are representative of the outer membrane and periplasmic bacterial compartments and allow the presentation of membrane proteins in their natural composition and structure. In the broadest sense, OMVs relates to any such proteoliposomic vesicles. However, the term OMVs includes 'Native OMVs' (nOMVs), microvesicles (MVs), detergent-extracted OMVs (DOMVs), and blebs, which are outer-membrane protrusions that remain attached to bacteria prior to release as MVs. All of these form part of the invention and are collectively referred to as OMVs herein, unless otherwise specifically mentioned. In a preferred embodiment of the invention, the OMVs are nOMVs. As used herein the term outer membrane vesicle(s) or OMV's may also be referred to as GMMA.

As used herein the term "isogenic" refers to two individual organisms having substantially identical genomes. In an embodiment isogenic means two individual organisms having identical genomes. In the context of the present disclosure, two organisms may be isogenic with the exception of particular specified genetic modification.

As used herein the term "heterologous gene sequence" refers to a nucleotide sequence (e.g. a gene sequence or part of a gene sequence) that is not naturally occurring in relation to a reference organism. In the context of the present invention a heterologous gene sequence refers to a sequence that is not naturally present within the genome of the gonococcal FA1090 strain.

As used herein the term "genomic recombination" refers to a process of exchange of genetic information between two polynucleotides. For gene deletion/knockout purposes, homologous recombination involves creating a DNA construct containing an antibiotic resistance marker in place of the desired knockout gene. The construct also contains a gene sequence with homology to the target sequence. This approach relies upon the cells repair mechanisms to recombine the DNA construct into the existing DNA. This results in the sequence of the endogenous gene being altered.

As used herein the term "immunogenic composition" relates to a composition of matter suitable for administration to a human or animal subject (e.g., in an experimental or clinical setting) that is capable of eliciting a specific immune response, e.g., against a pathogen, such as Neisseria. As such, an immunogenic composition includes one or more antigens (for example, polypeptide antigens) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject, wholly or partially, against symptoms or conditions induced by a pathogen. In the context of this disclosure, the term immunogenic composition will be understood to encompass compositions that are intended for administration to a subject or population of subjects for the purpose of eliciting a protective pre-exposure immune response against Neisseria or palliative post-exposure immune response against Neisseria.

By "immunologically effective amount", it is meant that the administration of that amount to an individual, either in a single dose or as part of a series, is effective for treatment, protection or prevention. Administration of an immunologically effective amount elicits an immune response, including a protective immune response. This amount can vary depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range.

As used herein the term "pharmaceutically acceptable" means that the referent is suitable for administration to a subject (e.g., a human or animal subject). Remington's Pharmaceutical Sciences, by E. W. Martin, Mack Publishing Co., Easton, PA, 15$^{th}$ Edition 25 (1975), describes compositions and formulations (including diluents) suitable for pharmaceutical delivery of therapeutic and/or prophylactic compositions, including immunogenic compositions.

As used herein the term "antibody" is used in the broadest sense to refer to molecules with an immunoglobulin-like domain (for example IgG, IgM, IgA, IgD or IgE) and includes monoclonal, recombinant, polyclonal, chimeric, human, humanised, multispecific antibodies, including bispecific antibodies, and heteroconjugate antibodies; a single variable domain (e.g., VH, VHH, VL, domain antibody (dAb™)), antigen binding antibody fragments, Fab, F(ab')$_2$, Fv, disulphide linked Fv, single chain Fv, disulphide-linked scFv, diabodies, TANDABS™, etc. and modified versions of any of the foregoing (for a summary of alternative "antibody" formats see [Holliger P, Hudson P. J. *Engineered antibody fragments and the rise of single domains. Nat Biotechnol.* 2005; 23(9):1126-36]). Alternative antibody formats include alternative scaffolds in which the one or more CDRs of the antigen binding protein can be arranged onto a suitable non-immunoglobulin protein scaffold or skeleton, such as an affibody, a SpA scaffold, an LDL receptor class A domain, an avimer or an EGF domain.

"Sequence identity" can be determined by the Smith-Waterman homology search algorithm as implemented in the MPSRCH program (Oxford Molecular), using an affine gap search with parameters gap open penalty=12 and gap extension penalty=1, but is preferably determined by the Needleman-Wunsch global alignment algorithm (see e.g. Rubin (2000) *Pediatric. Clin. North Am.* 47: 269-285), using default parameters (e.g. with Gap opening penalty=10.0, and with Gap extension penalty=0.5, using the EBLOSUM62 scoring matrix). This algorithm is conveniently implemented in the needle tool in the EMBOSS package. Where the application refers to sequence identity to a particular SEQ ID, the identity is intended to be calculated over the entire length of that SEQ ID.

Gonococcus

In a first aspect the present invention provides, a genetically modified gonococcal bacterium of strain FA1090, comprising genetic modification(s) that:

a) decreases or abolishes expression and/or function of the lipid A biosynthesis lauroyl acyltransferase (lpxl1) gene, mRNA, and/or polypeptide; and b) decreases or abolishes expression and/or function of the reduction modifiable protein (rmp) gene, mRNA, and/or polypeptide.

In an embodiment, the starting organism to which the genetic modification(s) is/are then introduced is a substantially or completely unmodified gonococcal bacterium of strain FA1090. As such the present invention provides a genetically modified gonococcal bacterium, comprising genetic modification(s) that:

a) decreases or abolishes expression and/or function of the lpxl1 gene mRNA and/or polypeptide; and b) decreases or abolishes expression and/or function of the rmp gene mRNA and/or polypeptide, wherein the unmodified gonococcal bacterium is an FA1090 strain gonococcal bacterium.

In an embodiment, the starting organism to which the genetic modification(s) of the invention are then introduced is a gonococcal bacterium of strain FA1090 that comprises no genetic modification(s) to its lpxl1 and/or rmp genes. As such the present invention provides a genetically modified gonococcal bacterium, comprising genetic modification(s) that:

a) decreases or abolishes expression and/or function of the lpxl1 gene mRNA and/or polypeptide; and b) decreases or abolishes expression and/or function of the rmp gene mRNA and/or polypeptide, wherein the unmodified gonococcal bacterium is an FA1090 strain gonococcal bacterium comprising wild type lpxl1 and rmp genes.

In an embodiment there is provided a *Neisseria gonorrhoeae* strain FA1090 comprising modifications, which at least: decrease total activity of lipid A biosynthesis lauroyl acyltransferase (Lpxl1) and decrease functional reduction modifiable protein (Rmp) compared to functional Lpxl1 and functional Rmp in a *N. gonorrhoeae* strain FA1090 lacking said modifications.

Gonococcal bacteria of strain FA1090 are known in the art. The FA1090 strain (a porin serotype PIB-3 strain) of *N. gonorrhoeae* was originally isolated from the endocervix of a patient with probable disseminated gonococcal infection [Nachamkin I, Cannon J G, Mittler R S. *Infect Immun.* 1981 May; 32(2):641-8]. The FA1090 gonococcus is commercially available from the American Type Culture Collection (ATCC, see for example Deposit Number #700825, 1081 University Blvd, Manassas, Virginia 20110, US) and the FA1090 genome sequence is publicly available from GenBank (accession ID: AE004969.1).

Whilst it will be understood in the art that FA1090 strains may differ marginally (for example between different laboratories) due to natural variation, the skilled person will be aware of methods to determine whether a given gonococcus is of the strain FA1090. For example, the person skilled in the art is aware of methods to sequence the gonococcal genome (for example using the method described in Example 9) and align the genome with the genome of a known FA1090 strain, for example the genome of FA1090 as set forth in GenBank Accession ID: AE004969.1. Said alignment, will provide the skilled person with a level of sequence identity compared to the genome as set forth in GenBank Accession ID: AE004969.1. If said level of sequence identity is above 95%, above 97% or above 99% identical, the skilled person may deduce that said gonococcus is an FA1090 strain gonococcus.

In an embodiment, the FA1090 gonococcus, to which the genetic modification(s) are introduced is a gonococcus that is at least 80%, at least 85%, at least 90%, at least 91%, at least 92%, at least 93%, at least 94%, at least 95%, at least 96%, at least 97%, at least 98%, at least 99% or is 100% identical to the FA1090 gonococcal genome as set forth in GenBank Accession: AE004969.1 (dated 1, Jul. 2015). In an embodiment, the FA1090 gonococcus, to which the genetic modification(s) are introduced is a gonococcus that is 99.97% identical to the FA1090 gonococcal genome as set forth in GenBank Accession: AE004969.1 (dated 1, Jul. 2015) as calculated using the OrthoANI algorithm as described in [Lee I, Ouk Kim Y, Park S C, Chun J. *OrthoANI: An improved algorithm and software for calculating average nucleotide identity. Int J Syst Evol Microbiol.* 2016; 66(2): 1100-1103.]. In an embodiment, the unmodified gonococcal bacterium is an FA1090 strain gonococcal bacterium that is at least 80%, at least 85%, at least 90%, at least 91%, at least 92%, at least 93%, at least 94%, at least 95%, at least 96%, at least 97%, at least 98%, at least 99% or is 100% identical to the FA1090 gonococcal genome as set forth in GenBank Accession: AE004969.1 (dated 1 Jul. 2015). In an embodiment, the unmodified gonococcal bacterium is an FA1090 strain gonococcal bacterium that is 99.97% identical to the FA1090 gonococcal genome as set forth in GenBank Accession: AE004969.1 (dated 1, Jul. 2015) as calculated using the OrthoANI algorithm as described in [Lee I, Ouk Kim Y, Park S C, Chun *OrthoANI: An improved algorithm and software for calculating average nucleotide identity. Int J Syst Evol Microbiol.* 2016; 66(2): 1100-1103.].

In an embodiment, the FA1090 gonococcus to which the genetic modification(s) are introduced (i.e. the unmodified gonococcal bacterium) is an FA1090 strain gonococcus comprising sequences with at least 80%, at least 85%, at least 90%, at least 95% or at least 97% identity to SEQ ID NO: 1 and SEQ ID NO: 3. In said embodiment, the FA1090 gonococci comprising sequences with at least 80%, at least 85%, at least 90%, at least 95% or at least 97% identity to SEQ ID NO: 1 and SEQ ID NO: 3 retain functional Lpxl1 and Rmp proteins. In an embodiment, the FA1090 gonococcus to which the genetic modification(s) are introduced (i.e. the unmodified gonococcal bacterium) is an FA1090 strain gonococcus comprising SEQ ID NO: 1 and SEQ ID NO: 3.

In an embodiment, the invention further provides a genetically modified gonococcal bacterium of strain FA1090, comprising genetic modification(s) that:

a) decreases or abolishes expression and/or function of the lpxl1 gene mRNA and/or polypeptide and b) decreases or abolishes expression and/or function of the rmp gene mRNA and/or polypeptide wherein the decreased or abolished expression and/or function is in comparison to gonococcal bacterium of strain FA1090 that comprises the wild type lpxl1 and rmp genes.

In an embodiment the gonococcal bacterium of strain FA1090 that comprises the wild type lpxl1 and rmp is an unmodified FA1090 strain gonococcus. An example of such a strain may be the FA1090 strain gonococcus that is available from ATCC (#700825).

In an embodiment the lpxl1 gene comprises a sequence at least 80% identical to the sequence as set forth in SEQ ID NO: 3 and the rmp gene comprises a sequence at least 80% identical to the sequence set forth in SEQ ID NO: 1.

In an embodiment, the lpxl1 gene comprises a sequence at least 80%, at least 85%, at least 90%, at least 91%, at least 92%, at least 93%, at least 94%, at least 95%, at least 96%, at least 97%, at least 98%, at least 99% or 100% identical to the sequence as set forth in SEQ ID NO: 3. The lpxl1 gene (also referred to as msbB) encodes the polypeptide Lipid A biosynthesis lauroyl acyltransferase (Lpxl1). Lpxl1 plays a role in lipid A biosynthesis. Neisserial organisms genetically modified to provide for decreased or no detectable functional lpxl1 encoded protein produce OMVs with reduced endotoxicity. This is because the amount of lipid A acylation and the nature of the acylation are major factors that affect LOS toxicity [Makda Fisseha et al. *Infection and Immunity June* 2005, 73 (7) 4070-4080]. Lpxl1 (polypeptide) may also be referred to as the Lpxl1 enzyme.

In an embodiment the rmp gene comprises a sequence at least 80%, at least 85%, at least 90%, at least 91%, at least 92%, at least 93%, at least 94%, at least 95%, at least 96%, at least 97%, at least 98%, at least 99% or 100% identical to the sequence as set forth in SEQ ID NO: 1. The rmp gene encodes the polypeptide reduction modifiable protein (Rmp).

In an embodiment, the lpxl1 gene comprises a sequence at least 90% identical to the sequence as set forth in SEQ ID NO: 3 and the rmp gene comprises a sequence at least 90% identical to the sequence set forth in SEQ ID NO: 1. In an embodiment the lpxl1 gene comprises SEQ ID NO 3 and the rmp gene comprises SEQ ID NO: 1.

In an embodiment, the genetically modified gonococcal bacterium of the invention comprises genetic modification (s) that:

a) decreases or abolishes expression of the lpxl1 gene mRNA and/or polypeptide; and b) decreases or abolishes expression of the rmp gene mRNA and/or polypeptide.

In an embodiment, the genetically modified gonococcal bacterium of the invention comprises genetic modification (s) that:

a) decreases or abolishes expression and/or function of the Lpxl1 polypeptide; and b) decreases or abolishes expression and/or function of the Rmp polypeptide.

In an embodiment, the genetically modified gonococcal bacterium of the invention comprises genetic modification (s) that:

a) decreases or abolishes expression of the Lpxl1 polypeptide; and b) decreases or abolishes expression of the Rmp polypeptide.

In an embodiment, the genetically modified gonococcal bacterium of the invention comprises genetic modification (s) that:

a) abolishes expression of the Lpxl1 polypeptide; and b) abolishes expression of the Rmp polypeptide.

In an embodiment the Lpxl1 polypeptide comprises an amino acid sequence at least 80% identical to SEQ ID NO: 4 and the Rmp polypeptide comprises an amino acid sequence at least 80% identical to SEQ ID NO: 2.

In an embodiment, the Lpxl1 polypeptide comprises an amino acid sequence at least 85%, at least 90%, at least 91%, at least 92%, at least 93%, at least 94%, at least 95%, at least 96%, at least 97%, at least 98%, at least 99% or 100% identical to the sequence as set forth in SEQ ID NO: 4. In an embodiment the Rmp polypeptide comprises an amino acid sequence at least 85%, at least 90%, at least 91%, at least 92%, at least 93%, at least 94%, at least 95%, at least 96%, at least 97%, at least 98%, at least 99% or 100% identical to the sequence as set forth in SEQ ID NO: 2.

In an embodiment, the Lpxl1 polypeptide comprises an amino acid sequence at least 90% identical to SEQ ID NO: 4 and the Rmp polypeptide comprises an amino acid sequence at least 90% identical to SEQ ID NO: 2. In an embodiment the Lpxl1 polypeptide comprises the amino acid sequence of SEQ ID NO: 4 and the Rmp polypeptide comprises the amino acid sequence of SEQ ID NO: 2.

In an embodiment, the gonococcal bacterium of the invention expresses less than 10%, less than 5% or less than 1% of the Lpxl1 polypeptide compared to the expression of the Lpxl1 polypeptide in an unmodified (e.g. wild-type) gonococcal FA1090 strain and less than 10%, less than 5% or less than 1% of the Rmp polypeptide compared to the expression of the Rmp polypeptide in an unmodified (e.g. wild-type) gonococcal FA1090 strain. In an embodiment, the gonococcal bacterium of the invention expresses less than 10%, less than 5% or less than 1% of the Lpxl1 polypeptide compared to the expression of the Lpxl1 polypeptide in a gonococcal FA1090 strain that comprises the wild-type lpxl1 gene and less than 10%, less than 5% or less than 1% of the Rmp polypeptide compared to the expression of the Rmp polypeptide in a gonococcal FA1090 strain comprising the wild type rmp gene.

In an embodiment, the gonococcal bacterium of the invention expresses a de minimus level of the Lpxl1 polypeptide compared to the level of the Lpxl1 polypeptide in an unmodified (wild-type) gonococcal FA1090 strain and a de minimus level of the Rmp polypeptide compared to the level of Rmp polypeptide in an unmodified (wild-type) gonococcal FA1090 strain.

In an embodiment the gonococcal bacterium of the invention does not express the Lpxl1 polypeptide or the Rmp polypeptide. In an embodiment, the gonococcal bacterium of the invention does not express the Lpxl1 and/or Rmp polypeptide at a detectable level as measured for example by immunoassay. In an embodiment, the gonococcal bacterium of the invention does not express the Lpxl1 and/or Rmp polypeptide at a detectable level as measured by Western Blot or ELISA.

In the context of the present disclosure, "Decreased expression" means that the gonococcal bacterium of the invention expresses less lpxl1 and rmp mRNA and/or Lpxl1 and Rmp protein compared to an unmodified (wild type) gonococcal FA1090 strain or a gonococcal FA1090 strain comprising the wild type lpxl1/rmp genes. Expression may be considered decreased when any reduction in mRNA and/or protein expression is observed compared to an unmodified (wild type) gonococcal FA1090 strain or a gonococcal FA1090 strain comprising the wild type lpxl1/rmp genes. Expression may be considered decreased when an over 5%, over 10%, over 25%, over 50%, over 60%, over 70%, over 80% over 90% or over 95% reduction in mRNA and/or protein expression is observed compared to the mRNA and/or protein expression, respectively, in an unmodified (wild-type) gonococcal FA1090 strain or a gonococcal FA1090 strain comprising the wild type lpxl1/rmp genes. In the context of the present disclosure, "abolished expression" means that no Lpxl1 mRNA and/or protein and no Rmp mRNA and/or protein can be detected in the gonococcal bacterium of the invention using the technique used by the skilled person to measure expression.

The level of expression of the lpxl1 and rmp genes can be measured using techniques well known to the skilled person, for example using polymerase chain reaction (PCR) based techniques (for example using Q/RT-PCR). The level of expression of the Lpxl1 and Rmp polypeptides can be measured using techniques well known to the skilled person. For example, the level of expression of both the Lpxl1 and Rmp polypeptides can be measured using Western Blotting or ELISA. The level of expression of the Rmp polypeptide can be measured using SDS-PAGE and LC/MS-MS, for example using the technique essentially as described in Example 11.

The genetic modification(s) may decrease or abolish the expression and/or function of the lpxl1 gene mRNA and/or polypeptide. As such, said genetic modification(s) may result in retained expression of the Lpxl1 polypeptide but wherein the polypeptide is non-functional. The function of Lpxl1 can be determined for example by examining the extent to which the Lipid A component of the outer membrane vesicle lipooligosaccharide is penta-acylated (for example using the method as described in Example 6) as opposed to being hexa-acylated. If the genetically modified gonococcal bacterium comprises a genetic modification that decreases or abolishes the function of the Lpxl1 protein, the Lipid A will be penta-acylated (for example it will be at least 80%; at least 90%; at least 90%, at least 91%, at least 92%, at least 93%, at least 94%, at least 95%, at least 96%, at least 97%, at least 98%, at least 99%; or is 100% penta-acylated), despite evidence to suggest presence of lpxl1 mRNA and/or protein.

In an embodiment, decreased or abolished expression and/or function of the Lpxl1 polypeptide results in the FA1090 strain gonococcus comprising a ratio of penta-acylated lipid A to hexa-acylated lipid A from 50:50 to 99:1 (wherein the percentage of lipid A that is penta-acylated compared to total lipid A is from 50% to 100%).

In an embodiment decreased or abolished expression and/or function of the Lpxl1 polypeptide results in penta-acylation of lipid A, optionally wherein the acylation of lipid A is determined by Matrix-Assisted Laser Desorption/Ionization-Time of Flight (MALDI-TOF) spectrometry. In an embodiment, the genetically modified gonococcal bacterium of the invention comprises lipooligosaccharide (LOS) with penta-acylated lipid A. The acylation of Lipid A can be determined for example by extracting lipid A followed by analysis by MADI-TOF spectrometry, for example essentially as described in Example 6. Specifically, decreased or abolished expression and/or function of the Lpxl1 polypeptide results in lipooligosaccharide (LOS) comprising a lipid A lacking the lauric acid that LpxL1 would have added, had it been functionally expressed. Decreased or abolished expression and/or function of the Lpxl1 polypeptide results in a LOS comprising a lipid A lacking the secondary lauroyl chain from the nonreducing end of the GlcN disaccharide of lipid A. Decreased or abolished expression and/or function of the Lpxl1 polypeptide results in a LOS comprising a lipid A lacking the C12 acyloxyacyl chain (from the non-reducing end). Decreased or abolished expression and/or function of the Lpxl1 polypeptide results in a LOS comprising a lipid A lacking the lauric acid in the secondary 2'-O-position of the distal nonreducing terminal glucosamine of the $\beta$-(1→6) D-glucosamine dimer (consequently a lone 3-hydroxymyristyl moiety exists in amide linkage on the distal glucosamine of the lipid A).

In an embodiment, decreased or abolished expression and/or function of the lpxl1 polypeptide results in above 50% penta-acylation of lipid A, for example above 60%, above 70%, above 80%, above 90%, above 95% or above 99%. In an embodiment, decreased or abolished expression and/or function of the Lpxl1 polypeptide results in 100% penta-acylation of lipid A. In an embodiment, the genetically modified gonococcal bacterium of the invention has a reduced capacity for activating Toll-like receptor 4 (TLR4) compared to an FA1090 strain gonococcus comprising the wild-type lpxl1 gene.

Similarly, the genetic modification(s) may decrease or abolish the expression and/or the function of the rmp gene mRNA and/or polypeptide. As such, said genetic modification(s) may result in the retention of expression of the Rmp polypeptide but wherein the polypeptide is non-functional. The function of Rmp can be determined for example by examining the extent to which the gonococcus blebs. If the genetically modified gonococcal bacterium comprises a genetic modification that decreases or abolishes the function of the Rmp protein the gonococcus may be "hyperblebbing" compared to a gonococcal bacterium that comprises the wild type rmp gene, despite evidence to suggest the presence of rmp mRNA and/or Rmp protein. Accordingly, in some embodiment the genetically modified FA1090 may be tested for whether it produces more OMVs (e.g. whether a strain is hyperblebbing) compared to the same measures from the gonococcal bacterium that comprises the wild type rmp gene i.e. by comparing the OMV yield obtained from one strain with the OMV yield from another (using the same OMV blebbing protocol). Such methods are for example disclosed in [Maharjan et al. (2016). Dissection of the function of the RmpM periplasmic protein from Neisseria meningtidis. Microbiology, 1620, 364-375]. An example of such an experiment can be found in Example 18.

In an embodiment the genetically modified FA1090 gonococcus of the present invention (FA1090 double-mutant ΔLpxl1, Δrmp) demonstrates improved OMV productivity (in terms of increase in OMV productivity versus the single-mutant ΔLpxl1) compared to comparator strains e.g. GC_b 0817560.

In an embodiment the decreased or abolished expression and/or function of the Rmp polypeptide results in a gonococcus that is hyper-blebbing compared to the blebbing of a gonococcal FA1090 strain comprising the wild type rmp gene. As such, the gonococcal bacteria of the present disclosure are, relative to their corresponding wild-type strains (or strains comprising the wild-type rmp gene), hyperblebbing i.e. they release into their culture medium larger quantities of blebs than either the wild-type strain or strains comprising the wild-type rmp gene. In an embodiment, the decreased or abolished expression and/or function of the Rmp polypeptide results in a gonococcus that blebs 10%, 20%, 30%, 40%, 50%, 60%, 70%, 80%, or 90% more OMVs compared to a gonococcal FA1090 strain comprising the wild type rmp gene. In an embodiment, the decreased or abolished expression and/or function of the Rmp polypeptide results in a gonococcus that blebs between 80% and 120% more OMVs compared to a gonococcal FA1090 strain comprising the wild type rmp gene. In an embodiment, a gonococcal FA1090 strain comprising the wild type rmp gene comprises a sequence that is at least 90%, 95% or 100% identical to SEQ ID NO: 1.

In an embodiment the gonococcal bacterium of the invention comprises genetic modification(s) wherein the genetic modification(s) consist of or comprise;

a) disruption or deletion of the endogenous lpxl1 and rmp genes; or b) suppression of lpxl1 and rmp polypeptide expression in a strain comprising the wild type lpxl1 and rmp genes.

In an embodiment, the genetically modified gonococcal bacterium of the invention is produced by either a) disruption or deletion of the endogenous lpxl1 and rmp genes; or b) suppression of Lpxl1 and Rmp polypeptide expression in a strain comprising the wild type lpxl1 and rmp genes.

In an embodiment, the genetic modification(s) (i.e. that decrease or abolish the expression and/or function of lpxl1 and rmp) is achieved by suppression of Lpxl1 and Rmp polypeptide expression in a strain comprising the wild type lpxl1 and rmp genes. In said embodiment, the FA1090 gonococcal strain comprises the wild type (i.e. unmodified) lpxl1 and rmp gene sequences and said genetic modification (s) made to the bacterium results in decreased or abolished expression of the Lpxl1 and Rmp proteins. Techniques to suppress Lpxl1 and Rmp protein expression in a strain comprising the wild type lpxl1 and rmp genes include for example antisense inhibition and inhibitory RNA (i.e. small interfering RNA [siRNA], micro RNA [miRNA], short-hairpin RNA [shRNA] etc.), although these techniques are more typically used in eukaryotic hosts. In the resulting bacterium, mRNA encoding the suppressed protein will be substantially absent and/or its translation will be substantially inhibited (e.g. to less than 90%, less than 80%, less than 70%, less than 60%, less than 50%, less than 40%, less than 25%, less than 15%, less than 10%, less than 5% or less than 1% of the level of expression that would be seen in the absence of suppression). Said suppression of Lpxl1 and Rmp protein expression in a strain comprising the wild-type lpxll and rmp genes is measured in comparison to a strain which has not been modified such that the expression of Lpxll and Rmp protein is suppressed.

It is however preferred to disrupt or delete the endogenous lpxll and rmp genes. As such, in an embodiment the genetic modification(s) consist of or comprise disruption and/or deletion of the endogenous lpxll and rmp genes.

Where the genetic modifications(s) involve disruption of the endogenous lpxll and rmp gene this may result in decreased or abolished expression of Lpxll and/or Rmp protein for example if said disruption is to a promoter region. However, disruption of the endogenous lpxll and/or rmp gene may result in expression of mutant Lpxll and/or Rmp proteins, for example Lpxll and/or Rmp proteins with a different amino acid sequence to the wild type Lpxll and/or Rmp proteins. In an embodiment disruption of the endogenous lpxll and/or rmp results in expression of non-functional Lpxll and/or Rmp polypeptides.

In an embodiment disruption of the endogenous lpxll and/or rmp gene includes an addition to, a deletion from or a substitution of the endogenous lpxll and/or rmp gene sequence. An "addition" refers to the insertion of one or more non-native nucleotides into the gene sequence. Additions may be made to coding or non-coding regions including upstream promoter regions and may be made at terminal and/or non-terminal residues. In some embodiments, the addition is to the promoter region such that there is no or reduced transcription of the coding region or the addition is to the coding region such that there is a codon shift or early stop codon. A "substitution" refers to the exchange of one nucleotide base for another. Substitutions have the ability to change a codon to one that encodes a different amino acid thus resulting in a minor (yet functional) change in the protein produced. Alternatively, substitutions have the ability to change an amino acid coding codon to a "stop" codon thus resulting an incomplete (non-functional) protein. A "deletion" in the context of disrupting of endogenous genes, refers to removal of one or more nucleotides from the polynucleotide gene sequence. In some embodiments, the deletion comprises deletion of the promoter region (or portion thereof) such that there is no or reduced transcription of the coding region or the deletion is within the coding region such that there is a codon shift or early stop codon.

In an embodiment, the gonococcal bacterium of the invention comprises genetic modification(s) wherein the genetic modification(s) comprise deletion of the endogenous lpxll and rmp genes. In an embodiment, the gonococcal bacterium of the invention comprises genetic modification(s) wherein the genetic modification(s) comprise deletion of the endogenous lpxll and rmp genes resulting in the double-mutant FA1090 gonococcus (Δlpxll, Δrmp). In an embodiment, the genetically modified gonococcal bacterium of the invention is a double-mutant FA1090 gonococcus (Δlpxll, Δrmp).

As such, the present invention provides a genetically modified gonococcal bacterium of strain FA1090, comprising genetic modification(s) that:
   a. decreases or abolishes expression and/or function of the lpxll gene mRNA and/or polypeptide; and
   b. decreases or abolishes expression and/or function of the rmp gene mRNA and/or polypeptide.
wherein the genetic modification(s) comprise deletion of the endogenous lpxll and rmp genes resulting in the double mutant FA1090 gonococcus (Δlpxll, Δrmp).

In an embodiment there is provided a genetically modified gonococcal bacterium of strain FA1090, comprising genetic modification(s) that decreases or abolishes expression of the lpxll gene mRNA and/or polypeptide and decreases or abolishes expression of the rmp gene mRNA and/or polypeptide, wherein the genetic modification(s) comprise deletion of the endogenous lpxll and rmp genes resulting in the double-mutant FA1090 gonococcus (Δlpxll, Δrmp).

In an embodiment there is provided a genetically modified gonococcal bacterium of strain FA1090, comprising genetic modification(s) that decreases or abolishes expression of the Lpxll polypeptide and decreases or abolishes expression of the rmp polypeptide, wherein the genetic modification(s) comprise deletion of the endogenous lpxll and rmp genes resulting in the double-mutant FA1090 gonococcus (Δlpxll, Δrmp)).

In an embodiment, the gonococcal bacterium of the invention comprises genetic modification(s) wherein the genetic modification(s) are gene deletions.

In an embodiment there is provided a genetically modified gonococcal bacterium of strain FA1090, comprising genetic modification(s) that decreases or abolishes expression of the lpxll gene, mRNA and/or Lpxll polypeptide and decreases or abolishes expression of the rmp gene, mRNA and/or Rmp polypeptide, wherein the genetic modification(s) are gene deletions. In an embodiment the gene deletion is a result of a sequence addition, substitution or deletion modification within the lpxll and rmp loci. Gene deletion may be a result of said modification(s) or may be achieved by said modification(s).

In an embodiment there is provided a genetically modified gonococcal bacterium of strain FA1090, comprising genetic modification(s) that decreases or abolishes expression of the lpxll gene, mRNA and/or Lpxll polypeptide and decreases or abolishes expression of the rmp gene, mRNA and/or Rmp polypeptide, wherein the genetic modification(s) are gene deletions wherein the gene deletion is a result of replacing a portion (or portions) of the lpxll and rmp genes with heterologous sequences, optionally wherein said heterologous sequences encode antibiotic resistance genes. In an embodiment there is provided a genetically modified gonococcal bacterium of strain FA1090, comprising genetic modification(s) that decreases or abolishes expression of the lpxll gene, mRNA and/or Lpxll polypeptide and decreases or abolishes expression of the rmp gene, mRNA and/or Rmp polypeptide, wherein the genetic modification(s) are gene deletions wherein the gene deletion is a result of adding a heterologous gene sequences into the lpxll and rmp coding regions, optionally wherein said heterologous sequences encode antibiotic resistance genes.

In an embodiment there is provided a genetically modified gonococcal bacterium of strain FA1090, comprising genetic modification(s) that decreases or abolishes expression of the Lpxll polypeptide and decreases or abolishes expression of the rmp polypeptide, wherein the genetic modification(s) are gene deletions, resulting in the double-mutant FA1090 gonococcus (Δlpxll, Δrmp).).

Any suitable technique can be used to delete the endogenous lpxll and rmp genes (i.e. to generate a gene knockout). Gene knockouts in gonococci can for example be made by transposon mutagenesis, in vitro genetic engineering to modify genes contained on plasmids or Bacterial Artificial Chromosomes (BACs) and moving the modified construct to the organism of interest, and in vivo homologous recombination. In an embodiment the genes are knocked out by disabling an endogenous promoter, operon or regulatory element that is essential for transcription or translation of the genes. In an embodiment, the genes are deleted using CRISPR-Cas9 technology.

In an embodiment the endogenous lpxl1 and rmp genes are deleted by homologous recombination. Homologous recombination may be performed for example as described in WO01/09350A2 or using techniques described in [Dillard J. P. (2011). *Genetic Manipulation of Neisseria gonorrhoeae. Current protocols in microbiology Chapter* 4, Unit4A.2]. During the process of homologous recombination, the endogenous lpxl1 and rmp genes are deleted by either adding a different gene into the coding sequence of the lpxl1 and rmp genes or by replacing the gene or fragment thereof with the different gene (e.g., a heterologous gene, or non-functional gene) by recombination. In an embodiment, the heterologous gene is an antibiotic resistance gene.

In an embodiment, the genetic modification(s) may be to coding and/or non-coding regions. The coding region is the portion of a gene's DNA sequence that codes for a protein. The non-coding region (e.g. intronic DNA) is the components of an organism's (i.e. *N. gonorrhoea*) DNA that do not encode protein sequences. In an embodiment, the genetic modification(s) are to the coding region, non-coding region or combination thereof of the lpxl1 gene and to the coding region, non-coding region or combination thereof of the rmp gene. It is within the realm of the skilled person to identify coding and non-coding regions in a given DNA sequence.

In an embodiment, the gonococcal bacterium of the invention is isogenic with a wild-type gonococcal FA1090 strain, except for the genetic modification(s) that, a) decreases or abolishes expression and/or function of the lpxl1 gene mRNA and/or polypeptide; and
b) decreases or abolishes expression and/or function of the rmp gene mRNA and/or polypeptide.

As used herein the term "isogenic" refers to a substantially identical genome. As such, in an embodiment, the gonococcal bacterium of the invention is isogenic with a wild-type (i.e. substantially unmodified) gonococcal FA1090 strain except for the specified genetic modification(s). In an embodiment, the gonococcal bacterium of the invention is isogenic with a gonococcal FA1090 strain comprising wild type lpxl1 and rmp genes except for the specified genetic modification(s).

In an embodiment, the gonococcal bacterium of the invention is identical with a wild-type gonococcal FA1090 strain, except for the genetic modification(s) that, a) decreases or abolishes expression and/or function of the lpxl1 gene mRNA and/or polypeptide; and
b) decreases or abolishes expression and/or function of the rmp gene mRNA and/or polypeptide.

In an embodiment, the gonococcal bacterium of the invention is identical with a wild-type (i.e. substantially unmodified) gonococcal FA1090 strain except for the specified genetic modification(s). In an embodiment, the gonococcal bacterium of the invention is isogenic with a gonococcal FA1090 strain comprising wild type lpxl1 and rmp genes except for the specified genetic modification(s).

An example of a wild-type gonococcal FA1090 strain (or gonococcal FA1090 strain comprising wild-type lpxl1 and rmp genes) is the gonococcal FA1090 strain obtainable from ATCC (#700825).

In an embodiment, the gonococcal bacterium of the invention further comprises additional genetic modification (s) that result(s) in over-expression and/or decreased or abolished expression of up to 3, up to 5, up to 10 or up to 20 further Neisserial antigens. By "further" Neisserial antigens, it is meant "in addition" to (i.e. not including) the modifications to Lpxl1 and Rmp. In an embodiment the gonococcal bacterium of the invention comprises additional genetic modification(s) that result in over-expression and/or decreased or abolished expression of 1, 2, 3, 4, 5, 6, 7, 8, 9, 10, 11, 12, 13, 14, 15, 16, 17, 18, 19 or 20 further Neisserial antigens i.e. in addition to the genetic modification(s) that a) decreases or abolishes expression and/or function of the lpxl1 gene mRNA and/or polypeptide; and b) decreases or abolishes expression and/or function of the rmp gene mRNA and/or polypeptide.

In an embodiment, said further genetic modifications result in over-expression and/or decreased or abolished expression of further Neisseria antigens wherein said over-expression and/or decreased expression is compared to an FA1090 strain gonococcus that has not been genetically modified or an FA1090 strain gonococcus that contains the corresponding wild type gene. In the case where the additional genetic modification(s) result in over-expression of further Neisserial antigens, said antigens are preferably present in the bacterial outer membrane such that they are surface exposed on OMVs obtained or obtainable from the genetically modified gonococcus. In such embodiment, the further Neisserial antigens may be in the form of separate polypeptides or may be present in the same polypeptide as a fusion protein.

The skilled person is aware of techniques in order to over-express antigens, particularly techniques to over-express an antigen(s) such that increased levels are present on the surface of OMVs (see for example the methods summarised in WO2012/032498A2). OMVs can be obtained from bacteria which have been genetically modified to over-express particular antigen(s). The bacterium may express the antigen(s) already, but may include a genetic modification which, compared to a bacterium without said modification, increases expression of the antigen. This modification will usually be introduced using recombinant techniques for example, site-directed mutagenesis or targeted homologous recombination. As a result of the over-expression, outer membrane vesicles prepared from the modified bacterium contain higher levels of the overexpressed antigen(s).

Said Neisseria antigens may be antigens derived from any member of the Neisseria genus for example *N. animalis, N. animaloris, N. bacilliformis, N. canis, N. cinerea, N. dentiae, N. elongata, N. flava, N. flavescens, N. gonorrhoeae, N. iguanae, N. lactamica, N. macacae, N. meningitidis, N. mucosa, N. oralis, N. perflava, N. pharyngis, N. polysaccharea, N. shayeganii, N. sicca, N. subflava, N. wadsworthii, N. weaveri* or *N. zoodegmatis*. In an embodiment, said *Neisseria* antigens are antigens derived from Neisseria meningitidis. In an embodiment, said *Neisseria* antigens are antigens derived from *Neisseria gonorrhoea*.

In an embodiment, the gonococcal bacterium of the invention comprises additional genetic modification(s) that result in over-expression of up to 3, up to 5, up to 10 or up to 20 further *Neisserial* antigens.

Process for Producing Genetically Modified Bacterium

In a further aspect the present invention provides, a process for producing the gonococcal bacterium of the invention the process comprising either:

a) decreasing or abolishing the expression and/or function of the lpxl1 gene mRNA and/or polypeptide in a gonococcal FA1090 bacterium to produce a first gonococcal FA1090 bacterium and decreasing or abolishing the expression and/or function of the rmp gene mRNA and/or polypeptide from the first gonococcal FA1090 bacterium to produce a second gonococcal FA1090 bacterium; or
b) decreasing or abolishing the expression and/or function of the rmp gene mRNA and/or polypeptide from the first gonococcal FA1090 bacterium to produce a first gonococcal FA1090 bacterium and decreasing or abolishing the expression and/or function of the lpxl1 gene mRNA and/or polypeptide from the first gonococcal FA1090 bacterium to produce a second gonococcal FA1090 bacterium.

In the process described in a) the first gonococcal FA1090 bacterium is the single-mutant (Δlpxl1) and the second gonococcal FA1090 bacterium is the double-mutant (Δlpxl1, Δrmp). In the process described in b) the first gonococcal FA1090 bacterium is the single-mutant (Δrmp) and the second gonococcal FA1090 bacterium is the double-mutant (Δlpxl1, Δrmp).

In a preferred embodiment, the process of the invention comprises decreasing or abolishing the expression and/or function of the lpxl1 gene mRNA and/or polypeptide in a gonococcal FA1090 bacterium to produce a first gonococcal FA1090 bacterium and decreasing or abolishing the expression and/or function of the rmp gene mRNA and/or polypeptide from the first gonococcal FA1090 bacterium to produce a second gonococcal FA1090 bacterium. In said preferred embodiment, the first gonococcal FA1090 bacterium is the single-mutant (Δlpxl1). The single-mutant ((Δlpxl1) is an FA1090 strain gonococcus that has been genetically modified such that its lpxl1 gene has been deleted. In an embodiment the second gonococcal FA1090 bacterium is the double-mutant (Δlpxl1, Δrmp).

In an embodiment the process of the invention comprises the steps of decreasing or abolishing the expression of the lpxl1 gene mRNA and/or polypeptide in a gonococcal FA1090 bacterium to produce a first gonococcal FA1090 bacterium and decreasing or abolishing the expression of the rmp gene mRNA and/or polypeptide from the first gonococcal FA1090 bacterium to produce a second gonococcal FA1090 bacterium. In an embodiment the process of the invention comprises the steps of decreasing or abolishing the expression of the Lpxl1 polypeptide in a gonococcal FA1090 bacterium to produce a first gonococcal FA1090 bacterium; and decreasing or abolishing the expression of the Rmp polypeptide from the first gonococcal FA1090 bacterium to produce a second gonococcal FA1090 bacterium.

In an embodiment, said genetic modification(s) to decrease or abolish the expression and/or function of the lpxl1 and rmp gene mRNA and/or polypeptides may consist of or comprise,
  a) disruption or deletion of the endogenous lpxl1 and rmp genes; or
  b) decreasing or abolishing lpxl1 and rmp expression in a strain comprising the wild type lpxl1 and rmp genes.

It is however preferred that the genetic modification(s) involve disruption or deletion of the endogenous lpxl1 and rmp genes. It is particularly preferred to delete the endogenous lpxl1 and rmp genes. In a preferred embodiment, the genetic modification(s) are gene deletions.

The person skilled in the art is aware of conventional gene knockout techniques with which to generate the "second gonococcal FA1090 bacterium" (i.e. the double-mutant Δlpxl1, Δrmp strain). Techniques for gene knockout are well known, and *Neisserial* knockout mutants of have been reported previously [see for example, Makda Fisseha et al. *Infection and Immunity June* 2005, 73 (7) 4070-4080]. For example, the knockout may be achieved by deletion of at least a portion of the coding region, but any other suitable technique may be used e.g. deletion or mutation of the promoter, deletion or mutation of the start codon, etc. The bacterium may contain a marker gene in place of the knocked-out gene e.g. an antibiotic resistance marker. Whichever technique (or combination of techniques) is chosen, the resulting bacterium will be substantially free from Lpxl1 and Rmp.

In a preferred embodiment decreasing or abolishing the expression of both the lpxl1 gene and the rmp gene is performed by genomic recombination. In an embodiment the genomic recombination is homologous recombination in which the lpxl1 and rmp genes or a portion thereof are replaced. In an embodiment decreasing or abolishing the expression of both the lpxl1 gene and the rmp gene is performed by replacing the lpxl1 and rmp coding sequences, or a portion thereof with a heterologous gene sequence. However, in a preferred embodiment, decreasing or abolishing the expression of both the lpxl1 gene and the rmp gene is performed by replacing the lpxl1 and rmp coding sequences, or a portion thereof with antibiotic resistance cassettes or antibiotic resistance genes.

In an embodiment, decreasing or abolishing the expression of both the lpxl1 gene and the rmp gene are gene deletions, optionally wherein said gene deletions are a result of sequence addition, substitution or deletion modifications within the lpxl1 and rmp loci. In an embodiment decreasing or abolishing the expression of both the lpxl1 gene and the rmp gene is performed by the addition or insertion of a heterologous gene sequence (or heterologous sequence) within the lpxl1 and rmp coding sequences and/or replacing the lpxl1 and rmp gene sequences, or a portion thereof with a heterologous gene sequence. In an embodiment, the heterologous gene sequence is an antibiotic resistance gene carried within a cassette, said cassette also comprising a recombination site.

In an embodiment, decreasing or abolishing the expression of both the lpxl1 gene and the rmp gene is performed by addition of antibiotic resistance cassettes within the lpxl1 and rmp coding sequences and/or replacing the lpxl1 and rmp coding sequences, or a portion thereof with antibiotic resistance cassettes. An antibiotic resistance cassette is a gene cassette that carries a recombination site and an antibiotic resistance gene e.g. KanMX which confers kanamycin resistance upon bacteria.

Addition of a gene that confers antibiotic resistance to the lpxl1 and/or rmp genes, or replacing the lpxl1 and/or rmp genes sequences (e.g. coding regions), or a portion thereof with a gene that confers antibiotic resistance enables selection of transformants carrying the inserted antibiotic resistance gene (as opposed to the gene being deleted). Successful transformants (i.e. successfully produced mutants) are thus sensitive when streaked on a plate in the presence of said antibiotic or when grown in its presence. Any bacteria that have not been successfully transformed will not survive. However, transformants should be subsequently tested a) to ensure that decreased or abolished expression and/or function of said gene has been achieved and b) to ensure that no residual wild type (i.e. non-transformed) bacteria remain present.

A subsequent transformation using an unmarked mutation construct can be used to replace the antibiotic cassette if desired. As such, in an embodiment the antibiotic resistance cassette is subsequently replaced.

Outer Membrane Vesicles

In a further aspect of the invention there is provided the use of the gonococcal bacterium of the invention (i.e. the genetically modified gonococcal bacterium of strain FA1090, wherein the genetic modification(s) a) decreases or abolishes expression and/or function of the lpxl1 gene mRNA and/or polypeptide; and b) decreases or abolishes expression and/or function of the rmp gene mRNA and/or polypeptide) in the production of OMVs.

To the Extent Lpxl1 is Expressed in Outer Membrane Vesicles:

In a further aspect of the invention there is provided an outer membrane vesicle obtained or obtainable from an FA1090 strain gonococcus, wherein said outer membrane vesicle comprises either reduced levels or no detectable level of both Lpxl1 and Rmp polypeptides. In an embodiment, there is provided an outer membrane vesicle obtained or obtainable from an FA1090 strain gonococcus, wherein said outer membrane vesicle comprises reduced or abolished levels of Lpxl1 and Rmp. In an embodiment reduced levels or no detectable level of both Lpxl1 and Rmp polypeptides is measured in comparison to OMVs from a wild-type FA1090 bacterium. In an embodiment reduced levels or no detectable level of both Lpxl1 and Rmp polypeptides is measured in comparison to OMVs from a gonococcal bacterium of strain FA1090, said strain comprising the wild type (i.e. unmodified) lpxl1 and rmp genes. In an embodiment reduced levels or no detectable level of Lpxl1 and Rmp polypeptide is measured by immunoassay (for example by Western Blot or ELISA assay).

In a further aspect of the invention there is provided an outer membrane vesicle obtained or obtainable from a gonococcal bacterium of the invention. As such, there is provided an outer membrane vesicle obtained or obtainable from a genetically modified gonococcal bacterium of strain FA1090, wherein the genetic modification(s) a) decreases or abolishes expression and/or function of the lpxl1 gene mRNA and/or polypeptide; and b) decreases or abolishes expression and/or function of the rmp gene mRNA and/or polypeptide. In an embodiment, the outer membrane vesicle of the invention is obtained or obtainable from a genetically modified gonococcal bacterium of strain FA1090, wherein the genetic modification(s) a) decreases or abolishes expression of the lpxl1 gene mRNA and/or polypeptide; and b) decreases or abolishes expression of the rmp gene mRNA and/or polypeptide. The genetic modification(s) made to the gonococcal genome result in OMVs from said genetically modified gonococcal bacterium of strain FA1090 with decreased or abolished expression and/or function of the Lpxl1 polypeptide and decreased or abolished expression and/or function of the Rmp polypeptide, compared to the levels of expression and/or function of the Lpxl1 and Rmp polypeptides in a comparator OMV, said comparator OMV being from a *N. gonorrhoeae* strain FA1090 that lacks said genetic modifications (or comprising the wild-type lpxl1 and rmp genes).

In an embodiment, the outer membrane vesicles of the invention comprise decreased or abolished expression and/or function of the Lpxl1 polypeptide and decreased or abolished expression and/or function of the Rmp polypeptide. In an embodiment, the outer membrane vesicles of the invention comprise decreased or abolished expression of the Lpxl1 polypeptide and decreased or abolished expression of the Rmp polypeptide. In an embodiment the outer membrane vesicles of the invention comprise decreased or abolished expression of the Lpxl1 polypeptide and decreased or abolished expression of the Rmp polypeptide on the surface of the OMV. Said decreased or abolished expression and/or function is in comparison to OMVs from a FA1090 strain gonococcal bacterium that comprises the wild type lpxl1 and rmp genes.

In an embodiment, the outer membrane vesicle of the invention does not express Lpxl1 or Rmp. In an embodiment, the outer membrane vesicle of the invention does not express Lpxl1 or Rmp on the surface of the OMVs.

In an embodiment there is provided an outer membrane vesicle obtained or obtainable from a genetically modified gonococcal bacterium of strain FA1090, wherein the genetic modification(s) decreases or abolishes expression of the Lpxl1 polypeptide; and decreases or abolishes expression of the rmp polypeptide, wherein the genetic modification(s) comprise deletion of the endogenous lpxl1 and rmp genes. In an embodiment there is provided an outer membrane vesicle obtained or obtainable from a genetically modified gonococcal bacterium of strain FA1090, wherein the genetic modification(s) decreases or abolishes expression of the Lpxl1 polypeptide; and decreases or abolishes expression of the rmp polypeptide, wherein the genetic modification(s) comprise deletion of the endogenous lpxl1 and rmp genes resulting in the double-mutant FA1090 gonococcus (Δlpxl1, Δrmp).

In an embodiment there is provided an outer membrane vesicle obtained or obtainable from a genetically modified gonococcal bacterium of strain FA1090, wherein the genetic modification(s) decreases or abolishes expression of the Lpxl1 polypeptide and decreases or abolishes expression of the Rmp polypeptide, wherein the genetic modification(s) are gene deletions wherein said gene deletions are a result of a sequence addition, substitution or deletion modification within the lpxl1 and rmp loci, optionally wherein said gene deletion is a result of replacing a portion or portions of the lpxl1 and rmp genes with heterologous sequences, optionally wherein said heterologous sequences encode antibiotic resistance genes.

To the Extent Lpxl1 is not Expressed in Outer Membrane Vesicles:

In a further aspect of the invention there is provided an outer membrane vesicle (OMV) from a genetically modified FA1090 strain gonococcus, said genetically modified FA1090 strain gonococcus comprising genetic modification(s) that a) decreases or abolishes expression and/or function of the lpxl1 gene, lpxl1 mRNA, and/or Lpxl1 polypeptide; and b) decreases or abolishes expression and/or function of the rmp gene, rmp mRNA, and/or Rmp polypeptide, said OMV comprising:

I. reduced levels of Rmp polypeptide compared to the levels of Rmp polypeptide in a comparator OMV wherein said comparator OMV is from a *N. gonorrhoeae* strain FA1090 that lacks said genetic modifications; and II. reduced levels of hexa-acylated lipid A compared to the levels of hexa-acylated lipid A from the comparator OMV.

In an embodiment, the OMV comprises lipooligosaccharide (LOS) with reduced levels of hexa-acylated lipid A. In an embodiment, the OMV comprises lipooligosaccharide (LOS) with a lipid A component, said lipid A component having reduced levels of hexa-acylated lipid A compared to the levels of hexa-acylated lipid A from the comparator OMV (wherein the comparator OMV from a *N. gonorrhoeae* strain FA1090 that lacks genetic modification(s) that a) decreases or abolishes expression and/or function of the lpxl1 gene, lpxl1 mRNA, and/or Lpxl1 polypeptide; and b) decreases or abolishes expression and/or function of the rmp gene, rmp mRNA, and/or Rmp polypeptide).

In an embodiment said OMV further comprises iii. increased levels of penta-acylated lipid A that lacks lauric acid compared to the levels of penta-acylated lipid A that lacks lauric acid from the comparator OMV.

In an embodiment, the OMV further comprises a lipoo-ligosaccharide (LOS) with increased levels of penta-acy-lated lipid A that lacks lauric acid. In an embodiment, the OMV further comprises a lipooligosaccharide (LOS) with a lipid A component, said lipid A component having increased levels of penta-acylated lipid A that lacks lauric acid com-pared to the levels of penta-acylated lipid A that lacks lauric acid from the comparator OMV. In an embodiment, said penta-acylated lipid A that lacks lauric acid lacks the sec-ondary lauroyl chain from the non-reducing end of the GlcN disaccharide.

There is further provided an outer membrane vesicle (OMV) from a genetically modified *N. gonorrhoeae* strain FA1090, the OMV comprising:

I. reduced levels of Rmp polypeptide compared to the levels of Rmp polypeptide in a comparator OMV from a *N. gonorrhoeae* strain FA1090 that lacks said genetic modifications; and II. reduced levels of hexa-acylated lipid A compared to the levels of hexa-acylated lipid A from the comparator OMV.

III. increased levels of penta-acylated lipid A that lacks lauric acid compared to the levels of penta-acylated lipid A that lacks lauric acid from the comparator OMV;

The levels of hexa/penta-acylated lipid A can be deter-mined as previously described, an example of such method is provided in Example 6.

The outer membrane vesicles obtained or obtainable from a gonococcal bacterium of the invention comprise PorB, said PorB protein comprising eight loop domains (loop domains 1-8). Said loop domains are provided herein as SEQ ID NO: 26, 27, 28, 29, 30, 31, 32 and 33 (i.e. the PorB loop domains from the FA1090 2KO Δlpxll, Δrmp strain). In an embodiment, the outer membrane vesicles obtained or obtainable from a gonococcal bacterium of the invention comprises a PorB protein, said PorB protein comprising SEQ ID NO: 26, SEQ ID NO: 27, SEQ ID NO: 28, SEQ ID NO: 29, SEQ ID NO: 30, SEQ ID NO: 31. SEQ ID NO: 32 and SEQ ID NO: 33. In an embodiment, the outer membrane vesicles obtained or obtainable from a gonococcal bacterium of the invention comprises a PorB protein, said PorB protein comprising eight loop domains, each loop domain having at least 90%, at least 91%, at least 92%, at least 93%, at least 94%, at least 95%, at least 96%, at least 97%, at least 98%, or at least 99% identity to SEQ ID NO: 26, SEQ ID NO: 27, SEQ ID NO: 28, SEQ ID NO: 29, SEQ ID NO: 30, SEQ ID NO: 31. SEQ ID NO: 32 and SEQ ID NO: 33 respectively. In other words the loop 1 domain may comprise a sequence having at least at least 90%, at least 91%, at least 92%, at least 93%, at least 94%, at least 95%, at least 96%, at least 97%, at least 98%, or at least 99% identity to SEQ ID NO: 26, the loop 2 domain may comprise a sequence having at least at least 90%, at least 91%, at least 92%, at least 93%, at least 94%, at least 95%, at least 96%, at least 97%, at least 98%, or at least 99% identity to SEQ ID NO: 27 etc.

In an embodiment, the outer membrane vesicles obtained or obtainable from a gonococcal bacterium of the invention comprise a PorB protein sequence having at least 85%, at least 90%, at least 91%, at least 92%, at least 93%, at least 94%, at least 95%, at least 96%, at least 97%, at least 98%, or at least 99% identity to SEQ ID NO: 25. In an embodi-ment, the outer membrane vesicles obtained or obtainable from a gonococcal bacterium of the invention comprises the PorB protein sequence of SEQ ID NO: 25.

In an embodiment the outer membrane vesicles of the invention exhibit reduced toll-like receptor 4 (TLR4) activation compared to the activation with comparator OMVs from a gonococcal FA1090 strain that lacks the genetic modification(s). A method used to determine TLR4 activa-tion is as disclosed in Example 13

In a further aspect of the invention there is provided an outer membrane vesicle obtained or obtainable from a gonococcal bacterium of the invention. As such, there is provided an outer membrane vesicle obtained or obtainable from a genetically modified gonococcal bacterium of strain FA1090, wherein the genetic modification(s) a) decreases or abolishes expression and/or function of the lpxll gene mRNA and/or polypeptide; and b) decreases or abolishes expression and/or function of the rmp gene mRNA and/or polypeptide. In an embodiment, the outer membrane vesicle of the invention is obtained or obtainable from a genetically modified gonococcal bacterium of strain FA1090, wherein the genetic modification(s) a) decreases or abolishes expres-sion of the lpxll gene mRNA and/or polypeptide; and b) decreases or abolishes expression of the rmp gene mRNA and/or polypeptide. The genetic modification(s) made to the gonococcal genome result in OMVs from said genetically modified gonococcal bacterium of strain FA1090 compris-ing reduced levels of the Rmp polypeptide compared to the levels of the Rmp polypeptide in a comparator OMV from a *N. gonorrhoeae* strain FA1090 that lacks said genetic modification(s) and reduced levels of hexa-acylated lipid A compared to the levels of hexa-acylated lipid A from the comparator OMV.

The invention thus provides gonococcal outer membrane vesicles. Outer membrane vesicles include any proteolipo-somic vesicle obtained by disruption of or blebbing from a gonococcal outer membrane to form vesicles therefrom that retain antigens from the outer membrane. OMVs can be prepared by various methods that are known to the person skilled in the art. For example, OMVs can be prepared artificially from bacteria, and may be prepared using deter-gent treatment (e.g. with deoxycholate), or by non-detergent means. A preferred method for OMV preparation is, for example, by centrifugation followed by filtration of culture supernatant and its concentration using Tangential Flow Filtration (TFF) (for example, as described in Example 10).

In a preferred embodiment, the outer membrane vesicle of the invention is a native outer membrane vesicle i.e. not detergent extracted. In a preferred embodiment, the outer membrane vesicles of the invention are obtained via non-detergent extraction. The outer membrane vesicles of the invention are obtained from blebbing or is obtained from disruption of the outer membrane, wherein said disruption does not substantially comprise detergent extraction of the OMV from the outer membrane. Preferred methods for obtaining outer membranes vesicles of the invention are therefore performed substantially in the absence of detergent using techniques such as sonication, homogenisation, micro-fluidisation, cavitation, osmotic shock, grinding, French press, blending, etc. Methods using no or low detergent can retain useful antigens as described in [WO2004/019977].

In an embodiment the outer membrane vesicle of the invention is, when administered to a subject, cross-bacteri-cidal. In an embodiment the outer membrane vesicle of the invention, when administered to a subject, is able to induce cross-bactericidal antibody titres. In an embodiment, the outer membrane vesicle of the invention is, when adminis-tered to a subject, cross-bactericidal against heterologous and homologous strain(s) of *N. gonorrhoeae* wherein the homologous strain is an FA1090 strain gonococcus and the heterologous strain(s) are non-FA1090 strains of gonococcus, for example WHO-M, F62, MS11, WHO-N, BG27, BG8, WHO-F, WHO-G, and GC14.

The outer membrane vesicles of the invention have a diameter of between 40-nm and 120-nm by electron microscopy (for example between 60-nm and 80-nm by electron microscopy). Furthermore, the OMVs of the invention are substantially free from cytoplasmic contamination OMVs are released spontaneously during bacterial growth and can be purified from the culture medium. The purification ideally involves separating the OMVs from living and/or intact *N. gonorrhoea* bacteria e.g. by using low speed centrifugation to pellet cells while leaving blebs in suspension and/or by size-based filtration using a filter, such as a 0.22 μm filter, which allows the blebs to pass through but which does not allow intact bacteria to pass through. Thus, unlike the culture medium, OMV containing compositions of the disclosure will generally be substantially free from whole bacteria, whether living or dead. The size of the blebs means that they can readily be separated from whole bacteria by filtration e.g. as typically used for filter sterilisation. Although blebs will pass through a standard 0.22 μm filters, these can rapidly become clogged by other material, and so it may be useful to perform sequential steps of filter sterilisation through a series of filters of decreasing pore size before using a 0.22 μm filter. Examples of preceding filters would be those with pore size of 0.8 μm, 0.45 μm, etc. In an embodiment, the outer membrane vesicle of the invention is purified via filtering through a sterile filter with a pore size of less than 0.5, 0.4 or 0.3 μm.

A useful process for OMV preparation is described in [WO2005/004908] and involves ultrafiltration on crude OMVs, rather than high speed centrifugation. The process may involve a step of ultracentrifugation after the ultrafiltration takes place.

The obtained vesicles may lack LOS altogether, or they may lack hexa-acylated LOS e.g. LOS in the vesicles may have a reduced number of secondary acyl chains per LOS molecule. For example, OMVs obtained from the genetically modified gonococcus of the invention (i.e. a strain which has a lpxl1 deletion or mutation) results in production of a penta-acylated LOS [Koeberling et al. (2008) *J Infect Dis* 198:262-70 and Zollinger et al. (2010) *Vaccine* 28:5057-67]. The obtained OMVs may comprise LOS comprising a lipid A lacking the secondary lauroyl chain from the non-reducing end of the GlcN disaccharide of lipid A. The obtained OMVs comprise diminished endotoxin activity.

In an embodiment, the outer membrane vesicles of the invention comprise the double-mutant FA1090 (ΔlpxL1, Δrmp) protein profile, wherein said double-mutant FA1090 (ΔlpxL1, Δrmp) protein profile is measured by mass spectrometry analysis (for example as disclosed in Example 12). In an embodiment the double-mutant FA1090 (ΔlpxL1, Δrmp) protein profile comprises PorB, Opa, PilQ, BamA, BamD and Ton-B Dependent Receptor protein (NG00952). In an embodiment the double mutant FA1090 (ΔlpxL1, Δrmp) protein profile comprises PorB 1B, PilQ, BamA and BamD.

Immunogenic Compositions and Vaccines

In a further aspect of the invention there is provided an immunogenic composition comprising the outer membrane vesicles of the invention.

This aspect of the invention thus provides an immunogenic composition comprising outer membrane vesicles obtained or obtainable from an FA1090 strain gonococcus, wherein said outer membrane vesicle comprises either reduced levels or no detectable level of both Lpxl1 and Rmp polypeptides.

This aspect of the invention thus provides an immunogenic composition comprising outer membrane vesicles (OMVs) from a genetically modified FA1090 strain gonococcus, said genetically modified FA1090 strain gonococcus comprising genetic modification(s) that a) decreases or abolishes expression and/or function of the lpxl1 gene, lpxl1 mRNA, and/or Lpxl1 polypeptide; and b) decreases or abolishes expression and/or function of the rmp gene, rmp mRNA, and/or Rmp polypeptide, said OMV comprising:

I. reduced levels of Rmp polypeptide compared to the levels of Rmp polypeptide in a comparator OMV wherein said comparator OMV is from a *N. gonorrhoeae* strain FA1090 that lacks said genetic modifications; and II. reduced levels of hexa-acylated lipid A compared to the levels of hexa-acylated lipid A from the comparator OMV.

In an embodiment said OMV further comprises III. increased levels of penta-acylated lipid A that lacks lauric acid compared to the levels of penta-acylated lipid A that lacks lauric acid from the comparator OMV.

This aspect of the invention also provides an immunogenic composition comprising outer membrane vesicles obtained or obtainable from a genetically modified gonococcal bacterium of strain FA1090, wherein said bacterium comprises genetic modification(s) that:

a) decreases or abolishes expression and/or function of the lpxl1 gene mRNA and/or polypeptide; and b) decreases or abolishes expression and/or function of the rmp gene mRNA and/or polypeptide.

In an embodiment, there is provided an immunogenic composition comprising outer membrane vesicles obtained or obtainable from a genetically modified gonococcal bacterium of strain FA1090, wherein said bacterium comprises genetic modification(s) that:

a) decreases or abolishes expression of the lpxl1 gene mRNA and/or polypeptide; and b) decreases or abolishes expression of the rmp gene mRNA and/or polypeptide.

In an embodiment, there is provided an immunogenic composition comprising outer membrane vesicles obtained or obtainable from a genetically modified gonococcal bacterium of strain FA1090, wherein said bacterium comprises genetic modification(s) that:

a) decreases or abolishes expression of the Lpxl1 polypeptide; and b) decreases or abolishes expression of the Rmp polypeptide.

In an embodiment, there is provided an immunogenic composition comprising outer membrane vesicles obtained or obtainable from a genetically modified gonococcal bacterium of strain FA1090, wherein said bacterium comprises genetic modification(s) that:

a) abolishes expression of the Lpxl1 polypeptide; and b) abolishes expression of the Rmp polypeptide.

In an embodiment, there is provided an immunogenic composition comprising outer membrane vesicles obtained or obtainable from a genetically modified gonococcal bacterium of strain FA1090, wherein said bacterium comprises genetic modification(s) that decreases or abolishes expression of the Lpxl1 polypeptide and decreases or abolishes expression of the Rmp polypeptide, wherein the genetic modification(s) comprise deletion of the endogenous lpxl1 and rmp genes. In an embodiment there is provided an immunogenic composition comprising outer membrane vesicles obtained or obtainable from a genetically modified gonococcal bacterium of strain FA1090, wherein said bacterium comprises genetic modification(s) that decreases or abolishes expression of the Lpxl1 polypeptide and decreases or abolishes expression of the Rmp polypeptide, wherein the genetic modification(s) are gene deletions wherein said gene deletions are a result of a sequence addition, substitution or deletion modification within the lpxl1 and rmp loci, optionally wherein said gene deletion is a result of replacing a portion or portions of the lpxl1 and rmp genes with heterologous sequences, optionally wherein said heterologous sequences encode antibiotic resistance genes.

The term "immunogenic" in the context of a composition comprising OMVs is used to mean that antigens present on the surface (or substantially surface exposed) are capable of eliciting an immune response, such as a cell-mediated and/or an antibody response, for example when used to immunise a subject. Immunogenic compositions of the invention may be useful for vaccines. Immunogenic compositions and vaccines may thus be pharmaceutically acceptable. The term "obtained or obtainable" means OMVs that are isolated from the genetically modified gonococcus of the invention, said isolation resulting in an enriched population of OMVs. Said OMVs may also be purified to remove contamination, for example to remove cytoplasmic protein contamination.

In an embodiment, the immunogenic composition of the invention does not comprise any living and/or whole bacteria. In an embodiment, the immunogenic composition of the invention is pharmaceutically acceptable.

In an embodiment, the immunogenic composition of the invention further comprises an adjuvant. The compositions of the present invention may further comprise an adjuvant such that, when administered to a subject in conjunction with outer membrane vesicles of the invention, an increased or enhanced immune response to the antigen or antigens present on the surface of the OMVs is observed. The compositions of the present invention may further comprise an adjuvant such that, when administered to a subject in conjunction with outer membrane vesicles of the invention, reduced reactogeneicity is observed.

The composition of the invention may comprise an aluminium salt adjuvant. Suitable aluminium salt adjuvant includes hydroxides, phosphates or mixtures thereof. The salts can take any suitable form (e.g. gel, crystalline, amorphous etc.) with adsorption of the antigen to the salt being preferred. In an embodiment the adjuvant is an aluminium salt adjuvant, for example aluminium hydroxide. In an embodiment the adjuvant is aluminium hydroxide. In an embodiment, the OMVs of the invention are adsorbed onto aluminium hydroxide. In an embodiment, the adjuvant is not gel-based. In an embodiment, the adjuvant is not ALHYDROGEL.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 cm$^{-1}$ and a strong shoulder at 3090-3100 cm$^{-1}$ [Chapter 9 of Vaccine Design: *The Subunit and Adjuvant Approach* (eds. Powell & Newman) Plenum Press 1995]. The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminium hydroxide adjuvants.

The compositions of the invention may be prepared in various forms. Compositions will generally be administered to a subject (e.g. a mammal) in aqueous form however, prior to administration, the composition may have been in a non-aqueous form (e.g. dried or lyophilized). The compositions may be prepared in liquid form as injectables (either as solutions or suspensions). Compositions of the invention may include a preservative for example thiomersal and/or 2-phenoxyethanol. It is preferred however that the composition be substantially free form mercurial material. Vaccines containing no mercury are more preferred.

Compositions or vaccines of the invention may further comprise excipients. Compositions of the invention may include sodium salts (e.g. sodium chloride) to provide tonicity. Other salts that may be present include potassium chloride, potassium dihydrogen phosphate, disodium phosphate dehydrate, magnesium chloride, calcium chloride etc. Compositions of the invention may further comprise detergent e.g. a Tween (polysorbate).

Compositions may include one or more buffers. Typical buffers include: a phosphate buffer; a Tris buffer; a borate buffer; a succinate buffer; a histidine buffer (particularly with an aluminium hydroxide adjuvant); or a citrate buffer.

In an embodiment the immunogenic composition of the invention, when administered to a subject, elicits antibodies against homologous and/or heterologous strains of Neisseria gonorrhoea for example antibodies that are bactericidal against homologous and/or heterologous strains of N gonorrhoea. In general compositions of the invention are able to induce serum bactericidal antibody responses after being administered to a subject. These responses are typically measured, for example, following administration to mice and are standard indicators of vaccine efficacy. Serum bactericidal activity (SBA) measured bacterial killing mediated by complement and can be assaying using human or rabbit complement (an exemplar method to measure SBA can be found in Example 16 herein). As used herein, the term "heterologous strain(s)" refers to strain(s) of N. gonorrhoeae which are different from the N. gonorrhoeae strain from which the OMVs used to immunize the subject was derived. Since the OMVs used to immunize the subject are herein derived from an FA1090 strain gonococcus, heterologous strain(s) refer to non-FA1090 strain gonococci. As used herein, the term "homologous strain(s)" refers to an FA1090 strain of N. gonorrhoeae. In an embodiment, the immunogenic composition or vaccine of the invention is able to elicit cross-bactericidal titres.

In a further aspect of the invention there is provided a vaccine comprising the outer membrane vesicle of the invention or the immunogenic composition of the invention and a pharmaceutically acceptable excipient.

Vaccines according to the invention may either be prophylactic (i.e. prevent infection) or therapeutic (i.e. to treat infection) but will typically be prophylactic. The vaccines of the invention comprise an immunologically effective amount of antigens, wherein said antigens are present on the surface of the OMVs of the invention.

Treatment

The present disclosure provides immunogenic compositions and vaccines for us as medicaments. It also provides the use of the outer membrane vesicles of the invention as medicaments in the format of the immunogenic compositions and vaccines of the invention. Thus, in a further aspect there is provided the immunogenic composition of the invention or vaccine of the invention for use in medicine.

In a further aspect there is provided the immunogenic composition of the invention or vaccine of the invention, for use in immunising a subject against *Neisseria* infection for example *N. gonorrhoea* infection. The immunogenic composition of the invention or vaccine of the invention may thus be used in immunising a subject against other bacteria of the genus *Neisseria*, most particularly *N. meninigitidis* and *N. gonorrhoea*.

In a further aspect there is provided the immunogenic composition of the invention or vaccine of the invention for use in the treatment or prevention of disease caused by Neisseria for example *N. gonorrhoea*. In an embodiment, the immunogenic composition or vaccine of the invention is used in the treatment or prevention of gonorrhoea infection at the urogenital, anorectal and/or oropharyngeal site. In a further embodiment, the immunogenic composition or vaccine of the invention is used in the treatment or prevention of gonococcal associated pelvic inflammatory disease, disseminated gonococcal infection, ectopic pregnancy and/or infertility.

Efficacy of prophylactic and therapeutic treatment can be tested by monitoring the N gonorrhoea infection after administration of the immunogenic composition or vaccine of the invention. The World Health Organisation (WHO) suggests that prevention of infection is measured by diagnostic tests as the clinical endpoint for efficacy rather than disease endpoints; this would ensure the control of the transmission also in asymptomatic state [Gottlieb S L et al. Gonococcal vaccines: Public health value and preferred product characteristics; report of a WHO global stakeholder consultation, January 2019. Vaccine 2020 Jun. 9; 38(28): 4362-4373]. The protective effect of vaccination can be tested by monitoring immune responses against immunogenic proteins in the outer membrane vesicles or other antigens after administration of the composition or vaccine. Immunogenicity of compositions of the disclosure can be determined by administering them to test subjects and then determining standard serological parameters (e.g. levels/concentration of anti-OMV IgG and presence of functional antibodies). These immune responses will generally be determined after administration of the composition and compared to values determined before administration of the composition. Where more than one dose of the composition is administered, more than one post-administration determination may be made. The immunogenic composition or vaccine of the invention is also considered efficacious if gonococcal infection at specific anatomical sites is reduced/lower in subjects that received the immunogenic composition or vaccine of the invention, compared to subjects administered a control/placebo vaccine. In an embodiment the immunogenic composition or vaccine of the invention is at least 40%, at least 50%, at least 60%, at least 70%, at least 80% or at least 90% protective against *N. gonorrhoea* infection.

In a further aspect there is provided a method for the treatment or prevention of disease caused by *Neisseria* (for example *N. gonorrhoea*) in a subject in need thereof, said method comprising administering to said subject a therapeutically effective amount of the immunogenic composition of the invention or the vaccine of the invention.

In a further aspect there is provided, a method for immunizing a subject in need thereof against *Neisseria* (for example *N. gonorrhoea*), comprising administering an immunologically effective amount of the immunogenic composition of the invention or vaccine of the invention to the subject.

In a further aspect there is provided a method for raising an immune response in a subject, comprising administering an immunogenic composition of the invention or vaccine of the invention to a subject. In a further aspect there is provided a method for raising an immune response against *Neisseria* infection (for example *N. gonorrhoeae* infection) in a subject, comprising administering an immunogenic composition of the invention or vaccine of the invention to a subject.

In a further aspect there is provided the use of the immunogenic composition of the invention or the vaccine of the invention in the manufacture of a medicament for the treatment or prevention of disease caused by *Neisseria*. In a further aspect there is provided the use of the immunogenic composition of the invention or the vaccine of the invention in the manufacture of a medicament for the treatment or prevention of disease caused by *N. gonorrhoea*.

Dosage treatment can be a single dose schedule or a multiple dose schedule. In a further aspect there is provided the immunogenic composition or vaccine for use, the method or the use of the invention wherein at least 2 doses of the composition are administered to a subject. Multiple doses may be used in a primary immunisation schedule and/or in a booster immunisation schedule. A primary dose schedule may be followed by a booster dose schedule. Therefore, in a further embodiment there is provided the immunogenic composition or vaccine for use, the method or the use of the invention wherein at least 2 doses of the composition are administered to a subject, wherein at least one dose is a booster dose.

In a further aspect there is provided the immunogenic composition or vaccine for use, the method or the use of the invention wherein the subjects are adolescents and/or adults (e.g. young adults). The World Health Organization (WHO) recommends to vaccinate before the first sexual exposure while providing maximal protection during the period of highest incidence, which is generally in late adolescence and young adulthood. WHO defines adolescents as people between 10 and 19 years of age [Rosen J E. *Adolescent health and development* (AHD): *a resource guide for World Bank operations staff and government counterparts*. Washington, D.C., The World Bank, 2004]. As such, as used herein the term "adolescents" means subjects who are between 10 and 19 years old. As used herein "adults" refers to subjects who are 20 years of age or older (for example 20-25 years old, 20-45 years old, 20-55 years old etc).

To identify subjects for prophylaxis or treatment according to the methods or uses disclosed herein, screening methods may be employed to determine risk factors associated with the targeted or suspected disease or condition or to determine the status of an existing disease or condition in a subject. These screening methods induce for example determination of environmental, familial, occupation and other such risk factors that may be associated with gonococcal infection or gonococcal related diseases, as well as diagnostic methods (e.g. bacterial culture or immunoassay methods). These and other routine methods allow clinicians to select patients in need of therapy. In a further aspect there is provided the immunogenic composition or vaccine for use, the method or the use of the invention wherein the subject is at increased risk of infection with *N. gonorrhoea* relative to the average risk in the general population. Examples of subjects that are at an increased risk of infection with *N. gonorrhoea* infection relative to the average risk in the general population might include (but is not limited to) sex workers, men who have sex with men (MSM), pre-exposure prophylaxis (PreP) users, individuals with current or past STI diagnosis, HIV+ individuals who are engaged in care and individuals who are seeking or have sought STI screening or other STI services at a healthcare centre.

In a further aspect there is provided the immunogenic composition or vaccine for use, method or the use of the invention wherein the subject is co-immunised against one or more further infectious agents. Co-immunisation may include immunisation against one or more further infectious agents within the vaccine of the invention (i.e. wherein the vaccine of the invention further comprises antigens against one or more further infectious agents). Co-immunisation may however also include, immunisation against one or more further infectious agents wherein further vaccines are administered at substantially the same time as the vaccine of the invention (for example at the same clinical appointment). For example, the immunogenic composition or vaccine of the invention may be administered to a subject alongside a further immunogenic composition or vaccine which comprises antigens against one or more further infectious agents. In an embodiment the one or more further infectious agents are infectious agents that cause sexually transmitted infections.

In a further aspect there is provided the immunogenic composition or vaccine for use, the method or the use of the invention wherein said immunogenic composition or vaccine is administered via the intramuscular or intraperitoneal route of administration. In an embodiment the immunogenic composition or vaccine of the invention is administered via the intramuscular route of administration. In an embodiment the route of administration remains unchanged between the first and any subsequent immunisation. In an embodiment the route of administration does not comprise the intranasal route.

Embodiments of the invention are further described in the subsequent numbered paragraphs:

1. A genetically modified gonococcal bacterium of strain FA1090, comprising genetic modification(s) that:
   a. decreases or abolishes expression and/or function of the lipid A biosynthesis lauroyl acyltransferase (lpxl1) gene, mRNA, and/or polypeptide; and
   b. decreases or abolishes expression and/or function of the reduction modifiable protein (rmp) gene, mRNA, and/or polypeptide.

2. The gonococcal bacterium of paragraph 1 wherein the decreased or abolished expression and/or function is in comparison to a gonococcal bacterium of strain FA1090 that comprises the wild type lpxl1 and rmp genes.

3. The gonococcal bacterium of paragraph 1 or paragraph 2 wherein the lpxl1 gene comprises a sequence at least 80% identical to the sequence as set forth in SEQ ID NO: 3 and wherein the rmp gene comprises a sequence at least 80% identical to the sequence set forth in SEQ ID NO: 1.

4. The gonococcal bacterium of paragraph 1-3 wherein the lpxl1 gene comprises a sequence at least 90% identical to the sequence as set forth in SEQ ID NO: 3 and wherein the rmp gene comprises a sequence at least 90% identical to the sequence set forth in SEQ ID NO: 1.

5. The gonococcal bacterium of paragraphs 1-4 wherein the lpxl1 gene comprises SEQ ID NO: 3 and wherein the rmp gene comprises SEQ ID NO: 1.

6. The gonococcal bacterium of any preceding paragraph, wherein the genetic modification(s):
   a. decreases or abolishes expression and/or function of the Lpxl1 polypeptide; and
   b. decreases or abolishes expression and/or function of the Rmp polypeptide.

7. The gonococcal bacterium of paragraphs 1-6 wherein the Lpxl1 polypeptide comprises an amino acid sequence at least 80% identical to SEQ ID NO: 4 and the Rmp polypeptide comprises an amino acid sequence at least 80% identical to SEQ ID NO: 2.

8. The gonococcal bacterium of paragraphs 1-7 wherein the Lpxl1 polypeptide comprises an amino acid sequence at least 90% identical to SEQ ID NO: 4 and the Rmp polypeptide comprises an amino acid sequence at least 90% identical to SEQ ID NO: 2.

9. The gonococcal bacterium of paragraphs 1-8 wherein the Lpxl1 polypeptide comprises the amino acid sequence of SEQ ID NO: 4 and the Rmp polypeptide comprises the amino acid sequence of SEQ ID NO: 2.

10. The gonococcal bacterium of any preceding paragraph, wherein the bacterium expresses less than 10%, less than 5% or less than 1% of the Lpxl1 polypeptide compared to a gonococcal FA1090 strain comprising the wild type Lpxl1 gene and less than 10%, less than 5% or less than 1% of the Rmp gene compared to a gonococcal FA1090 strain comprising the wild type rmp gene.

11. The gonococcal bacterium of paragraphs 1-10, wherein the bacterium does not express the Lpxl1 polypeptide and/or the Rmp polypeptide.

12. The gonococcal bacterium of paragraphs 1-11, wherein decreased or abolished expression and/or function of the lpxl1 polypeptide results in penta-acylation of lipid A, optionally wherein the acylation of lipid A is determined by MALDI-TOF spectrometry.

13. The gonococcal bacterium of paragraph 12, wherein decreased or abolished expression and/or function of the Lpxl1 polypeptide results in above 50% penta-acylation of lipid A, for example above 60%, above 70%, above 80%, above 90%, above 95% or above 99%.

14. The gonococcal bacterium of paragraph 12 or paragraph 13, wherein decreased or abolished expression and/or function of the Lpxl1 polypeptide results in 100% penta-acylation of lipid A.

15. The gonococcal bacterium of paragraphs 1-14, wherein the decreased or abolished expression and/or function of the Rmp polypeptide results in a gonococcus that is hyper-blebbing compared to a gonococcal FA1090 strain comprising the wild type rmp gene.

16. The gonococcal bacterium of paragraphs 1-15, wherein the genetic modification(s) consist of or comprise,
   a) disruption or deletion of the endogenous Lpxl1 and rmp genes; or
   b) suppression of Lpxl1 and Rmp polypeptide expression in a strain comprising the wild type lpxl1 and rmp genes.

17. The gonococcal bacterium of paragraphs 1-16, wherein the genetic modification(s) consists of or comprise disruption or deletion of the endogenous lpxl1 and rmp genes.

18. The gonococcal bacterium of paragraph 17, wherein disruption of the endogenous lpxl1 and/or rmp results in expression of non-functional Lpxl1 and/or Rmp polypeptides.

19. The gonococcal bacterium of paragraph 17 or paragraph 18, wherein disruption includes addition to, deletion from or substitution of the endogenous lpxl1 and/or rmp gene sequence.

20. The gonococcal bacterium of any preceding paragraph wherein the genetic modification(s) comprise deletion of the endogenous lpxl1 and rmp genes, i.e. are gene deletions.

21. The gonococcal bacterium of paragraph 20 wherein deletion of the endogenous lpxl1 and rmp genes results in the double-mutant FA1090 gonococcus (Δlpxl1, Δrmp).

22. The gonococcal bacterium of paragraph 20 or paragraph 21, wherein the endogenous lpxl1 and rmp genes are deleted by homologous recombination.

23. The gonococcal bacterium of any preceding paragraph wherein the genetic modification(s) may be to coding and/or non-coding regions.

24. The gonococcal bacterium of any preceding paragraph, wherein the bacterium is isogenic with a wild-type gonococcal FA1090 strain, except for the genetic modification(s) of paragraphs 1-23.

25. The gonococcal bacterium of any preceding paragraph further comprising additional genetic modification(s) that result in over-expression and/or decreased or abolished expression of up to 3, up to 5, up to 10 or up to 20 further Neisserial antigens.

26. A process for producing the gonococcal bacterium according to paragraphs 1-25, the process comprising either:
   a) decreasing or abolishing the expression and/or function of the lpxl1 gene mRNA and/or polypeptide in a gonococcal FA1090 bacterium to produce a first gonococcal FA1090 bacterium and decreasing or abolishing the expression and/or function of the rmp gene mRNA and/or polypeptide from the first gonococcal FA1090 bacterium to produce a second gonococcal FA1090 bacterium; or
   b) decreasing or abolishing the expression and/or function of the rmp gene mRNA and/or polypeptide from the first gonococcal FA1090 bacterium to produce a first gonococcal FA1090 bacterium and decreasing or abolishing the expression and/or function of the lpxl1 gene mRNA and/or polypeptide from the first gonococcal FA1090 bacterium to produce a second gonococcal FA1090 bacterium.

27. The process of paragraph 26, wherein a) the first gonococcal FA1090 bacterium is the single-mutant (Δlpxl1) and the second gonococcal FA1090 bacterium is the double-mutant (Δlpxl1,Δrmpl and wherein b) the first gonococcal FA1090 bacterium is the single-mutant (Δrmpl and the second gonococcal FA1090 bacterium is the double-mutant (Δlpxl1,Δrmpl.

28. The process of paragraph 26 or paragraph 27, wherein decreasing or abolishing the expression of both the lpxl1 gene and the rmp gene is performed by genomic recombination.

29. The process of paragraphs 26-28, wherein decreasing or abolishing the expression of both the lpxl1 gene and the rmp gene are gene deletions, optionally wherein said gene deletions are a result of sequence addition, substitution or deletion modifications within the lpxl1 and rmp loci.

30. The process of paragraphs 26-29, wherein decreasing or abolishing the expression of both the lpxl1 gene and the rmp gene is performed by addition of a heterologous gene sequence within the lpxl1 and rmp coding sequence and/or replacing the lpxl1 and rmp coding sequences, or a portion thereof with a heterologous gene sequence.

31. The process of paragraphs 26-30, wherein decreasing or abolishing the expression of both the lpxl1 gene and the rmp gene is performed by addition of antibiotic resistance cassettes within the lpxl1 and rmp coding sequence and/or replacing the lpxl1 and rmp coding sequences, or a portion thereof with antibiotic resistance cassettes.

32. The use of the gonococcal bacterium according to any of paragraphs 1-25 in the production of outer membrane vesicles.

33. An outer membrane vesicle obtained or obtainable from an FA1090 strain gonococcus, wherein said outer membrane vesicle comprises either reduced levels or no detectable level of both Lpxl1 and Rmp polypeptides.

34. The outer membrane vesicle of paragraph 33 wherein the reduced levels or no detectable level of both Lpxl1 and Rmp polypeptides is measured in comparison to an OMV from a wild-type FA1090 bacterium or an FA1090 bacterium comprising the wild-type Lpxl1 and Rmp genes.

35. An outer membrane vesicle (OMV) from a genetically modified FA1090 strain gonococcus, said genetically modified FA1090 strain gonococcus comprising genetic modification(s) that a) decreases or abolishes expression and/or function of the lpxl1 gene, lpxl1 mRNA, and/or Lpxl1 polypeptide; and b) decreases or abolishes expression and/or function of the rmp gene, rmp mRNA, and/or Rmp polypeptide,
said OMV comprising:
   I. reduced levels of Rmp polypeptide compared to the levels of Rmp polypeptide in a comparator OMV from a *N. gonorrhoeae* strain FA1090 that lacks said genetic modifications; and
   II. reduced levels of hexa-acylated lipid A compared to the levels of hexa-acylated lipid A from the comparator OMV 36. The outer membrane vesicle (OMV) according to paragraph 35 wherein said OMV further comprises: III. increased levels of penta-acylated lipid A that lacks lauric acid compared to the levels of penta-acylated lipid A that lacks lauric acid from the comparator OMV.

37. An outer membrane vesicle obtained or obtainable from a gonococcal bacterium according to any of paragraphs 1-25.

38. The outer membrane vesicle of paragraph 37, comprising decreased or abolished expression of the Lpxl1 polypeptide and decreased or abolished expression of the Rmp polypeptide.

39. The outer membrane vesicle of paragraph 37 or paragraph 38 which does not express Lpxl1 or Rmp.

40. The outer membrane vesicle of paragraph 37 comprising reduced levels of the Rmp polypeptide compared to the levels of the Rmp polypeptide in a comparator OMV from a *N. gonorrhoeae* strain FA1090 that lacks said genetic modification(s) and reduced levels of hexa-acylated lipid A compared to the levels of hexa-acylated lipid A from the comparator OMV.

41. The outer membrane vesicle of paragraph 40 which further comprises increased levels of penta-acylated lipid A that lacks lauric acid compared to the levels of penta-acylated lipid A that lacks lauric acid from the comparator OMV.

42. The outer membrane vesicle of any of paragraphs 33-41, wherein said outer membrane vesicle is a native outer membrane vesicle i.e. not detergent extracted.

43. The outer membrane vesicle of any of paragraphs 33-42 which is purified via filtering through a sterile filter with a pore size of less than 0.5, 0.4 or 0.3 μm.

44. The outer membrane vesicle of any of paragraphs 33-43 wherein said outer membrane vesicle comprises the double-mutant FA1090 (ΔlpxL1, Δrmp) protein profile, wherein said protein profile is measured by mass spectrometry analysis.

45. The outer membrane vesicle of paragraph 44 wherein the double-mutant FA1090 (ΔlpxL1, Δrmp) protein profile comprises PorB 1B, PilQ, BamA and BamD.

46. An immunogenic composition comprising an outer membrane vesicle according to any of paragraphs 33-45.

47. The immunogenic composition of paragraph 46 further comprising an adjuvant.

48. The immunogenic composition of paragraph 47, wherein the adjuvant is an aluminium salt adjuvant, for example aluminium hydroxide.

49. The immunogenic composition of paragraphs 46-48 that when administered to a subject, elicits antibodies against homologous and/or heterologous strains of *Neisseria gonorrhoea* for example antibodies that are bactericidal against homologous and/or heterologous strains of *N. gonorrhoea.*

50. A vaccine comprising the outer membrane vesicle of any of paragraphs 33-45 or the immunogenic composition of paragraphs 46-49 and a pharmaceutically acceptable excipient.

51. The immunogenic composition according to paragraphs 46-49 or vaccine according to paragraph 50 for use in medicine.

52. The immunogenic composition according to paragraphs 46-49 or vaccine according to paragraph 50, for use in immunising a subject against *Neisseria* infection for example *N. gonorrhoea* infection.

53. The immunogenic composition according to paragraphs 46-49 or vaccine according to paragraph 50 for use in the treatment or prevention of disease caused by Neisseria for example *N. gonorrhoea.*

54. A method for the treatment or prevention of disease caused by *Neisseria* (for example *N. gonorrhoea*) in a subject in need thereof, said method comprising administering to said subject a therapeutically effective amount of the immunogenic composition according to paragraphs 46-49 or the vaccine of paragraph 50.

55. A method for immunizing a subject in need thereof against *Neisseria* (for example *N. gonorrhoea*), comprising administering an immunologically effective amount of the immunogenic composition according to paragraphs 46-49 or vaccine according to paragraph 50 to the subject.

56. A method for raising an immune response in a subject, comprising administering an immunogenic composition according to paragraphs 46-49 or vaccine according to paragraph 50 to a subject.

57. The use of the immunogenic composition according to paragraphs 46-49 or the vaccine according to paragraph 50 in the manufacture of a medicament for the treatment or prevention of disease caused by *Neisseria.*

58. The use of the immunogenic composition according to paragraphs 46-49 or the vaccine according to paragraph 50 in the manufacture of a medicament for the treatment or prevention of disease caused by *N. gonorrhoea.*

59. The immunogenic composition or vaccine for use, the method or the use according to any of paragraphs 51-58, wherein at least 2 doses of the composition are administered to a subject.

60. The immunogenic composition or vaccine for use, the method or the use according to any of paragraphs 51-58 wherein the subjects are adolescents and/or adults.

61. The immunogenic composition or vaccine for use, the method or the use according to any of paragraphs 51-58 wherein the subject is at increased risk of infection with *N. gonorrhoea* relative to the average risk in the general population.

62. The immunogenic composition or vaccine for use, the method or the use according to any of paragraphs 51-58 wherein the subject is co-immunised against one or more further infectious agents.

63. The immunogenic composition or vaccine for use, the method or the use according to any of paragraphs 51-58 wherein said immunogenic composition or vaccine is administered via the intramuscular or intraperitoneal route of administration.

The following examples are intended for illustration only and are not intended to limit the scope of the invention in any way.

EXAMPLES

Example 1: Genomic Comparison of FA1090 with the Global Variability of Gonococci Two FA1090 whole genomes were selected for comparative genomic analysis as follows:

(1) FA1090—GenBank (see GenBank accession ID: AE004969.1)

(2) FA1090—FA1090 strain gonococcus obtained from Prof Lee Wetzler, Boston University School of Medicine.

The genome of FA1090 strain (1) was downloaded from GenBank (accession id: AE004969.1). The genome of FA1090 strain (2) was sequenced with the Illumina Miseq technology (performed as described in Example 9). The sequenced genome was assembled to determine the whole chromosome sequence.

The identity between FA1090 genomes (1) and (2) was calculated using the method described in Lee I, Ouk Kim Y, Park S C, Chun J. OrthoANI: *An improved algorithm and software for calculating average nucleotide identity. Int J Syst Evol Microbiol.* 2016; 66(2):1100-1103.1. The genomes are 99.97% identical.

The genomes of these two FA1090 strains were compared against a large number of other gonococcal genomes including:

14 World Health Organization Strains (present in internal collection), 12 strains obtained from ATCC (present in internal collection), 30 gonococcal strains forming part of an in-house gonococcal library and, 4000 publicly available genomes of *Neisseria gonorrhoeae* strains, representing a global collection of the species.

Figure 1:
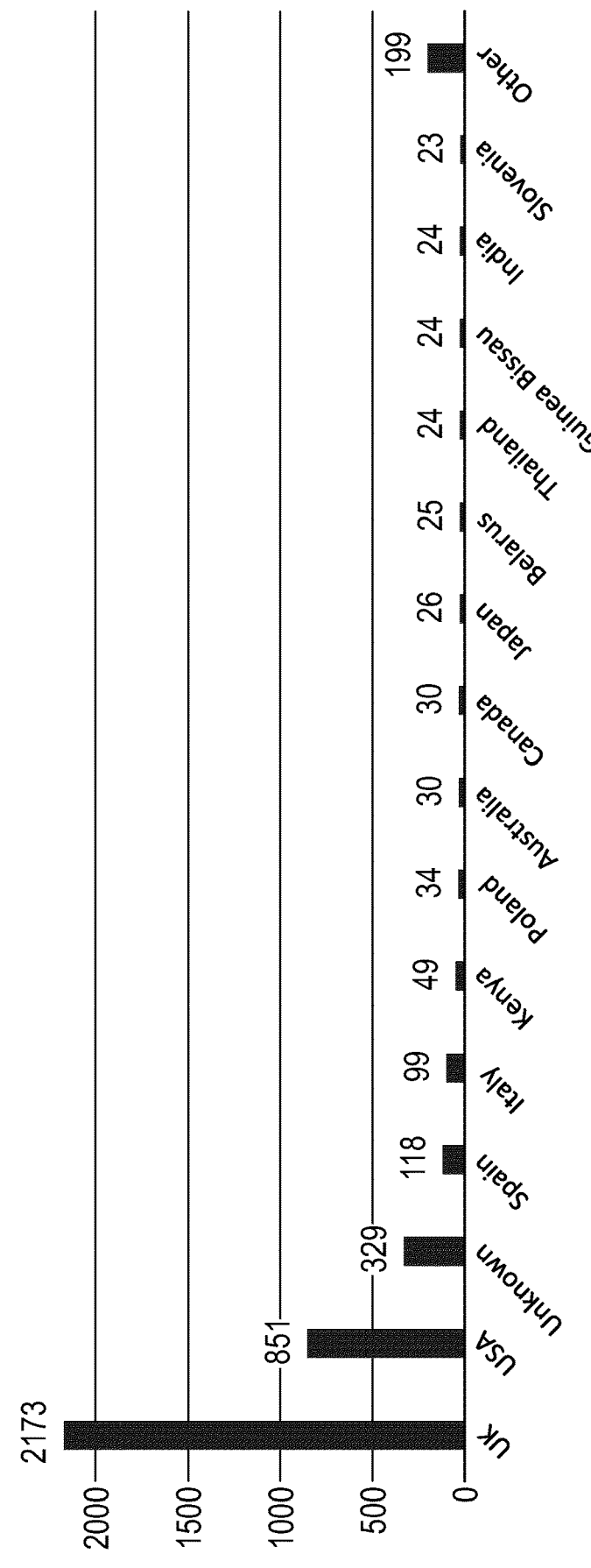
FIG. 1: Frequency of gonococcal isolates considered for the genomic analysis (as described in Example 1) by country of origin (*=frequency<0.5%). 4058 *N. gonorrhoeae* whole genomes were available for analysis.

A total of 4058 genomes were therefore available for analysis. Overall, the strains considered for this analysis were representative of different countries and correspond to relevant collections of gonococcal circulating strains (see FIG. 1)

Materials and Methods

Data sources: The global collection of gonococci genomes (4000 publicly available genomes) was downloaded from the PubMLST database (accessed MAR/2019). The FA1090 GenBank strain (accession AE004969.1) genome and WHO genomes (accession PRJEB14020) were downloaded from GenBank and European Nucleotide Archive (ENA) databases respectively. The genomes of the FA1090 (2), ATCC collection (12 strains) and the in-house gonococcal library (30 strains) was obtained by next-generation sequencing.

Assembly: The assembly of the sequenced strains was performed with spades (v. 3.6.2) assembly software.

Single nucleotide polymorphisms (snps) detection and comparison: Genome sequences were compared with kSNP3 software (v. 021). kSNP3 allows detection of core and non-core snps among the genome sequences provided as input. The raw result of the analysis is a multifasta file of aligned snps, including insertions and deletions. This mfasta file can be the input of any software pipeline for the phylogeny and the population structure reconstruction. For these phylogenetic analyses, an ad hoc pipeline was developed in R programming language (based on ape, phangom, clValid and cluster R packages) or it was directly performed with splitstree software (v. 4.14).

Extended multi-locus sequence typing (MLST): Genome sequences were also characterised with Bigsdb software (v. 1.20) to assign alleles and protein identifiers to the list of loci defined by the public core genome MLST schema for Neisseria genus (NM_cgMLST_v1.0). In all cases, these extended MLST typing profiles were used to compute genetic distances between strains (on the basis of the number of varying alleles) and reconstruct population phylogeny.

Genomes annotation: Coding sequences detection and annotation were performed with prokka software pipeline (v. 1.13.3). For genome (1) the originally published genome annotation was used, but it was also reannotated. For genome (2) by mauve pipeline the contigs were reordered on the (1) genome scaffold and then fused with a 6-frame stop linker motif to form a virtual single contig (labelled r1c). The general overview of the assemblies is reported in Table 1.

TABLE 1

General overview of the FA1090 assemblies.

| | Strain | Assembly name | n. of contigs (length) | n. of plasmids (length) | n. of genes |
|---|---|---|---|---|---|
| (1) | FA1090 AE004969 | AE004969 | 1 (2153922) | — | 2002[a] |
| (2) | FA1090 | FA1090 [FA1090_r1c][b] | 110 (2086558) [1 (2093390)][b] | 1 (4302) [—][b] | 2089 [2124][b] |

[a]this number is 2201 if the published genome AE004969 is reannotated with the prokka pipeline.
[b]these numbers refer to the single virtual contig FA1090_r1c annotation.

Whole genome comparisons: Genome comparison was performed using two techniques, based on core and non-core single nucleotide polymorphisms (snps) detection and extended multilocus allele assignment (cgMLST_v1.0 scheme from PubMLST database).

Single Nucleotide Polymorphisms Phylogeny

The phylogenetic reconstruction based on snps is a computationally demanding task and to facilitate the comparisons among genomes and their visualization, the analysis was produced on a subset of selected genomes. In total 369 genomes were included in the analysis and were randomly selected out of the 4058 genomes available. Core and non-core snps were determined and aligned with kSNP pipeline.

Figure 2:
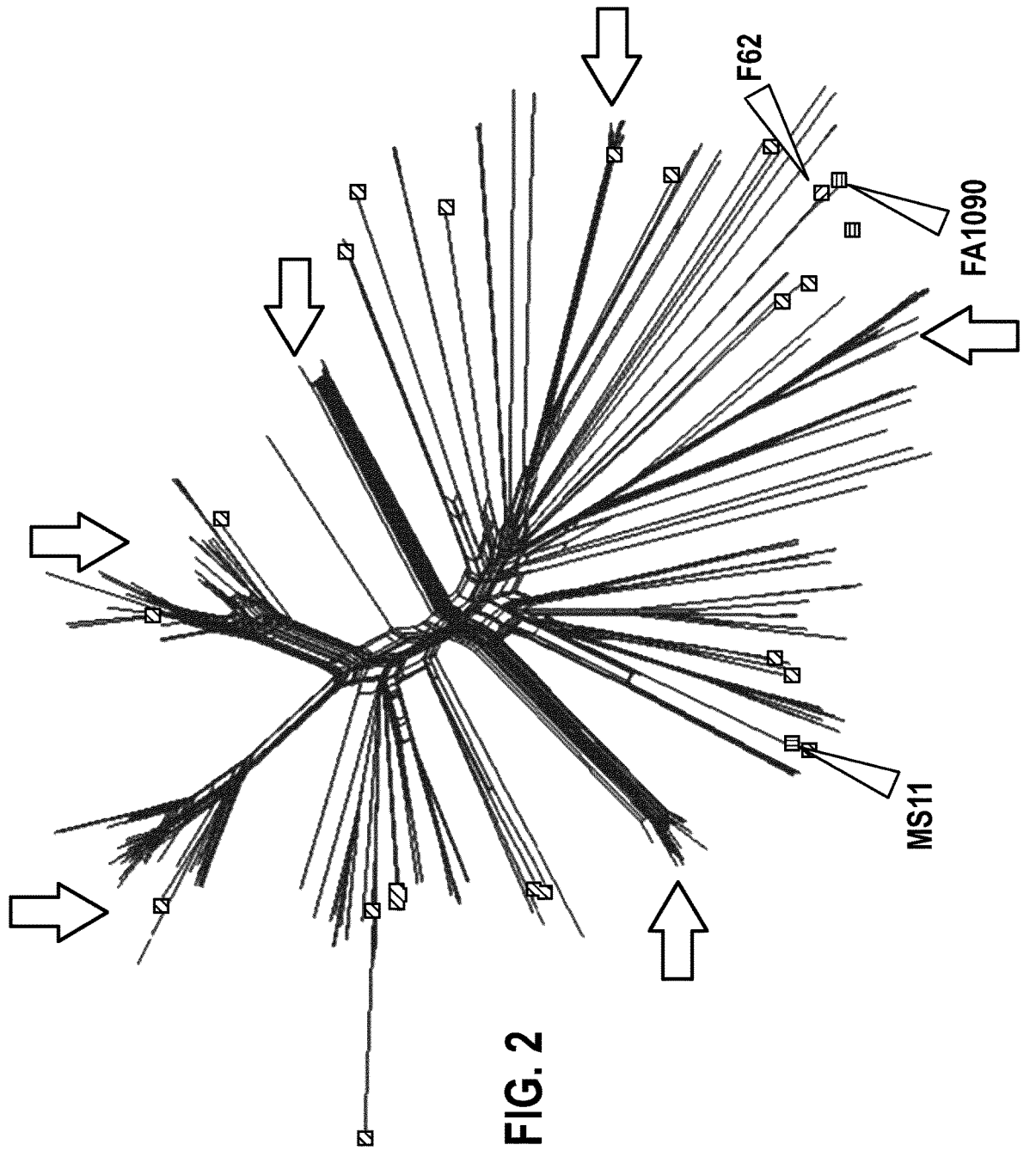
FIG. 2: Core and non-core single nucleotide polymorphisms (snps) phylogeny of gonococcal genomes, including genomes of strains present in an internal collection (marked with a □ symbol). Branch lengths are proportional to the genetic distance. Six compact clusters were identified and are highlighted with black arrows.

A phylogenetic network representation of the similarity of strains is represented in FIG. 2. The FA1090 genome shows a certain level of similarity to the F62 strain genome, but in general, it appears to be very distant from all the genomes of the collection. In general, the network shows a star like structure with the presence of about 6 compact clusters (black arrows in FIG. 2).

cgMLST Phylogeny

A comprehensive genomic analysis of all 4058 strains was conducted by the Neisseria meningitidis typing schema (NM cgMLST v1.0) characterization. The schema assigns numerical identifiers to the sequence of 1605 gene loci in each genome. This extended multilocus profile (a list of numerical identifiers) was used to compare genomes to each other and to define a genetic distance (in order to reconstruct the phylogeny of the strains).

A genetic symmetric matrix (shown in FIG. 3) was prepared which shows the genetic matrix distance computed between strain pairs. In agreement with the reconstruction shown in FIG. 2, the structure of the population was characterized by well-defined clusters separated from each other. A hierarchical relationship based on pair distances is represented on both sides of the matrix. In this tree, clusters are well separated and defined.

Figure 4:
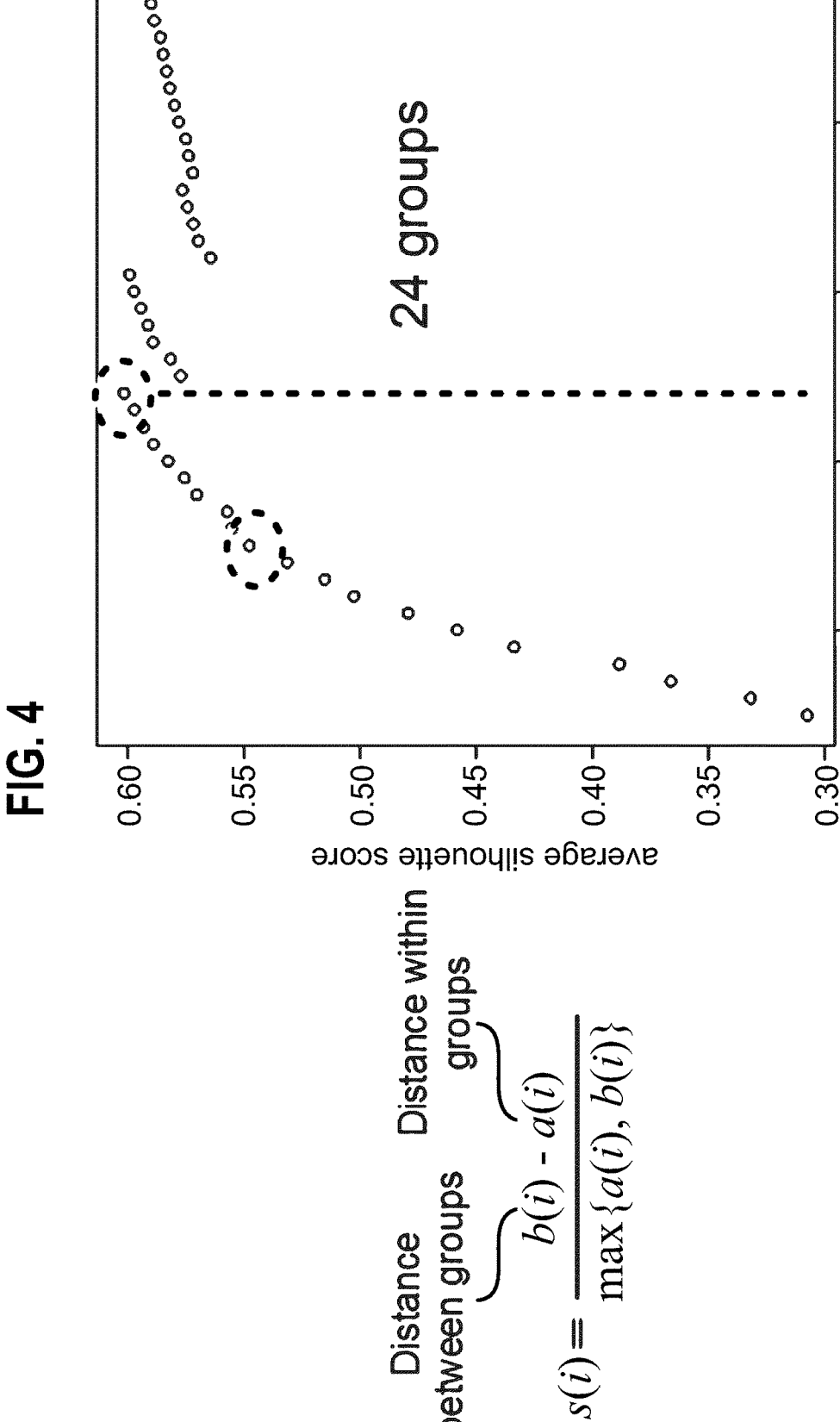
FIG. 4: Silhouette parameter optimization was used to determine the optimal number of partitions of the gonococcal population. Whole genome variability shows that isolates group in 24 distinct clusters.

The optimal number of clusters was then determined by silhouette optimization technique (FIG. 4). This procedure identifies partitionings in the tree that maximise the average distance between the clusters. The number of partitions that maximized the score was 24.

Figure 3:
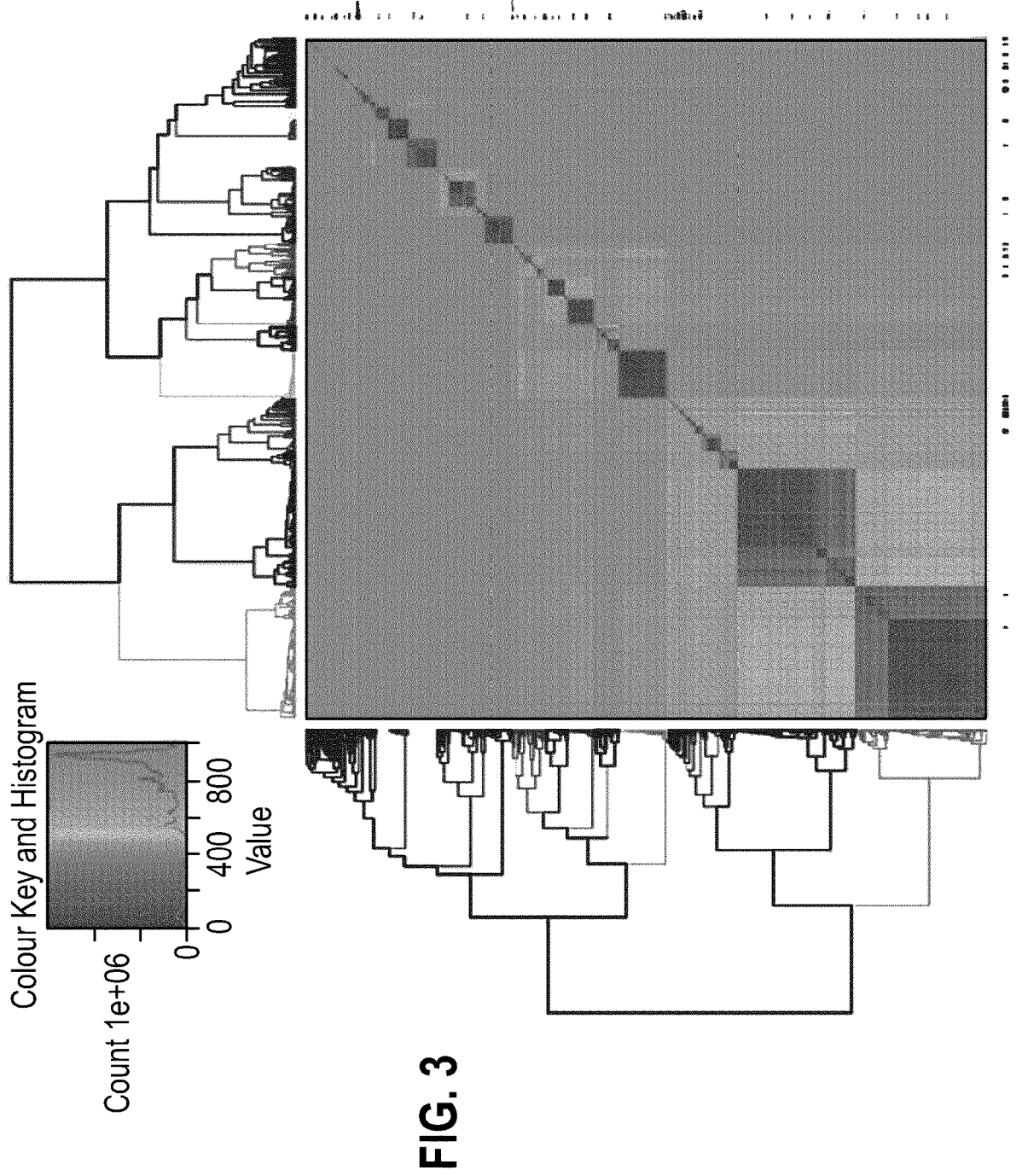
FIG. 3: Phylogenetic reconstruction and population structure of 4058 gonococcal genomes, including strains of the internal collection (NM_cgMLST_v1.0 schema). Clustering on 4058 strains profiles defined by the typing of whole genome.
Figure 5:
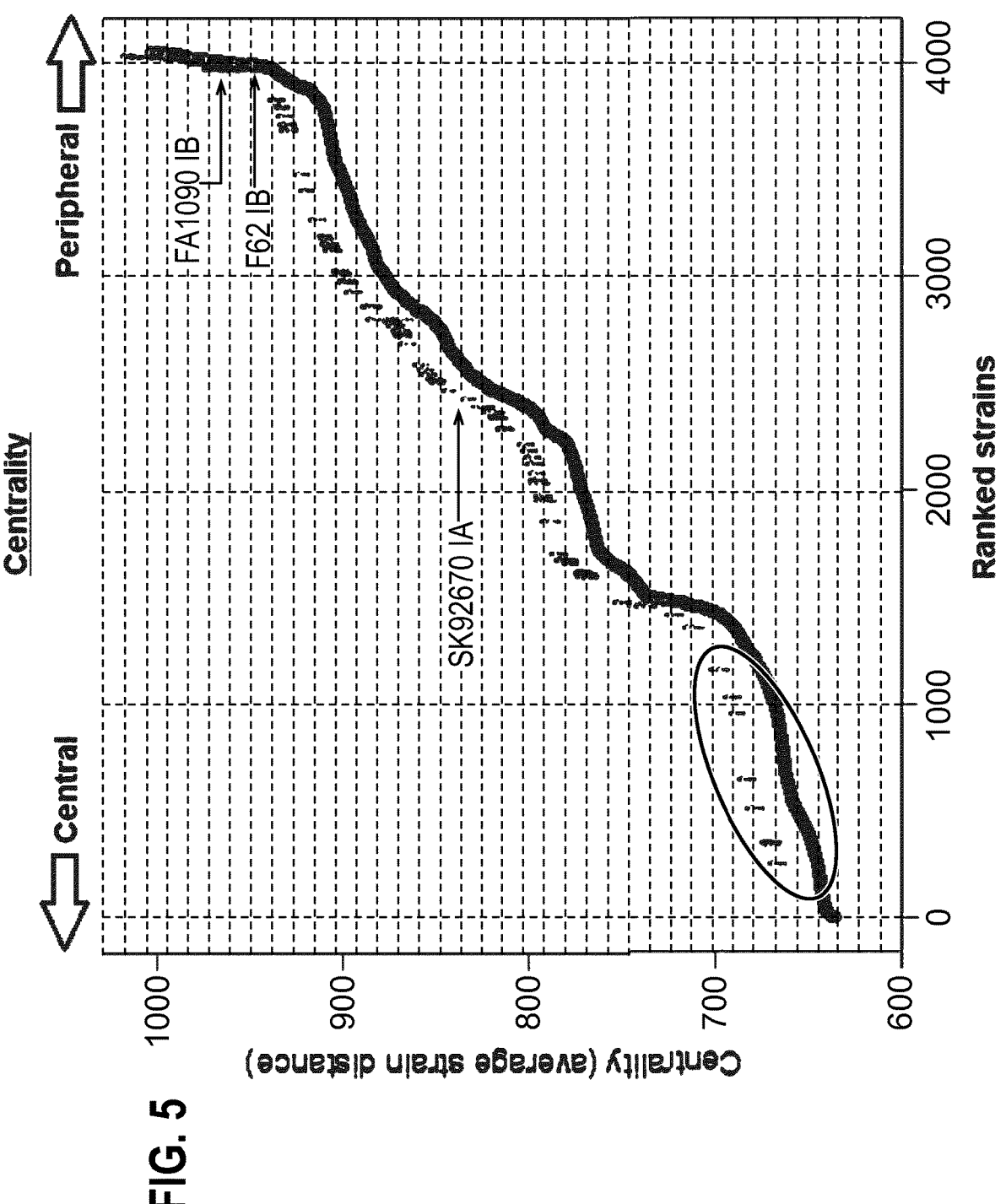
FIG. 5: Centrality defined as average distance of each strain with respect to others based on whole genome analysis. Phylogenetic average distance of each strain from all the others (centrality), based on NM_cgMLST_v1.0 allelic variations of 1605 gene loci.

On the basis of the matrix of genetic distances between pair of strains represented in FIG. 3, for each strain its average distance from all the other strains was also computed. This analysis represents the strains 'centrality' with respect to the entire population and is represented in FIG. 5 for all the analysed strains.

The centrality score measures how much each strain is central or peripheral in the gonococcal population in terms of genetic distance. Strains that are more central are on average more similar to the other strains of the population. On the basis of this score we can infer that in general, stains that are peripheral are not good candidates to be representative of the features of the average of the population. These strains tend to be particular and unique in the population (i.e. dissimilar from the others). Centrality scores for a subset of strains is shown in Table 2 below.

TABLE 2

| Strain | Centrality Score |
|---|---|
| FA1090 (1) Genbank | 965 |
| FA1090 (2) | 941 |
| F62 | 944 |
| SK92-679 | 803 |
| GC_0817560 | 692 |

As shown in FIG. 5, the strains (circled) are in the most "central" region of the plot. The reference strain FA1090 is in the right corner of the plot and was among the most peripheral strains. This position suggests that the FA1090 strain is genetically diverse from the other strains of the collection.

Conclusion: An analysis of FA1090 whole genome compared to the available genomes of other gonococcus strains indicated that the average genetic distance of this strain from all other Gonococcus strain is much higher compared to that of other strains. Based on these analyses, an OMV based vaccine (wherein the OMVs are blebbed from the FA1090 strain) may not be broadly cross-protective based on genomic similarity.

Example 2: Bacterial Strain and Culture Conditions

A gonococcal FA1090 strain with 99.97% identity to the FA1090 strain disclosed in Genbank Accession ID:

Rmp: The amplification of the up and downstream regions of the rmp gene was performed with the primer couples UpIII-FOR/REV and DpIII-FOR/REV using as template 50 ng of genomic DNA of the FA1090 strain. Meanwhile the amplification of the erythromycin resistance gene (eryR) was performed with the primer couple EryR_gono_SmaI-Fw/Rev using as template 10 ng of a plasmid carrying the gene (Serruto et al., 2010). See table 3 below. Purified PCR products were cloned as XbaI-SuraI (UP rmp), SmaI (eryR) and SmaI-XhoI (DOWN rmp) into a pBluescript KS+ (Agilent, #212207) digested with XbaI-XhoI (NEB). The correct cloning was confirmed by double digestions and electrophoresis.

TABLE 3

| Name | Sequence | Restriction Site | SEQ ID NO |
|------|----------|------------------|-----------|
| UpIII-FOR | gctctagaGGTCGTCTATCCGTTCCGTA | XbaI | 11 |
| UpIII-REV | tcccccgggCTCAACGCCTGAAAACAACC | SmaI | 12 |
| DpIII-FOR | tcccccgggTCAAGCGCAAATGACTCAAG | SmaI | 13 |
| DpIII-REV | cccgctcgagGGGAAAGGCGTGAATTTGTA | XhoI | 14 |
| EryR_gono_SmaI-Fw | ATTCGCCCGGGAAACTTAAGAGTGTGTTGATAGTG | SmaI | 15 |
| EryR_gono_SmaI-Rev | ATTCGCCCGGGACCTCTTTAGCTTCTTGG | SmaI | 16 |

AE004969.1) was used in the experiments described below (I.e. FA1090 strain (2) from Example 1). Strains were routinely cultured for 18-24 hours on Gonococcus (GC) agar medium (Difco) with 1% Isovitalex at 37° C. in an atmosphere of 5% $CO_2$.

Example 3: Construction of Plasmids and Transformation

DNA manipulations were carried out routinely as described for standard laboratory methods [Sambrook J F E, Maniatis T. *Molecular cloning: a laboratory manual. Cold Spring Harbor Laboratory*. 2012; 4th ed].

Lpxl1: The plasmid pBS-ΔlpxL1 kanR [see Oliver Koeberling, Anja Seubert, Dan M Granoff. Bactericidal Antibody Responses Elicited by a Meningococcal Outer Membrane Vesicle Vaccine with Overexpressed Factor H—Binding Protein and Genetically Attenuated Endotoxin, The Journal of Infectious Diseases, Volume 198, Issue 2, 15 Jul. 2008, Pages 262-270], which contains the kanamycin resistance gene and the upstream and downstream regions for the homologous recombination was used as a template for the amplification of the DNA needed for the transformation. The PCR was performed using the primers lpxl1 UP FW (GGCATTTGTATTTTGCCGTCTG, SEQ ID NO: 9) and lpxl1 DO REV (GCGAAATGTACGCCATTTC-TACGC, SEQ ID NO: 10) and the KAPA Hifi 2× mastermix (Roche), with reaction conditions as follow: 94° C. for 5 min, 40 cycles of 94° C. 30 s, 60° C. 30 s and 72° C. 3 min, with a final step at 72° C. for 5 min. DNA purifications were performed using the QIAquick PCR purification kit (QIAGEN) following the manufacturer's protocol.

Transformation: Either the PCR product (for Lpxl1 deletion) or the XbaI-linearized plasmid (for Rmp deletion) were used for the transformations. Wild-type FA1090 was transformed with the PCR product described above to generate the FA1090 (1KO) ΔlpxL1 strain. This 1KO strain was then subsequently transformed with the XbaI-linearized plasmid to generate the FA1090 (2KO) Δlpxl1,Δrmp. Transformations were carried out as previously described (Dillard J P. *Genetic Manipulation of Neisseria gonorrhoeae. Curr Protoc Microbiol*. 2011; Chapter 4: Unit4A.2) and transformants were selected into GC agar plates+1% Isovitalex with either kanamycin 40 μg/ml (Δlpxl1) or erythromycin 2 μg/ml (Δrmpl.

All transformants were tested by PCR analysis using Accuprime Taq Polymerase (Thermo Scientific) and with external primers (primer couples lpxl1 est FW/REV and UP CHECK NG01577-Fw/DW CHECK NG01577-Rev for ΔlpxL1 and Δrmp, respectively) to check the correct event of double recombination (see Example 4 and 7 below).

Example 4: Generation of FA1090 Single Mutant (ΔLpxl1)

Lipopolysaccharide (LPS) has an endotoxin activity primarily due to the lipid A. Its toxicity can result in significant reactogenicity. Therefore, to decrease the reactogenicity of an OMV based vaccine against *N. gonorrhoeae*, the lpxl1 gene (NGO0154) was deleted.

The FA1090 strain, which contains a PorB IB allele, was used as the background strain for the deletions.

FA1090 ΔlpxL1 was obtained by double homologous recombination where a region of the coding sequence of the lpxL1 gene was replaced with an antibiotic resistance cassette (Kanamycin).

Figure 6:
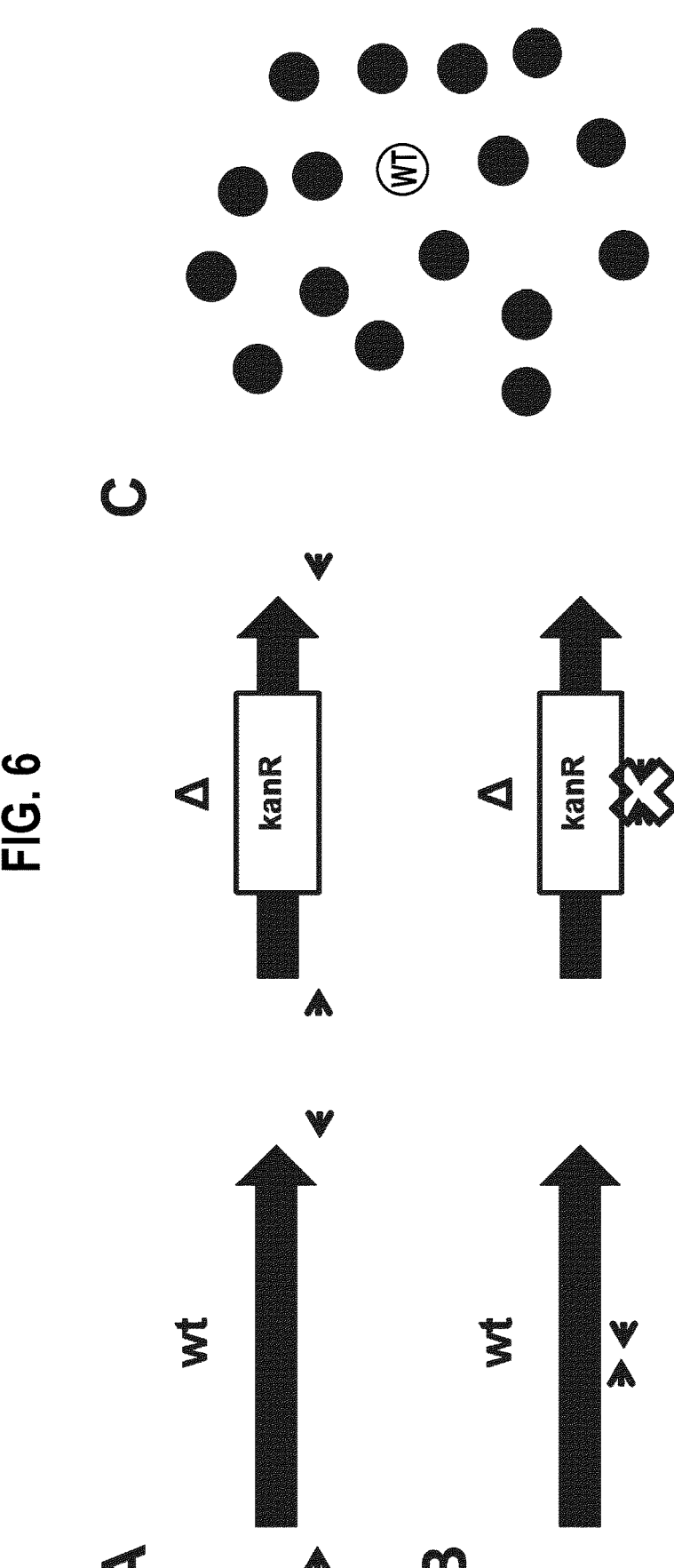
FIG. 6A, FIG. 6B and FIG. 6C: Schematic representation of the controls for the mutant generation. To check the occurrence of the double homologous recombination and the generation of the mutant clone a pair of primers external to the deletion region were designed as depicted (FIG. 6A). The presence of wild-type cells mixed in the total mutant population (FIG. 6C) was investigated with primers that pair specifically to the wild-type genome but not to the mutant (FIG. 6B).

Mutant ΔlpxL1 clones resistant to the kanamycin were selected and amplified and their DNA tested for the presence of the correct mutation (FIG. 6).

Clone #2 was streaked in plates with kanamycin and from the derived clone (#2.1), a glycerol stock was prepared, and a DNA lysate was generated. By using primers external to the recombination event (FIG. 6A) the selected clones were screened for the loss of the lpxl1 gene and the acquisition of the gene for the kanamycin resistance.

All transformants were tested by PCR analysis using Accuprime Taq Polymerase (Thermo Scientific) and with external primers (primer couples lpxl1 est FW (CCGC-CAAACTCAATCCTTCG, SEQ ID NO: 17) and lpxl1 est REV (GCAAACTTTTGTTTCACCGTTTCCG, SEQ ID NO: 18) to check the correct event of double recombination.

Figure 7:
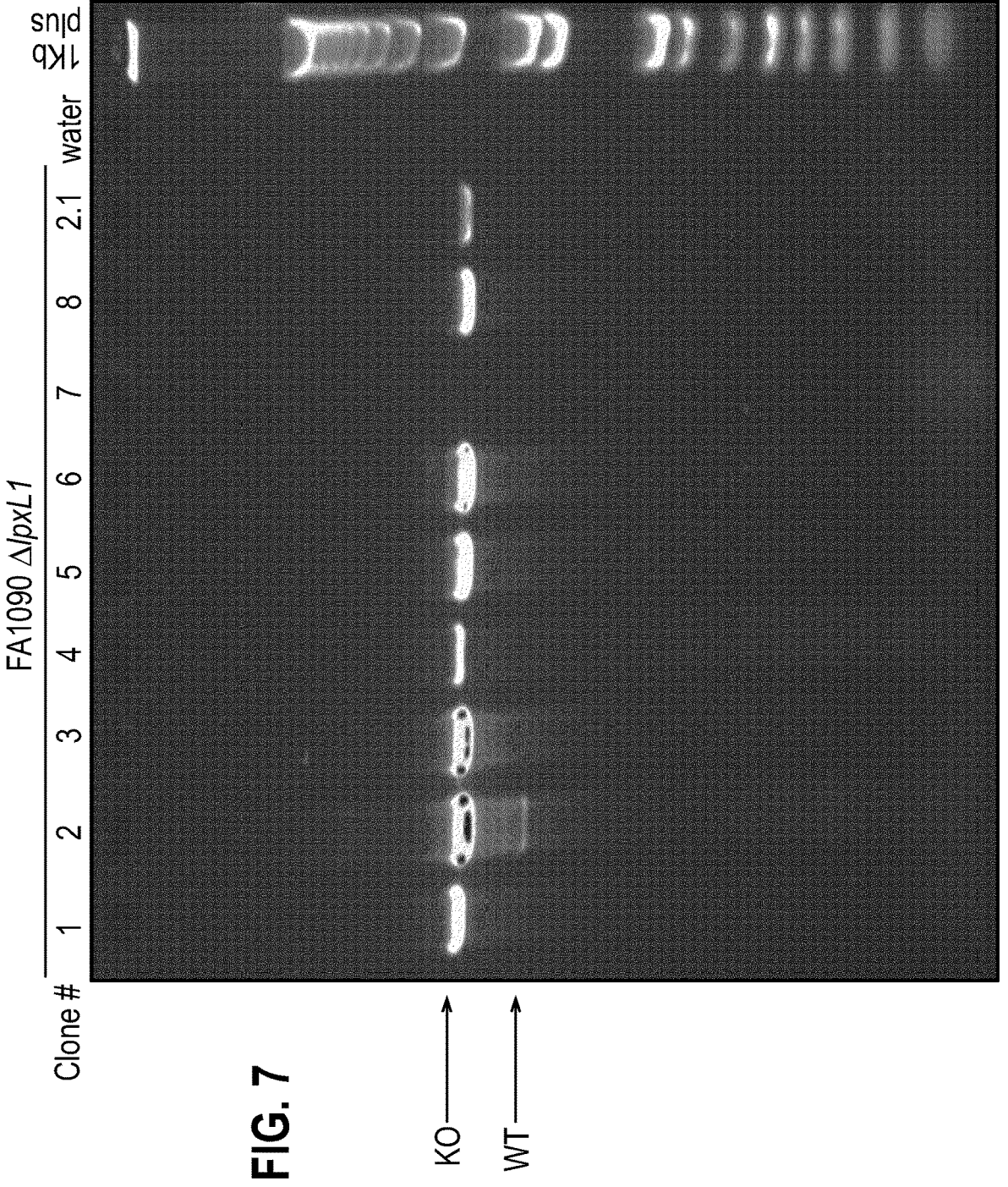
FIG. 7: Agarose gel of the PCR external check of FA1090 Δlpxl1 clones. PCRs were performed with primers external to the recombination event and PCR products were separated by electrophoresis in a 1% agarose gel. Water was used as a negative control for the PCR reaction. The 1 kb plus ladder was used as marker. Arrows indicate the expected bands for the knock-out (KO) mutant and for the wild-type (WT) strain.

The expected length of the amplicon in the wild-type strain was shorter (1703 bp) than the one in the deletion mutant (2344 bp). As shown in FIG. 7, the PCR product from the DNA of the clone #2 has two bands, a shorter one that represents the wild-type and a longer one of the expected lengths of the deletion mutant. All other clones have the longer band, including the subclone #2.1, suggesting that in all these clones the recombination occurred and that these clones are deficient for the lpxl1 gene.

Example 5: Investigating the Presence of Residual FA1090 WT Gonococcus in the FA1090 Single Mutant (Δlpxl1)

During transformation some bacteria acquire natural resistance to the antibiotic used, while not acquiring the resistance cassette from the recombination.

To investigate the presence of residual FA1090 (i.e. WT) cells (FIG. 6C) a PCR with primers specific for the wild-type genome was performed (FIG. 6B). As the primers are specific for the parental strain genome, the presence of a product is indicating the presence of wild-type cells within the total population. On the contrary, the absence of a product indicates a homogenous mutant population.

PCR screenings were performed using Accuprime Taq Polymerase (Thermo Scientific) with internal primers, specific for the wild-type DNA (NGO_lpxL1wtcheck-Fw (CCGCGTTCGAGATGG, SEQ ID NO: 19) and NGO_lpxL1wtcheck-Rev (GCGGAACTGTTTGACGAG, SEQ ID NO: 20).

Figure 8:
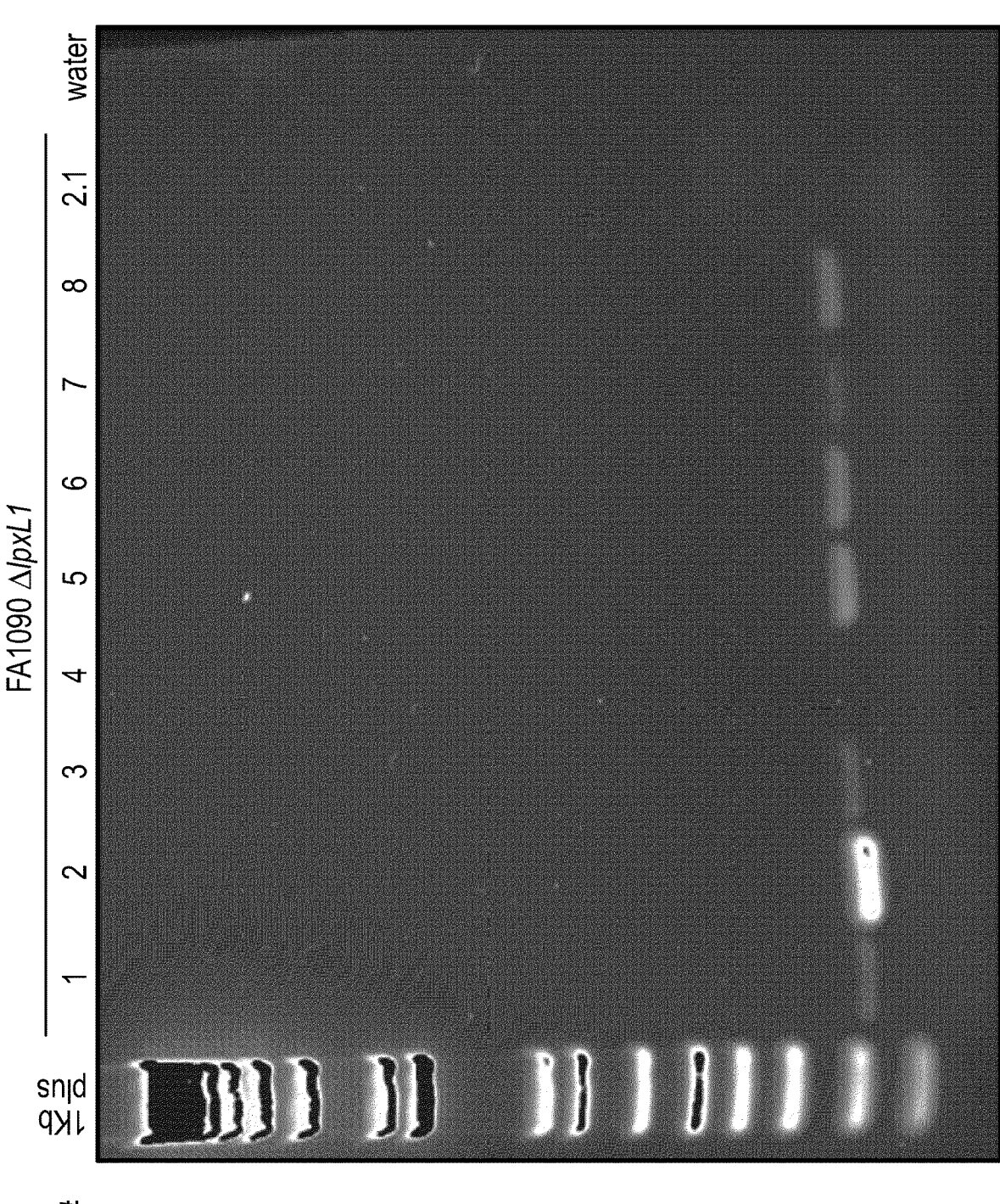
FIG. 8: Agarose gel of the PCR internal check of FA1090 ΔlpxL1 clones. PCRs were performed with primers specific for the wild-type population and PCR products were separated by electrophoresis in a 1% agarose gel. The presence of a band is correlated with the presence of residual wild-type cells in the population. Water was used as a negative control for the PCR reaction. The 1 kb plus ladder was used as marker.

For the generation of the lpxl1 deletion mutant the expected length of the wild-type specific amplicon was 176 bp. Therefore, in clones FA1090 ΔlpxL1 #4 and #2.1 in which no band was observed (FIG. 8), the mutant population was clean from wild-type cells contamination. Hence, the FA1090 ΔlpxL1 #2.1, which also had the proper amplification profile using the external primers, was chosen for further experiments.

Example 6: Penta-acylation of LOS

Deletion of lpxl1 is known to result in a lipooligosaccharide content with penta-acylated form of lipid A. As such, the acylation state of lipid A was assessed using MALDI-TOF spectrometry to confirm loss of Lpxl1 function in OMV's obtained from the FA1090 single mutant (Δlpxl1).
Methods:

Lipid A extraction: Lipid A was precipitated from 100 µg of OMVs released and purified from gonococcus FA1090 wild type and Δlpxl1 (single mutant) strains respectively, using a mild acid hydrolysis with 1% (vol/vol) acetic acid for 3 h at 100° C. Samples were centrifuged at 14,000×g for 15 min; the pellets were resuspended in water and washed twice with water. The pellets were then dried overnight using a SpeedVac, resuspended in 20 µL of chloroform/methanol (4:1 ratio), and mixed with an equal volume of Super DHB solution (Sigma) as previously reported in [Rossi et al. Modulation of endotoxicity of Shigella generalized modules for membrane antigens (GMM4) by genetic lipid A modifications: relative activation of TLR4 and TLR2 pathways in different mutants. J Biol Chem. 2014, 289(36): 24922-35].

MALDI TOF analysis: 2 µL of the Lipid A extract was loaded on the target plate (MTP 384 target plate ground steel BC, Bruker Daltonics) and analysed by Ultraflex MALDI-TOF (Bruker Daltonics) in reflectron ion-negative mode (see Rossi et al reference provided above). A peptide calibration standard (Bruker Daltonics), mixed with the Super DHB solution, was included in each analysis. For MS/MS analysis of lipid A, main peaks from the linear mode analysis were selected for collision-induced dissociation and the resulting fragments were detected by MALDI TOF-TOF in ion negative mode. The spectra represent the integration of 50 single laser shots on 20 different spot areas.

Results: MS analysis of lipid A: Lipid A structures from the wild-type OMVs (i.e. OMVs blebbed from a wild-type FA1090 with no genetic modifications) and the ΔLpxl1 OMV was assessed by MS analysis.

Figure 9A:
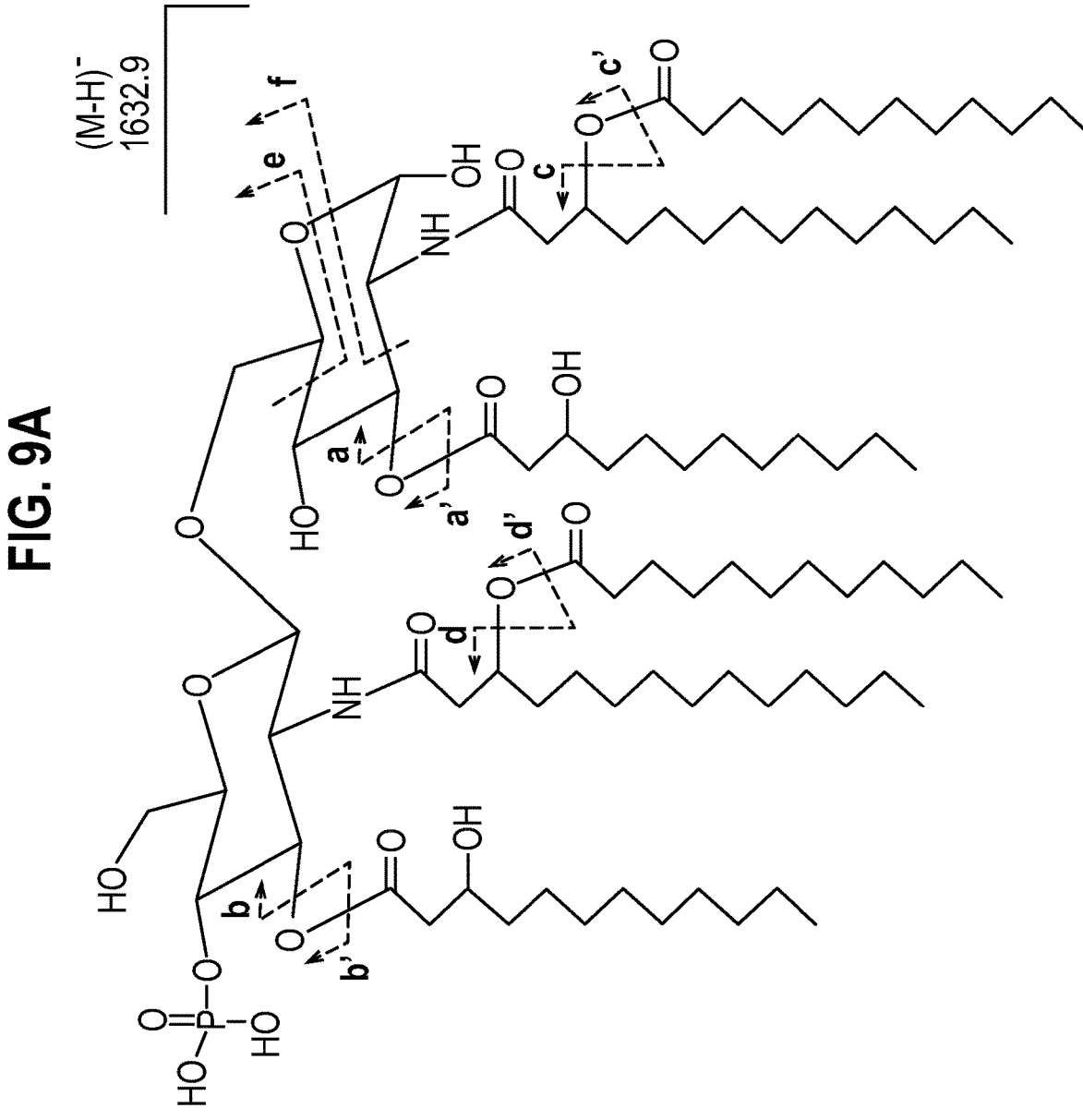
FIG. 9A: The structures of the lipid A purified from the reference batch FA1090 and the mass spectroscopy spectrum thereof, using MALDI-TOF. The recorded spectra show unmodified hexa-acylated lipid A: the highest peak corresponding to the MPLA form, the second to the BPLA form. MALDI-TOF profile of lipid

Lipid A from wild-type OMVs was observed with a major molecular ion at m/z 1,632.03, that agreed with the theoretical mass of hexa-acyl, mono-phosphoryl structure of lipid A (MPLA). In addition to this major form, a diphosphoryl species (BPLA) at m/z 1,711.97 was also identified (FIG. 9A).

Figure 9B:
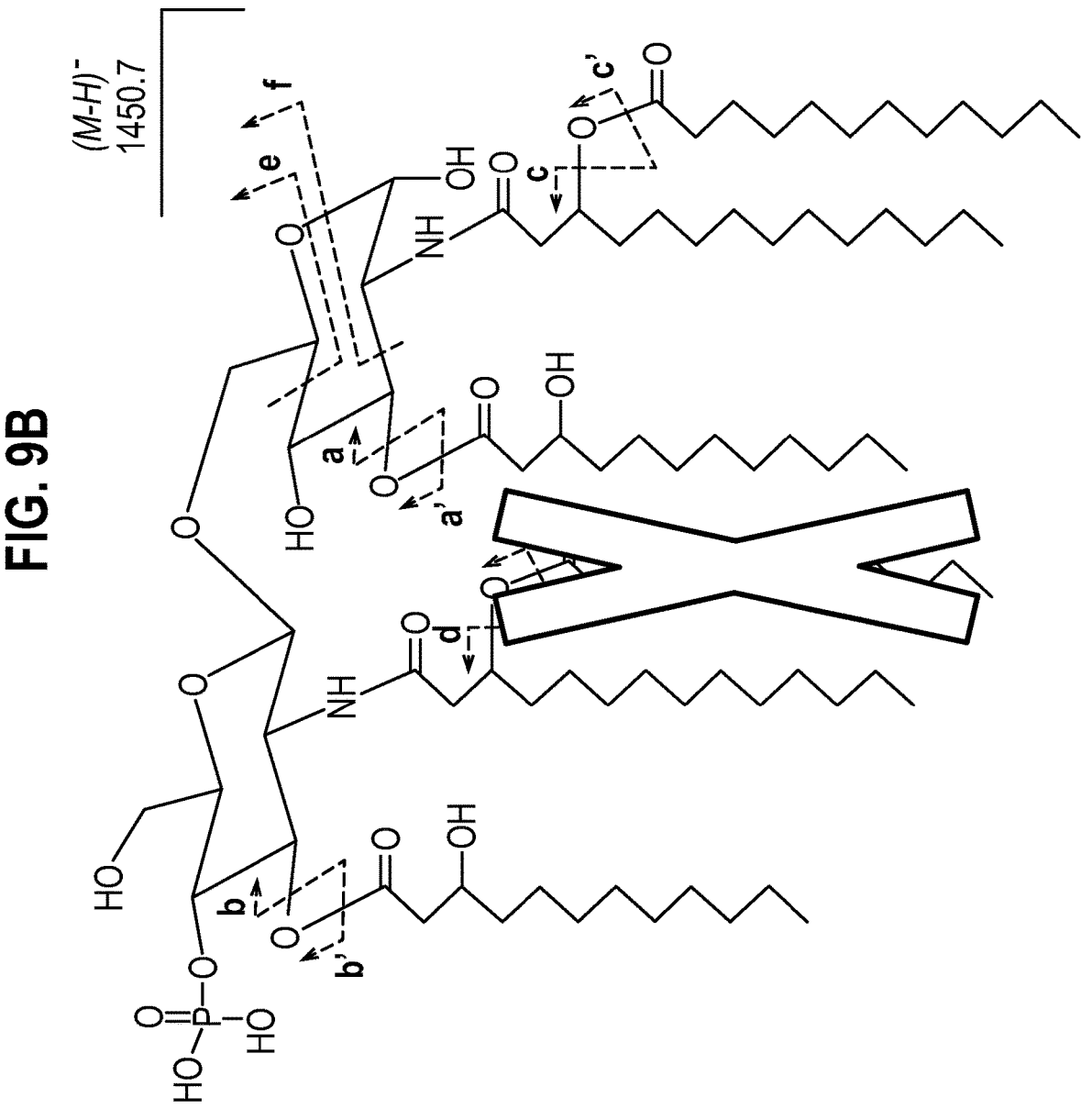
FIG. 9B: The structure of lipid A corresponding to the penta-acylated form purified from genetically modified FA1090 Δlpxl1 and the mass spectroscopy spectrum thereof using MALDI-TOF. When compared to the spectrum from FIG. 9A, the mass differences between the each of the corresponding peaks (MPLA and BPLA) are 182 Da, which is the mass of a lauric acid chain. A signal at m/z 1572, corresponding to a non-identified lipid, is present in both spectra.

A major component with a molecular ion at m/z 1,449.84 was observed from MALDI spectrum acquired from the ΔLpxl1 OMV lipid A (FIG. 9B). The difference of mass of 182 Da observed with the MPLA form of the wild type lipid A is consistent with the lack of a single lauric acid chain (calculated mass: 182.3 Da). In addition, the spectrum of the ΔLpxl1 OMV also revealed a signal at m/z 1,529.79 corresponding to the di-phosphoryl form of the lipid A also lacking the lauric acid chain. No MS signal that could be attributed to the wild type form of the lipid A were observed.

As a result, OMVs produced from FA1090 Δlpxl1 were confirmed by MALDI TOF-analysis to have LOS content with 100% penta-acylated form both mono- and di-phosphoryl species (FIG. 9).

Example 7: Generation of the Double Mutant FA1090 (ΔlpxL1, ΔRmp)

Reduction modifiable protein (Rmp), previously known as PIII, has been shown to induce blocking antibodies which could inhibit the effect of other bactericidal antibodies [Gulati S, et al. Antibody to reduction modifiable protein increases the bacterial burden and the duration of gonococcal infection in a mouse model. J Infect Dis. 2015; 212(2): 311-315] [Joiner K A, Scales R, Warren K A, Frank M M, Rice P A. Mechanism of action of blocking immunoglobulin G for Neisseria gonorrhoeae. J Clin Invest. 1985; 76(5): 1765-1772].

To remove Rmp from the Δlpxl1 single-mutant FA1090 strain (and thus produce the double mutant FA1090 Δlpxl1, Δrmp) the FA1090 Δlpxl1 #2.1 strain was transformed with the pBS Δrmp eryR linearized construct.

FA1090 Δlpxl1, Amp was obtained by double homologous recombination where a region of the coding sequence of the rmp gene was replaced with an antibiotic resistance cassette (Erythromycin).

Figure 10:
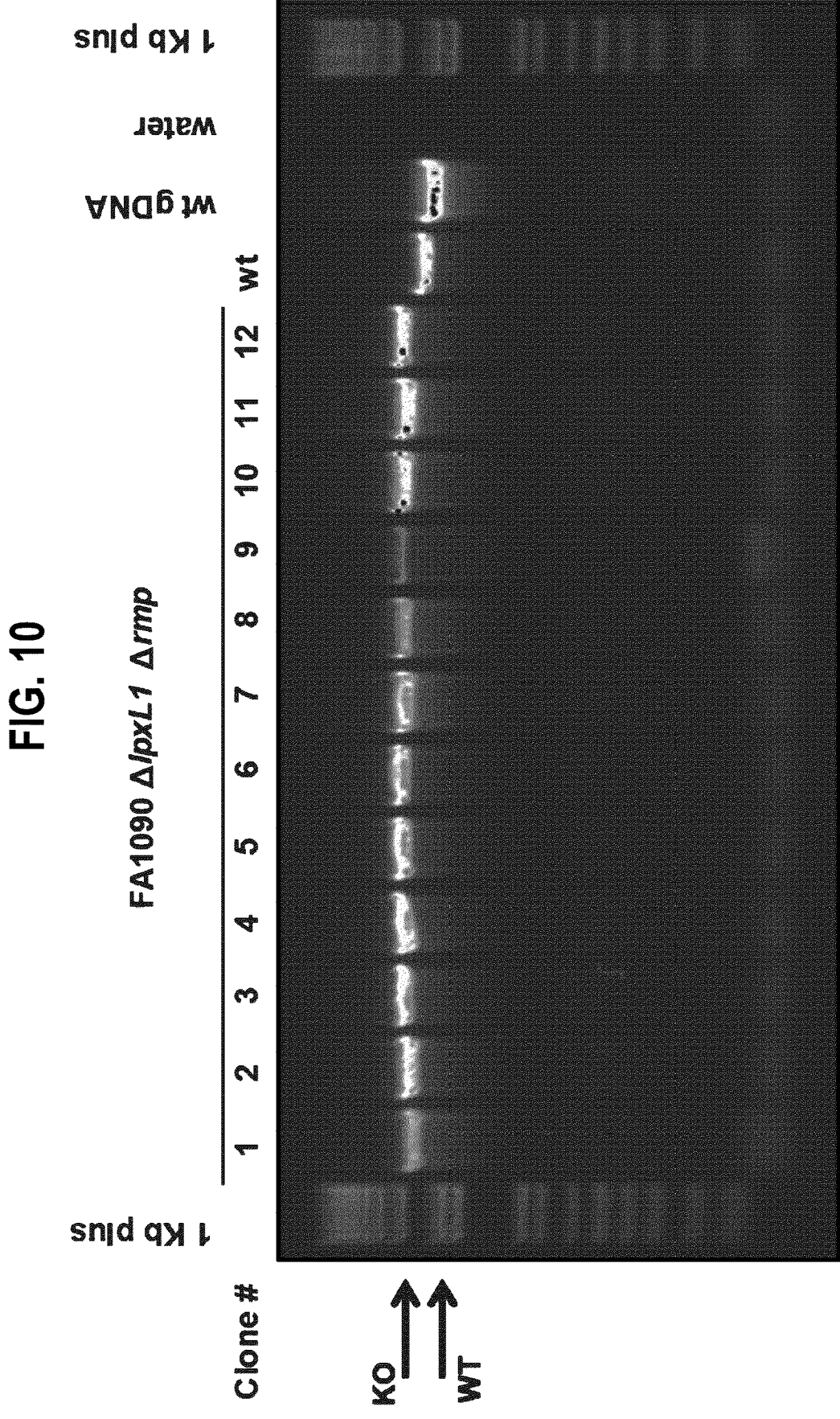
FIG. 10: Agarose gel of the PCR external check of FA1090 Δlpxl1, Δrmp clones. PCRs were performed with primers external to the recombination event and PCR products were separated by electrophoresis in a 1% agarose gel. Both a DNA lysate and a genomic DNA (gDNA) of the wild-type strain were used as a positive control of the PCR reaction and as a comparison with the mutant clones. Water was used as a negative control for the PCR reaction. The 1 kb plus ladder was used as marker. Arrows indicate the expected bands for the knock-out (KO) mutant and for the wild-type (WT) strain.

Mutant Δlpxl1, Amp clones resistant to the erythromycin were selected and amplified and their DNA tested for the presence of the correct mutation (FIG. 10). Using primers external to the recombination event, clones that lost the rmp gene and acquired the gene for the erythromycin resistance were selected.

All transformants were tested by PCR analysis using Accuprime Taq Polymerase (Thermo Scientific) and with external primers (UP_CHECK_NG01577-Fw (GTGTGTCCAGTCGTAGCAGG, SEQ ID NO: 21) DW_CHECK NGO_1577-Rev (AGGGATGATGA-TAAAACCATATCC, SEQ ID NO: 22) to check the correct event of double recombination.

The expected length of the amplicon in the wild-type strain is 2089 bp and the expected length of the amplicon in the deletion mutant is 2590 bp. As shown in FIG. 10, the PCR products of all clones have the expected length for the deletion mutant, while the bands in the wild-type control have shorter apparent size, thus suggesting that the recombination occurred in all clones and that these were deleted for the rmp gene.

Example 8: Investigating the Presence of Residual Single-Mutant FA1090 (ΔLpxl1) Gonococcus Clone #1 (from Example 7) was streaked in a plate with erythromycin and from the derived clone (#1.1), a glycerol stock and a DNA lysate were generated.

To investigate the presence of residual FA1090 Δlpxl1 cells in the generated double-mutant, a PCR was performed with primers specific for the original genome (see FIG. 11). PCR screenings were performed using Accuprime Taq Polymerase (Thermo Scientific) and with internal primers, specific for the wild-type DNA (INTwt_NGO1577-Fw (TCGTACGCAACAACTATGGAG, SEQ ID NO: 23) and INTwt_NGO1577-Rev (CATCAACATATTGAG-GAGCCTG, SEQ ID NO: 24)).

The expected length of the wild-type specific amplicon was 150 bp. A band was observed using the original FA1090 ΔlpxL1 #2.1 as a template.

From the agarose gel it was possible to observe a faint band with DNA of the clone FA1090 ΔlpxL1 Δrmp #1, while in clone FA1090 ΔlpxL1 Δrmp #1.1 no band was observed, suggesting that the mutant population was clean from contamination with the original cells.

The FA1090 ΔlpxL1 Δrmp #1.1 was chosen for further experiments.

Example 9: Confirmation of lpxl1 and rmp Deletion by Next-Generation sequencing Methods: A loopful of bacteria from frozen FA1090 wild-type (wild type), Δlpxl1 (single-mutant, 1KO) and Δlpxl1, Δrmp (double-mutant, 2KO) stock was streaked on an GC+1% Isovitalex agar plate and incubated at 37° C. and 5% $CO_2$ for 24 h. Bacteria were resuspended in 5 mL of PBS up to an optical density of 0.6 at 600 nm (Ultrospec 10 cell density meter GE Healthcare). Two milliliters of bacterial suspension were centrifuged in duplicate for 5 minutes at 13000 rpm at 4° C., the supernatant was discarded, and the resulting pellet was used for DNA purification using the GenElute Bacterial Genomic DNA Kits (Sigma Aldrich Cat #NA2110) according to manufacturer's instructions for Gram-negative bacteria. Elution was performed with 100 μL of pre-warmed (70° C.) nuclease-free water (ThermoFisher cat #10977-035). Purified DNA concentration was determined with NanoDrop 1000 UV-Vis spectrophotometer and DNA integrity was checked by 0.8% TAE agarose gel electrophoresis.

Next generation sequencing libraries were prepared using Nextera XT DNA Library Prep, following the manufacturer's protocol (Document #15031942 v02 April 2017, Illumina). Time tagmentation was 8 minutes and library was tagged with sequencing adapters (Nextera XT Index kit 24 indexes-96 samples; REF 15055294; LOT 10026832). Library was normalized and diluted to 1:25. Other libraries were constructed using Nextera DNA Flex Library Prep kit, following the manufacturer's protocol (Document #1000000025416 v07;

May 2019; Illumina, USA). 300 ng of DNA were tagmented, cleaned up with magnetic beads and amplified for 5 cycles of PCR using Illumina Enhanced PCR Mix and dual index adapters. The indexes were chosen following Index Adapter Pooling guide, Nextera DNA CD Indexes, Illumina (Document #1000000041074 v09). Amplified DNAs were cleaned up and size selected for average fragment size of 500-600 base pairs. The final libraries were checked on Agilent 2100 Bioanalyzer with a High Sensitivity DNA kit. Libraries were pooled and diluted to 4 nM concentration. The pool was denatured and spiked with 1% non-indexed PhiX control library, following MiSeq System (Denature and Dilute Libraries Guide Document #15039740 v10, Illumina). Denatured libraries were loaded at a concentration of 12 pM. All libraries were run on an Illumina MiSeq sequencer to perform sequencing using the 500-cycle MiSeq Reagent Kit v2 (Illumina, Cat. No. MS-103-1003) with paired-end reads of 250 base pairs (2×250).

Results: Genomic DNA of the FA1090 Δlpxl1, Δrmp #1.1 strain was isolated and the complete genome was assembled. From this, the sequence of the two deleted loci was extracted.

Next-generation sequencing was used to confirm,
- a) the presence of lpxl1 locus in the wild-type FA1090 (2) isolate strain (FIG. 12),
- b) the expected deletion of lpxl1 in the FA1090 Δlpxl1 Δrmp mutant (FIG. 13).
- c) the presence of rmp locus in the wild-type FA1090 (2) isolate strain (FIG. 14); and,
- d) the expected deletion of rmp in the FA1090 Δlpxl1 Δmutant (FIG. 15).

Example 10: OMV Preparation

OMVs were prepared in the absence of detergent and are therefore native OMVs (nOMVs).

To produce OMVs for the analyses presented herein, 500 mL of bacterial growth was centrifuged at 12,000 xg for 30 minutes. The pellet was discarded.

The 500 mL supernatant was incubated with 100 μl of Benzonase (1000 U/mL) for 24-72 hours at 4° C. The inoculant was filtered through a 0.22 μm filter and then a series of concentration and washing steps were performed using Tangential Flow Filtration (TFF) with a 300 kDa cut off. A first concentration to 250 ml was followed by a buffer exchange with 5 L PBS (20 CV). A second concentration to 50 ml was then followed by a second wash with 2 L PBS (40 CV). A final concentration step to 5-15 ml was then performed.

Purified OMVs in PBS were then obtained by filtering again with a 0.22 μm syringe filter.

Example 11: Confirmation of Rmp Protein Deletion

SDS-PAGE and Peptide Mass Fingerprinting Method: OMVs isolated from wild-type FA1090 gonococcus, FA1090 ΔlpxL1 (single mutant) and FA1090 ΔlpxL1, Δrmp (double mutant), respectively was denatured for 5 min at 95° C. in SDS sample buffer containing 2% SDS final. Subsequently, 10 μg of each preparation was loaded onto 4-12% polyacrylamide gels (Bio-Rad). The gel was stained with Coomassie blue and the bands of interest were excised from the gel, washed once with 50 mM ammonium bicarbonate and acetonitrile (50:50, vol/vol), once with pure acetonitrile and air-dried. 50 μl of 0.012 μg/μl sequencing grade modified trypsin (Promega, Madison, WI) in 50 mM ammonium bicarbonate was added to the dried bands and the digestion was allowed to proceed overnight at 37° C. The solution containing the peptide mixtures was loaded onto a C18-reversed phase column Acquity UPLC peptide CSH C18 130 Å, 1.7 μm 1×150 mm and separated with a linear gradient of 28-85% buffer B (0.1% (v/v) formic acid in ACN) at a flow rate of 50 μl/min and 50° C. MS data was acquired in positive mode on a Q-Exactive biopharma plus mass spectrometer using a data-dependent acquisition mode (DDA) dynamically choosing the five most abundant precursor ions from the survey scan (300-1600 m/z) at 70,000 resolution for HCD fragmentation. Automatic Gain Control (AGC) was set at 3×106. For MS/MS acquisition, the isolation of precursors was performed with a 3 m/z window and MS/MS scans were acquired at a resolution of 17,500 at 200 m/z with normalized collision energy of 26 eV. MS spectra were analysed for protein identification using by Peaks X software (Bioinphormatics solution) using a database containing protein sequences deduced from a sequenced *Neisseria gonorrhoeae* FA1090 genome.

Results: OMVs obtained from wild-type, Δlpxll (single mutant) and Δlpx1, Δrmp (double mutant) FA1090 gonococcus were analysed by SDS-PAGE. Following Coomassie staining of the gel, the protein content of the band which migrated with an apparent molecular weight of ~28 kDa were identified. Proteins were in gel tryptic digested and the generated peptides were analysed by LC-MS/MS. Rmp and Opacity proteins B and D were identified from the bands observed from the wild type OMVs and the Δlpxll (single mutant) OMVs. Only the Opacity proteins B and D were identified from the band observed from the ΔLpxll, Δrmp (double mutant) OMVs (see FIG. 16).

Example 12: Comparison of the Genetic Variability Across Global Gonococci Strains Based on the Protein Components Present in OMVs Produced by FA1090 Double Mutant Essentially the same genomic comparisons (as outlined in Example 1) were performed considering only the protein components of the outer membrane vesicles blebbed from the FA1090 double mutant gonococcus Δlpxll, Δrmp.

The list of protein components of the OMVs was derived by mass spectrometry characterization of the OMV products as follows.

Four different OMV productions from FA1090 ΔLpxll, Δrmp double mutant (2KO) strain were considered for mass spectrometry (MS) analysis. Three of these four productions were analysed twice with two different digestion protocols. In total 7 preparations were analysed by MS. MS data of each sample were analysed independently to identify proteins and their relative abundance. Proteins were annotated in comparison to FA1090 public genome annotation and by PSORTb software to predict cellular localization. The list of proteins of each independents MS analysis were filtered by removing proteins predicted as cytoplasmic and having a relative abundance below 0.05%. Finally, the resulting final list of 59 proteins was determined by joining the seven filtered lists revealed by each MS experiment.

Of the 59 proteins that were identified by MS, a number of proteins were identified across all OMV productions (outlined in Table 4 below) and were observed at concentrations of over 0.6% (w/w) of the total OMV protein.

TABLE 4

| Known proteins quantified in each lot with an average abundance ≥0.6% w/w and commonly identified in all the 7 lots are reported. | | | | | | | | | | | |
|---|---|---|---|---|---|---|---|---|---|---|---|
| Uniprot Code | Description | Cell Local- isation [b] | Protein Amount (%, w/w) in each of the seven samples analysed | | | | | | | Average | StDev |
| | | | TRD4 | TRD5 | TRD6 | TRD7 | TRD8 | TRD9 | TRD10 | | |
| Q5F5V7 | major outer membrane protein (PorB 1B) | Outer Membrane | 72.2 | 72.4 | 79.1 | 64.0 | 60.2 | 77.1 | 70.4 | 70.8 | 6.7 |
| — | opacity protein family (Opa) [a] | Outer Membrane | 9.1 | 6.9 | 5.7 | 4.8 | 9.0 | 6.5 | 6.7 | 7.0 | 1.6 |
| Q5FAD2 | type IV pilus secretin (PilQ) | Outer Membrane | 1.7 | 2.0 | 1.6 | 1.3 | 1.8 | 2.1 | 1.6 | 1.7 | 0.3 |
| Q5F5W8 | outer membrane protein assembly factor (BamA) | Outer Membrane | 1.6 | 1.6 | 1.4 | 1.3 | 1.7 | 1.6 | 1.5 | 1.5 | 0.1 |
| Q5F845 | TonB-dependent | Outer Membrane | 0.7 | 0.6 | 0.4 | 0.6 | 0.9 | 0.3 | 0.8 | 0.6 | 0.2 |

TABLE 4-continued

Known proteins quantified in each lot with an average abundance ≥0.6% w/w and commonly identified in all the 7 lots are reported.

| Uniprot Code | Description | Cell Local-isation [b] | Protein Amount (%, w/w) in each of the seven samples analysed | | | | | | | Average | StDev |
|---|---|---|---|---|---|---|---|---|---|---|---|
| | | | TRD4 | TRD5 | TRD6 | TRD7 | TRD8 | TRD9 | TRD10 | | |
| Q5F9W0 | receptor protein Outer membrane protein assembly factor (BamD) | Lipoprotein | 0.6 | 0.7 | 0.6 | 0.7 | 0.9 | 0.8 | 0.6 | 0.7 | 0.1 |

[a] Due to primary sequence redundancy the amount of Opa proteins is representative of the family.
[b] Cell localization predicted by PSORTb Version 3.0.2 and manually revised fore lipoprotein prediction The 59 proteins that were identified using MS characterisation were used to define a multilocus typing schema (at protein sequence level). All the 4058 strains of the collection were typed to assign protein alleles identifiers to each strain.

As described in Example 1, these extended profiles were used to measure variations between strains and to measure a genetic distance. The optimal number of clusters derived from the silhouette score analysis, was 22 groups.

As described previously, the centrality score measures how much each strain is central or peripheral in the gonococcal population in terms of genetic distance. Based on genetic distance the centrality of the FA1090 double mutant OMV composition is reported in FIG. 17). Centrality scores for a subset of strains is shown in Table 5 below.

TABLE 5

| Strain | Centrality Score |
|---|---|
| FA1090 (1) Genbank | 33.9 |
| FA1090 (2) | 32.2 |
| F62 | 31 |
| SK92-679 | 28.3 |
| GC_0817560 | 25.1 |

This analysis is in agreement with the previous analysis conducted at whole genome level (see Example 1). Moreover, the analysis also confirms that, for the protein components of FA1090 OMVs, the FA1090 is genomically distant from the other strains of the collection.

Example 13: Testing Capacity of OMVs from FA1090 Mutants to Activate TLR-4

Deletion of the lpxl1 gene results in bacteria that produce only a penta-acylated lipid A and exhibits reduced toll-like receptor 4 (TLR4) signaling [Zhou X, Gao X, Broglie P M, et al. Hexa-acylated lipid A is required for host inflammatory response to Neisseria gonorrhoeae in experimental gonorrhoea. Infection and Immunity. 2014 January; 82(1):184-192].

To evaluate the capacity of penta-acylated form of lipid A expressed by FA1090 Δlpxl1 mutant and FA1090 ΔlpxL1, Δrmpmutant to activate TLR4, OMVs (referred to as GMMA in FIG. 18) prepared from these mutants as well as OMVs from the wild-type FA1090 strain were tested on HEK293 cells stably transfected with human TLR4 and a reporter plasmid expressing luciferase under the control of NF-kB.

These data confirm that both FA1090 Δlpxl1 (single-mutant or 1KO) and FA1090 ΔlpxL1, Δrmp (double-mutant or 2KO) mutants express a mutated form of lipid A which has a highly reduced capacity of activating TLR4 compared to that expressed by the wild-type FA1090 strain (see FIG. 18).

Example 14: Comparison of Liquid Growth of FA1090 Double-Mutant (Δlpxl1, Δrmp) Against Liquid Growth of Double-Mutants (ΔlpxL1, Δrmp) Prepared in Other Gonococcal Strains The objective of this experiment was to directly compare the growth profiles of a number of Δlpxl1, Δrmp strains in liquid cultures from plate (not adapted to liquid growth). The ability of double-mutant strains to grow in liquid cultures was an important consideration to assess the scale-up potential of the chosen vaccine strain.

Double-mutant (Δlpxl1, Δrmp) were generated in the FA1090, F62, SK92-679, BG13, BG17 and BG27 strains as described in Examples 3-4 and 7.

The following strains were streaked on GC+isovitalex 1% plates from frozen glycerol stocks.

1. FA1090 Δlpxl1, Δrmp (FA1090ΔΔ)

2. F62 Δlpxl1, Δrmp(F62ΔΔ)

3. SK92-679 Δlpxl1, Δrmp(SK92-679ΔΔ)

4. BG13 Δlpxl1, Δrmp(BG13ΔΔ)

5. BG17 Δlpxl1, Δrmp(BG17ΔΔ)

6. BG27 Δlpxl1, Δrmp(BG27ΔΔ)

A loopful of bacteria from glycerol stock was streaked in order to obtain single colonies. 4 plates were prepared for each strain. Plates were incubated at 37° C. and 5% $CO_2$ for 30 hours.

Two different media were prepared for this experiment:

1. GC+isovitalex 1%+lactate 7.5 g/L (or GC+lactate): 3 g of Na-(DL)lactate (Sigma Aldrich) were solubilized in 400 mL of GC+isovitalex 1% medium and filter sterilized with 500 mL 0.22 μm filter bottle (Millipore).

2. MCDMI-mod (or MCDMI-5 g/L lactate): 1 L of medium was prepared according to the recipe below (Table 6): PH was adjusted to 7 with NaOH and then the medium was filter sterilized with 1 L 0.22 μm filter bottle (Millipore)

TABLE 6

| Medium composition (MCDMI-mod) | |
| --- | --- |
| Component | Flask (g/L) |
| Soy peptone (BBL Phytone*) | 15.00 |
| NaCl | 5.80 |
| MgSO4—7H20 | 2.56 |
| K2HPO4—3H20 | 5.24 |
| L-Glutamic Acid | 3.00 |
| L-Argenine | 0.20 |
| L-Serine | 0.50 |
| L-Cysteine | 0.30 |
| L-Glycine | 0.25 |
| Fe(III) Citrate | 0.01 |
| CaCl2 | 0.02 |
| Na-(DL)Lactate | 5.00 |
| Betaine-H20 | 0.34 |
| Vitamin Mix-0.5 g/L Tiamina, 0.5 g/L Riboflavina, 0.5 g/L Piridossina, 0.5 g/L Niacinamide (500x) | 5x |

All strains were resuspended from agar plates in 6 mL of GC+lactate. Only single colonies were used.

Suspensions were then diluted in 50 mL of both GC+lactate and MCDMI-mod media in 250 mL disposable baffled shaking flasks with vented cup (Corning) to an $OD_{600\ nm}$ (optical density at 600 nnm) of about 0,3. Starting $OD_{600\ nm}$ was recorded and flasks were incubated at 37° C. and 160 rpm shaking.

$OD_{600\ nm}$ was monitored until stationary phase was reached.

Different growth performances were observed in the two different media (data shown in FIG. 19)

In GC supplemented with lactate, poor growth was only observed with F62ΔΔ and SK92-679ΔΔ.

Growth of other strains was successful. In MCDMI, F6244 was the best performer. In general, the MCDMI medium appeared to be suitable for the growth of both F62 and FA1090 double mutant strains ("ΔΔ" denoting double mutants), while BG13ΔΔ and BG27ΔΔ were able to grow but with were limited in terms of growth rate and biomass yield. For BG17ΔΔ, the MCDMI-mod medium seems to be not suitable for liquid growth. SK92-679ΔΔ showed growth defects in both media tested.

In summary,

BG13ΔΔ and BG27ΔΔcan be cultivated in both media with strong preference for GC based medium. The opposite situation was observed for F62 ΔΔ (strong preference for MCDMI medium)

BG17ΔΔcan exclusively be cultivated in GC based medium

SK92-672 ΔΔshows growth defects in both media tested with a slight growth observed only in GC based medium.

FA1090 ΔΔcan be cultivated in both media making it a flexible strain for possible future scale up. It shows comparable growth rate in both media tested. However, depending on the medium, other double mutant strains show comparable growth (F6244 in MCDMI-mod and BG13ΔΔ, BG17ΔΔ and BG27ΔΔ in GC+lactate).

Example 15: Evaluation of OMV Productivity by Direct Quantification of OMV from Culture Supernatant Using the six Δlpxl1,Δrmp strains (as utilized in Example 14) OMV productivity was assessed:

Cultures were pelleted at 4000 rpm for 30 min and the supernatants were filtered with the stericup 0.22 μm filters.

OMV productivity was estimated for each strain in the two growth conditions (described in Example 14) using the fluorescent dye, FM4-64. The dye fluoresces when intercalated in the membrane double layer. Fluorescent intensity is proportional to the amount of membranes in culture supernatants (OMVs) in a linearity range determined using a standard curve. For each sample the dye was diluted 1:100 directly into the sample supernatants. The standard curve was prepared by serially diluting purified OMV from FA1090 in the same medium used for growth and with FM4-64 dye diluted 1:100.

For each sample fluorescence was recorded with and without dye addition and background fluorescence of supernatants without dye were subtracted from the dye-treated samples values. A blank with medium only was also subtracted. OMV concentration in culture supernatant was evaluated by value extrapolation from standard curve and reported in FIG. 20 as an average of the two biological replicates for each strain and growth condition.

As shown in FIG. 20A, the OMV volumetric productivity was higher in GC based medium with the exception of F6244 strain reflecting the different biomass reached by the different strains into the two media. Surprisingly, high values were obtained also for SK92-67944 strain despite the very poor growth observed especially in MCDMI medium. The highest productivity was reached by FA1090ΔΔ in GC based medium.

The calculated values were also normalized on the different OD600 nm reached by each strain in each condition to compare the specific productivity (see FIG. 20B). In terms of specific productivity, the SK92-67944 strain shows very high value as expected considering the low OD600 nm reached in both media and the relatively high volumetric productivity of OMVs registered. However, it is unclear whether these productivity values are due to actual OMV release or just to cell debris nonspecifically released in the culture supernatant.

Regarding the other strains in GC based medium the range of productivity is 20-30 mg/L/OD for FA1090ΔΔ, BG13ΔΔ and BG17ΔΔ while it is slightly higher for F6244 and lower for BG2744. A similar situation was observed in MCDMI-mod medium where most of the strains show productivity range of 10-20 mg/L/OD and slightly lower for BG2744.

Since the double-mutant mutants from FA1090 and F62 both demonstrated sound growth performance and were deemed the most productive strains in terms of OMV production, (excluding the anomalous finding with SK92-679 which was caused by low biomass), OMVs from these two strains were selected for immunogenicity analysis.

Example 16: Evaluate Immunogenicity of OMV from FA1090 Mutants

OMVs were prepared from FA1090 Δlpxl1,Δrmp double-mutant (2KO) and also from a similar ΔlpxL1,Δrmp double-mutants of the F62 strain of N. gonorrhoeae.

Immunogenicity of these OMVs was tested in vivo in CD1 mice.

7-week-old CD1 female mice were immunized two times on days 1 and 29 via the intraperitoneal (IP) route of administration with these OMV preparations (10 μg) formulated in Alum (3 mg/ml) or with Alum alone. Sera were collected before the first dose of vaccine (pre-immune sera) and after the second dose of vaccine (post2 sera).

Functional antibodies were measured by human serum bactericidal assay (hSBA) and bacterial adhesion inhibition (BAI).

hSBA Method

Bacteria were streaked from a frozen aliquot on a round GC+1% Isovitalex agar plate and incubated for 16 (±2) hours at 37° C. with 5% $CO_2$.

Following incubation colonies were picked using a 10 μl sterile bacterial loop and inoculated in 10 ml of GC Broth containing 1% Isovitalex (pre-heated at 37° C.) to give a starting level of optical density (OD, 600 nm) of 0.1. The bacterial suspension was then incubated at 37° C. with gentle shaking (180 rpm) until the culture reached an OD600 nm≅0.3-0.4. Bacteria were then diluted 1:10.000 in SBA buffer (DPBS, 1% BSA, 0.1% glucose).

Heat inactivated mouse sera was then diluted in SBA buffer to have a final volume in plate of 25 μl/well. 17 μl/well of diluted bacteria and 8 μl/well of normal human serum were then added. The reaction mixture was incubated for one hour at 37° C. with gentle shaking. After the reaction, 7 μl of each well was plated onto square GC+1% Isovitalex plates and incubated at 37° C. 5% $CO_2$ overnight.

Following incubation, the number of colonies in each spot on the plates was manually counted and recorded (colony forming units, CFU) in each spot on each of the plates. The plates were acquired by MACROLAB instrument.

Negative controls were bacteria tested in the presence of heat inactivated complement and serum sample to detect the potential serum toxicity and bacteria tested in the presence of active human complement without serum sample to detect potential complement toxicity.

The bactericidal titer was calculated as the reciprocal of the serum dilution giving 50% of killing compared to the control without serum.

BAI Method

Day −4: SV-HUC-1 cells were seeded (35000 cells/well) in 96-well plate in F-12 Nut mix medium+10% FBS.

Day −1: Bacteria were streaked from a frozen aliquot on a round GC+1% Isovitalex agar plate and incubated overnight at 37° C.

Day 0:

Step 1) Bacterial preparation: Bacteria were grown up to $A_{600}$ nm=0.5 in medium GC 1% isovitalex. Bacteria were then stained with oregon green to reach a final A600=0.05.

To perform the staining bacteria were centrifuged for 5 minutes at 8000 rpm and then resuspended in 1 mg/ml Oregon green diluted 1:200 in PBS. The stained bacteria were then incubated for 15 minutes at 37° C., washed in PBS and resuspended in 1 ml PBS/BSA 2%.

Step 2) Sera Dilutions: In a 96 round wells plate, sera were diluted 1:100 and then were serially diluted (depending on homologous or heterologous strains) for 10 dilutions points (1:100 to 1:51200 or 1:100 to 1:1968300).

Step 3) Neutralization: 60 microliters of sera+60 microliters of bacteria was then incubated for 15 minutes at room temperature.

Cells were washed 3 times in PBS before adding sera+bacteria (100 μl/well) and then incubated for 1h at 37° C. Following a second wash (3 times in PBS) cells were resuspend in formaldehyde 4%, for 20 minutes at room temperature in the dark. After another wash (1 time in PBS) they were then resuspended in 100 μl $H_2O$ per well.

Plates were read on an Opera Phenix (or stored at +4° C. in the dark). BAI was calculated as a percentage of Bacterial Adhesion Inhibition induced by each dilutions of serum sample compared to bacteria in the absence of serum as follows;

% Bacterial adhesion inhibition is computed for each sample j at each dilution i as, $$100 - \frac{\text{All bacteria Volume }[\mu m^3]_{ji}}{\text{Mean all bacteria volume alum}} * 100$$

0% bacteria volume is equal to the Average of Bacteria Volume observed for serum from Alum immunized samples 100% bacteria volume is equal to 0—no adhesion is observed.

Results:

hSBA was measured against FA1090, WHO-M, F62, MS11, WHO-N, and SK92-679 strains in pooled sera collected after two immunizations using human serum as complement source (FIG. 21).

The results show that for five out of six tested strains, OMVs (referred to as GMMA in FIG. 21) from FA1090 double-mutants were surprisingly able to induce SBA titers higher than the titers induced by OMVs produced from a similar Δlpxll, Δrmp double-mutant in the F62 strain. Both OMVs from FA1090 and F62 double-mutants (Δlpxll, Δrmp) were unable to induce bactericidal titers against the SK92-679 strain.

BAI was tested against FA1090 (FIG. 22A), SK-92-679 (FIG. 22B) and WHO-M (FIG. 22C) strains in pooled sera collected after two immunizations.

The results show that for all tested strains, OMVs (referred to as GMMA in FIG. 22) from FA1090 2KO induce functional antibodies able to inhibit bacterial adhesion to cells.

Example 17: Evaluate Induction of Anti-Rmp Antibodies by OMVs from FA1090 Mutants 7-week-old CD1 female mice were immunized two times on days 1 and 29 IP with 1 lot of OMVs from FA1090 ΔlpxL1 mutant (or 1KO) and two lots of OMVs from FA1090 Δlpxll,Δrmp double-mutant (or 2KO) formulated in Alum (as described above).

Anti-rmp IgG were measured by Luminex assay on pooled sera.

The results in FIG. 23 show that while the OMVs (referred to as GMMA in FIG. 23) from FA1090 ΔlpxL1 single-mutant (1KO) are able to induce production of antibodies against rmp, OMVs from FA1090 double-mutant (2KO) does not induce anti-rmp IgG, further demonstrating the absence of this protein in FA1090 2KO.

Example 18: Rmp Deletion Results in a Gonococcus that is Hyperblebbing

Ten 2-L scale fermentations were performed. Three with FA1090 Δlpxll (Runs #1 to 3) and seven with FA1090 Δlpxll, Δrmp (2KO) strain (runs #4 to 10). The yield of OMVs were calculated at the point of concentrated bulk (CB) which corresponds to the OMV fraction obtained following the final filtration step (in the process outlined in Example 10). Data is presented below in Table 7.

TABLE 7

| Run | Gono Strain | OD590 at harvest | Process yield @ CB mg TP/L SNF | Productivity per OD | Average productivity per OD (STDEV) |
|---|---|---|---|---|---|
| 1 | 1KO FA1090 Δlpxl1 | 6.7 | 16 | 2.39 | 2.26 (0.14) |
| 2 | 1KO FA1090 Δlpxl1 | 6.6 | 15 | 2.27 | |
| 3 | 1KO FA1090 Δlpxl1 | 7.1 | 15 | 2.11 | |
| 4 | 2KO FA1090 Δlpxl1, ΔRmp | 4.8 | 36 | 7.5 | 11.93 (3.86) |
| 5 | 2KO FA1090 Δlpxl1, ΔRmp | 3.9 | 56 | 14.36 | |
| 6 | 2KO FA1090 Δlpxl1, ΔRmp | 4.3 | 36 | 8.37 | |
| 7 | 2KO FA1090 Δlpxl1, ΔRmp | 4.4 | 52 | 11.82 | |
| 8 | 2KO FA1090 Δlpxl1, ΔRmp | 3.0 | 57 | 19.00 | |
| 9 | 2KO FA1090 Δlpxl1, ΔRmp | 4.1 | 45 | 10.98 | |
| 10 | 2KO FA1090 Δlpxl1, ΔRmp | 5.5 | 63 | 11.45 | |

The Δlpxl1 (single mutant) reaches a higher final OD OD590 at harvest compared to the Δlpx1,Δrmp (double mutant), i.e. 6.8±0.3 vs 4.3±0.8. However, OMV yield determined at concentrated bulk is more than double for the Δlpx1,Δrmp (double mutant) (49±11 versus 15±1 mg proteins/L filtered supernatant). Therefore the productivity (per OD) is 5.28 (2 dp) times higher in the double mutant.

Example 19: Follow-Up Immunogenicity Study in CD1 Mice

Study Design: Female CD1 mice aged between 7 and 8 weeks old (10/group) were immunized intraperitoneally (IP) 3 times at days 1, 29 and 57 with seven different lots (labelled TRD4 to TRD10) of 2KO (Δlpxl1,Δrmp) FA1090 OMVs (10 µg in 200 µL), adsorbed to Alum (3 mg/mL), or Alum alone (200 µL) or the comparator vaccine Bexsero (200 µL).

Bexsero was used as a comparator vaccine due to observations that the meningococcal group B outer-membrane vesicle component of Bexsero is able to cross-protect against gonococcal infection (Petousis-Harris H et al. *Lancet* 2017; 390: 1603-1610).

The OMV Lots were prepared as previously described (see Example 10) with the exception that the fermentations were performed at 2 L scale and an aliquot corresponding to 400-550 mL of filtered supernatant for each run was processed in order to purify the OMVs.

Blood samples were taken before 1st vaccination (day 0), 4 weeks after 2nd vaccination (4wp2) and 2 weeks after 3rd vaccination (2wp3). Vaginal washes were taken at 2wp3.

The analysis of the immune response was performed on pooled sera from animals immunized with all seven lots of 2KOFA1090 OMVs testing 4wp2 and 2wp3. A more extensive and statistically powered analysis of the immune response was performed on single sera 2wp3 and vaginal washes 2wp3 from animals immunized with three (TRD4, TRD5 and TRD9) out of seven lots. TRD4, TRD5 and TRD9 were selected based on their purity (less GROEL protein contamination), as determined by Western Blot (data not shown).

Methods:

hSBA was measured as described in Example 16. Ten heterologous strains were selected based on the genetic analyses conducted in Example 12 (i.e. a panel of strains was selected which are representative across different genetic clusters). Strains were also selected that express different PorB variants as follows:

PorB 1a Strains— SK92-679, WHO-F, WHO-G, WHO-N

PorB 1b Stains— FA1090, F62, MS11, BG27, WHO-M, BG8. GC14

Quantification of IgG in sera and vaginal washes or IgA in vaginal washes against the FA1090 2KO vaccine candidate was made using Luminex essentially as described below.

Luminex Magplex beads were equilibrated at room temperature and prepared for use according to the manufacturer's instructions. The activated and washed beads were incubated for 2 hours with 40 ug/mL of 2KOFA1090 OMVs (TRD9) suspended in 50 mM MES pH 5. Coupled beads were finally washed twice with PBS/0.05% Tween and stored in 500 µL of PBS/ 0.05% Tween/0.5% BSA (Assay buffer) at 4° C.

For individual sera testing, each plate was considered as an independent test and contained 8 blank wells, 2 replicates of Standard serum (STD) and 9 sera to be tested. For individual vaginal washes testing, each plate was considered as an independent test and contained 10 blank wells, 2 replicates of Standard serum (STD) and 10 vaginal washes to be tested.

Sera and STD were pre-diluted in Assay buffer then, 8 consecutive 3-fold dilution steps were performed in a 96-well microtiter plate (final volume 50 µL/well). For vaginal washes 7 consecutive 3-fold dilution steps were analysed.

Beads coupled with 2KOFA1090 OMVs TRD9 were prepared to dispense 3000 beads/well. Immediately before dispensing in the plate, beads were mixed by vortex for approximately 20 seconds then 50 µL were added to prediluted sera in a final volume of 100 µL per well.

Plates were incubated for 60 min at RT in the dark on a plate shaker at 700 rpm and after incubation, unbound antibodies were removed by washing plates three times with 200 µL PBS (wash buffer).

For specific anti-OMVs IgG detection, each well was then loaded with 50 µL of 2.5 µg/mL of R-Phycoerythrin-AffiniPure F(ab')₂ Fragment Goat Anti-Mouse-IgG Fcγ fragment specific (Jackson Immunoresearch 115-116-071) in PBS pH 7.2, 0.05% Tween 20, 0.5% BSA and plates and were incubated for 60 min at RT in the dark on a plate shaker at 700 rpm.

For specific anti-OMV IgA detection, each well was then loaded with 50 µL of 5 µg/mL of R-Phycoerythrin Goat Anti-Mouse IgA (Southern Biotech 1040-09) in PBS pH 7.2, 0.05% Tween 20, 0.5% BSA and plates and were incubated for 60 min at RT in the dark on a plate shaker at 700 rpm.

After washing, beads were suspended in 100 µL of PBS and shaken before analysis with Bioplex 200. Data were acquired in real time by Bioplex Manager Software 6.2 (BioRad) used also to fit the model of the Standard curve.

Results: Immunization of CD1 mice with FA1090 2KO OMV vaccine candidate adsorbed to Alum resulted in induction of:

Comparable hSBA titres in 4wp2 and 2wp3 pooled sera
against FA1090 homologous strain for all FA1090 2KO
OMV vaccine lots tested (7 lots)— see FIG. 24

Statistically significant higher SBA using human comple-
ment (hSBA) titres of single 2wp3 sera of all FA1090
2KO OMV tested lots (3 lots) on the homologous strain
FA1090 and 8 out of 10 heterologous strains tested as
compared to both Alum and Bexsero—see FIG. 25

Comparable specific anti-OMV IgG titres in 4wp2 and
2wp3 pooled sera for all FA1090 2KO OMV vaccine
lots tested (7 lots)— FIG. 26

Figure 28B:
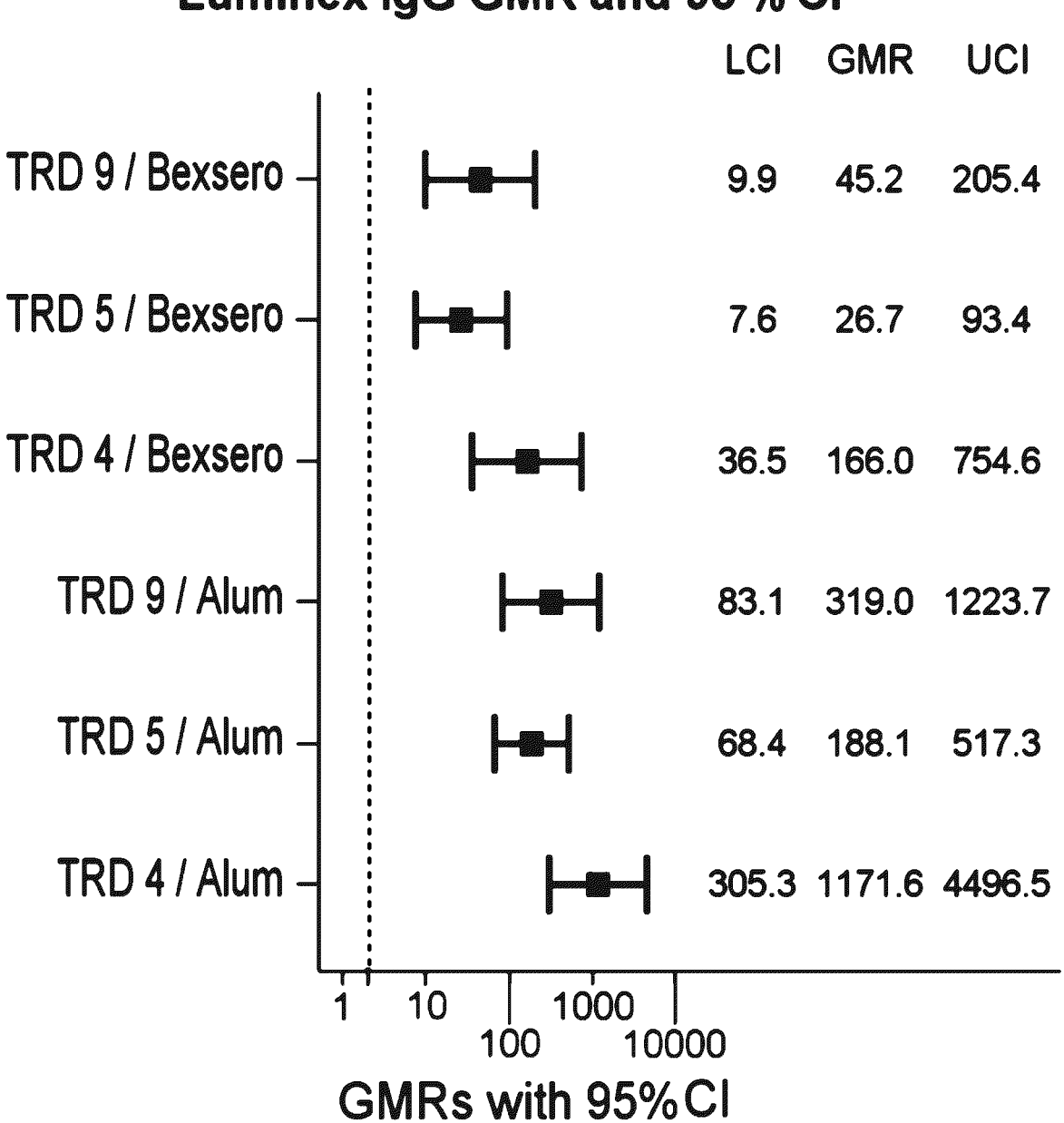
Figure 29B:

Statistically significant higher Anti-OMV IgG titres of
single 2wp3 sera of all 3 FA1090 2KO OMV tested lots
(FIG. 27) and vaginal washes as compared to both
Alum and Bexsero (FIG. 28A and FIG. 28B);

Statistically significant higher Anti-OMV IgA titres of
vaginal washes of all 3 FA1090 2KO OMV tested lots
as compared to both Alum and Bexsero—FIG. 29A and
FIG. 29B Conclusion: Demonstration of a functional immune
response able to block different immunological mechanism
and the superiority compared to Bexsero commercial vac-
cine constitutes important evidence supporting the FA1090
2KO (Δlpxl1,Δrmp) OMV vaccine candidate.

FA1090 2KO OMV vaccine was able to induce statisti-
cally superior bactericidal titres (compared to both Alum and
Bexsero), on the homologous strain FA1090 and the major-
ity of heterologous strains tested.

The immunogenicity response as measured by Luminex
analysis of mice sera and vaginal washes demonstrated
significant induction of OMV specific antibodies. In par-
ticular, the FA1090 2KO OMV vaccine was able to induce
higher anti-OMV IgG titres with a GMR≥2 (LL 95% CI)
compared to Alum and Bexsero in both sera and vaginal
washes and anti-OMV IgA titres with a GMR≥2 (LL 95%
CI) compared to Alum and Bexsero in vaginal washes.

Finally, data in mice (presented in Example 16) demon-
strated the capability of FA1090 2KO OMV vaccine candi-
date to elicit antibodies that inhibit the adhesion of three
different gonococcal strains (the homologous strain FA1090
and two selected heterologous strains) to the primary ure-
teral cell line SVHUC-1 cells which are representative of the
urinary epithelial tract.

Taken together these pre-clinical results support the
immunogenicity of the FA1090 2KO OMV vaccine candi-
date adsorbed to Alum.

Example 20: Comparison of FA1090 Vaccine Strain Versus GC_0817560

Objective: To retrieve the protein sequence from publicly
available and internally sequenced genomes of the most
abundant proteins present in FA1090 2KOOMVs (see
Example 12) and compare the protein sequence and diver-
sity of the most abundant proteins present in the OMVs
between FA1090 2KO ((Δlpxl1,Δrmp) and GC_0817640
strains and characterise the phase variable tracts that control
the expression of functional OpaB.

Materials and Methods

Assembly of FA1090_2KOgenome: The genome of the
FA1090 2KOstrain used in the Examples presented herein
(Δlpxl1,Δrmpl was sequenced as described in Example 9.
The raw data from two sequencing runs was mixed and assembled together to produce a final, closed and complete,
assembly of the chromosome and an accessory short plasmid
for a total of 2,161,273 bp.

Assembly of GC_0817560 genome: The genome
sequence (at contig level) of the *Neisseria gonorrhoeae*
strain GC_0817560 was publicly available from the Pub-
MLST database. The available sequence is not closed and
composed by 151 contigs for a total of 2,154,632 bp of
length. The database also referred to the original Illumina
raw data available from the European Nucleotide Archive
(ENA) with accession id ERR349896.

Identification of protein sequence of the most abundant
GMMA protein components: As described in Example 12
the top protein components accounted for the >80% of the
protein mass of the OMVs. The most abundant proteins
were: PorB and the Opa family proteins.

Identification of PorB gene on FA1090 2KO,
GC_0817560 and other publicly available genomes: The
protein sequence of PorB were extracted by homology
BLAST search at DNA and protein sequence level. The
searches were performed with Bigsdb software based on
BLAST homology searches. The assumed start and stop
gene sequence positions for PorB are those annotated by
PubMLST database (Gene locus NEIS2020, FA1090
genome identifier NGO1812).

Bigsdb software allowed the identification of the position
of the loci on the genome sequences and assigned gene and
protein unique identifiers for these loci in each genome.
Multiple alignments of the protein sequence of all gonococ-
cal strains available from PubMLST database to date were
performed for PorB with MUSCLE software. Protein phy-
logeny reconstructions were performed with MEGA soft-
ware by NJ method and p-distance between sequences.

Graphic view of the protein sequences that were extracted
from FA1090 2KO and GC_0817560 genomes was pro-
duced with BioEdit software. Variable codons were coloured
by Blosum62 identity/similarity distance matrix (variable
codons in black, variable codons with similar physicochemi-
cal properties in boxes, as defined by Blosum62 matrix and
reported by BioEdit software).

Identification of Opa genes on FA1090 2KO genome: The
annotation of the *Neisseria gonorrhoeae* FA1090 strain
genome (accession identifier NC 002946 from GenBank
Refseq database) was used to annotate the genes on the
FA1090 2KO (Δlpxl1,Δrmp) closed genome, which was
internally sequenced. Gene sequences were extracted with
Bedtools getfasta function and then BLAST was used to get
the closest matches.

Identification of Opa genes on GC_0817560 genome: The
identification of the loci on GC_0817560 genome, was done
in essentially the same way as for the FA1090 2KO genome,
starting from the sequences extracted from the FA1090 2KO
genome plus their flanking regions (1000 nucleotides
upstream and downstream). These sequences were used to
identify the exact location of the genes with BLAST. The
approach was also complemented by searching on the
GC_0817560 genome for the position of the flanking genes
that were annotated upstream and downstream to each Opa
gene.

Population quantification for opaB: The analysis pipeline
that was used to evaluate the number of bacteria in the
population having a sequence that was translated in a
complete version of the protein starts with mapping the
Illumina sequencing reads to the closed genome sequence of
the FA1090 2KO genome.

Samples included in this Example are:

FA1090_wild-type (wild-type FA1090 strain with no genetic modifications)

FA1090_2KO_adapted ((Δlpxl1, Δrmp)

GC_0817560 reads downloaded from ENA (id: ERR349896)

Other strains: including the sequences for F62, SK92-679, WHO-F and WHO-G and the public sequences of WHO-M and WHO-N downloaded from ENA (id: ERR352751 and ERR388420 for WHO-M and ERR363586 for WHO-N)

For the mapping, the Burrows-Wheeler Aligner (BWA) mem algorithm with default parameters was utilised because it automatically uses the mate-pairs, and it assigns each read to a single position on the genome. These two characteristics are particularly important for an accurate alignment of reads in genes that have closely similar paralogs. After alignment, the files produced were sorted and indexed with samtools suite. An R script was used for the extraction of all the reads aligning to the regions of interest through the iteration of samtools tview until the reference sequence (after removing the spaces) reaches the length of the short sequence repeat (SSR) on the closed genome plus two flanking bases. After, the script removed the reads that do not cover entirely the region and then summarized the length of the SSR observed in each read.

The translation script assembled the sequence of that locus by joining:

The sequence extracted from FA1090 2KO genome from the start codon to the beginning of the SSR The sequence of the SSR cut from each read aligned spanning the entire SSR The sequence extracted from FA1090 2KO genome from the end of the SSR to the stop codon Each assembled sequence is then translated using the specific function from seqinr R package and the percentage of ON/OFF population is computed.

Results

PorB: PorB is the most abundant protein in the OMVs from the FA1090 2KOstrain (see Example 12). The overall *Neisseria gonorrhoeae* diversity of the PorB molecule is represented in the phylogenetic tree of FIG. 30.

A direct comparison of PorB protein sequences from FA1090_2KO and GC_0817560 is depicted in the protein sequence alignment of FIG. 31, where the extracellular variable Loops (1-8) are identified from the PubMLST classification.

The molecules harboured by the two strains are classified as PorB IB allelic forms. FIG. 31 shows that PorB diversity between the two strains is mainly focused on extracellular Loop 5, 6 and 7. The functional role of the extracellular loops was deeply investigated for gonococcal PorB molecule (Infect Immun. 2013 December; 81(12): 4383-4391) and in particular Loops 4-7 were demonstrated to bind complement regulatory factor C4bp and play a role in variations to resistance to serum-mediated killing.

Opa: In the FA1090 2KO strain, 11 Opa loci were identified (see Table 8). Most of them were in OFF phase variation, in the consensus sequence. For opaD, which has an ON sequence on the public databases, we have observed an OFF sequence in the sample sequenced internally. In the 2KO FA1090 strain, opaB predominates.

TABLE 8

| Identified coordinates of Opa loci on FA1090 2KO genome | | | | |
| --- | --- | --- | --- | --- |
| Chromosome | Start | End | Gene | Strand |
| 1 | 69142 | 69956 | opaA | − |
| 1 | 74894 | 75692 | opaB | − |
| 1 | 1000502 | 1001347 | opaC | − |
| 1 | 1483931 | 1484763 | opaD | + |
| 1 | 1833181 | 1834022 | opaE | − |
| 1 | 925679 | 926526 | opaF | + |
| 1 | 2039329 | 2040161 | opaG | − |
| 1 | 1533814 | 1534603 | opaH | + |
| 1 | 1428325 | 1429157 | opaI | − |
| 1 | 1035967 | 1036736 | opaJ | + |
| 1 | 1232206 | 1233036 | opaK | + |

This analysis successfully assessed the proportion of bacteria in the sequenced population resulting in complete amino acid sequences of opaB.

opaB is the second most abundant antigen in FA1090 gonococcal OMVs, and nearly the entire population expresses a sequence that can be translated in a complete protein both in FA1090 WT (89%) and in the 2KO (median 96%). On the contrary, GC_0817560, as well as other strains reported in this analysis, has lower amount of complete protein accounting to 20% and a median of 19%, respectively (see FIG. 32).

CONCLUSION

This data shows that the PorB sequences of the two strains analysed differ in the loop regions and that functional OpaB protein is expected to be less abundant in GC_0817560 strain compared to FA1090 2KO (Δlpxl1,Δrmp).

PorB and OpaB are two of the most abundant proteins present in gonococcal OMVs.

---

SEQUENCE LISTING:

SEQ ID NO: 1-FA1090 Rmp nucleotide Sequence
ATGACCAAACAGCTGAAATTAAGCGCATTATTCGTTGCATTGCTCGCTTCCGGCACTGCTGTTG
CGGGCGAGGCGTCCGTTCAGGGTTACACCGTAAGCGGCCAATCGAACGAAATCGTACGCAACA
ACTATGGAGAATGCTGGAAAAACGCCTACTTTGATAAAGCAAGCCAAGGTCGCGTAGAATGCG
GCGATGCGGTTGCCGTCCCCGAGCCCGAACCCGCGCCTGTCGCCGTTGTGGAGCAGGCTCCTCA
ATATGTTGATGAAACCATTTCCCTGTCTGCCAAAACCCTGTTCGGTTTCGATAAGGATTCATTGC
GCGCCGAAGCTCAAGACAACCTGAAAGTATTGGCGCAACGCCTGAGTCGAACCAATGTCCAAT
CTGTCCGCGTCGAAGGCCATACCGACTTTATGGGTTCTGAAAAATACAATCAGGCTCGTCCGA
ACGCCGCGCATACGTAGTGGCAAACAACCTGGTCAGCAACGGCGTACCTGCTTCTAGAATTTCT
GCTGTCGGCTTGGGCGAATCTCAAGCGCAAATGACTCAAGTTTGTCAAGCCGAAGTTGCCAAAC
TGGGTGCGAAAGCCTCTAAAGCCAAAAAACGTGAGGCTCTGATTGCATGTATCGAACCTGACC
GCCGCGTAGATGTGAAAATCCGCAGCATCGTAACCCGTCAGGTTGTGCCGGCACGCAATCATC
ACCAACACTAA SEQ ID NO: 2-FA1090 Rmp protein sequence
MTKQLKLSALFVALLASGTAVAGEASVQGYTVSGQSNEIVRNNYGECWKNAYFDKASQGRVECG
DAVAVPEPEPAPVAVVEQAPQYVDETISLSAKTLFGFDKDSLRAEAQDNLKVLAQRLSRTNVQSVR VEGHTDFMGSEKYNQALSERRAYVVANNLVSNGVPASRISAVGLGESQAQMTQVCQAEVAKLGA
KASKAKKREALIACIEPDRRVDVKIRSIVTRQVVPARNHHQH SEQ ID NO: 3-FA1090 lpxl1 nucleotide sequence
ATGAAATTTATATTTTTTGTACTGTATGTTTTGCAGTTTCTGCCGTTTGCGCTGCTGCACAAGATT
GCCGGCCTGATCGGTTCGCTTGCCTACCTTCTGGTCAAACCGCGCCGCCGTATCGGCGAAATCA
ATTTGGCAAAATGTTTTCCCGAATGGGACGAAGAAAAGCGTAAAACCGTGTTGAAACAGCATT
TCAAACACATGGCAAAACTGATGCTCGAATACGGCTTATATTGGTACGCGTCTGCCAAATGCCT
GAAATCGCTGGTGCGCTACCGCAATAAGCATTATTTGGACGACGCGCTGGCGGCGGGGGAAAA
AGTCATCATCCTGTACCCGCACTTTACCGCGTTCGAGATGGCGGTGTACGCGCTTAATCAGGAT
GTCCCGCTGATCAGTATGTATTCCCACCAAAAAAACAAGATATTGGACGAACAGATTTTGAAA
GGCCGCAACCGCTATCACAACGTCTTCCTTATCGGGCGCACCGAAGGGCTGCGCGCCCTCGTCA
AACAGTTCCGCAAAAGCAGTGCGCCGTTCCTGTATCTGCCCGATCAGGATTTCGGACGCAACAA
TTCGGTTTTTGTGGATTTTTTCGGCATTCAGACGGCAACGATTACCGGCTTGAGCCGCATTGCCG
CGCTTGCAAATGCAAAGTGATACCCGCCATTCCCGTCCGCGAGGCGGACAATACGGTTACATT
GCAATTCTATCCCGCTTGGAAATCCTTTCCGAGTGAAGACGCGCAAGCCGACGCGCAACGTATG
AACCGCTTTATCGAAGAACGCGTGCGCGAACACCCGGAACAATATTTCTGGCTGCACAAGCGTT
TCAAAACCCGTCCGGAAGGCAGCCCCGATTTTTACTGA SEQ ID NO: 4-FA1090 Lpxl1 protein sequence
MKFIFFVLYVLQFLPFALLHKIAGLIGSLAYLLVKPRRRIGEINLAKCFPEWDEEKRKTVLKQHFKH
MAKLMLEYGLYWYASAKCLKSLVRYRNKHYLDDALAAGEKVIILYPHFTAFEMAVYALNQDVPLI
SMYSHQKNKILDEQILKGRNRYHNVFLIGRTEGLRALVKQFRKSSAPFLYLPDQDFGRNNSVFVDFF
GIQTATITGLSRIAALANAKVIPAIPVREADNTVTLQFYPAWKSFPSEDAQADAQRMNRFIEERVREH
PEQYFWLHKRFKTRPEGSPDFY SEQ ID NO: 5-Lpxl1 Locus (corresponding to FIG. 12)
CCGGCATCGACGCTGATGCTCGGTCAGGCGCGCGGAGCGGCATTGGCGGCTTTGGTCAGCCAT
AAGCTGCCCGTTTCGGAATACACGGCCTTGCAGGTCAAACAGGCGGTGGTCGGCAAAGGCAAG
GCGGCGAAAGAACAGGTGCAGCATATGGTGGTGCAAATGCTGGGACTTTCGGGAACGCCGCAG
GCGGATGCGGCGGACGGTCTTGCCGTCGCGCTGACCCACGCCTTACGCAACCACGGGCTTGCCG
CCAAACTCAATCCTTCGGGGATGCAGGTCAAGCGCGGAAGGTTTCAATAGTTTCAGACGGCATT
TGTATTTTGCCGCCTGAAAAGAAAATGTGTACCGAGATGAAATTTATATTTTTTGTACTGTATGT
TTTGCAGTTTCTGCCGTTTGCGCTGCTGCACAAGATTGCCGGCCTGATCGGTTCGCTTGCCTACC
TTCTGGTCAAACCGCGCCGCCGTATCGGCGAAATCAATTTGGCAAAATGTTTTCCCGAATGGGA
CGAAGAAAAGCGTAAAACCGTGTTGAAACAGCATTTCAAACACATGGCAAAACTGATGCTCGA
ATACGGCTTATATTGGTACGCGTCTGCCAAATGCCTGAAATCGCTGGTGCGCTACCGCAATAAG
CATTATTTGGACGACGCGCTGGCGGCGGGGGAAAAAGTCATCATCCTGTACCCGCACTTTACCG
CGTTCGAGATGGCGGTGTACGCGCTTAATCAGGATGTCCCGCTGATCAGTATGTATTCCCACCA
AAAAAACAAGATATTGGACGAACAGATTTTGAAAGGCCGCAACCGCTATCACAACGTCTTCCT
TATCGGGCGCACCGAAGGGCTGCGCGCCCTCGTCAAACAGTTCCGCAAAAGCAGTGCGCCGTT
CCTGTATCTGCCCGATCAGGATTTCGGACGCAACAATTCGGTTTTTGTGGATTTTTTCGGCATTC
AGACGGCAACGATTACCGGCTTGAGCCGCATTGCCGCGCTTGCAAATGCAAAGTGATACCCG
CCATTCCCGTCCGCGAGGCGGACAATACGGTTACATTGCAATTCTATCCCGCTTGGAAATCCTT
TCCGAGTGAAGACGCGCAAGCCGACGCGCAACGTATGAACCGCTTTATCGAAGAACGCGTGCG
CGAACACCCGGAACAATATTTCTGGCTGCACAAGCGTTTCAAAACCCGTCCGGAAGGCAGCCC
CGATTTTTACTGACTACATAAAATTACAAACAAATCAGGCGTTTCAGATCAAAAACCCCGATT
GTTTTTGGGAATTTGAAACCCGGGTTGTACAAACAGGATTTGCCGGACGGTTTTAACGGTTCAG
TTGTTTGTAAAAACAATGCTTTTTTAAAATTGACAAAAAACAAGTATCTCATATAAGCCTTTTT
CATTAAACAGATAGTCAGATATTTTGTGCTAAAAATTTATATAATATTTAAATTAATATCAAGTT
ATAAAAAATATATGGAATTTTATTTTGTTTATTTATAATTTTAAGCA SEQ ID NO: 6-Lpxl1 Locus extracted from FA1090 Δlpxl1, Δrmp strain
(corresponding to FIG. 13)
CCGGCATCGACGCTGATGCTCGGTCAGGCGCGCGGAGCGGCATTGGCGGCTTTGGTCAGCCAT
AAGCTGCCCGTTTCGGAATACACGGCCTTGCAGGTCAAACAGGCGGTGGTCGGCAAAGGCAAG
GCGGCGAAAGAACAGGTGCAGCATATGGTGGTGCAAATGCTGGGACTTTCGGGAACGCCGCAG
GCGGATGCGGCGGACGGTCTTGCCGTCGCGCTGACCCACGCCTTACGCAACCACGGGCTTGCCG
CCAAACTCAATCCTTCGGGGATGCAGGTCAAGCGCGGAAGGTTTCAATAGTTTCAGACGGCATT
TGTATTTTGCCGTCTGAAAAGAAAATGTGTATCGAGATGAAATTTATATTTTTTGTACTGTATGT
TTTGCAGTTTCTGCCGTTTGCGCTGCTGCACAAGATTGCCGACCTGACGGGTTTGCTTGCCTACC
TTCTGGTCAAACCGCGCCGCCGTATCGGCGAAATCAATTTGGCAAAATGTTTTCCGAATGGAG
TGAGGAAAAGCGTAAACCGTGTTGAAACAGCATTTCAAACACATGGCGAAACTGATGTTGGA
ATACGGTTTATATTGGTACGCGCCTGCCGGACGTTTGAAATCGCTGGTGCGCTACCGCAATAAG
CATTATTTGGACGACGCGCTGGCGGCGGGGGAAAAAGTCATCATCCTGTATCCGCACTTCACCG
CTGCAGTTGCAGTGACTAACTAGGAGGAATAAATGGCTAAATGAGAATATCACCGGAATTGA
AAAAACTGATCGAAAAATACCGCTGCGTAAAAGATACGGAAGGAATGTCTCCTGCTAAGGTAT
ATAAGCTGGTGGGAGAAAATGAAAACCTATATTTAAAAATGACGGACAGCCGGTATAAAGGGA
CCACCTATGATGTGGAACGGGAAAAGGACATGATGCTATGGCTGGAAGGAAAGCTGCCTGTTC
CAAAGGTCCTGCACTTTGAACGGCATGATGGCTGGAGCAATCTGCTCATGAGTGAGGCCGATG
GCGTCCTTTGCTCGGAAGAGTATGAAGATGAACAAAGCCCTGAAAAGATTATCGAGCTGTATG
CGGAGTGCATCAGGCTCTTTCACTCCATCGACATATCGGATTGTCCCTATACGAATAGCTTAGA
CAGCCGCTTAGCCGAATTGGATTACTTACTGAATAACGATCTGGCCGATGTGGATTGCGAAAAC

SEQUENCE LISTING:

TGGGAAGAAGACACTCCATTTAAAGATCCGCGCGAGCTGTATGATTTTTTAAAGACGGAAAAG
CCCGAAGAGGAACTTGTCTTTTCCCACGGCGACCTGGGGGACAGCAACATCTTTGTGAAAGATG
GCAAAGTAAGTGGCTTTATTGATCTTGGGAGAAGCGGCAGGGCGGACAAGTGGTATGACATTG
CCTTCTGCGTCCGGTCGATCAGGGAGGATATCGGGGAAGAACAGTATGTCGAGCTATTTTTTGA
CTTACTGGGGATCAAGCCTGATTGGGAGAAAATAAAATACTATATTTTACTGGATGAATTGTTT
TAGTACCTGGAAGGAATAATGAGTCGACAGGATTTCGGACGCAACGATTCGGTTTTTGTGGATT
TTTTCGGTATTCAGACGGCAACGATTACCGGATTGAGCCGCATTGCCGCGCTTGCAAATGCAAA
AGTGATACCCGCCATTCCCGTCCGCGAGGCAGACAATACGGTTACATTGCATTTCTATCCCGCT
TGGAAATCCTTTCCGGGTGAAGACGCGAAAGCCGACGCGCAGCGCATGAACCGTTTTATCGAA
GACAGGGTGCGCGAACATCCGGAACAATATTTTTGGCTGCACAAGCGTTTTAAAACCCGTCCGG
AAGGCAGCCCCGATTTTTACTGACTACATAAAATTACAAAACAAATCAGGCGTTTCAGATCAAA
AACCCCGATTGTTTTTGGGAATTTGAAACCCGGGTTGTACAAACAGGATTTGCCGGACGGTTTT
AACGGTTCAGTTGTTTGTAAAAACAATGCTTTTTTAAAATTGACAAAAAACGAAATCGGTTTTA
AAGGCTTATTCCGAGAACAAAGGGGAGTGGATGCCGAAAACCCGGTTAATATATTATAGTGGA
TTAACAAAAACCAATACGGCGTTGCTTCGCCTTAGCTCAAAGAGAACGATTCCCTAAGGTGCTG
AAGCACCAAGCGAATCGGTTCCGTACTATTTGTACTGTCTGCGGCTTCGCCGCCTTGTCCTGATT
TTTGTTAATCCACTATAAAATTAAATTTGTTTAAAAACATAAAGTTGTAAACAAGTATCTCATAT
AAGCCTTTTTCATTAAACAGATAGTCAGATATTTGTGCTAAAAATTTATATAATATTTAAATTA
ATATCAAGTTATAAAAAATATATGGAATTTTATTTTGTTTATTTATAATTTTAAGCA

SEQ ID NO: 7-Rmp Locus (corresponding to FIG. 14)
CAACGGCAATCGTGCGATATGGAAAAAATCCCCCTAAAGTAATGACACGGAATTGATTTTTCG
GCATGATAGACTATCAGGAAACAGGCTGTTTTACGGTTGTTTTCAGGCGTTGAGTATTGACAGT
CCGCCCCCTGTTTCTTTATAGTGGAGACTGAAATATCCGATTTGCCGCCATGTTTCTACAGCGGC
CTGTATGTTGGCAATTCAGCAGTTGCTTCTGTATCTGCTGTACAAATCTAATGAGGGAATAAAA
TGACCAAACAGCTGAAATTAAGCGCATTATTCGTTGCATTGCTCGCTTCCGGCACTGCTGTTGC
GGGCGAGGCGTCCGTTCAGGGTTACACCGTAAGCGGCCAATCGAACGAAATCGTACGCAACAA
CTATGGAGAATGCTGGAAAAACGCCTACTTTGATAAAGCAAGCCAAGGTCGCGTAGAATGCGG
CGATGCGGTTGCCGTCCCCGAGCCCGAACCCGCGCCTGTCGCCGTTGTGGAGCAGGCTCCTCAA
TATGTTGATGAAACCATTTCCCTGTCTGCCAAAACCCTGTTCGGTTTCGATAAGGATTCATTGCG
CGCCGAAGCTCAAGACAACCTGAAAGTATTGGCGCAACGCCTGAGTCGAACCAATGTCCAATC
TGTCCGCGTCGAAGGCCATACCGACTTTATGGGTTCTGAAAAATACAATCAGGCTCTGTCCGAA
CGCCGCGCATACGTAGTGGCAAACAACCTGGTCAGCAACGGCGTACCTGCTTCTAGAATTTCTG
CTGTCGGCTTGGGCGAATCTCAAGCGCAAATGACTCAAGTTTGTCAAGCCGAAGTTGCCAAACT
GGGTGCGAAAGCCTCTAAAGCCAAAAAACGTGAGGCTCTGATTGCATGTATCGAACCTGACCG
CCGCGTAGATGTGAAAATCCGCAGCATCGTAACCCGTCAGGTTGTGCCGGCACGCAATCATCAC
CAACACTAAGGCTAGGTAATATCTTGCCGATGCATGAGGTTAGCGGATTTTGTACCGGGTACTG
TTGCAATATTCGTGAAACGTCGGCCGGTATCGATGATGTGAAACAAACCCCGCTTTTGCGGGGT
TTGTTTTTTTGGGTGGTTTTCTGAAACGGCTATCGTCAGAATCGGGGTGCAGGTTCGGATTCGGA
TTCAGATTCATGTTTGTGTCCCATTGCCGCGCTTTATAGTGGATTAACAAAAATCAGGACAAGG
CGACGAAGCCGCAGACAGTACAATAGTACGGCAAGGCGAGGCAACGCCGTACCGGTTTAAATT
TAATCCACTATATCGGTTGAAACTCTGATTTTAAGGCGGTAGGATGTGGGTTTGCCCATAGCAA
GGGAATCCTTTCTGTATCAAGCCCCGAAAGGGATAATTCATACAAATTCACGCCTTTCCCCCTC
ATTGGGAAATGGATGGAATCGTGCCCGATGTGTGCGGCACTGTATGCCGGATATGGTTTTATCA
TCATCCCT SEQ ID NO: 8-Rmp Locus extracted from FA1090 Δlpxll, Δrmp strain
(corresponding to FIG. 15)
CAACGGCAATCGTGCGATATGGAAAAAATCCCCCTAAAGTAATGACACGGAATTGATTTTTCG
GCATGATAGACTATCAGGAAACAGGCTGTTTTACGGTTGTTTTCAGGCGTTGAGCCCGGGACCT
CTTTAGCTTCTTGGAAGCTGTCAGTAGTATATCTAATAATTTATCTCCATTCCCTTTAGTAACGT
GTAACTTTCCAAATTTAAAAAAGCGACTCATAGAATTATTTCCTCCCGTTAAATAATAGATAAC
TATTAAAAATAGACAATACTTGCTCATAAGTAATGGTACTTAAATTGTTTACTTTGGCGTGTTTC
ATTGCTTGATGAAACTGATTTTTAGTAAACAGTTGACGATATTCTCGATTGACCCATTTTGAAAC
AAAGTACGTATATAGCTTCCAATATTTATCTGGAACATCGTGGTATGGCGGGTAAGTTTTATT
AAGACACTGTTTACTTTTGGTTTAGGATGAAAGCATTCCGCTGGCAGCTTAAGCAATTGCTGAA
TCGAGACTTGAGTGTGCAAGAGCAACCCTAGTGTTCGGTGAATATCCAAGGTACGCTTGTAGAA
TCCTTCTTCAACAATCAGATAGATGTCAGACGCATGGCTTTCAAAAACCACTTTTTTAATAATTT
GTGTGCTTAAATGGTAAGGAATACTCCCAACAATTTTATACCTCTGTTTGTTAGGGAATTGAAA
CTGTAGAATATCTTGGTGAATTAAAGTGACACGAATGTTCAGTTTTAATTTTTCTGACGATAAGT
TGAATAGATGACTGTCTAATTCAATAGACGTTACCTGTTTACTTATTTTAGCCAGTTTCGTCGTT
AAATGCCCTTTACCTGTTCCAATTTCGTAAACGGTATCGGTTTCTTTTAAATTCAATTGTTTTATT
ATTTGGTTGAGTACTTTTTCACTCGTTAAAAAGTTTTGAGAATATTTTATATTTTTGTTCATGTAA
TTACTCCTGAAGTGATTACATCTGTAAATAAATACAGAAGTTAAACGATTTGTTTGTAATTTTAG
TTATCTGTTTAAAAAGTCATAAGATTAGTCACTGGTAGGAATTAATCTAACGTATTTATTTATCT
GCGTAATCACTGTTTTTAGTCTGTTTCAAAACAGTAGATGTTTTATCTACATTACGCATTTGGAA
TACCAACATGACGAATCCCTCCTTCTTAATTACAAATTTTTAGCATCTAATTTAACTTCAATTCC
TATTATACACAAAATTTTAAGATACTGCACTATCAACACACTCTTAAGTTTCCCGGGTCAAGCG
CAAATGACTCAAGTTTGTCAAGCCGAAGTTGCCAAACTGGGTGCGAAAGCCTCTAAAGCCAAA
AAACGTGAGGCTCTGATTGCATGTATCGAACCTGACCGCCGCGTAGATGTGAAAATCCGCAGC
ATCGTAACCCGTCAGGTTGTGCCGGCACGCAATCATCACCAACACTAAGGCTAGGTAATATCTT
GCCGATGCATGAGGTTAGCGGATTTTGTACCGGGTACTGTTGCAATATTCGTGAAACGTCGGCC
GGTATCGATGATGTGAAACAAACCCCGCTTTTGCGGGGTTTGTTTTTTTGGGTGGTTTTCTGAAA
CGGCTATCGTCAGAATCGGGGTGCAGGTTCGGATTCGGATTCAGATTCATGTTTGTGTCCCATT
GCCGCGCTTTATAGTGGATTAACAAAAATCAGGACAAGGCGACGAAGCCGCAGACAGTACAAT
AGTACGGCAAGGCGAGGCAACGCCGTACCGGTTTAAATTTAATCCACTATATCGGTTGAAACTC
TGATTTTAAGGCGGTAGGATGTGGGTTTGCCCATAGCAAGGGAATCCTTTCTGTATCAAGCCCC

SEQUENCE LISTING:

GAAAGGGATAATTCATACAAATTCACGCCTTTCCCCCTCATTGGGAAATGGATGGAATCGTGCC
CGATGTGTGCGGCACTGTATGCCGGATATGGTTTTATCATCATCCCT

SEQ ID NO: 9: lpxl1_UP FW
GGCATTTGTATTTTGCCGTCTG

SEQ ID NO: 10-lpxl1_DO REV
GCGAAATGTACGCCATTTTCTACGC

SEQ ID NO: 11-UpIII-FOR
gctctagaGGTCGTCTATCCGTTCCGTA

SEQ ID NO: 12-UpIII-REV
tcccccgggCTCAACGCCTGAAAACAACC

SEQ ID NO: 13-DpIII-FOR
tcccccgggTCAAGCGCAAATGACTCAAG

SEQ ID NO: 14-DpIII-REV
cccgctcgagGGGAAAGGCGTGAATTTGTA

SEQ ID NO: 15-EryR_gono_SmaI-Fw
ATTCGCCCGGGAAACTTAAGAGTGTGTTGATAGTG

SEQ ID NO: 16-EryR_gono_SmaI-Rev
ATTCGCCCGGGACCTCTTTAGCTTCTTGG

SEQ ID NO: 17-lpxl1 est FW
CCGCCAAACTCAATCCTTCG

SEQ ID NO: 18-lpxl1 est REV
GCAAACTTTTGTTTCACCGTTTCCG

SEQ ID NO: 19-NGO_lpxL1wtcheck-Fw
CCGCGTTCGAGATGG

SEQ ID NO: 20-NGO_lpxL1wtcheck-Rev
GCGGAACTGTTTGACGAG

SEQ ID NO: 21-UP_CHECK_NGO1577-Fw
GTGTGTCCAGTCGTAGCAGG

SEQ ID NO: 22-DW_CHECK_NGO1577-Rev
AGGGATGATGATAAAACCATATCC

SEQ ID NO: 23-INTwt_NGO1577-Fw
TCGTACGCAACAACTATGGAG

SEQ ID NO: 24-INTwt_NGO1577-Rev
CATCAACATATTGAGGAGCCTG

SEQ ID NO: 25-FA1090 2KO PorB Protein
MKKSLIALTLAALPVAAMADVTLYGAIKAGVQTYRSVEHTDGKVSKVETGSEIADFGSKI
GFKGQEDLGNGLKAVWQLEQGASVAGTNTGWGNKQSFVGLKGGFGTIRAGSLNSPLKNTG
ANVNAWESGKFTGNVLEISGMAQREHRYLSVRYDSPEFAGFSGSVQYAPKDNSGSNGESY
HVGLNYQNSGFFAQYAGLFQRYGEGTKKIEYDGQTYSIPSLFVEKLQVHRLVGGYDNNAL
YVSVAAQQQDAKLYGAMSGNSHNSQTEVAATAAYRFGNVTPRVSYAHGFKGTVDSANHDN
TYDQVVVGAEYDFSKRTSALVSAGWLQEGKGADKIVSTASAVVLRHKF SEQ ID NO: 26-FA1090 2KO PorB Protein (Loop 1)
TYRSVEHTDGKVSKVETGSEIA SEQ ID NO: 27-FA1090 2KO PorB Protein (Loop 2)
ASVAGTNTGWG SEQ ID NO: 28-FA1090 2KO PorB Protein (Loop 3)
LNSPLKNTGANVNAWESGKFTGNVLEISGMAQREHRY SEQ ID NO: 29-FA1090 2KO PorB Protein (Loop 4)
APKDNSGSNGE SEQ ID NO: 30-FA1090 2KO PorB Protein (Loop 5)
RYGEGTKKIEYDGQTYSIPSLFVEKL SEQ ID NO: 31-FA1090 2KO PorB Protein (Loop 6)
DAKLYGAMSGNSHN

SEQUENCE LISTING:

SEQ ID NO: 32-FA1090 2KO PorB Protein (Loop 7)
FKGTVDSANHDNT

SEQ ID NO: 33-FA1090 2KO PorB Protein (Loop 8)
GWLQEGKGADKIVSTA

The invention claimed is:

1. A genetically modified gonococcal bacterium of strain FA1090 suitable for liquid culture, comprising genetic modification(s) that:

a. decreases or abolishes expression and/or function of the lipid A biosynthesis lauroyl acyltransferase (lpxl1) gene, mRNA, and/or polypeptide; and b. decreases or abolishes expression and/or function of the reduction modifiable protein (rmp) gene, mRNA, and/or polypeptide.

2. The gonococcal bacterium of claim 1 wherein the lpxl1 gene comprises a sequence at least 80% identical to the sequence as set forth in SEQ ID NO: 3 and wherein the rmp gene comprises a sequence at least 80% identical to the sequence set forth in SEQ ID NO: 1.

3. The gonococcal bacterium of claim 1, wherein the genetic modification(s):

a. decreases or abolishes expression and/or function of the Lpxl1 polypeptide; and b. decreases or abolishes expression and/or function of the Rmp polypeptide.

4. The gonococcal bacterium of claim 1 wherein the Lpxl1 polypeptide comprises an amino acid sequence at least 80% identical to SEQ ID NO: 4 and the Rmp polypeptide comprises an amino acid sequence at least 80% identical to SEQ ID NO: 2.

5. The gonococcal bacterium of claim 1, wherein the genetic modification(s) consist of or comprise, a) disruption or deletion of the endogenous lpxl1 and rmp genes; or b) suppression of Lpxl1 and Rmp polypeptide expression in a strain comprising the wild-type lpxl1 and rmp genes.

6. A process for producing the gonococcal bacterium according to claim 1, the process comprising either:

a) decreasing or abolishing the expression and/or function of the lpxl1 gene mRNA and/or polypeptide in a gonococcal FA1090 bacterium to produce a first gonococcal FA1090 bacterium and decreasing or abolishing the expression and/or function of the rmp gene mRNA and/or polypeptide from the first gonococcal FA1090 bacterium to produce a second gonococcal FA1090 bacterium; or b) decreasing or abolishing the expression and/or function of the rmp gene mRNA and/or polypeptide from the first gonococcal FA1090 bacterium to produce a first gonococcal FA1090 bacterium and decreasing or abolishing the expression and/or function of the lpxl1 gene mRNA and/or polypeptide from the first gonococcal FA1090 bacterium to produce a second gonococcal FA1090 bacterium.

7. An outer membrane vesicle obtained or obtainable from an FA1090 strain gonococcus, wherein said outer membrane vesicle comprises either reduced levels or no detectable level of both Lpxl1 and Rmp polypeptides, optionally wherein said reduced levels or no detectable level of both Lpxl1 and Rmp polypeptides is measured in comparison to an outer membrane vesicle obtained from a wild-type FA1090 bacterium.

8. An outer membrane vesicle (OMV) from a genetically modified FA1090 strain gonococcus, said genetically modified FA1090 strain gonococcus comprising genetic modification(s) that: a) decreases or abolishes expression and/or function of the lpxl1 gene, lpxl1 mRNA, and/or Lpxl1 polypeptide; and b) decreases or abolishes expression and/or function of the rmp gene, rmp mRNA, and/or Rmp polypeptide, said OMV comprising:

I. reduced levels of Rmp polypeptide compared to the levels of Rmp polypeptide in a comparator OMV from a N. gonorrhoeae strain FA1090 that lacks said genetic modifications; and II. reduced levels of hexa-acylated lipid A compared to the levels of hexa-acylated lipid A from the comparator OMV.

9. An outer membrane vesicle obtained or obtainable from a gonococcal bacterium according to claim 1.

10. The outer membrane vesicle of claim 9, comprising decreased or abolished expression of the Lpxl1 polypeptide and decreased or abolished expression of the Rmp polypeptide.

11. The outer membrane vesicle of claim 9 comprising reduced levels of the Rmp polypeptide compared to the levels of the Rmp polypeptide in a comparator OMV from a N. gonorrhoeae strain FA1090 that lacks said genetic modification(s) and reduced levels of hexa-acylated lipid A compared to the levels of hexa-acylated lipid A from the comparator OMV.

12. The outer membrane vesicle of claim 7, wherein said outer membrane vesicle is a native outer membrane vesicle that is not detergent extracted.

13. An immunogenic composition comprising an outer membrane vesicle according to claim 7, wherein the immunogenic composition further comprises an adjuvant, wherein the adjuvant is an aluminium salt adjuvant.

14. A vaccine comprising the outer membrane vesicle of claim 7 and a pharmaceutically acceptable excipient.

15. The outer membrane vesicle of claim 9, wherein said outer membrane vesicle is a native outer membrane vesicle that is not detergent extracted.

16. An immunogenic composition comprising an outer membrane vesicle according to claim 9, wherein the immunogenic composition further comprises an adjuvant, wherein the adjuvant is an aluminium salt adjuvant.

17. The immunogenic composition comprising an outer membrane vesicle according to claim 13, wherein the aluminium salt adjuvant is aluminium hydroxide.

18. The immunogenic composition comprising an outer membrane vesicle according to claim 16, wherein the aluminium salt adjuvant is aluminium hydroxide.

19. A vaccine comprising the outer membrane vesicle of claim 8 and a pharmaceutically acceptable excipient.

20. A vaccine comprising the outer membrane vesicle of claim 9 and a pharmaceutically acceptable excipient.

21. A method for immunizing a subject in need thereof against Neisseria comprising administering an immunologically effective amount of the immunogenic composition according to claim 7 to the subject.

* * * * *

SEQUENCE LISTING

<160> NUMBER OF SEQ ID NOS: 33

<210> SEQ ID NO 1
<211> LENGTH: 711
<212> TYPE: DNA
<213> ORGANISM: Neisseria gonorrhoeae

<400> SEQUENCE: 1
atgaccaaac agctgaaatt aagcgcatta ttcgttgcat tgctcgcttc cggcactgct        60
gttgcgggcg aggcgtccgt tcagggttac accgtaagcg gccaatcgaa cgaaatcgta       120
cgcaacaact atggagaatg ctggaaaaac gcctactttg ataaagcaag ccaaggtcgc       180
gtagaatgcg gcgatgcggt tgccgtcccc gagcccgaac ccgcgcctgt cgccgttgtg       240
gagcaggctc ctcaatatgt tgatgaaacc atttccctgt ctgccaaaac cctgttcggt       300
ttcgataagg attcattgcg cgccgaagct caagacaacc tgaaagtatt ggcgcaacgc       360
ctgagtcgaa ccaatgtcca atctgtccgc gtcgaaggcc ataccgactt tatgggttct       420
gaaaaataca tcaggctct gtccgaacgc cgcgcatacg tagtggcaaa caacctggtc       480
agcaacggcg tacctgcttc tagaatttct gctgtcggct tgggcgaatc tcaagcgcaa       540
atgactcaag tttgtcaagc cgaagttgcc aaactgggtg cgaaagcctc taaagccaaa       600
aaacgtgagg ctctgattgc atgtatcgaa cctgaccgcc gcgtagatgt gaaaatccgc       660
agcatcgtaa cccgtcaggt tgtgccggca cgcaatcatc accaacacta a              711

<210> SEQ ID NO 2
<211> LENGTH: 236
<212> TYPE: PRT
<213> ORGANISM: Neisseria gonorrhoeae

<400> SEQUENCE: 2

Met Thr Lys Gln Leu Lys Leu Ser Ala Leu Phe Val Ala Leu Leu Ala
1               5                   10                  15

Ser Gly Thr Ala Val Ala Gly Glu Ala Ser Val Gln Gly Tyr Thr Val
            20                  25                  30

Ser Gly Gln Ser Asn Glu Ile Val Arg Asn Asn Tyr Gly Glu Cys Trp
        35                  40                  45

Lys Asn Ala Tyr Phe Asp Lys Ala Ser Gln Gly Arg Val Glu Cys Gly
    50                  55                  60

Asp Ala Val Ala Val Pro Glu Pro Glu Pro Ala Pro Val Ala Val Val
65                  70                  75                  80

Glu Gln Ala Pro Gln Tyr Val Asp Glu Thr Ile Ser Leu Ser Ala Lys
                85                  90                  95

Thr Leu Phe Gly Phe Asp Lys Asp Ser Leu Arg Ala Glu Ala Gln Asp
            100                 105                 110

Asn Leu Lys Val Leu Ala Gln Arg Leu Ser Arg Thr Asn Val Gln Ser
        115                 120                 125

-continued

Val Arg Val Glu Gly His Thr Asp Phe Met Gly Ser Glu Lys Tyr Asn
130             135             140

Gln Ala Leu Ser Glu Arg Arg Ala Tyr Val Val Ala Asn Asn Leu Val
145             150             155             160

Ser Asn Gly Val Pro Ala Ser Arg Ile Ser Ala Val Gly Leu Gly Glu
165             170             175

Ser Gln Ala Gln Met Thr Gln Val Cys Gln Ala Glu Val Ala Lys Leu
180             185             190

Gly Ala Lys Ala Ser Lys Ala Lys Lys Arg Glu Ala Leu Ile Ala Cys
195             200             205

Ile Glu Pro Asp Arg Arg Val Asp Val Lys Ile Arg Ser Ile Val Thr
210             215             220

Arg Gln Val Val Pro Ala Arg Asn His His Gln His
225             230             235

<210> SEQ ID NO 3
<211> LENGTH: 870
<212> TYPE: DNA
<213> ORGANISM: Neisseria gonorrhoeae

<400> SEQUENCE: 3
atgaaattta tattttttgt actgtatgtt ttgcagtttc tgccgtttgc gctgctgcac      60
aagattgccg gcctgatcgg ttcgcttgcc taccttctgg tcaaaccgcg ccgccgtatc     120
ggcgaaatca atttggcaaa atgttttccc gaatgggacg aagaaaagcg taaaaccgtg     180
ttgaaacagc atttcaaaca catggcaaaa ctgatgctcg aatacggctt atattggtac     240
gcgtctgcca aatgcctgaa atcgctggtg cgctaccgca taagcatta tttggacgac     300 gcgctggcgg cggggaaaa agtcatcatc ctgtacccgc actttaccgc gttcgagatg     360
gcggtgtacg cgcttaatca ggatgtcccg ctgatcagta tgtattccca ccaaaaaaac     420
aagatattgg acgaacagat tttgaaaggc cgcaaccgct atcacaacgt cttccttatc     480
gggcgcaccg aagggctgcg cgccctcgtc aaacagttcc gcaaaagcag tgcgccgttc     540
ctgtatctgc cgatcagga tttcggacgc aacaattcgg tttttgtgga ttttttcggc     600
attcagacgg caacgattac cggcttgagc cgcattgccg cgcttgcaaa tgcaaaagtg     660
atacccgcca ttcccgtccg cgaggcggac aatacggtta cattgcaatt ctatcccgct     720
tggaaatcct ttccgagtga agacgcgcaa gccgacgcgc aacgtatgaa ccgctttatc     780
gaagaacgcg tgcgcgaaca cccggaacaa tatttctggc tgcacaagcg tttcaaaacc     840
cgtccggaag cagccccga tttttactga                                      870

<210> SEQ ID NO 4
<211> LENGTH: 289
<212> TYPE: PRT
<213> ORGANISM: Neisseria gonorrhoeae

<400> SEQUENCE: 4

Met Lys Phe Ile Phe Phe Val Leu Tyr Val Leu Gln Phe Leu Pro Phe
1               5               10              15

Ala Leu Leu His Lys Ile Ala Gly Leu Ile Gly Ser Leu Ala Tyr Leu
            20              25              30

Leu Val Lys Pro Arg Arg Arg Ile Gly Glu Ile Asn Leu Ala Lys Cys
            35              40              45

Phe Pro Glu Trp Asp Glu Glu Lys Arg Lys Thr Val Leu Lys Gln His
            50              55              60

-continued

```
Phe Lys His Met Ala Lys Leu Met Leu Glu Tyr Gly Leu Tyr Trp Tyr
65                  70                  75                  80

Ala Ser Ala Lys Cys Leu Lys Ser Leu Val Arg Tyr Arg Asn Lys His
                85                  90                  95

Tyr Leu Asp Asp Ala Leu Ala Ala Gly Glu Lys Val Ile Ile Leu Tyr
            100                 105                 110

Pro His Phe Thr Ala Phe Glu Met Ala Val Tyr Ala Leu Asn Gln Asp
            115                 120                 125

Val Pro Leu Ile Ser Met Tyr Ser His Gln Lys Asn Lys Ile Leu Asp
        130                 135                 140

Glu Gln Ile Leu Lys Gly Arg Asn Arg Tyr His Asn Val Phe Leu Ile
145                 150                 155                 160

Gly Arg Thr Glu Gly Leu Arg Ala Leu Val Lys Gln Phe Arg Lys Ser
            165                 170                 175

Ser Ala Pro Phe Leu Tyr Leu Pro Asp Gln Asp Phe Gly Arg Asn Asn
            180                 185                 190

Ser Val Phe Val Asp Phe Phe Gly Ile Gln Thr Ala Thr Ile Thr Gly
        195                 200                 205

Leu Ser Arg Ile Ala Ala Leu Ala Asn Ala Lys Val Ile Pro Ala Ile
    210                 215                 220

Pro Val Arg Glu Ala Asp Asn Thr Val Thr Leu Gln Phe Tyr Pro Ala
225                 230                 235                 240

Trp Lys Ser Phe Pro Ser Glu Asp Ala Gln Ala Asp Ala Gln Arg Met
            245                 250                 255

Asn Arg Phe Ile Glu Glu Arg Val Arg Glu His Pro Glu Gln Tyr Phe
            260                 265                 270

Trp Leu His Lys Arg Phe Lys Thr Arg Pro Glu Gly Ser Pro Asp Phe
        275                 280                 285

Tyr

<210> SEQ ID NO 5
<211> LENGTH: 1771
<212> TYPE: DNA
<213> ORGANISM: Neisseria gonorrhoeae

<400> SEQUENCE: 5
ccggcatcga cgctgatgct cggtcaggcg cgcggagcgg cattggcggc tttggtcagc        60
cataagctgc ccgtttcgga atacacggcc ttgcaggtca aacaggcggt ggtcggcaaa       120
ggcaaggcgg cgaaagaaca ggtgcagcat atggtggtgc aaatgctggg actttcggga       180
acgccgcagg cggatgcggc ggacggtctt gccgtcgcgc tgacccacgc cttacgcaac       240
cacgggcttg ccgccaaact caatccttcg gggatgcagg tcaagcgcgg aaggtttcaa       300
tagtttcaga cggcatttgt attttgccgc ctgaaaagaa aatgtgtacc gagatgaaat       360
ttatattttt tgtactgtat gttttgcagt ttctgccgtt tgcgctgctg cacaagattg       420
ccggcctgat cggttcgctt gcctaccttc tggtcaaacc gcgccgccgt atcggcgaaa       480
tcaatttggc aaaatgtttt cccgaatggg acgaagaaaa gcgtaaaacc gtgttgaaac       540
agcatttcaa acacatggca aaactgatgc tcgaatacgg cttatattgg tacgcgtctg       600
ccaaatgcct gaaatcgctg gtgcgctacc gcaataagca ttatttggac gacgcgctgg       660
cggcggggga aaaagtcatc atcctgtacc cgcactttac gcgttcgag atggcggtgt       720 acgcgcttaa tcaggatgtc ccgctgatca gtatgtattc ccaccaaaaa aacaagatat       780
tggacgaaca gattttgaaa ggccgcaacc gctatcacaa cgtcttcctt atcgggcgca       840
```

-continued

```
ccgaagggct gcgcgccctc gtcaaacagt tccgcaaaag cagtgcgccg ttcctgtatc    900
tgcccgatca ggatttcgga cgcaacaatt cggttttttgt ggattttttc ggcattcaga    960
cggcaacgat taccggcttg agccgcattg ccgcgcttgc aaatgcaaaa gtgatacccg   1020
ccattcccgt ccgcgaggcg gacaatacgg ttacattgca attctatccc gcttggaaat   1080
cctttccgag tgaagacgcg caagccgacg cgcaacgtat gaaccgcttt atcgaagaac   1140
gcgtgcgcga acaccggaa caatatttct ggctgcacaa gcgtttcaaa acccgtccgg   1200
aaggcagccc cgattttttac tgactacata aaattacaaa acaaatcagg cgtttcagat   1260
caaaaacccc gattgttttt gggaatttga aacccgggtt gtacaaacag gatttgccgg   1320
acggttttaa cggttcagtt gtttgtaaaa acaatgcttt tttaaaattg acaaaaaacg   1380
aaatcggttt taaaggctta ttccgagaac aaaggggagt ggatgccgaa aacccggtta   1440
atatattata gtggattaac aaaaaccaat acggcgttgc ttcgccttag ctcaaagaga   1500
acgattccct aaggtgctga agcaccaagc gaatcggttc cgtactattt gtactgtctg   1560
cggcttcgcc gccttgtcct gatttttgtt aatccactat aaaattaaat ttgtttaaaa   1620
acataaagtt gtaaacaagt atctcatata agccttttttc attaaacaga tagtcagata   1680
ttttgtgcta aaaatttata taatatttaa attaatatca agttataaaa aatatatgga   1740
attttatttt gtttatttat aattttaagc a                                  1771
```

<210> SEQ ID NO 6
<211> LENGTH: 2416
<212> TYPE: DNA
<213> ORGANISM: Neisseria gonorrhoeae

<400> SEQUENCE: 6

```
ccggcatcga cgctgatgct cggtcaggcg cgcggagcgg cattggcggc tttggtcagc     60
cataagctgc ccgtttcgga atacacggcc ttgcaggtca aacaggcggt ggtcggcaaa    120
ggcaaggcgg cgaaagaaca ggtgcagcat atggtggtgc aaatgctggg actttcggga    180
acgccgcagg cggatgcggc ggacggtctt gccgtcgcgc tgacccacgc cttacgcaac    240
cacgggcttg ccgccaaact caatccttcg gggatgcagg tcaagcgcgg aaggtttcaa    300
tagtttcaga cggcatttgt attttgccgt ctgaaaagaa aatgtgtatc gagatgaaat    360 ttatatttttt tgtactgtat gttttgcagt ttctgccgtt tgcgctgctg cacaagattg    420
ccgacctgac gggtttgctt gcctaccttc tggtcaaacc gcgccgccgt atcggcgaaa    480
tcaatttggc aaaatgtttt tccgaatgga gtgaggaaaa gcgtaaaacc gtgttgaaac    540
agcatttcaa acacatggcg aaactgatgt tggaatacgg tttatattgg tacgcgcctg    600
ccggacgttt gaaatcgctg gtgcgctacc gcaataagca ttatttggac gacgcgctgg    660 cggcgggga aaaagtcatc atcctgtatc cgcacttcac cgctgcagtt gcagtgacta    720
actaggagga ataaatggct aaaatgagaa tatcaccgga attgaaaaaa ctgatcgaaa    780
aataccgctg cgtaaaagat acggaaggaa tgtctcctgc taaggtatat aagctggtgg    840
gagaaaatga aaacctatat ttaaaaatga cggacagccg gtataaaggg accacctatg    900
atgtggaacg ggaaaaggac atgatgctat ggctggaagg aaagctgcct gttccaaagg    960
tcctgcactt tgaacggcat gatggctgga gcaatctgct catgagtgag gccgatggcg   1020
tcctttgctc ggaagagtat gaagatgaac aaagccctga aaagattatc gagctgtatg   1080
cggagtgcat caggctcttt cactccatcg acatatcgga ttgtccctat acgaatagct   1140
```

```
tagacagccg cttagccgaa ttggattact tactgaataa cgatctggcc gatgtggatt   1200
gcgaaaactg ggaagaagac actccattta aagatccgcg cgagctgtat gattttttaa   1260
agacggaaaa gccccgaagag gaacttgtct tttcccacgg cgacctgggg gacagcaaca   1320
tctttgtgaa agatggcaaa gtaagtggct ttattgatct tgggagaagc ggcagggcgg   1380
acaagtggta tgacattgcc ttctgcgtcc ggtcgatcag ggaggatatc ggggaagaac   1440
agtatgtcga gctattttt gacttactgg ggatcaagcc tgattgggag aaaataaaat   1500
actatatttt actggatgaa ttgttttagt acctggaagg aataatgagt cgacaggatt   1560
tcggacgcaa cgattcggtt tttgtggatt ttttcggtat tcagacggca acgattaccg   1620
gattgagccg cattgccgcg cttgcaaatg caaaagtgat acccgccatt cccgtccgcg   1680
aggcagacaa tacggttaca ttgcatttct atcccgcttg gaaatccttt ccgggtgaag   1740
acgcgaaagc cgacgcgcag cgcatgaacc gttttatcga agacagggtg cgcgaacatc   1800
cggaacaata ttttttggctg cacaagcgtt ttaaaacccg tccggaaggc agccccgatt   1860
tttactgact acataaaatt acaaaacaaa tcaggcgttt cagatcaaaa accccgattg   1920
tttttgggaa tttgaaaccc gggttgtaca aacaggattt gccggacggt tttaacggtt   1980
cagttgtttg taaaaacaat gcttttttaa aattgacaaa aaacgaaatc ggtttttaaag   2040 gcttattccg agaacaaagg gggagtggatg ccgaaaaccc ggttaatata ttatagtgga   2100
ttaacaaaaa ccaatacggc gttgcttcgc cttagctcaa agagaacgat tccctaaggt   2160
gctgaagcac caagcgaatc ggttccgtac tatttgtact gtctgcggct tcgccgcctt   2220
gtcctgattt ttgttaatcc actataaaat taaatttgtt taaaaacata aagttgtaaa   2280
caagtatctc atataagcct ttttcattaa acagatagtc agatattttg tgctaaaaat   2340
ttatataata tttaaattaa tatcaagtta taaaaaatat atggaatttt attttgttta   2400
tttataattt taagca                                                    2416

<210> SEQ ID NO 7
<211> LENGTH: 1477
<212> TYPE: DNA
<213> ORGANISM: Neisseria gonorrhoeae

<400> SEQUENCE: 7
caacggcaat cgtgcgatat ggaaaaaatc cccctaaagt aatgacacgg aattgatttt     60
tcggcatgat agactatcag gaaacaggct gttttacggt tgttttcagg cgttgagtat    120
tgacagtccg ccccctgttt ctttatagtg gagactgaaa tatccgattt gccgccatgt    180
ttctacagcg gcctgtatgt tggcaattca gcagttgctt ctgtatctgc tgtacaaatc    240
taatgaggga ataaaatgac caaacagctg aaattaagcg cattattcgt tgcattgctc    300
gcttccggca ctgctgttgc gggcgaggcg tccgttcagg gttacaccgt aagcggccaa    360
tcgaacgaaa tcgtacgcaa caactatgga gaatgctgga aaaacgccta ctttgataaa    420
gcaagccaag gtcgcgtaga atgcggcgat gcggttgccg tccccgagcc cgaacccgcg    480
cctgtcgccg ttgtggagca ggctcctcaa tatgttgatg aaaccatttc cctgtctgcc    540
aaaaccctgt tcggtttcga taaggattca ttgcgcgccg aagctcaaga caacctgaaa    600
gtattggcgc aacgcctgag tcgaaccaat gtccaatctg tccgcgtcga aggccatacc    660
gactttatgg gttctgaaaa atacaatcag gctctgtccg aacgccgcgc atacgtagtg    720
gcaaacaacc tggtcagcaa cggcgtacct gcttctagaa tttctgctgt cggcttgggc    780
gaatctcaag cgcaaatgac tcaagtttgt caagccgaag ttgccaaact gggtgcgaaa    840
```

-continued

```
gcctctaaag ccaaaaaacg tgaggctctg attgcatgta tcgaacctga ccgccgcgta        900
gatgtgaaaa tccgcagcat cgtaacccgt caggttgtgc cggcacgcaa tcatcaccaa        960
cactaaggct aggtaatatc ttgccgatgc atgaggttag cggattttgt accgggtact       1020
gttgcaatat tcgtgaaacg tcggccggta tcgatgatgt gaaacaaacc ccgctttttgc      1080 ggggtttgtt tttttggggtg gttttctgaa acggctatcg tcagaatcgg ggtgcaggtt      1140
cggattcgga ttcagattca tgtttgtgtc ccattgccgc gctttatagt ggattaacaa       1200
aaatcaggac aaggcgacga agccgcagac agtacaatag tacggcaagg cgaggcaacg       1260
ccgtaccggt ttaaatttaa tccactatat cggttgaaac tctgatttta aggcggtagg       1320
atgtgggttt gcccatagca agggaatcct ttctgtatca agccccgaaa gggataattc       1380
atacaaattc acgcctttcc ccctcattgg gaaatggatg gaatcgtgcc cgatgtgtgc       1440
ggcactgtat gccggatatg gttttatcat catccct                                1477
```

```
<210> SEQ ID NO 8
<211> LENGTH: 1978
<212> TYPE: DNA
<213> ORGANISM: Neisseria gonorrhoeae

<400> SEQUENCE: 8
caacggcaat cgtgcgatat ggaaaaaatc cccctaaagt aatgacacgg aattgatttt         60
tcggcatgat agactatcag gaaacaggct gttttacggt tgttttcagg cgttgagccc        120
gggacctctt tagcttcttg gaagctgtca gtagtatatc taataatttta tctccattcc       180 ctttagtaac gtgtaacttt ccaaatttaa aaaagcgact catagaatta tttcctcccg        240
ttaaataata gataactatt aaaaatagac aatacttgct cataagtaat ggtacttaaa        300
ttgtttactt tggcgtgttt cattgcttga tgaaactgat ttttagtaaa cagttgacga        360
tattctcgat tgacccattt tgaaacaaag tacgtatata gcttccaata tttatctgga        420
acatctgtgg tatggcgggt aagttttatt aagacactgt ttacttttgg tttaggatga        480
aagcattccg ctggcagctt aagcaattgc tgaatcgaga cttgagtgtg caagagcaac        540
cctagtgttc ggtgaatatc caaggtacgc ttgtagaatc cttcttcaac aatcagatag        600
atgtcagacg catggctttc aaaaaccact tttttaataa tttgtgtgct taaatggtaa        660
ggaatactcc caacaatttt atacctctgt ttgttaggga attgaaactg tagaatatct        720
tggtgaatta aagtgacacg aatgttcagt tttaattttt ctgacgataa gttgaataga        780
tgactgtcta attcaataga cgttacctgt ttacttattt tagccagttt cgtcgttaaa        840
tgccctttac ctgttccaat ttcgtaaacg gtatcggttt cttttaaatt caattgtttt        900
attatttggt tgagtacttt ttcactcgtt aaaaagtttt gagaatattt tatatttttg        960
ttcatgtaat tactcctgaa gtgattacat ctgtaaataa atacagaagt taaacgattt       1020
gtttgtaatt ttagttatct gtttaaaaag tcataagatt agtcactggt aggaattaat       1080
ctaacgtatt tatttatctg cgtaatcact gttttttagtc tgtttcaaaa cagtagatgt      1140
tttatctaca ttacgcattt ggaataccaa catgacgaat ccctccttct taattacaaa       1200
tttttagcat ctaatttaac ttcaattcct attatacaca aaattttaag atactgcact       1260
atcaacacac tcttaagttt cccgggtcaa gcgcaaatga ctcaagtttg tcaagccgaa       1320
gttgccaaac tgggtgcgaa agcctctaaa gccaaaaaac gtgaggctct gattgcatgt       1380
atcgaacctg accgccgcgt agatgtgaaa atccgcagca tcgtaacccg tcaggttgtg       1440
```

```
ccggcacgca atcatcacca acactaaggc taggtaatat cttgccgatg catgaggtta      1500
gcggattttg taccgggtac tgttgcaata ttcgtgaaac gtcggccggt atcgatgatg      1560
tgaaacaaac cccgcttttg cggggtttgt ttttttgggt ggttttctga aacggctatc      1620
gtcagaatcg gggtgcaggt tcggattcgg attcagattc atgtttgtgt cccattgccg      1680
cgctttatag tggattaaca aaaatcagga caaggcgacg aagccgcaga cagtacaata      1740
gtacggcaag gcgaggcaac gccgtaccgg tttaaattta atccactata tcggttgaaa      1800
ctctgatttt aaggcggtag gatgtgggtt tgcccatagc aagggaatcc tttctgtatc      1860
aagccccgaa aggggataatt catacaaatt cacgcctttc cccctcattg ggaaatggat      1920
ggaatcgtgc ccgatgtgtg cggcactgta tgccggatat ggttttatca tcatccct       1978
```

```
<210> SEQ ID NO 9
<211> LENGTH: 22
<212> TYPE: DNA
<213> ORGANISM: Artificial
<220> FEATURE:
<223> OTHER INFORMATION: PCR primer

<400> SEQUENCE: 9
ggcatttgta ttttgccgtc tg                                                22
```

```
<210> SEQ ID NO 10
<211> LENGTH: 25
<212> TYPE: DNA
<213> ORGANISM: Artificial
<220> FEATURE:
<223> OTHER INFORMATION: PCR primer

<400> SEQUENCE: 10
gcgaaatgta cgccattttc tacgc                                             25
```

```
<210> SEQ ID NO 11
<211> LENGTH: 28
<212> TYPE: DNA
<213> ORGANISM: Artificial
<220> FEATURE:
<223> OTHER INFORMATION: PCR primer

<400> SEQUENCE: 11
gctctagagg tcgtctatcc gttccgta                                          28
```

```
<210> SEQ ID NO 12
<211> LENGTH: 29
<212> TYPE: DNA
<213> ORGANISM: Artificial
<220> FEATURE:
<223> OTHER INFORMATION: PCR primer

<400> SEQUENCE: 12
tcccccgggc tcaacgcctg aaaacaacc                                         29
```

```
<210> SEQ ID NO 13
<211> LENGTH: 29
<212> TYPE: DNA
<213> ORGANISM: Artificial
<220> FEATURE:
<223> OTHER INFORMATION: PCR primer

<400> SEQUENCE: 13
tcccccgggt caagcgcaaa tgactcaag                                         29
```

-continued

```
<210> SEQ ID NO 14
<211> LENGTH: 30
<212> TYPE: DNA
<213> ORGANISM: Artificial
<220> FEATURE:
<223> OTHER INFORMATION: PCR primer

<400> SEQUENCE: 14
cccgctcgag gggaaaggcg tgaatttgta                                   30

<210> SEQ ID NO 15
<211> LENGTH: 35
<212> TYPE: DNA
<213> ORGANISM: Artificial
<220> FEATURE:
<223> OTHER INFORMATION: PCR primer

<400> SEQUENCE: 15
attcgcccgg gaaacttaag agtgtgttga tagtg                             35

<210> SEQ ID NO 16
<211> LENGTH: 29
<212> TYPE: DNA
<213> ORGANISM: Artificial
<220> FEATURE:
<223> OTHER INFORMATION: PCR primer

<400> SEQUENCE: 16
attcgcccgg gacctcttta gcttcttgg                                    29

<210> SEQ ID NO 17
<211> LENGTH: 20
<212> TYPE: DNA
<213> ORGANISM: Artificial
<220> FEATURE:
<223> OTHER INFORMATION: PCR primer

<400> SEQUENCE: 17
ccgccaaact caatccttcg                                              20

<210> SEQ ID NO 18
<211> LENGTH: 25
<212> TYPE: DNA
<213> ORGANISM: Artificial
<220> FEATURE:
<223> OTHER INFORMATION: PCR primer

<400> SEQUENCE: 18
gcaaactttt gtttcaccgt ttccg                                        25

<210> SEQ ID NO 19
<211> LENGTH: 15
<212> TYPE: DNA
<213> ORGANISM: Artificial
<220> FEATURE:
<223> OTHER INFORMATION: PCR primer

<400> SEQUENCE: 19
ccgcgttcga gatgg                                                   15

<210> SEQ ID NO 20
<211> LENGTH: 18
<212> TYPE: DNA
<213> ORGANISM: Artificial
<220> FEATURE:
<223> OTHER INFORMATION: PCR prime
```

-continued

<400> SEQUENCE: 20
gcggaactgt ttgacgag                                                        18

<210> SEQ ID NO 21
<211> LENGTH: 20
<212> TYPE: DNA
<213> ORGANISM: Artificial
<220> FEATURE:
<223> OTHER INFORMATION: PCR primer

<400> SEQUENCE: 21
gtgtgtccag tcgtagcagg                                                      20

<210> SEQ ID NO 22
<211> LENGTH: 24
<212> TYPE: DNA
<213> ORGANISM: Artificial
<220> FEATURE:
<223> OTHER INFORMATION: PCR primer

<400> SEQUENCE: 22
agggatgatg ataaaaccat atcc                                                 24

<210> SEQ ID NO 23
<211> LENGTH: 21
<212> TYPE: DNA
<213> ORGANISM: Artificial
<220> FEATURE:
<223> OTHER INFORMATION: PCR primer

<400> SEQUENCE: 23
tcgtacgcaa caactatgga g                                                    21

<210> SEQ ID NO 24
<211> LENGTH: 22
<212> TYPE: DNA
<213> ORGANISM: Artificial
<220> FEATURE:
<223> OTHER INFORMATION: PCR primer

<400> SEQUENCE: 24
catcaacata ttgaggagcc tg                                                   22

<210> SEQ ID NO 25
<211> LENGTH: 348
<212> TYPE: PRT
<213> ORGANISM: Neisseria gonorrhoeae

<400> SEQUENCE: 25

Met Lys Lys Ser Leu Ile Ala Leu Thr Leu Ala Ala Leu Pro Val Ala
1               5                   10                  15

Ala Met Ala Asp Val Thr Leu Tyr Gly Ala Ile Lys Ala Gly Val Gln
                20                  25                  30

Thr Tyr Arg Ser Val Glu His Thr Asp Gly Lys Val Ser Lys Val Glu
            35                  40                  45

Thr Gly Ser Glu Ile Ala Asp Phe Gly Ser Lys Ile Gly Phe Lys Gly
        50                  55                  60

Gln Glu Asp Leu Gly Asn Gly Leu Lys Ala Val Trp Gln Leu Glu Gln
65                  70                  75                  80

Gly Ala Ser Val Ala Gly Thr Asn Thr Gly Trp Gly Asn Lys Gln Ser
                85                  90                  95

Phe Val Gly Leu Lys Gly Gly Phe Gly Thr Ile Arg Ala Gly Ser Leu

```
                    100                 105                 110

Asn Ser Pro Leu Lys Asn Thr Gly Ala Asn Val Asn Ala Trp Glu Ser
        115                 120                 125

Gly Lys Phe Thr Gly Asn Val Leu Glu Ile Ser Gly Met Ala Gln Arg
    130                 135                 140

Glu His Arg Tyr Leu Ser Val Arg Tyr Asp Ser Pro Glu Phe Ala Gly
145                 150                 155                 160

Phe Ser Gly Ser Val Gln Tyr Ala Pro Lys Asp Asn Ser Gly Ser Asn
                165                 170                 175

Gly Glu Ser Tyr His Val Gly Leu Asn Tyr Gln Asn Ser Gly Phe Phe
                180                 185                 190

Ala Gln Tyr Ala Gly Leu Phe Gln Arg Tyr Gly Glu Gly Thr Lys Lys
        195                 200                 205

Ile Glu Tyr Asp Gly Gln Thr Tyr Ser Ile Pro Ser Leu Phe Val Glu
        210                 215                 220

Lys Leu Gln Val His Arg Leu Val Gly Gly Tyr Asp Asn Asn Ala Leu
225                 230                 235                 240

Tyr Val Ser Val Ala Ala Gln Gln Gln Asp Ala Lys Leu Tyr Gly Ala
                245                 250                 255

Met Ser Gly Asn Ser His Asn Ser Gln Thr Glu Val Ala Ala Thr Ala
                260                 265                 270

Ala Tyr Arg Phe Gly Asn Val Thr Pro Arg Val Ser Tyr Ala His Gly
        275                 280                 285

Phe Lys Gly Thr Val Asp Ser Ala Asn His Asp Asn Thr Tyr Asp Gln
        290                 295                 300

Val Val Val Gly Ala Glu Tyr Asp Phe Ser Lys Arg Thr Ser Ala Leu
305                 310                 315                 320

Val Ser Ala Gly Trp Leu Gln Glu Gly Lys Gly Ala Asp Lys Ile Val
                325                 330                 335

Ser Thr Ala Ser Ala Val Val Leu Arg His Lys Phe
                340                 345
```

```
<210> SEQ ID NO 26
<211> LENGTH: 22
<212> TYPE: PRT
<213> ORGANISM: Neisseria gonorrhoeae

<400> SEQUENCE: 26

Thr Tyr Arg Ser Val Glu His Thr Asp Gly Lys Val Ser Lys Val Glu
1               5                   10                  15

Thr Gly Ser Glu Ile Ala
            20

<210> SEQ ID NO 27
<211> LENGTH: 11
<212> TYPE: PRT
<213> ORGANISM: Neisseria gonorrhoeae

<400> SEQUENCE: 27

Ala Ser Val Ala Gly Thr Asn Thr Gly Trp Gly
1               5                   10

<210> SEQ ID NO 28
<211> LENGTH: 37
<212> TYPE: PRT
<213> ORGANISM: Neisseria gonorrhoeae

<400> SEQUENCE: 28
```

```
Leu Asn Ser Pro Leu Lys Asn Thr Gly Ala Asn Val Asn Ala Trp Glu
1               5                   10                  15

Ser Gly Lys Phe Thr Gly Asn Val Leu Glu Ile Ser Gly Met Ala Gln
            20                  25                  30

Arg Glu His Arg Tyr
        35
```

```
<210> SEQ ID NO 29
<211> LENGTH: 11
<212> TYPE: PRT
<213> ORGANISM: Neisseria gonorrhoeae

<400> SEQUENCE: 29

Ala Pro Lys Asp Asn Ser Gly Ser Asn Gly Glu
1               5                   10
```

```
<210> SEQ ID NO 30
<211> LENGTH: 26
<212> TYPE: PRT
<213> ORGANISM: Neisseria gonorrhoeae

<400> SEQUENCE: 30

Arg Tyr Gly Glu Gly Thr Lys Lys Ile Glu Tyr Asp Gly Gln Thr Tyr
1               5                   10                  15

Ser Ile Pro Ser Leu Phe Val Glu Lys Leu
            20                  25
```

```
<210> SEQ ID NO 31
<211> LENGTH: 14
<212> TYPE: PRT
<213> ORGANISM: Neisseria gonorrhoeae

<400> SEQUENCE: 31

Asp Ala Lys Leu Tyr Gly Ala Met Ser Gly Asn Ser His Asn
1               5                   10
```

```
<210> SEQ ID NO 32
<211> LENGTH: 13
<212> TYPE: PRT
<213> ORGANISM: Neisseria gonorrhoeae

<400> SEQUENCE: 32

Phe Lys Gly Thr Val Asp Ser Ala Asn His Asp Asn Thr
1               5                   10
```

```
<210> SEQ ID NO 33
<211> LENGTH: 16
<212> TYPE: PRT
<213> ORGANISM: Neisseria gonorrhoeae

<400> SEQUENCE: 33

Gly Trp Leu Gln Glu Gly Lys Gly Ala Asp Lys Ile Val Ser Thr Ala
1               5                   10                  15
```